(12) United States Patent
Peto et al.

(10) Patent No.: US 11,072,600 B2
(45) Date of Patent: Jul. 27, 2021

(54) PHTHALAZINE DERIVATIVES AS INHIBITORS OF PARP1, PARP2, AND/OR TUBULIN USEFUL FOR THE TREATMENT OF CANCER

(71) Applicants: THE REGENTS OF THE UNIVERSITY OF CALIFORNIA, Oakland, CA (US); ATLASMEDX, INC., San Francisco, CA (US)

(72) Inventors: Csaba J. Peto, San Francisco, CA (US); David M. Jablons, San Francisco, CA (US); Tsze Tsang, El Cerrito, CA (US); Hassan Lemjabbar-Alaoui, San Francisco, CA (US)

(73) Assignees: THE REGENTS OF THE UNIVERSITY OF CALIFORNIA, Oakland, CA (US); ATLASMEDX, INC., San Francisco, CA (US)

( * ) Notice: Subject to any disclaimer, the term of this patent is extended or adjusted under 35 U.S.C. 154(b) by 0 days.

(21) Appl. No.: 16/310,606

(22) PCT Filed: Jun. 23, 2017

(86) PCT No.: PCT/US2017/039119
§ 371 (c)(1),
(2) Date: Dec. 17, 2018

(87) PCT Pub. No.: WO2017/223516
PCT Pub. Date: Dec. 28, 2017

(65) Prior Publication Data
US 2019/0337928 A1 Nov. 7, 2019

Related U.S. Application Data

(60) Provisional application No. 62/354,449, filed on Jun. 24, 2016, provisional application No. 62/426,095, filed on Nov. 23, 2016.

(51) Int. Cl.
| | | |
|---|---|---|
| *C07D 403/10* | (2006.01) | |
| *A61P 35/00* | (2006.01) | |
| *C07D 401/14* | (2006.01) | |
| *C07D 407/14* | (2006.01) | |
| *C07D 413/14* | (2006.01) | |
| *C07D 471/04* | (2006.01) | |

(52) U.S. Cl.
CPC ............ *C07D 403/10* (2013.01); *A61P 35/00* (2018.01); *C07D 401/14* (2013.01); *C07D 407/14* (2013.01); *C07D 413/14* (2013.01); *C07D 471/04* (2013.01)

(58) Field of Classification Search
CPC .................................................. C07D 403/10
See application file for complete search history.

(56) References Cited

U.S. PATENT DOCUMENTS

| | | |
|---|---|---|
| 3,401,171 A | 9/1968 | Craig et al. |
| 6,677,333 B1 | 1/2004 | Seko et al. |
| 7,151,102 B2 | 12/2006 | Martin et al. |
| 2004/0235886 A1 | 11/2004 | Charifson et al. |
| 2009/0270617 A1 | 10/2009 | Menear et al. |
| 2012/0286157 A1 | 11/2012 | Fuhrmann et al. |
| 2014/0221314 A1 | 8/2014 | Shen et al. |
| 2014/0336190 A1 | 11/2014 | Aktoudianakis |

FOREIGN PATENT DOCUMENTS

| | | |
|---|---|---|
| CN | 102372706 | 3/2012 |
| SU | 1019810 A1 | 4/1991 |
| SU | 1218649 | 4/1991 |
| WO | WO 1999/040072 | 8/1999 |
| WO | WO 2000/050419 | 8/2000 |
| WO | WO 2002/036576 | 5/2002 |
| WO | WO 2004/080976 | 9/2004 |
| WO | WO 2005/112932 | 12/2005 |
| WO | WO 2006/124874 | 11/2006 |

(Continued)

OTHER PUBLICATIONS

Pinedo et al. (2000).*
McMahon et al. (2000).*
Burger's Medicinal Chemistry, pp. 975-977 (1997).*
Banker et al., "Modern Pharmaceuticals", p. 596.*
Neidle et al. (2008).*
International Search Report and Written Opinion EP ISA dated Sep. 20, 2017 (PCT/US2017/039119).
Ferraris, D.V., Journal of Medicinal Chemistry, vol. 53, No. 12, pp. 4561-4584 (2010).
Papeo, G. et al., Expert Opinion on Therapeutic Patents, vol. 23, No. 4, pp. 503-514 (2013).

(Continued)

*Primary Examiner* — Paul V Ward
(74) *Attorney, Agent, or Firm* — Morgan, Lewis & Bockius LLP; Todd Esker

(57) ABSTRACT

The application relates to phthalazine derivatives of formula (I) which are inhibitors of PARP1, PARP2 and/or tubulin and thus useful for the treatment of cancer. Also disclosed are pharmaceutical formulations containing such compounds, as well as combinations of these compounds with at least one additional therapeutic agent.

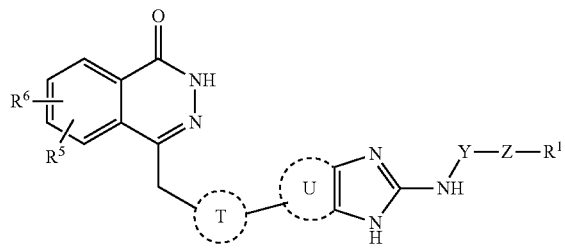

42 Claims, 15 Drawing Sheets

(56) References Cited

FOREIGN PATENT DOCUMENTS

| | | |
|---|---|---|
| WO | WO 2008/114023 | 9/2008 |
| WO | WO 2012/166983 | 12/2012 |
| WO | WO 2014/102817 | 7/2014 |
| WO | WO 2017/223516 | 12/2017 |

OTHER PUBLICATIONS

Peukert S. et al., Expert Opinion on Therapeutic Patents, vol. 14, No. 11, pp. 1531-1551 (2004).
Yuan, Z. et al., Expert Opinion on Therapeutic Patents, vol. 27, No. 3, pp. 363-382 (2016).
Zaremba, T. et al., Anti-Cancer Agents in Medicinal Chemistry, vol. 7, No. 5, pp. 515-523 (2007).
Grillot et al., "Second-Generation Antibacterial Benzimidazole Ureas: Discovery of a Preclinical Candidate with Reduced Metabolic Liability." Journal of Medicinal Chemistry, vol. 57, pp. 8792-8816 (2014).
Hong et al., "Discovery of New Benzothiazole-Based Inhibitors of Breakpoint Cluster Region-Abelson Kinase Including the T315I Mutant." Journal of Medicinal Chemistry, vol. 56, pp. 3531-3545 (2013).
Park et al., "Discovery of Picomolar ABL Kinase Inhibitors Equipotent for Wild Type and T315I Mutant via Structure-Based de Novo Design." Journal Am. Chem. Soc., vol. 135, pp. 8227-8237 (2013).
Sharma et al., "Virtual screening reveals allosteric inhibitors of the Toxoplasma gondii thymidylate synthase—dihydrofolate reductase." Bioorganic & Medicinal Chemistry Letters, 24, pp. 1232-1235 (2014).
Cheong et al., European Journal of Medicinal Chemistry, vol. 144, pp. 372-385 (2018).
Dubey et al., J. Med. Chem., vol. 28, pp. 1748-1750 (1985).
Hughes, D., Org. Process Res. Dev., vol. 21, No. 9, 1227-1244 (2017).
Kruse et al., J. Med. Chem., vol. 32, pp. 409-417 (1989).
Menear et al., J. Med. Chem., vol. 51, pp. 6581-6591 (2008).
Ram et al., J. Med. Chem., vol. 35, pp. 539-547 (1992).
Abbas et al., Single-agent Paclitaxel in Advanced Anal Cancer after Failure of Cisplatin and 5-Fluorouracil Chemotherapy, Anticancer Research 31: 4637-4640 (2011).
Ain et al., Treatment of Anaplastic Thyroid Carcinoma with Paclitaxel: Phase 2 Trial Using Ninety-Six-hour Infusion, Thyroid, vol. 10, No. 7, (2000).
Airoldi et al., Carboplatin plus taxol is an effective third-line regimen in recurrent undifferentiated nasopharyngeal carcinoma, Tumori, (2002); 88(4): 273-6.
Annino et al, Chemotherapy in Hairy Cell Leukemia, Cancer 53:2398-2400 (1984).
Carruthers et al., The potential of PARP inhibitors in neuro-oncology, CNS Oncol. (2012) 1(1), 85-97.
Castellano et al A phase I-II study to evaluate safety and efficacy of the combination of niraparib plus cabozantinib in patients with advanced kidney/urothelial carcinoma, Journal of Clinical Oncology 36, No. 15_suppl., (2018).
Chitapanarux et al., Induction chemotherapy with paclitaxel, ifosfamide, and cisplatin followed by concurrent chemoradiotherapy for unresectable locally advanced head and neck cancer, Biomed Imaging Interv J (2010); 6(3).
Chow et al., PARP1 Is Overexpressed in Nasopharyngeal Carcinoma and Its Inhibition Enhances Radiotherapy Mol Cancer Ther; 12(11) (2013).
Cook et al., Targeting Bone Metastatic Castration-Resistant Prostate Cancer, Am. J. Hematology/Oncology, vol. 12, No. 8, (2016) p. 17-22.
Costa et al., Chemotherapy for advanced adrenal cancer improvement from a molecular approach? BJU Int 108 1546-1554 (2011).
Cullinane et al., Abstract 1800: The PARP inhibitor, rucaparib enhances the antitumor activity of Lu-DOTA octreotate radionuclide therapy in preclinical models of neuroendocrine tumor, AACR 106th Annual Meeting 2015; Apr. 18-22 (2015); Philadelphia, PA.
D'Anneo et al. Paclitaxel and Beta-Lapachone Synergistically Induce Apoptosis in Human Retinoblastoma Y79 Cells by Downregulating the Levels of Phospho-Akt. J. Cell. Physiol. 222: 433-443, (2010).
Fam et al., TDP1 and PARP1 Deficiency Are Cytotoxic to Rhabdomyosarcoma Cells Mol Cancer Res; 11(10) (2013).
Garcia-Sanz et al., Waldenström macroglobulinaemia: presenting features and outcome in a series with 217 cases, British Journal of Haematology, vol. 115, Issue 3, (2001).
Hall et al., Taxol Inhibits Osteoclastic Bone Resorption, Celcif Tissue Int (1995) 57: 463-465.
Herman et al, Improved Outcomes With Carboplatin-Paclitaxel Compared to Docetaxel-Cisplatin-5-Fluorouracil Induction Chemotherapy in Locally-Advanced Squamous Cell Cancer of the Head and Neck, International Journal of Radiation Oncology, Biology, Physics, vol. 87, No. 2S, Supplement (2013) Poster Viewing Abstracts.
Horton et al, A Phase 1 and pharmacokinetic clinical trial of paclitaxel for the treatment of refractory leukemia in children—a Children's Oncology Group study Pediatr Blood Cancer. (2008); 50(4): 788-792.
Hu et al., Paclitaxel induces apoptosis and reduces proliferation by targeting epidermal growth factor receptor signaling pathway in oral cavity squamous cell carcinoma, Oncology Letters, 10: 2378-2384 (2015).
Jiang et al Lin Chuang Er Bi Yan Hou Ke Za Zhi, (2003);17(6):342-5.
Kivlin, Christine, Dissertation: Poly(ADP) Ribose Polymerase Inhibitors for the treatment of Malignant Peripheral Nerve Sheath Tumor, (2016).
Kondagunta et al., Carboplatin plus taxol is an effective third-line regimen in recurrent undifferentiated nasopharyngeal carcinoma, Journal of Clinical Oncology, vol. 23, No. 27, (2005).
Lemjabbar-Alaoui et al., Am J Cancer Res (2020); 10(8): 2649-2676.
Leong et al Paclitaxel, carboplatin, and gemcitabine in metastatic nasopharyngeal carcinoma, Cancer (2005) 103(3):569-75.
McCabe et al.. Cancer Res. (2006); 66:8109-8115.
Mego et al., PARP1 expression in testicular germ cell tumors, Journal of Clinical Oncology, vol. 30, No. 15, Abstract (2012).
Mizobe et al, Gemcitabine with Paclitaxel Therapy Against Mesocolic Leiomyosarcoma: A Case Report, Anticancer Research, 33: 2929-2934 (2013).
Musacchio et al., Cancer Management and Research (2020): 12 6123-6135.
Nakano et al., Combination chemotherapy of carboplatin and paclitaxel for advanced/metastatic salivary gland carcinoma patients: differences in responses by different pathological diagnoses, Acta Oto-Laryngologica, (2016) vol. 136, No. 9, 948-951.
Okano et al., The growth inhibition of liver cancer cells by paclitaxel and the involvement of extracellular signal-regulated kinase and apoptosis, Oncology Reports 17: 1195-1200, (2007).
Peng et al, Paclitaxel induces apoptosis in leukemia cells through a JNK activation-dependent pathway, Genetics and Molecular Research 15(1) (2016).
Protzel et al., Chemotherapy in Patients with Penile Carcinoma, Urol Int (2009); 82:1-7.
Reinecke et al, Antiproliferative Effects of Paclitaxel (Taxol) on Human Renal Clear Cell Carcinomas in Vitro. European Journal of Cancer vol. 33, No. 7, pp. 1122-1129, (1997).
Ruzich et al, Response to paclitaxel and carboplatin in metastatic salivary gland cancer: a case report, Head Neck 2002 (4):406-10.
Schaefer et al, Paclitaxel synergizes with exposure time adjusted CD22-targeting immunotoxins against B-cell malignancies Nucl Med Commun. (2011); 32(11): 1046-1051.
Shimo et al., Breast Cancer (2014) 21:75-85.
Shin et al, Phase II Study of Induction Chemotherapy with Paclitaxel, Ifosfamide, and Carboplatin (TIC) for Patients with Locally Advanced Squamous Cell Carcinoma of the Head and Neck, Cancer (2002), vol. 95, No. 2, 322-330.
Slichenmyer et al., Taxol: a new and effective anti-cancer drug, Anti-Cancer Drugs (1991) 2: 519-530.

(56) References Cited

OTHER PUBLICATIONS

Soumerai et al., Diagnosis and Management of Castleman Disease, Cancer Control (2014) vol. 21, No. 4, p. 266-278.
Tajima et al., Successful treatment of unresectable gallbladder cancer with low-dose paclitaxel as palliative chemotherapy after failure of gemcitabine and oral S-1: A case report, Oncology Letters 4: 1281-1284 (2012).
Takemoto et al., Primary adenocarcinoma of the vagina successfully treated with neoadjuvant chemotherapy consisting of paclitaxel and carboplatin, J. Obstet Gynaecol Res., (2009) Abstract 35(3): 579-83.
Termrungruanglert W, Kudelka AP, Piamsomboon S, et al. Remission of refractory gestational trophoblastic disease with high-dose paclitaxel. Anticancer Drugs (1996) 7:503.
Vormoor et al., Poly(ADP-ribose) polymerase inhibitors in Ewing sarcoma, Co-Oncology, vol. 26, No. 4, (2014), p. 428-433.
Witteveen et al., Phase II study on paclitaxel in patients with recurrent, metastatic or locally advanced vulvar cancer not amenable to surgery or radiotherapy: a study of the EORTC-GCG (European Organisation for Research and Treatment of Cancer—Gynaecological Cancer Group), Annals of Oncology 20: 1511-1516, (2009).
Xu et al., Efficacy and safety of the combination of paclitaxel and platinum in advanced thymic carcinoma, Thoracic Cancer, 7 (2016) 222-225.
Xu et al., The synergic antitumor effects of paclitaxel and temozolomide co-loaded in mPEG-PLGA nanoparticles on glioblastoma cells, Oncotarget, (2016) vol. 7, No. 15, 20890-20901.
Xu et al Potential biomarkers for paclitaxel sensitivity in hypopharynx cancer cell Int J Clin Exp Pathol (2013);6(12):2745-2756.
Yap et al., Poly(ADP-Ribose) Polymerase (PARP) Inhibitors: Exploiting a Synthetic Lethal Strategy in the Clinic, CA Cancer J Clin (2011); 61: 31-49.
Zeniou et al., Biochemical Pharmacology, vol. 167, Sep. 2019, pp. 107-115.
Zhang et al., Nab-Paclitaxel Is an Active Drug in Preclinical Model of Pediatric Solid Tumors, Clin Cancer Res; 19(21) (2013).
Cancer [online], [retrieved on Jul. 6, 2007] Retrieved from the Internet, URL: http://www.nlm.nih.gov/medlineplus/cancer.html (Year: 2007).
Golub et al., Molecular Classification of Cancer: Class Discovery and Class Prediction by Gene Expression Monitoring, Science ( 1999), vol. 286, 531-537 (Year: 1999).
Lala et al., Role of nitric oxide in tumor progression: Lessons from experimental tumors, Cancer and Metastasis Reviews (1998), 17 , 91-106 (Year: 1998).

\* cited by examiner

FIGURE 1A

| Name | PARP1 | Tubulin | A549 | OVCAR8 | MDA-MB-436 | Trapped PARP-DNA |
|---|---|---|---|---|---|---|
| Ethyl (5-(2-methyl-5-((4-oxo-3,4-dihydrophthalazin-1-yl)methyl)phenyl)-1H-benzoimidazol-2-yl)carbamate | 0.24 | 1.20 | 0.16 | 0.13 | 0.05 | NT |
| Methyl (5-(2-methyl-5-((4-oxo-3,4-dihydrophthalazin-1-yl)methyl)phenyl)-1H-benzoimidazol-2-yl)carbamate | 0.32 | 1.35 | 0.12 | 0.06 | 0.03 | NT |
| Ethyl (5-(2-methoxy-5-((4-oxo-3,4-dihydrophthalazin-1-yl)methyl)phenyl)-1H-benzoimidazol-2-yl)carbamate | 0.15 | 1.40 | 0.04 | 0.01 | 0.02 | NT |
| 2-Methoxyethyl (6-fluoro-5-(2-fluoro-5-((4-oxo-3,4-dihydrophthalazin-1-yl)methyl)phenyl)-1H-benzoimidazol-2-yl)carbamate | 0.04 | 1.70 | 0.15 | 0.07 | 0.36 | NT |
| Methyl (5-(2-(difluoromethoxy)-5-((4-oxo-3,4-dihydrophthalazin-1-yl)methyl)phenyl)-1H-benzoimidazol-2-yl)carbamate | 0.43 | 1.70 | 0.02 | 0.01 | 0.05 | NT |
| Methyl (5-(2-ethoxy-5-((4-oxo-3,4-dihydrophthalazin-1-yl)methyl)phenyl)-1H-benzoimidazol-2-yl)carbamate | 0.69 | 1.70 | 0.02 | 0.01 | 0.04 | NT |
| Ethyl (5-(2-fluoro-5-((4-oxo-3,4-dihydrophthalazin-1-yl)methyl)phenyl)-1H-benzoimidazol-2-yl)carbamate | 0.01 | 1.80 | 0.18 | 0.15 | 0.15 | NT |

FIGURE 1B

| Name | PARP1 | Tubulin | A549 | OVCAR8 | MDA-MB-436 | Trapped PARP-DNA |
|---|---|---|---|---|---|---|
| 1-Ethyl-3-(5-(2-methoxy-5-((4-oxo-3,4-dihydrophthalazin-1-yl)methyl)phenyl)-1H-benzoimidazol-2-yl)urea | 0.06 | 1.80 | 0.07 | 0.05 | 0.05 | NT |
| Ethyl (7-fluoro-5-(2-fluoro-5-((4-oxo-3,4-dihydrophthalazin-1-yl)methyl)phenyl)-1H-benzoimidazol-2-yl)carbamate | 0.64 | 1.80 | 0.31 | 0.05 | 0.09 | NT |
| Methyl (5-(2-methoxy-5-((4-oxo-3,4-dihydrophthalazin-1-yl)methyl)phenyl)-1H-benzoimidazol-2-yl)carbamate | 0.10 | 1.90 | 0.07 | 0.02 | 0.04 | NT |
| Ethyl (5-(2-ethoxy-5-((4-oxo-3,4-dihydrophthalazin-1-yl)methyl)phenyl)-1H-benzoimidazol-2-yl)carbamate | 0.91 | 1.90 | 0.03 | 0.01 | 0.05 | TC |
| 1-Ethyl-3-(6-(5-((4-oxo-3,4-dihydrophthalazin-1-yl)methyl)furan-2-yl)-1H-benzoimidazol-2-yl)urea | 0.02 | 2.00 | 0.12 | 0.04 | 0.25 | NT |
| Ethyl (5-(2-(difluoromethoxy)-5-((4-oxo-3,4-dihydrophthalazin-1-yl)methyl)phenyl)-1H-benzoimidazol-2-yl)carbamate | 0.65 | 2.00 | 0.03 | 0.01 | 0.10 | NT |
| Methyl (7-fluoro-5-(2-fluoro-5-((4-oxo-3,4-dihydrophthalazin-1-yl)methyl)phenyl)-1H-benzoimidazol-2-yl)carbamate | 2.00 | 2.00 | 0.13 | 0.06 | 0.24 | NT |

FIGURE 1C

| Name | PARP1 | Tubulin | A549 | OVCAR8 | MDA-MB-436 | Trapped PARP-DNA |
|---|---|---|---|---|---|---|
| Methyl (5-(5-((4-oxo-3,4-dihydrophthalazin-1-yl)methyl)-2-(trifluoromethoxy)phenyl)-1H-benzoimidazol-2-yl)carbamate | 3.10 | 2.00 | 0.11 | 0.07 | 0.08 | NT |
| Methyl (5-(2-chloro-5-((4-oxo-3,4-dihydrophthalazin-1-yl)methyl)phenyl)-1H-benzoimidazol-2-yl)carbamate | 0.22 | 2.10 | 0.16 | 0.04 | 0.12 | NT |
| Ethyl (5-(5-((4-oxo-3,4-dihydrophthalazin-1-yl)methyl)-2-(trifluoromethoxy)phenyl)-1H-benzoimidazol-2-yl)carbamate | 3.31 | 2.20 | 0.11 | 0.06 | 0.06 | NT |
| 1-(5-(2-(Difluoromethoxy)-5-((4-oxo-3,4-dihydrophthalazin-1-yl)methyl)phenyl)-1H-benzoimidazol-2-yl)-3-ethylurea | 0.07 | 2.50 | 0.80 | 0.06 | 0.07 | NT |
| 1-Ethyl-3-(5-(2-methyl-5-((4-oxo-3,4-dihydrophthalazin-1-yl)methyl)phenyl)-1H-benzoimidazol-2-yl)urea | 0.09 | 2.50 | 0.92 | 0.11 | 0.16 | NT |
| Ethyl (5-(2-chloro-5-((4-oxo-3,4-dihydrophthalazin-1-yl)methyl)phenyl)-1H-benzoimidazol-2-yl)carbamate | 0.30 | 2.50 | 0.30 | 0.09 | 0.20 | NT |
| 2-Methoxyethyl (4-fluoro-5-(2-fluoro-5-(((4-oxo-3,4-dihydrophthalazin-1-yl)methyl)phenyl)-1H-benzoimidazol-2-yl)carbamate | NT | 2.50 | 0.47 | 0.21 | 0.14 | NT |

FIGURE 1D

| Name | PARP1 | Tubulin | A549 | OVCAR8 | MDA-MB-436 | Trapped PARP-DNA |
|---|---|---|---|---|---|---|
| Ethyl (6-fluoro-5-(2-fluoro-5-((4-oxo-3,4-dihydrophthalazin-1-yl)methyl)phenyl)-1H-benzoimidazol-2-yl)carbamate | 0.03 | 2.60 | 0.57 | 0.15 | 0.31 | NT |
| Methyl (5-(4-fluoro-2-methoxy-5-((4-oxo-3,4-dihydrophthalazin-1-yl)methyl)phenyl)-1H-benzoimidazol-2-yl)carbamate | 0.51 | 2.60 | 0.08 | 0.09 | 0.07 | NT |
| Ethyl (5-(4-fluoro-2-methoxy-5-((4-oxo-3,4-dihydrophthalazin-1-yl)methyl)phenyl)-1H-benzoimidazol-2-yl)carbamate | 0.56 | 2.60 | 0.12 | 0.17 | 0.13 | NT |
| Ethyl (5-(2,4-difluoro-5-((4-oxo-3,4-dihydrophthalazin-1-yl)methyl)phenyl)-1H-benzoimidazol-2-yl)carbamate | 0.03 | 2.80 | 0.83 | 0.30 | 0.43 | NT |
| Ethyl (6-(5-((4-oxo-3,4-dihydrophthalazin-1-yl)methyl)furan-2-yl)-1H-benzoimidazol-2-yl)carbamate | 0.08 | 3.00 | 0.20 | 0.11 | 0.15 | NT |
| Methyl (5-(2,4-difluoro-5-((4-oxo-3,4-dihydrophthalazin-1-yl)methyl)phenyl)-1H-benzoimidazol-2-yl)carbamate | 0.03 | 3.20 | 0.92 | 0.24 | 0.30 | NT |
| Ethyl (4-fluoro-5-((4-oxo-3,4-dihydrophthalazin-1-yl)methyl)phenyl)-1H-benzoimidazol-2-yl)carbamate | 0.06 | 3.20 | 0.72 | 0.36 | 0.20 | NT |

FIGURE 1E

| Name | PARP1 | Tubulin | A549 | OVCAR8 | MDA-MB-436 | Trapped PARP-DNA |
|---|---|---|---|---|---|---|
| Methyl (6-(2-fluoro-5-((4-oxo-3,4-dihydrophthalazin-1-yl)methyl)phenyl)-1H-benzoimidazol-2-yl)carbamate | 0.00 | 3.34 | 0.28 | 0.10 | 0.26 | TC |
| Methyl (5-(3-methoxy-5-((4-oxo-3,4-dihydrophthalazin-1-yl)methyl)phenyl)-1H-benzoimidazol-2-yl)carbamate | 1.17 | 3.60 | 1.14 | 0.53 | 0.44 | NT |
| Ethyl (5-(3-((4-oxo-3,4-dihydrophthalazin-1-yl)methyl)phenyl)-1H-benzoimidazol-2-yl)carbamate | 0.05 | 3.73 | 0.41 | 0.23 | 0.26 | NT |
| Ethyl (5-(3-fluoro-5-((4-oxo-3,4-dihydrophthalazin-1-yl)methyl)phenyl)-1H-benzoimidazol-2-yl)carbamate | 0.10 | 3.86 | 0.35 | 0.21 | 0.22 | NT |
| Methyl (6-(5-((4-oxo-3,4-dihydrophthalazin-1-yl)methyl)furan-2-yl)-1H-benzoimidazol-2-yl)carbamate | 0.10 | 4.00 | 0.15 | 0.07 | 0.09 | NT |
| Methyl (5-(2-fluoro-3-((4-oxo-3,4-dihydrophthalazin-1-yl)methyl)phenyl)-1H-benzoimidazol-2-yl)carbamate | 0.73 | 4.50 | 0.37 | 0.30 | 0.35 | NT |
| Methyl (4-fluoro-5-(2-fluoro-5-((4-oxo-3,4-dihydrophthalazin-1-yl)methyl)phenyl)-1H-benzoimidazol-2-yl)carbamate | NT | 4.50 | 1.76 | 0.88 | 0.72 | NT |

FIGURE 1F

| Name | PARP1 | Tubulin | A549 | OVCAR8 | MDA-MB-436 | Trapped PARP-DNA |
|---|---|---|---|---|---|---|
| Methyl (5-(2-fluoro-5-((6-methyl-4-oxo-3,4-dihydrophthalazin-1-yl)methyl)phenyl)-1H-benzoimidazol-2-yl)carbamate | 4.97 | 4.59 | 0.34 | 0.11 | 0.46 | NT |
| Methyl (5-(3-fluoro-5-((4-oxo-3,4-dihydrophthalazin-1-yl)methyl)phenyl)-1H-benzoimidazol-2-yl)carbamate | 0.18 | 4.73 | 0.31 | 0.19 | 0.32 | NT |
| Methyl (5-(3-methoxy-5-((4-oxo-3,4-dihydrophthalazin-1-yl)methyl)phenyl)-1H-benzoimidazol-2-yl)carbamate | 1.28 | 4.80 | 1.41 | 0.62 | 0.62 | NT |
| Ethyl (5-(2-fluoro-5-((6-methyl-4-oxo-3,4-dihydrophthalazin-1-yl)methyl)phenyl)-1H-benzoimidazol-2-yl)carbamate | 8.23 | 4.85 | 0.36 | 0.16 | 0.48 | NT |
| Ethyl (5-(2-fluoro-5-((5-fluoro-4-oxo-3,4-dihydrophthalazin-1-yl)methyl)phenyl)-1H-benzoimidazol-2-yl)carbamate | 0.21 | 4.89 | 0.35 | 0.16 | 0.36 | NT |
| Methyl (5-(2-fluoro-5-((4-oxo-3,4-dihydrophthalazin-1-yl)methyl)phenyl)-1H-imidazo[4,5-b]pyridin-2-yl)carbamate | 0.01 | 5.00 | 0.32 | 0.06 | 0.15 | TC |

FIGURE 1G

| Name | PARP1 | Tubulin | A549 | OVCAR8 | MDA-MB-436 | Trapped PARP-DNA |
|---|---|---|---|---|---|---|
| Ethyl (5-(2-fluoro-3-((4-oxo-3,4-dihydrophthalazin-1-yl)methyl)phenyl)-1H-benzoimidazol-2-yl)carbamate | 0.59 | 5.00 | 0.58 | 0.50 | 0.80 | NT |
| Ethyl (6-(2-fluoro-5-((4-oxo-3,4-dihydrophthalazin-1-yl)methyl)phenyl)-5-methyl-3H-imidazo[4,5-b]pyridin-2-yl)carbamate | NT | 5.00 | 1.14 | 0.39 | 0.99 | NT |
| 1-Ethyl-3-(4-fluoro-5-(2-fluoro-5-((4-oxo-3,4-dihydrophthalazin-1-yl)methyl)phenyl)-1H-benzoimidazol-2-yl)urea | NT | 5.00 | 1.14 | 0.98 | 2.27 | NT |
| Ethyl (5-(2-fluoro-5-((8-fluoro-4-oxo-3,4-dihydrophthalazin-1-yl)methyl)phenyl)-1H-benzoimidazol-2-yl)carbamate | 0.16 | 5.02 | 0.37 | 0.22 | 0.48 | NT |
| Ethyl (6-(2-fluoro-5-((4-oxo-3,4-dihydrophthalazin-1-yl)methyl)phenyl)benzothiazol-2-yl)carbamate | 2.38 | 5.06 | 2.04 | 1.87 | 2.81 | NT |
| 1-Ethyl-3-(6-(2-fluoro-5-((4-oxo-3,4-dihydrophthalazin-1-yl)methyl)phenyl)-1H-benzoimidazol-2-yl)urea | 0.01 | 5.69 | 1.80 | 0.15 | 0.93 | NT |
| Ethyl (4-chloro-6-(2-fluoro-5-((4-oxo-3,4-dihydrophthalazin-1-yl)methyl)phenyl)-1H-benzoimidazol-2-yl)carbamate | 16.67 | 7.30 | 1.02 | 0.25 | 0.89 | NT |

FIGURE 1H

| Name | PARP1 | Tubulin | A549 | OVCAR8 | MDA-MB-436 | Trapped PARP-DNA |
|---|---|---|---|---|---|---|
| Ethyl (5-(4-fluoro-3-((4-oxo-3,4-dihydrophthalazin-1-yl)methyl)phenyl)-1H-benzoimidazol-2-yl)carbamate | 0.16 | 8.76 | 1.51 | 0.89 | 1.79 | NT |
| Methyl (5-(3-((4-oxo-3,4-dihydrophthalazin-1-yl)methyl)phenyl)-1H-benzoimidazol-2-yl)carbamate | 0.09 | 12.35 | 0.37 | 0.22 | 0.54 | NT |
| Methyl (5-(4-methoxy-3-((4-oxo-3,4-dihydrophthalazin-1-yl)methyl)phenyl)-1H-benzoimidazol-2-yl)carbamate | 0.12 | NA | 2.81 | 1.26 | 0.64 | NT |
| Ethyl (5-(2-fluoro-5-((4-oxo-3,4-dihydrophthalazin-1-yl)methyl)phenyl)benzooxazol-2-yl)carbamate | 0.18 | NA | 6.16 | 3.52 | 7.30 | NT |
| Methyl (5-(2-fluoro-5-((4-oxo-3,4-dihydrophthalazin-1-yl)methyl)phenyl)benzooxazol-2-yl)carbamate | 0.20 | NA | 9.07 | 3.64 | 3.60 | NT |
| Ethyl (5-(4-methoxy-3-((4-oxo-3,4-dihydrophthalazin-1-yl)methyl)phenyl)-1H-benzoimidazol-2-yl)carbamate | 0.30 | NA | 2.88 | 1.18 | 0.98 | NT |
| N-(5-(2-Fluoro-5-((4-oxo-3,4-dihydrophthalazin-1-yl)methyl)phenyl)benzooxazol-2-yl)butyramide | 0.34 | NA | 25.26 | 76.91 | 7.42 | TC |

FIGURE 1I

| Name | PARP1 | Tubulin | A549 | OVCAR8 | MDA-MB-436 | Trapped PARP-DNA |
|---|---|---|---|---|---|---|
| Methyl (5-(2-fluoro-4-methoxy-5-((4-oxo-3,4-dihydrophthalazin-1-yl)methyl)phenyl)-1H-benzoimidazol-2-yl)carbamate | 0.38 | NA | 4.46 | 3.22 | 0.95 | TC |
| Methyl (5-(2-(2-methoxyethoxy)-5-((4-oxo-3,4-dihydrophthalazin-1-yl)methyl)phenyl)-1H-benzoimidazol-2-yl)carbamate | 0.43 | NA | 5.42 | 1.59 | 3.32 | TC |
| Ethyl (5-(2-fluoro-4-methoxy-5-((4-oxo-3,4-dihydrophthalazin-1-yl)methyl)phenyl)-1H-benzoimidazol-2-yl)carbamate | 0.43 | NA | 5.60 | 2.15 | 1.35 | TC |
| Ethyl (5-(2-(2-methoxyethoxy)-5-((4-oxo-3,4-dihydrophthalazin-1-yl)methyl)phenyl)-1H-benzoimidazol-2-yl)carbamate | 0.46 | NA | 1.40 | 0.46 | 1.72 | NT |
| Ethyl (5-(2-fluoro-5-((4-oxo-3,4-dihydrophthalazin-1-yl)methyl)phenyl)benzothiazol-2-yl)carbamate | 0.49 | NA | 5.14 | 12.08 | 3.74 | NT |
| 4-(3-(2-Aminobenzothiazol-6-yl)-4-fluorobenzyl)phthalazin-1(2H)-one | 0.49 | NA | 20.15 | 57.22 | 13.39 | NT |

FIGURE 1J

| Name | PARP1 | Tubulin | A549 | OVCAR8 | MDA-MB-436 | Trapped PARP-DNA |
|---|---|---|---|---|---|---|
| Ethyl (5-(2-fluoro-5-((7-fluoro-4-oxo-3,4-dihydrophthalazin-1-yl)methyl)phenyl)-1H-benzoimidazol-2-yl)carbamate | 0.55 | NA | 2.38 | 0.36 | 0.50 | NT |
| 4-(4-Fluoro-3-(2-phenyl-1H-benzoimidazol-5-yl)benzyl)phthalazin-1(2H)-one | 0.61 | NA | 6.93 | 2.45 | 0.35 | NT |
| N-(6-(2-Fluoro-5-((4-oxo-3,4-dihydrophthalazin-1-yl)methyl)phenyl)-1H-benzoimidazol-2-yl)methanesulfonamide | 0.76 | NA | 31.57 | 1.52 | 147.30 | NT |
| 4-(3-(2-Aminobenzooxazol-5-yl)-4-fluorobenzyl)phthalazin-1(2H)-one | 0.77 | NA | 10.71 | 20.88 | 11.80 | TC |
| Methyl (5-(2,4-dimethoxy-5-((4-oxo-3,4-dihydrophthalazin-1-yl)methyl)phenyl)-1H-benzoimidazol-2-yl)carbamate | 0.95 | NA | 3.93 | 1.93 | 4.28 | TC |
| Ethyl (5-(2,4-dimethoxy-5-((4-oxo-3,4-dihydrophthalazin-1-yl)methyl)phenyl)-1H-benzoimidazol-2-yl)carbamate | 0.97 | NA | 1.26 | 0.42 | 2.02 | TC |
| 4-(3-(2-Aminobenzothiazol-5-yl)-4-fluorobenzyl)phthalazin-1(2H)-one | 1.45 | NA | 7.82 | 26.40 | 5.86 | NT |

FIGURE 1K

| Name | PARP1 | Tubulin | A549 | OVCAR8 | MDA-MB-436 | Trapped PARP-DNA |
|---|---|---|---|---|---|---|
| 4-(4-Fluoro-3-(2-methylbenzooxazol-6-yl)benzyl)phthalazin-1(2H)-one | 1.59 | NA | 53.91 | 139.40 | 67.25 | NT |
| 4-(4-Fluoro-3-(2-methyl-1H-benzoimidazol-5-yl)benzyl)phthalazin-1(2H)-one | 1.61 | NA | 34.30 | 16.56 | 1.40 | NT |
| 4-(4-Fluoro-3-(2-methylbenzothiazol-6-yl)benzyl)phthalazin-1(2H)-one | 2.34 | NA | 21.18 | 34.43 | 35.01 | NT |
| 4-(4-Fuoro-3-(2-methyl-3H-imidazo[4,5-b]pyridin-6-yl)benzyl)phthalazin-1(2H)-one | 4.08 | NA | 186.40 | NA | 215.10 | NT |
| 4-(4-Fluoro-3-(2-methylbenzothiazol-5-yl)benzyl)phthalazin-1(2H)-one | 4.94 | NA | 36.28 | 18.12 | 1.23 | NT |
| Methyl (6-(2-fluoro-5-((4-oxo-3,4-dihydrophthalazin-1-yl)methyl)phenyl)benzothiazol-2-yl)carbamate | 5.31 | NA | 4.91 | 13.87 | 9.46 | NT |
| Ethyl (4-(2-fluoro-5-((4-oxo-3,4-dihydrophthalazin-1-yl)methyl)phenyl)-1H-benzoimidazol-2-yl)carbamate | 7.50 | NA | 11.39 | 3.96 | 1.76 | NT |

FIGURE 1L

| Name | PARP1 | Tubulin | A549 | OVCAR8 | MDA-MB-436 | Trapped PARP-DNA |
|---|---|---|---|---|---|---|
| N-(5-(2-Fluoro-5-((4-oxo-3,4-dihydrophthalazin-1-yl)methyl)phenyl)benzothiazol-2-yl)butyramide | 7.73 | NA | 3.92 | 1458.00 | 11.19 | NT |
| N-(6-(2-Fluoro-5-((4-oxo-3,4-dihydrophthalazin-1-yl)methyl)phenyl)benzothiazol-2-yl)butyramide | 11.08 | NA | NA | NA | 84.50 | NT |
| 4-(4-Fluoro-3-(2-methylbenzooxazol-5-yl)benzyl)phthalazin-1(2H)-one | 15.98 | NA | 53.91 | 139.40 | 67.25 | NT |
| 4-(4-Fluoro-3-(1H-indol-5-yl)benzyl)phthalazin-1(2H)-one | 21.05 | NA | 24.15 | 22.82 | 1.24 | NT |
| Ethyl (5-(2,3-dimethoxy-5-((4-oxo-3,4-dihydrophthalazin-1-yl)methyl)phenyl)-1H-benzoimidazol-2-yl)carbamate | 27.84 | NA | 7.04 | 3.88 | 6.56 | TC |
| Methyl (5-(2-methoxy-3-((4-oxo-3,4-dihydrophthalazin-1-yl)methyl)phenyl)-1H-benzoimidazol-2-yl)carbamate | 32.96 | NA | 4.87 | 2.87 | 2.08 | NT |

FIGURE 1M

| Name | PARP1 | Tubulin | A549 | OVCAR8 | MDA-MB-436 | Trapped PARP-DNA |
|---|---|---|---|---|---|---|
| Ethyl (5-(2-methoxy-3-((4-oxo-3,4-dihydrophthalazin-1-yl)methyl)phenyl)-1H-benzoimidazol-2-yl)carbamate | 33.51 | NA | 4.14 | 2.26 | 1.84 | NT |
| Ethyl (6-(2-fluoro-4-((4-oxo-3,4-dihydrophthalazin-1-yl)methyl)phenyl)-1H-benzoimidazol-2-yl)carbamate | 116.80 | NA | 0.11 | 0.12 | 0.09 | TC |
| Methyl (5-(2,3-dimethoxy-5-((4-oxo-3,4-dihydrophthalazin-1-yl)methyl)phenyl)-1H-benzoimidazol-2-yl)carbamate | 122.80 | NA | NA | NA | 7.83 | TC |
| Methyl (6-(2-fluoro-4-((4-oxo-3,4-dihydrophthalazin-1-yl)methyl)phenyl)-1H-benzoimidazol-2-yl)carbamate | 157.30 | NA | 3.27 | 2.77 | 4.16 | TC |
| 4-(4-Fluoro-3-(1H-indol-6-yl)benzyl)phthalazin-1(2H)-one | 216.80 | NA | 32.23 | 19.87 | 1.17 | TC |
| 4-(3-(2-Aminothiazolo[5,4-b]pyridin-6-yl)-4-fluorobenzyl)phthalazin-1(2H)-one | NT | NA | NA | NA | NA | TC |
| Methyl (6-(2-fluoro-5-((4-oxo-3,4-dihydrophthalazin-1-yl)methyl)phenyl)-5-methyl-1H-imidazo[4,5-b]pyridin-2-yl)carbamate | NT | NA | 3.50 | 0.27 | 6.14 | NT |

FIGURE 1N

| Name | PARP1 | Tubulin | A549 | OVCAR8 | MDA-MB-436 | Trapped PARP-DNA |
|---|---|---|---|---|---|---|
| Methyl (4-(2-fluoro-5-((4-oxo-3,4-dihydrophthalazin-1-yl)methyl)phenyl)-1H-benzoimidazol-2-yl)carbamate | NT | NA | 10.07 | NA | 62.58 | NT |
| 1-Ethyl-3-(4-(2-fluoro-5-((4-oxo-3,4-dihydrophthalazin-1-yl)methyl)phenyl)-1H-benzoimidazol-2-yl)urea | NT | NA | 4.63 | 23.88 | 14.36 | NT |
| Ethyl (6-(2-fluoro-5-((4-oxo-3,4-dihydrophthalazin-1-yl)methyl)phenyl)thiazolo[5,4-b]pyridin-2-yl)carbamate | NT | NT | 17.37 | 8.14 | 3.36 | TC |
| N-(6-(2-Fluoro-5-((4-oxo-3,4-dihydrophthalazin-1-yl)methyl)phenyl)thiazolo[5,4-b]pyridin-2-yl)butyramide | NT | NT | NA | NA | 57.50 | TC |
| Methyl (5-(2-fluoro-5-((4-oxo-3,4-dihydrophthalazin-1-yl)methyl)phenyl)benzothiazol-2-yl)carbamate | NT | NT | 20.03 | 114.90 | 3.12 | NT |
| Methyl (6-fluoro-5-(2-fluoro-5-((4-oxo-3,4-dihydrophthalazin-1-yl)methyl)phenyl)-1H-benzoimidazol-2-yl)carbamate | NT | NT | 0.70 | 0.79 | 0.59 | NT |
| 1-Ethyl-3-(4-fluoro-5-(2-fluoro-5-((4-oxo-3,4-dihydrophthalazin-1-yl)methyl)phenyl)-1H-benzoimidazol-2-yl)urea | NT | NT | 3.60 | 1.34 | 2.15 | TC |

FIGURE 10

| Name | PARP1 | Tubulin | A549 | OVCAR8 | MDA-MB-436 | Trapped PARP-DNA |
|---|---|---|---|---|---|---|
| 2-Methoxyethyl (7-fluoro-5-(2-fluoro-5-((4-oxo-3,4-dihydrophthalazin-1-yl)methyl)phenyl)-1H-benzoimidazol-2-yl)carbamate | NT | NT | 0.40 | 0.23 | 0.29 | TC |
| 1-Ethyl-3-(7-fluoro-5-(2-fluoro-5-((4-oxo-3,4-dihydrophthalazin-1-yl)methyl)phenyl)-1H-benzoimidazol-2-yl)urea | NT | NT | 2.07 | 0.50 | 0.50 | TC |
| Methyl (4-fluoro-5-(2-fluoro-5-((4-oxo-3,4-dihydrophthalazin-1-yl)methyl)phenyl)-1H-benzoimidazol-2-yl)carbamate | NT | NT | 1.76 | 0.88 | 0.72 | TC |
| 2-Methoxyethyl (4-fluoro-5-(2-fluoro-5-((4-oxo-3,4-dihydrophthalazin-1-yl)methyl)phenyl)-1H-benzoimidazol-2-yl)carbamate | NT | NT | 0.47 | 0.21 | 0.14 | TC |
| Methyl (5-(5-((4-oxo-3,4-dihydrophthalazin-1-yl)methyl)-2-(trifluoromethyl)phenyl)-1H-benzoimidazol-2-yl)carbamate | 19.20 | 1.20 | 0.11 | 0.02 | 0.06 | NT |
| Ethyl (5-(5-((4-oxo-3,4-dihydrophthalazin-1-yl)methyl)-2-(trifluoromethyl)phenyl)-1H-benzoimidazol-2-yl)carbamate | 29.01 | NT | 0.14 | 0.03 | 0.07 | NT |

US 11,072,600 B2

PHTHALAZINE DERIVATIVES AS INHIBITORS OF PARP1, PARP2, AND/OR TUBULIN USEFUL FOR THE TREATMENT OF CANCER

CROSS REFERENCE TO RELATED APPLICATIONS

The present application claims benefit of priority to U.S. Provisional Patent Application No. 62/354,449, filed Jun. 24, 2016, and U.S. Provisional Patent Application No. 62/426,095 filed Nov. 23, 2016, both of which are incorporated by reference in their entireties.

BACKGROUND OF THE INVENTION

The high proliferation rate of cancer cells is a result not only of decreased cell death but also of improperly regulated cell cycling, allowing evasion of growth suppressing signals. Although multiple cell cycle checkpoints can be impaired in cancer, the mitotic or spindle assembly checkpoint is of great importance both in tumorigenesis and as an anticancer target. This point of regulation, which is responsible for ensuring appropriate chromosome segregation, is required for cell viability. Cells with a weakened mitotic checkpoint are capable of survival but do not maintain proper chromosome segregation, resulting in genomic instability and aneuploidy. PARP (poly(ADP-ribose) polymerase) is an important protein in DNA repair pathways especially the base excision repair (BER). BER is involved in DNA repair of single strand breaks (SSBs). If BER is impaired, inhibiting PARP, SSBs accumulate and become double stand breaks (DSBs). In addition, PARP can act on many mediators of cell cycle progression through its effects on gene expression. However, direct regulation of the mitotic checkpoint by PARP is another important factor that may be exploited in the development of an optimal cancer therapy.

Recent reports suggest multiple roles for PARP in the structural machinery of mitosis. First, PAR, which is primarily synthesized by PARP, is required for assembly and function of the bipolar spindle. In addition, PARP-1 both localizes to and PARylates proteins at centromeres and centrosomes during mitosis. PARP-1 also mediates PARylation of p53, which is responsible for regulating centrosome duplication and monitoring chromosomal stability. Loss of PARP activity is associated with mislocalization of centromeric and centrosomal proteins, resulting in incomplete synapsis of homologous chromosomes, defective chromatin modifications, and failure to maintain metaphase arrest, indicating loss of mitotic checkpoint integrity. Similarly, inhibition of PARP-1 is associated with genomic instability characterized by reduced stringency of mitotic checkpoints, centrosome hyper-amplification, and chromosomal aneuploidy. Furthermore, PARP-1 has been shown to interact with the E3 ubiquitin ligase, CHFR, a tumor suppressor with an important role in the early mitotic checkpoint. Binding of these two proteins results in cell cycle arrest in prophase, an effect stimulated by microtubule inhibitors resulting in resistance to this class of drugs in cancer cells. Thus, inhibition of PARP or microtubules, or both, could significantly increase cancer cells death, and may be a promising anticancer strategy.

The present invention relates to compounds having microtubule-perturbing and/or anti-PARP activity. These compounds may be used for treatment in the animal of a disease associated with tubulin polymerization or PARP, or both. This, and other uses of these compounds are described herein.

SUMMARY OF THE INVENTION

This invention provides, among other things, compounds useful for treating diseases associated with PARP1 (Poly ADP Ribose Polymerase1) and/or PARP2 (Poly ADP Ribose Polymerase2) and/or tubulin, pharmaceutical formulations containing such compounds, as well as combinations of these compounds with at least one additional therapeutic agent.

BRIEF DESCRIPTION OF THE DRAWINGS

FIG. 1A-FIG. 1O provides biological data for compounds of the invention. For the Trapped PARP-DNA column, TC=Induces Trapped PARP-DNA complex formation in cells, NT=Not Tested.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; MgSO$_4$ is magnesium sulfate; mins or min is minutes; Mp or MP is melting point; NaCNBH$_3$ is sodium cyanoborohydride; NaOH is sodium hydroxide; Na$_2$SO$_4$ is sodium sulfate; NBS is N-bromosuccinimide; NH$_4$Cl is ammonium chloride; NIS is N-iodosuccinimide; N$_2$ is nitrogen; NMM is N-methylmorpholine; n-BuLi is n-butyllithium; overnight is O/N; PdCl$_2$(pddf) is 1,1'-Bis(diphenylphosphino) ferrocene]dichloropalladium(II); Pd/C is the catalyst known as palladium on carbon; Pd$_2$(dba)$_3$ is an organometallic catalyst known as tris(dibenzylideneacetone) dipalladium(O); Ra Ni or Raney Ni is Raney nickel; Ph is phenyl; PMB is p-methoxybenzyl; PrOH is 1-propanol; iPrOH is 2-propanol; POCl$_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—NH$_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclobutyl, cyclohexyl, (cyclohexyl)methyl, cyclopropyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —O—CH$_3$, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 2-(4-methylpiperazin-1-yl)ethyl, 3-(4-methylpiperazin-1-yl)propyl, 2-morpholinoethyl, 3-morpholinopropyl, 1-methylazetidin-3-yl, 1-ethylazetidin-3-yl, 1-isopropylazetidin-3-yl, 1-methylpiperidin-4-yl, 1-ethylpiperidin-4-yl or, 1-isopropylpiperidin-4-yl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 2-fluoroethyl, 2,2-difluoroethyl, 2-chloroethyl, 3-chloropropyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR'""—C(NR' R"R'")=NR"", —NR""—C(NR'R") =NR'", —S(O)R', —S(O)₂R', —S(O)₂NR'R", —NR"SO₂R', —CN, —NO₂, —N₃, —CH(Ph)₂, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""" each preferably independently refer to hydrogen, substituted or unsubstituted haloalkyl, substituted or unsubstituted heteroalkyl, substituted or unsubstituted heterocycloalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR'""—C(NR' R"R'")=NR"", —NR""—C(NR'R") =NR'", —S(O)R', —S(O)₂R', —S(O)₂NR'R", —NR"SO₂R', —CN, —NO₂, —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R'", R"" and R""" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5 to 7-membered ring" or "5 or 6 or 7 membered ring" includes, for example phenyl, pyridinyl and piperidinyl. The term "5 to 7-membered heterocycloalkyl ring" "5 or 6 or 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), and aluminum (Al).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical formulation administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as PARP1 (Poly ADP Ribose Polymerase1) and/or PARP2 and/or tubulin.

Embodiments of the invention also encompass compounds that are poly- or multi-valent species, including, for example, species such as dimers, trimers, tetramers and higher homologs of the compounds of use in the invention or reactive analogues thereof.

II. Introduction

The invention provides novel compounds. The novel compounds, as well as pharmaceutical formulations containing such compounds or combinations of these compounds with at least one additional therapeutic agent, can be used for, among other things, treating diseases, including cancer.

III. The Compounds

III.a)

In one aspect, the invention provides a compound of the invention. In an exemplary embodiment, the invention is a compound described herein. In an exemplary embodiment, the invention is a compound according to a formula described herein.

In another aspect, the invention provides a compound, or a salt or a hydrate or a solvate thereof, having a structure according to formula (I):

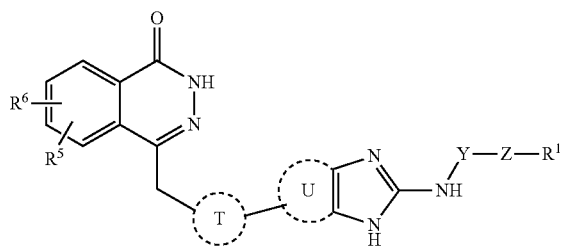

(I)

wherein T has a structure which is

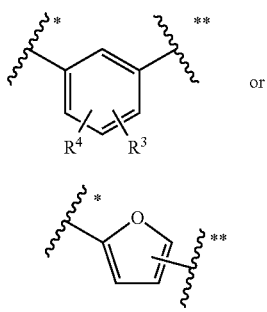

wherein $\overset{*}{\xi}$ presents a covalent bond to the methylene group in formula (I) and $\overset{**}{\xi}$ represents a covalent bond to the U ring in formula (I)

wherein formula (C)

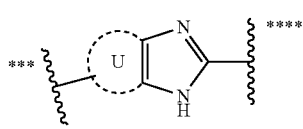

(C)

wherein $\overset{*}{\xi}$ represents a covalent bond to the T ring in formula (I) and $\overset{**}{\xi}$ represents a covalent bond to —NH—Y—Z—R$^1$ in formula (I), has a structure which is

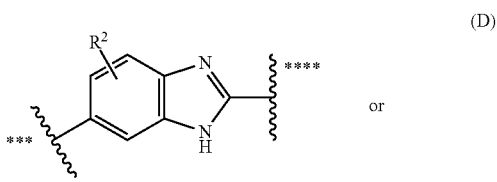

(D)

or

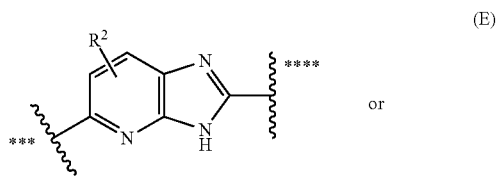

(E)

or

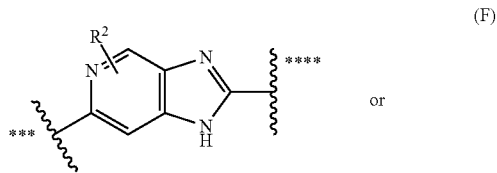

(F)

or

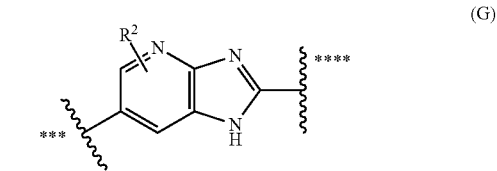

(G)

wherein Y is C(O) or S(O)$_2$; Z is —O— or —CH$_2$— or —NH— or —N(CH$_2$R$^7$)— wherein R$^7$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl; R$^1$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ heteroalkyl or substituted or unsubstituted aryl or substituted or unsubstituted arylalkyl or substituted or unsubstituted cycloalkyl or substituted or unsubstituted heterocycloalkyl; R$^2$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl; R$^3$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ alkoxy; R$^4$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ alkoxy; R$^5$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl; and R$^6$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl.

In another aspect, the invention provides a compound, or a salt or a hydrate or a solvate thereof, having a structure according to formula (Ia):

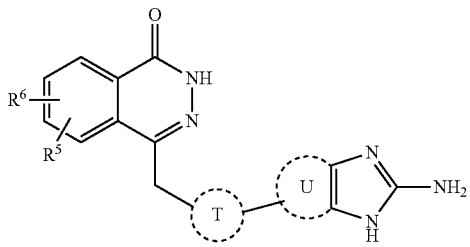

(Ia)

wherein T has a structure which is

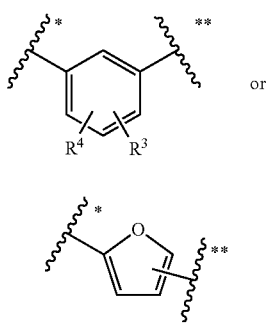

(A)

or (B)

wherein ⸸* represents a covalent bond to the methylene group in formula (Ia) and ⸸* represents a covalent bond to the U ring in formula (Ia)

wherein formula (C1)

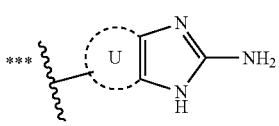

(C1)

wherein ⸸* represents a covalent bond to the T ring in formula (Ia), has a structure which is

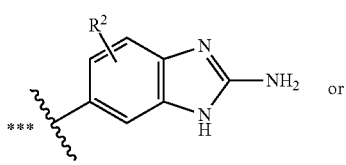

(D1)

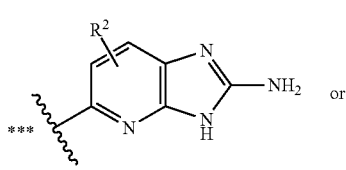

(E1)

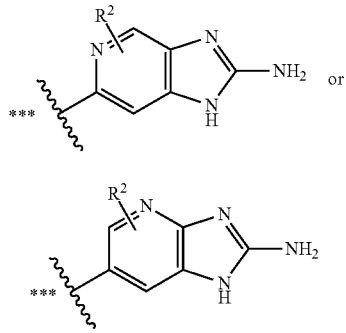

(F1)

or (G1)

wherein $R^2$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl; $R^3$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl or substituted or unsubstituted $C_1$ or $C_2$ or $C_3$ or $C_4$ or $C_5$ or $C_6$ or $C_7$ or $C_8$ or $C_9$ or $C_{10}$ alkoxy; $R^4$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl or substituted or unsubstituted $C_1$ or $C_2$ or $C_3$ or $C_4$ or $C_5$ or $C_6$ or $C_7$ or $C_8$ or $C_9$ or $C_{10}$ alkoxy; $R^5$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl; and $R^6$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl.

In an exemplary embodiment, according to formula (I), Z, $R^1$, $R^2$, $R^3$, $R^4$, $R^5$, and $R^6$ are as described herein, Y is C(O). In an exemplary embodiment, according to formula (I), Z, $R^1$, $R^2$, $R^3$, $R^4$, $R^5$, and $R^6$ are as described herein, Y is $S(O)_2$. In an exemplary embodiment, according to formula (I), Y, $R^1$, $R^2$, $R^3$, $R^4$, $R^5$, and $R^6$ are as described herein, Z is —O—. In an exemplary embodiment, according to formula (I), Y, $R^1$, $R^2$, $R^3$, $R^4$, $R^5$, and $R^6$ are as described herein, Z is —$CH_2$—. In an exemplary embodiment, according to formula (I), Y, $R^1$, $R^2$, $R^3$, $R^4$, $R^5$, and $R^6$ are as described herein, Z is —NH—. In an exemplary embodiment, according to formula (I), Y, $R^1$, $R^2$, $R^3$, $R^4$, $R^5$, $R^6$, and $R^7$ are as described herein, Z is —N($CH_2R^7$)—.

In an exemplary embodiment, according to formula (I), $R^1$, $R^2$, $R^3$, $R^4$ and $R^7$ are as described herein, Y is C(O), Z is —O— or —NH— or —N($CH_2R^7$)—, $R^5$ is halogen, and $R^6$ is halogen. In an exemplary embodiment, according to formula (I), $R^1$, $R^2$, $R^3$, $R^4$ and $R^7$ are as described herein, Y is C(O), Z is —O— or —NH— or —N($CH_2R^7$)—, $R^5$ is halogen, and $R^6$ is fluorine or chlorine. In an exemplary embodiment, according to formula (I), $R^1$, $R^2$, $R^3$, $R^4$ and $R^7$ are as described herein, Y is C(O), Z is —O— or —NH— or —N($CH_2R^7$)—, Y is C(O), Z is —O—, $R^5$ is hydrogen, and $R^6$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^4$ and $R^7$ are as described herein, Y is C(O), Z is —O— or —NH— or —N($CH_2R^7$)—, $R^6$ is hydrogen, and $R^5$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl.

In an exemplary embodiment, according to formula (I), $R^1$, $R^2$, and $R^7$ are as described herein, Y is C(O), Z is —O— or —NH— or —N($CH_2R^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, and $R^6$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen, and $R^6$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, and $R^7$ are as described herein, Y is C(O), Z is —O— or —NH— or —N(CH$_2$R$^7$)—, $R^3$ is halogen, and $R^4$ is fluorine or chlorine, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is unsubstituted $C_1$ or $C_2$ or $C_3$ or heteroalkyl, and $R^4$ is fluorine or chlorine, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, Y is C(O), Z is —O—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is $C_1$ or $C_2$ or $C_3$ alkoxy, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen, $R^4$ is hydrogen or halogen or $C_1$ or $C_2$ or $C_3$ alkoxy, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is fluorine, $R^4$ is hydrogen or halogen or $C_1$ or $C_2$ or $C_3$ alkoxy, $R^5$ is hydrogen or halogen, and $R^6$ is hydrogen or halogen. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen, and $R^6$ is fluorine or chlorine. In an exemplary embodiment, according to formula (I), $R^1$, $R^2$, and $R^7$ are as described herein, Y is C(O), Z is —O— or —NH— or —N(CH$_2$R$^7$)—, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen, and $R^6$ is fluorine or chlorine. In an exemplary embodiment, according to formula (I), $R^1$, $R^2$, and $R^7$ are as described herein, Y is C(O), Z is —O— or —NH— or —N(CH$_2$R$^7$)—, $R^3$ is fluorine, $R^4$ is hydrogen or halogen or $C_1$ or $C_2$ or $C_3$ alkoxy, $R^5$ is hydrogen, and $R^6$ is hydrogen.

In an exemplary embodiment, according to formula (I), $R^1$ and $R^7$ are as described herein, Y is C(O), Z is —O— or —NH— or —N(CH$_2$R$^7$)—, $R^2$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, and $R^6$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$ and $R^7$ are as described herein, Y is C(O), Z is —O— or —NH— or —N(CH$_2$R$^7$)—, $R^2$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, and $R^6$ is hydrogen or halogen. In an exemplary embodiment, according to formula (I), $R^1$ and $R^7$ are as described herein, Y is C(O), Z is —O— or —NH— or —N(CH$_2$R$^7$)—, $R^2$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl, $R^3$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl, $R^4$ is hydrogen or halogen or $C_1$ or $C_2$ or $C_3$ alkoxy, $R^5$ is hydrogen or halogen, and $R^6$ is hydrogen or halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$ and $R^7$ are as described herein, Y is C(O), Z is —O— or —NH— or —N(CH$_2$R$^7$)—, $R^2$ is halogen, $R^3$ is halogen, $R^4$ is fluorine or chlorine, $R^5$ is hydrogen or halogen, and $R^6$ is hydrogen or halogen. In an exemplary embodiment, according to formula (I), $R^1$ and $R^7$ are as described herein, Y is C(O), Z is —O— or —NH— or —N(CH$_2$R$^7$)—, $R^2$ is hydrogen, $R^3$ is halogen, $R^4$ is fluorine or chlorine, $R^5$ is hydrogen or halogen, and $R^6$ is hydrogen or halogen. In an exemplary embodiment, according to formula (I), $R^1$ and $R^7$ are as described herein, Y is C(O), Z is —O— or —NH— or —N(CH$_2$R$^7$)—, $R^2$ is hydrogen, $R^3$ is unsubstituted $C_1$ or $C_2$ or $C_3$ or heteroalkyl, $R^4$ is fluorine or chlorine, $R^5$ is hydrogen or halogen, and $R^6$ is hydrogen or halogen. In an exemplary embodiment, according to formula (I), $R^1$ and $R^7$ are as described herein, Y is C(O), Z is —O— or —NH— or —N(CH$_2$R$^7$)—, R$^2$ is hydrogen, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is C$_1$ or C$_2$ or C$_3$ alkoxy, R$^5$ is hydrogen or halogen, and R$^6$ is hydrogen or halogen. In an exemplary embodiment, according to formula (I), R$^1$ and R$^7$ are as described herein, Y is C(O), Z is —O— or —NH— or —N(CH$_2$R$^7$)—, R$^2$ is hydrogen, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is hydrogen, R$^5$ is hydrogen or halogen, and R$^6$ is hydrogen or halogen. In an exemplary embodiment, according to formula (I), R$^1$ and R$^7$ are as described herein, Y is C(O), Z is —O— or —NH— or —N(CH$_2$R$^7$)—, R$^2$ is hydrogen, R$^3$ is hydrogen, R$^4$ is hydrogen or halogen or C$_1$ or C$_2$ or C$_3$ alkoxy, R$^5$ is hydrogen or halogen, and R$^6$ is hydrogen or halogen. In an exemplary embodiment, according to formula (I), R$^1$ and R are as described herein, Y is C(O), Z is —O— or —NH— or —N(CH$_2$R)—, R$^2$ is hydrogen, R$^3$ is fluorine, R$^4$ is hydrogen or halogen or C$_1$ or C$_2$ or C$_3$ alkoxy, R$^5$ is hydrogen or halogen, and R$^6$ is hydrogen or halogen. In an exemplary embodiment, according to formula (I), R$^1$ and R$^7$ are as described herein, Y is C(O), Z is —O— or —NH— or —N(CH$_2$R')—, R$^2$ is hydrogen, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is hydrogen or halogen or C$_1$ or C$_2$ or C$_3$ alkoxy, R$^5$ is hydrogen or halogen, and R$^6$ is fluorine or chlorine. In an exemplary embodiment, according to formula (I), R$^1$ and R$^7$ are as described herein, Y is C(O), Z is —O— or —NH— or —N(CH$_2$R)—, R$^2$ is hydrogen, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is hydrogen or halogen or C$_1$ or C$_2$ or C$_3$ alkoxy, R$^5$ is hydrogen or halogen, and R$^6$ is fluorine or chlorine. In an exemplary embodiment, according to formula (I), R$^1$ and R$^7$ are as described herein, Y is C(O), Z is —O— or —NH— or —N(CH$_2$R')—, R$^2$ is methyl, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is hydrogen or halogen or C$_1$ or C$_2$ or C$_3$ alkoxy, R$^5$ is hydrogen or halogen, and R$^6$ is fluorine or chlorine. In an exemplary embodiment, according to formula (I), R$^1$ and R$^7$ are as described herein, Y is C(O), Z is —O— or —NH— or —N(CH$_2$R')—, R$^2$ is fluorine or chlorine, R$^3$ is hydrogen or halogen or unsubstituted C$_1$ or C$_2$ or C$_3$ haloalkyl or C$_1$ or C$_2$ or C$_3$ alkoxy or unsubstituted C$_1$ or C$_2$ or C$_3$ or C$_4$ or C$_5$ or C$_6$ or C$_7$ or C$_8$ or C$_9$ or C$_{10}$ alkyl, R$^4$ is hydrogen or halogen or C$_1$ or C$_2$ or C$_3$ alkoxy, R$^5$ is hydrogen or halogen, and R$^6$ is fluorine or chlorine. In an exemplary embodiment, according to formula (I), R$^1$ and R$^7$ are as described herein, Y is C(O), Z is —O— or —NH— or —N(CH$_2$R')—, R$^2$ is hydrogen, R$^3$ is fluorine, R$^4$ is hydrogen or halogen or C$_1$ or C$_2$ or C$_3$ alkoxy, R$^5$ is hydrogen, and R$^6$ is hydrogen. In an exemplary embodiment, according to formula (I), R$^1$ and R$^7$ are as described herein, Y is C(O), Z is —O— or —NH— or —N(CH$_2$R$^7$)—, R$^2$ is hydrogen, R$^3$ is fluorine, R$^4$ is hydrogen, R$^5$ is hydrogen, and R$^6$ is hydrogen.

In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is substituted C$_1$ or C$_2$ or C$_3$ or C$_4$ or C$_5$ or C$_6$ or C$_7$ or C$_8$ or C$_9$ or C$_{10}$ alkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is unsubstituted C$_1$ or C$_2$ or C$_3$ or C$_4$ or C$_5$ or C$_6$ or C$_7$ or C$_8$ or C$_9$ or C$_{10}$ alkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is CH$_3$. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is H. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is halogen. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is fluorine or chlorine. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^2$ is chlorine.

In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is hydrogen or halogen or substituted or unsubstituted C$_1$ or C$_2$ or C$_3$ or C$_4$ or C$_5$ or C$_6$ or C$_7$ or C$_5$ or C$_9$ or C$_{10}$ haloalkyl or substituted or unsubstituted C$_1$ or C$_2$ or C$_3$ or C$_4$ or C$_5$ or C$_6$ or C$_7$ or C$_8$ or C$_9$ or C$_{10}$ heteroalkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is substituted C$_1$ or C$_2$ or C$_3$ or C$_4$ or C$_5$ or C$_6$ or C$_7$ or C$_8$ or C$_9$ or C$_{10}$ alkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is unsubstituted C$_1$ or C$_2$ or C$_3$ or C$_4$ or C$_5$ or C$_6$ or C$_7$ or C$_8$ or C$_9$ or C$_{10}$ alkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is CH$_3$. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is C$_1$-C$_4$ alkyl substituted with one or more halogen. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is —CF$_3$. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is C$_1$ or C$_2$ or C$_3$ alkoxy. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is —OCH$_3$. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is C$_1$ or C$_2$ or C$_3$ haloalkyl. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is CF$_3$. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is H. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R)—, and R$^3$ is halogen. In an exemplary embodiment, according to formula (I), R$^1$, R$^3$, R$^4$, R$^5$, R$^6$, and R$^7$ are as described herein, Y is C(O), Z is —O— or —NH— or —N(CH$_2$R$^7$)—, and R$^3$ is fluorine or chlorine. In an exemplary embodiment, according to formula (I), R$^1$, R$^3$, $R^4$, $R^5$, $R^6$, and $R^7$ are as described herein, Y is C(O), Z is —O— or —NH— or —N(CH$_2$R$^7$)—, and $R^3$ is fluorine.

In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is halogen. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is fluorine or chlorine. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is CH$_3$. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is unsubstituted $C_1$ or $C_2$ or $C_3$ or heteroalkyl. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is $C_1$ or $C_2$ or $C_3$ alkoxy. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is —OCH$_3$. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is $C_1$ or $C_2$ or $C_3$ haloalkyl. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is CF$_3$. In an exemplary embodiment, according to formula (I), $R^1$, $R^2$, $R^3$, $R^5$, $R^6$, and $R^7$ are as described herein, Y is C(O), Z is —O— or —NH— or —N(CH$_2$R$^7$)—, and $R^4$ is hydrogen.

In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is halogen. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is fluorine or chlorine or bromine. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is substituted $C_1$ or $C_2$ or $C_3$ or $C_4$ or $C_5$ or $C_6$ or $C_7$ or C or $C_9$ or $C_{10}$ alkyl. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is CH$_3$. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is unsubstituted $C_1$ or $C_2$ or $C_3$ or heteroalkyl. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is $C_1$ or $C_2$ or $C_3$ alkoxy. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is —OCH$_3$. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is $C_1$ or $C_2$ or $C_3$ haloalkyl. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is CF$_3$. In an exemplary embodiment, according to formula (I), $R^1$, $R^2$, $R^3$, $R^4$, $R^6$, and $R^7$ are as described herein, Y is C(O), Z is —O— or —NH— or —N(CH$_2$R$^7$)—, and $R^5$ is hydrogen.

In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is hydrogen or halogen or substituted or unsubstituted $C_1$ or $C_2$ or $C_3$ or $C_4$ or $C_5$ or $C_6$ or $C_7$ or $C_5$ or $C_9$ or $C_{10}$ haloalkyl or substituted or unsubstituted $C_1$ or $C_2$ or $C_3$ or $C_4$ or $C_5$ or $C_6$ or $C_7$ or C or $C_9$ or $C_{10}$ heteroalkyl. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is halogen. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is fluorine or chlorine or bromine. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is CH$_3$. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is $C_1$ or $C_2$ or $C_3$ heteroalkyl. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is $C_1$ or $C_2$ or $C_3$ alkoxy. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is —OCH$_3$. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is unsubstituted $C_1$ or $C_2$ or $C_3$ haloalkyl. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is CF$_3$. In an exemplary embodiment, according to formula (I), $R^1$, $R^2$, $R^3$, $R^4$, $R^5$, and $R^7$ are as described herein, Y is C(O), Z is —O— or —NH— or —N(CH$_2$R$^7$)—, and $R^6$ is hydrogen. In an exemplary embodiment, according to formula (I), $R^1$, $R^2$, $R^5$, and $R^7$ are as described herein, Y is C(O), Z is —O— or —NH— or —N(CH$_2$R$^7$)—, $R^3$ is halogen, and $R^4$ is halogen. In an exemplary embodiment, according to formula (I), $R^1$, $R^2$, $R^5$, and $R^7$ are as described herein, Y is C(O), Z is —O— or —NH— or —N(CH$_2$R$^7$)—, $R^3$ is halogen, and $R^4$ is fluorine or chlorine. In an exemplary embodiment, according to formula (I), $R^1$, $R^2$, $R^5$, and $R^7$ are as described herein, Y is C(O), Z is —O— or —NH— or —N(CH$_2$R$^7$)—, $R^4$ is halogen, and $R^3$ is unsubstituted $C_1$ or $C_2$ or $C_3$ or heteroalkyl. In an exemplary embodiment, according to formula (I), $R^1$, $R^2$, $R^5$, and $R^7$ are as described herein, Y is C(O), Z is —O— or —NH— or —N(CH$_2$R$^7$)—, $R^3$ is halogen, and $R^4$ is $C_1$ or $C_2$ or $C_3$ alkoxy. In an exemplary embodiment, according to formula (I), $R^1$, $R^2$, $R^5$, and $R^7$ are as described herein, Y is C(O), Z is —O— or —NH— or —N(CH$_2$R)—, $R^3$ is fluorine or chlorine, and $R^4$ is —OCH$_3$. In an exemplary embodiment, according to formula (I), $R^1$, $R^2$, $R^5$, and $R^7$ are as described herein, Y is C(O), Z is —O— or —NH— or —N(CH$_2$R$^7$)—, $R^4$ is hydrogen, and $R^3$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^5$, and $R^7$ are as described herein, Y is C(O), Z is —O— or —NH— or —N(CH$_2$R$^7$)—, $R^3$ is hydrogen, and $R^4$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl.

In an exemplary embodiment, according to formula (I), $R^1$, $R^2$, $R^3$, $R^4$, $R^5$, and $R^6$ are as described herein, Y is C(O), Z is —N(CH$_2$R$^7$)—, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, $R^3$, and $R^4$ are as described herein, Y is C(O), Z is —N(CH$_2$R$^7$)—, $R^5$ is H, $R^6$ is H, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^2$, and $R^3$ are as described herein, Y is C(O), Z is —N(CH$_2$R$^7$)—, $R^4$ is H, $R^5$ is H, $R^6$ is H, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$, $R^3$, and $R^4$ are as described herein, Y is C(O), Z is —N(CH$_2$R$^7$)—, $R^2$ is H or F or CH$_3$, $R^5$ is H, $R^6$ is H, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$ and $R^3$ are as described herein, Y is C(O), Z is —N(CH$_2$R$^7$)—, $R^2$ is H or F or CH$_3$, $R^4$ is H, $R^5$ is H, $R^6$ is H, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$ is as described herein, Y is C(O), Z is —N(CH$_2$R$^7$)—, $R^2$ is H or F or CH$_3$, $R^3$ is F, $R^4$ is H, $R^5$ is H, $R^6$ is H, and $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^1$ is as described herein, Y is C(O), Z is —N(CH$_2$R$^7$)—, $R^2$ is H or F or CH$_3$, $R^3$ is F, $R^4$ is H, $R^5$ is H, $R^6$ is H, and $R^7$ is methyl or ethyl or propyl or isopropyl. In an exemplary embodiment, according to formula (I), $R^1$, $R^2$, $R^3$, $R^4$, $R^5$, and $R^6$ are as described herein, Y is C(O), Z is —N(CH$_2$R$^7$)—, and $R^7$ is methyl or ethyl or propyl or isopropyl. In an exemplary embodiment, according to formula (I), $R^2$, $R^3$, $R^4$, $R^5$, and $R^6$ are as described herein, Y is C(O), Z is —N(CH$_2$R$^7$)—, $R^7$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^2$, $R^3$, $R^4$, $R^5$, and $R^6$ are as described herein, Y is C(O), Z is —N(CH$_2$R$^7$)—, $R^7$ is methyl or ethyl or propyl or isopropyl and $R^1$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, according to formula (I), $R^2$, $R^3$, $R^4$, $R^5$, and $R^6$ are as described herein, Y is C(O), Z is —N(CH$_2$R)—, $R^7$ is unsubstituted $C_1$ or $C_2$ or $C_3$ or $C_4$ or $C_5$ or $C_6$ or $C_7$ or $C_8$ or $C_9$ or $C_{10}$ alkyl and $R^1$ is methyl or ethyl or propyl or isopropyl. In an exemplary embodiment, according to formula (I), $R^2$, $R^3$, $R^4$, $R^5$, and $R^6$ are as described herein, Y is C(O), Z is —N(CH$_2$R$^7$)—, $R^7$ is methyl or ethyl or propyl or isopropyl and $R^1$ is methyl or ethyl or propyl or isopropyl. In an exemplary embodiment, according to formula (I), $R^2$, $R^3$, and $R^4$ are as described herein, Y is C(O), Z is —N(CH$_2$R$^7$)—, $R^5$ is H, $R^6$ is H, and $R^7$ is methyl or ethyl or propyl or isopropyl and $R^1$ is methyl or ethyl or propyl or isopropyl. In an exemplary embodiment, according to formula (I), $R^2$ and $R^3$ are as described herein, Y is C(O), Z is —N(CH$_2$R$^7$)—, $R^4$ is H, $R^5$ is H, $R^6$ is H, $R^1$ is methyl or ethyl or propyl or isopropyl and $R^7$ is methyl or ethyl or propyl or isopropyl. In an exemplary embodiment, according to formula (I), $R^3$ and $R^4$ are as described herein, Y is C(O), Z is —N(CH$_2$R$^7$)—, $R^2$ is H or F or CH$_3$, $R^5$ is H, $R^6$ is H, $R^1$ is methyl or ethyl or propyl or isopropyl and $R^7$ is methyl or ethyl or propyl or isopropyl. In an exemplary embodiment, according to formula (I), $R^3$ is as described herein, Y is C(O), Z is —N(CH$_2$R$^7$)—, $R^2$ is H or F or CH$_3$, $R^4$ is H, $R^5$ is H, $R^6$ is H, $R^1$ is methyl or ethyl or propyl or isopropyl and $R^7$ is methyl or ethyl or propyl or isopropyl. In an exemplary embodiment, according to formula (I), Y is C(O), Z is —N(CH$_2$R$^7$)—, $R^2$ is H or F or CH$_3$, $R^3$ is F, $R^4$ is H, $R^5$ is H, $R^6$ is H, $R^1$ is methyl or ethyl or propyl or isopropyl and $R^7$ is methyl or ethyl or propyl or isopropyl. In an exemplary embodiment, according to formula (I), $R^1$ is as described herein, Y is C(O), Z is —N(CH$_2$R$^7$)—, $R^2$ is H or F or CH$_3$, $R^3$ is F, $R^4$ is H, $R^5$ is H, $R^6$ is H, and $R^7$ is methyl or ethyl or propyl or isopropyl.

In an exemplary embodiment, the compound, or a salt or a hydrate or a solvate thereof, has a structure which is

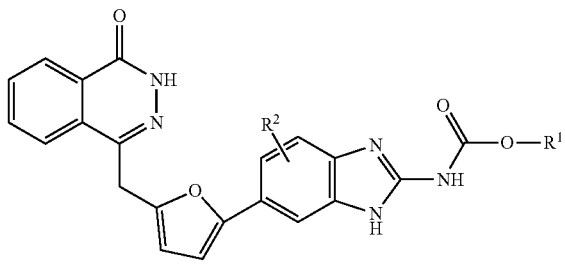

(II)

or

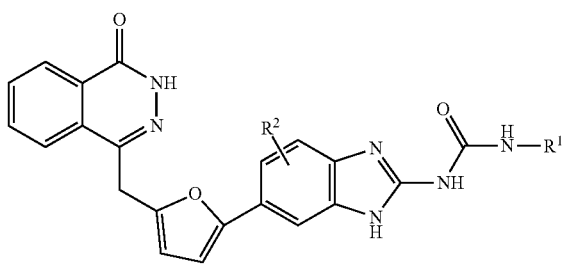

(III)

or
(IIa)
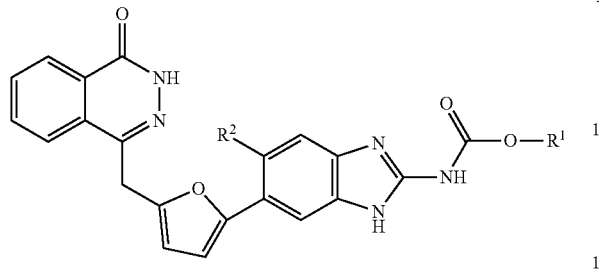
or
(IIIa)
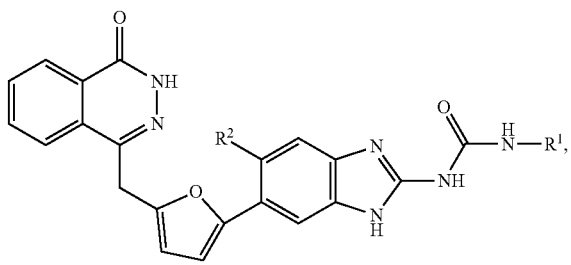
wherein R¹ and R² are as described herein. In an exemplary embodiment, the compound, or a salt or a hydrate or a solvate thereof, has a structure which is
(IV)
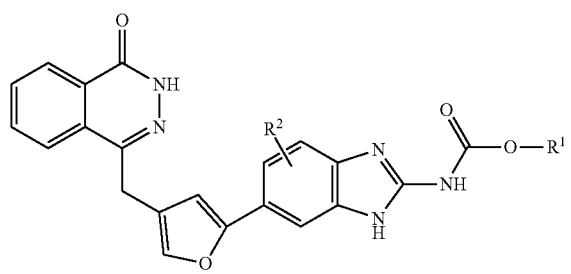
or
(V)
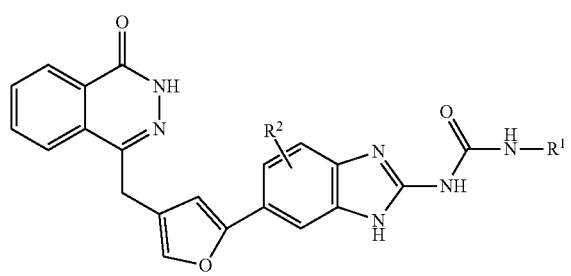
or
(IVa)
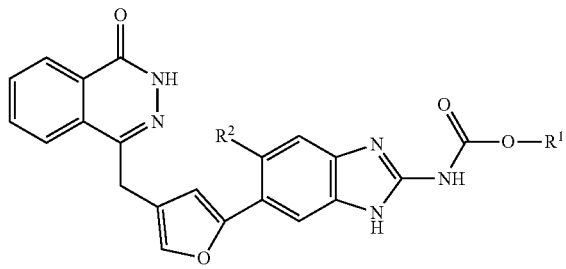
or
(Va)
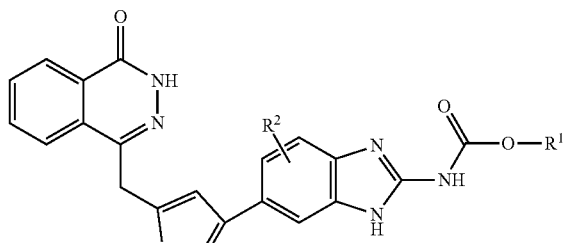
wherein R¹ and R² are as described herein. In an exemplary embodiment, the compound, or a salt or a hydrate or a solvate thereof, has a structure which is
(VI)
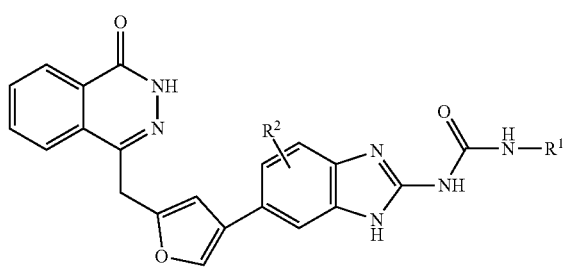
or
(VII)
or -continued

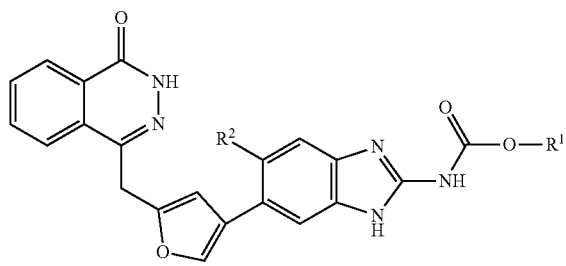
(VIa)

or

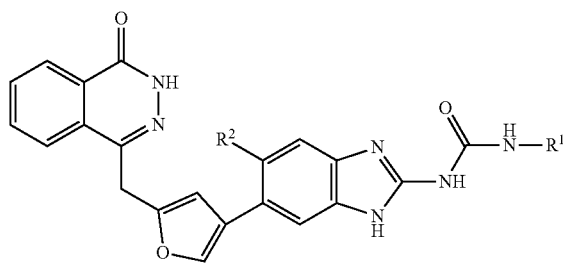
(VIIa)

wherein R¹ and R² are as described herein.

In an exemplary embodiment, the compound, or a salt or a hydrate or a solvate thereof, has a structure which is

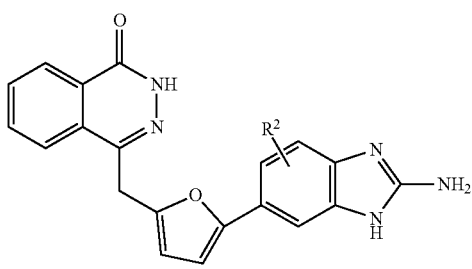
(IIb)

or

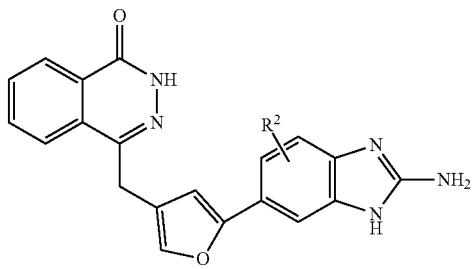
(IVb)

or

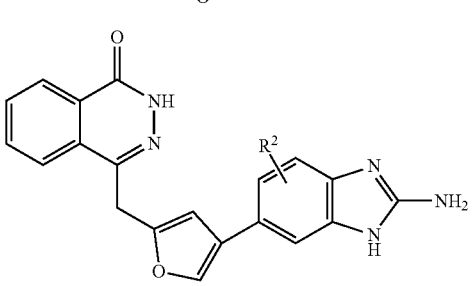
(VIb)

wherein R² is as described herein. In an exemplary embodiment, the structure is according to one of the following table, wherein R¹ is as described herein, where applicable

| Cmpd | Form | R² |
|------|------|-----|
| 1 | II | H |
| 2 | II | F |
| 3 | II | CH₃ |
| 4 | IIa | H |
| 5 | IIa | F |
| 6 | IIa | CH₃ |
| 7 | III | H |
| 8 | III | F |
| 9 | III | CH₃ |
| 10 | IIIa | H |
| 11 | IIIa | F |
| 12 | IIIa | CH₃ |
| 13 | IV | H |
| 14 | IV | F |
| 15 | IV | CH₃ |
| 16 | IVa | H |
| 17 | IVa | F |
| 18 | IVa | CH₃ |
| 19 | V | H |
| 20 | V | F |
| 21 | V | CH₃ |
| 22 | Va | H |
| 23 | Va | F |
| 24 | Va | CH₃ |
| 25 | VI | H |
| 26 | VI | F |
| 27 | VI | CH₃ |
| 28 | VIa | H |
| 29 | VIa | F |
| 30 | VIa | CH₃ |
| 31 | VII | H |
| 32 | VII | F |
| 33 | VII | CH₃ |
| 34 | VIIa | H |
| 35 | VIIa | F |
| 36 | VIIa | CH₃ |
| 37 | IIb | H |
| 38 | IIb | F |
| 39 | IIb | CH₃ |
| 40 | IVb | H |
| 41 | IVb | F |
| 42 | IVb | CH₃ |
| 43 | VIb | H |
| 44 | VIb | F |
| 45 | VIb | CH₃ |

In an exemplary embodiment, the compound, or a salt or a hydrate or a solvate thereof, has a structure which is

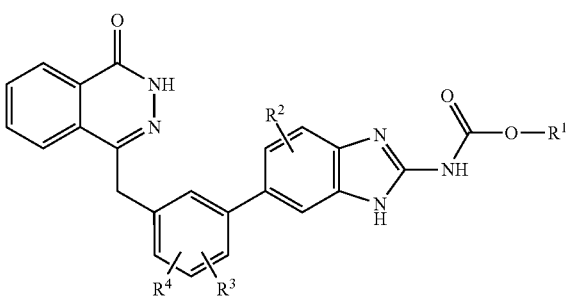
(VIII)

or (IX)

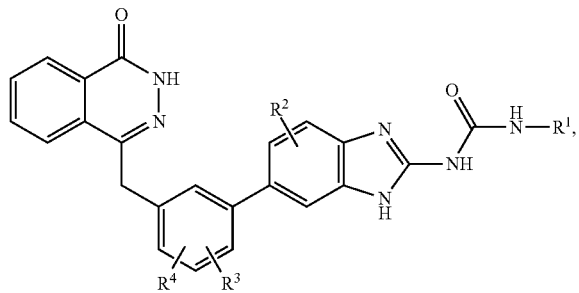

wherein R¹, R², R³, and R⁴ are as described herein.

In an exemplary embodiment, the compound, or a salt or a hydrate or a solvate thereof, has a structure which is (X)

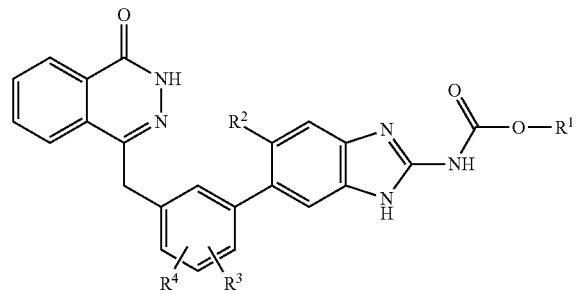

or (XI)

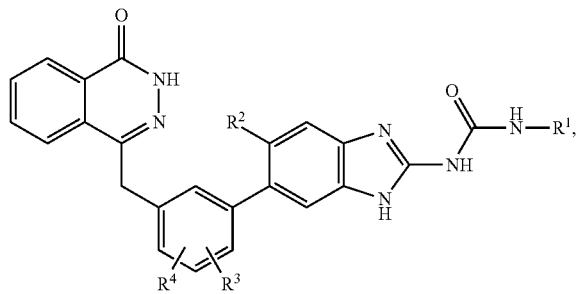

wherein R¹, R², R³, and R⁴ are as described herein.

In an exemplary embodiment, the compound, or a salt or a hydrate or a solvate thereof, has a structure which is (XII)

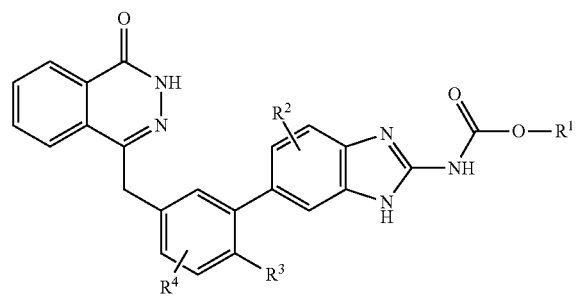

or (XIII)

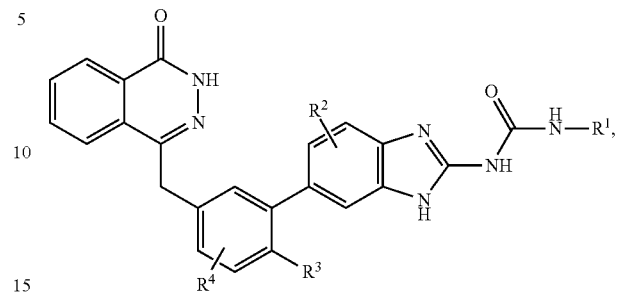

wherein R¹, R², R³, and R⁴ are as described herein.

In an exemplary embodiment, the compound, or a salt or a hydrate or a solvate thereof, has a structure which is (XIV)

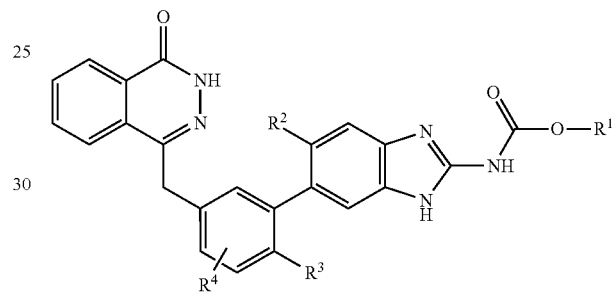

or (XV)

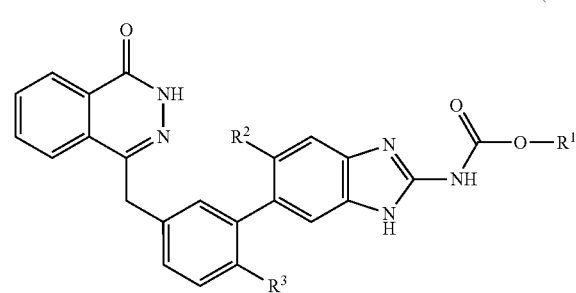

wherein R¹, R², R³, and R⁴ are as described herein.

In an exemplary embodiment, the compound, or a salt or a hydrate or a solvate thereof, has a structure which is (XVI)

-continued or

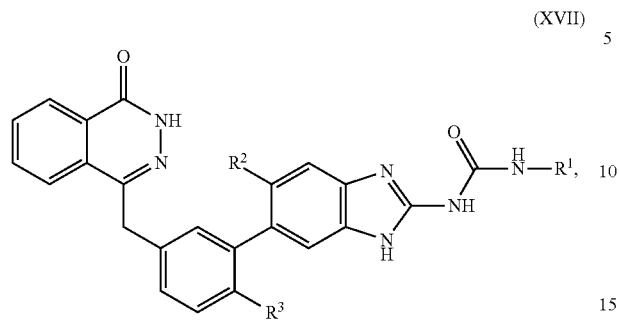

(XVII)

wherein R¹, R², and R³ are as described herein.

In an exemplary embodiment, the compound, or a salt or a hydrate or a solvate thereof, has a structure which is

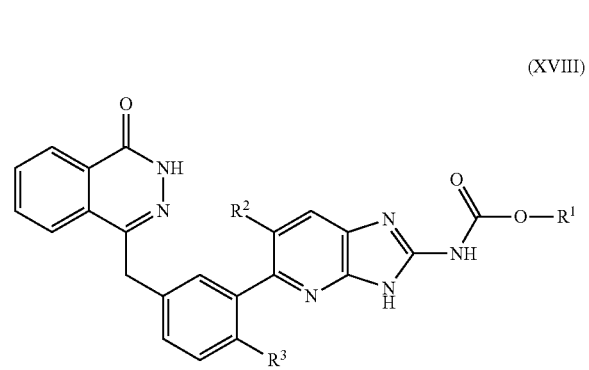

(XVIII)

or

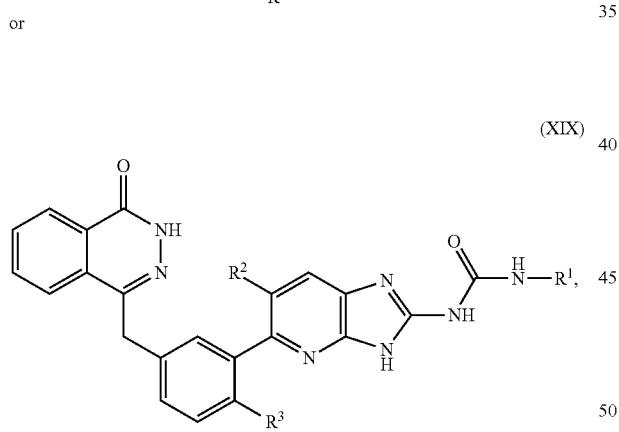

(XIX)

wherein R¹, R², and R³ are as described herein. In an exemplary embodiment, the compound, or a salt or a hydrate or a solvate thereof, is according to formulae (XVIII) or (XIX) wherein R² is hydrogen or F or Cl or unsubstituted $C_1$ or $C_2$ or $C_3$ alkyl; R³ is hydrogen or unsubstituted $C_1$ or $C_2$ or $C_3$ or alkyl or substituted or unsubstituted $C_1$ or $C_2$ or $C_3$ alkoxy; and R¹ is as described herein. In an exemplary embodiment, the compound, or a salt or a hydrate or a solvate thereof, is according to formulae (XVIII) or (XIX) wherein R² is H; R³ is F; and R¹ is as described herein.

In an exemplary embodiment, the compound, or a salt or a hydrate or a solvate thereof, has a structure which is

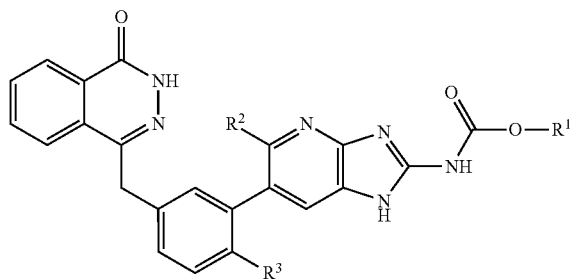

(XX)

or

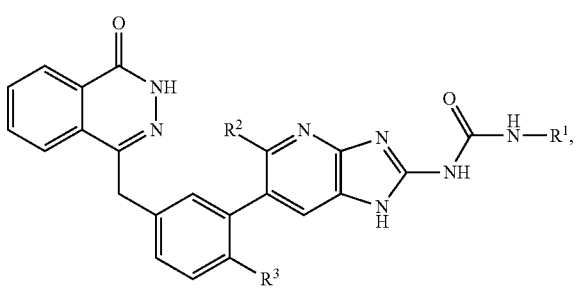

(XXI)

wherein R² and R³ are as described herein.

In an exemplary embodiment, the compound, or a salt or a hydrate or a solvate thereof, has a structure which is

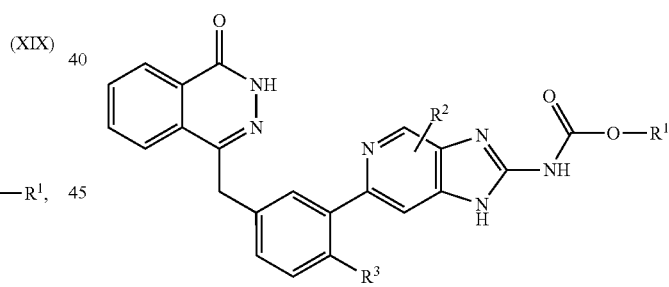

(XXII)

or

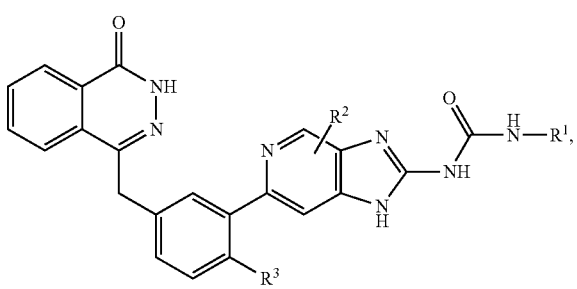

(XXIII)

wherein R² and R³ are as described herein.

In an exemplary embodiment, the compound, or a salt or a hydrate or a solvate thereof, has a structure which is

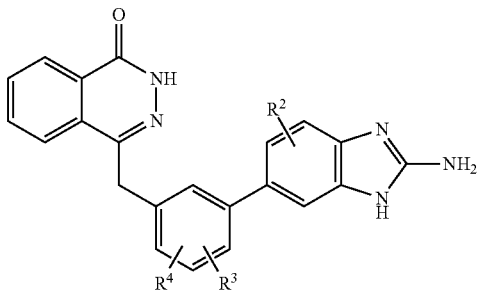
(VIIIb)

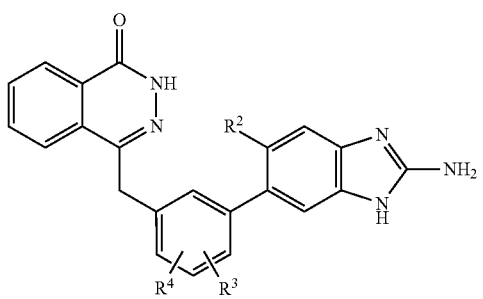
(Xb)

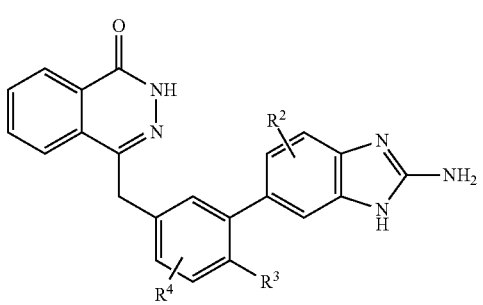
(XIIb)

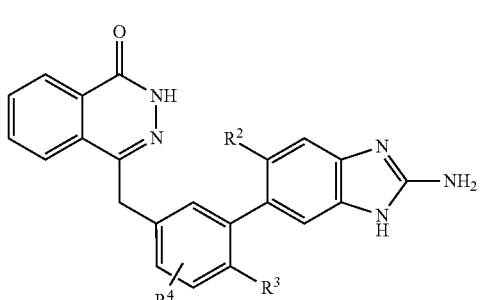
(XIVb)

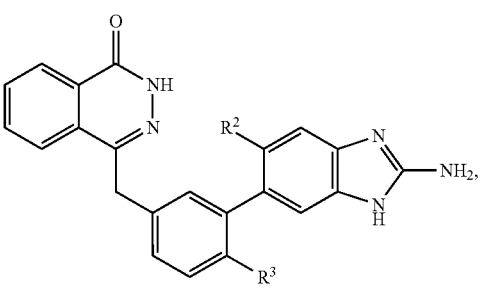
(XVIb)

wherein $R^2$ and $R^3$ are as described herein.

In an exemplary embodiment, the compound, or a salt or a hydrate or a solvate thereof, is according to formulae (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is hydrogen or F or Cl or unsubstituted $C_1$ or $C_2$ or $C_3$ alkyl; $R^3$ is hydrogen or F or Cl or unsubstituted $C_1$ or $C_2$ or $C_3$ or alkyl or substituted or unsubstituted $C_1$ or $C_2$ or $C_3$ alkoxy; and $R^4$ is hydrogen or F or Cl or unsubstituted $C_1$ or $C_2$ or $C_3$ or alkyl or substituted or unsubstituted $C_1$ or $C_2$ or $C_3$ alkoxy.

In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is H. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is F and $R^3$ is H. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is F. In an exemplary embodiment, the compound, or a salt or a hydrate or a solvate thereof, is according to formula (XVIb), wherein $R^2$ is H and $R^3$ is F. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is F and $R^3$ is F. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is Cl. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is F and $R^3$ is Cl. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$OCH_3$. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$OCHF_2$. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$OCF_3$. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$CH_3$. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$CF_3$. In an exemplary embodiment, the compound, or a salt or a hydrate or a solvate thereof, is according to formulae (I) or (Ia) or (VIII) or (VIIIb) or (IX) or (X) or (Xb) or (XI) or (XII) or (XIIb) or (XIII) or (XIV) or (XIVb) or (XV) or (XVI) or (XVIb) or (XVII) or (XX) or (XXI) or (XXII) or (XXIII), wherein $R^2$ is H and $R^3$ is —$OCH_2CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is substituted or unsubstituted $C_1$ or $C_2$ or $C_3$ or $C_4$ or $C_5$ or $C_6$ or $C_7$ or $C_8$ or $C_9$ or $C_{10}$ alkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl or substituted or unsubstituted aryl or substituted or unsubstituted arylalkyl or substituted or unsubstituted cycloalkyl or substituted or unsubstituted heterocycloalkyl. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_m OR^{1a}$, wherein $R^{1a}$ is substituted or unsubstituted $C_1$ or $C_2$ or $C_3$ alkyl, and m is 1 or 2 or 3. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is propyl or —$CH_2CH_2F$ or —$CH_2CHF_2$ or —$CH_2CF_3$ or —$CH(CH_3)_2$ or —$CH(CH_3)(CH_2CH_3)$ or cyclopropyl or cyclobutyl or cyclopentyl or cyclohexyl or oxetanyl or tetrahydropyranyl or azetidinyl or methylazetidinyl or piperidinyl or methylpiperidinyl or phenyl or benzyl or —$(CH_2)_m NR^{1b}R^{1c}$, wherein $R^{1b}$ is hydrogen or substituted or unsubstituted $C_1$ or $C_2$ or $C_3$ alkyl and $R^{1c}$ is hydrogen or substituted or unsubstituted $C_1$ or $C_2$ or $C_3$ alkyl and m is 1 or 2 or 3, with the proviso that $R^{1b}$ and $R^{1c}$ can optionally be joined to form a 4-7 membered ring.

In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$, $R^2$ is H, and $R^3$ is H. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$, $R^2$ is H, and $R^3$ is F. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl, $R^2$ is F, and $R^3$ is F. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl, $R^2$ is F, and $R^3$ is F. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$, $R^2$ is F, and $R^3$ is F. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl; $R^2$ is H; and $R^3$ is —$CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl; $R^2$ is H; and $R^3$ is —$CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$, $R^2$ is H; and $R^3$ is —$CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl; $R^2$ is H; and $R^3$ is —$OCH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl; $R^2$ is H; and $R^3$ is —$OCH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2 OCH_3$, $R^2$ is H; and $R^3$ is —$OCH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl; $R^2$ is H; and $R^3$ is —$OCHF_2$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl; $R^2$ is H; and $R^3$ is —$OCHF_2$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2OCH_3$, $R^2$ is H; and $R^3$ is —$OCHF_2$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl; $R^2$ is H; and $R^3$ is —$OCH_2CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl; $R^2$ is H; and $R^3$ is —$OCH_2CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is —$(CH_2)_2OCH_3$, $R^2$ is H; and $R^3$ is —$OCH_2CH_3$. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is methyl; $R^2$ is H; and $R^3$ is F. In an exemplary embodiment, the compound, or a salt or a hydrate or a solvate thereof, is according to formulae (I) or (VIII) or (IX) or (X) or (XI) or (XII) or (XIII) or (XIV) or (XV) or (XVI) or (XVII) or (XVIII) or (XIX) or (XX) or (XXI) or (XXII) or (XXIII), wherein $R^1$ is ethyl; $R^2$ is H; and $R^3$ is F.

In another aspect, the invention provides a compound, or a salt or a hydrate or a solvate thereof, having a structure according to formula (I):

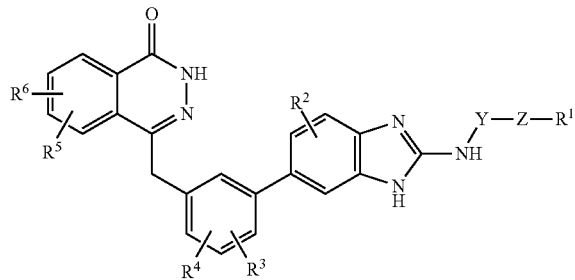

(I)

wherein Y is C(O) or S(O)$_2$; Z is —O— or —CH$_2$— or —NH— or —N(CH$_2$R$^7$)— wherein R$^7$ is hydrogen or substituted or unsubstituted $C_1$ or $C_2$ or $C_3$ or $C_4$ or $C_5$ or $C_6$ or $C_7$ or $C_8$ or $C_9$ or $C_{10}$ alkyl; $R^1$ is hydrogen or substituted or unsubstituted $C_1$ or $C_2$ or $C_3$ or $C_4$ or $C_5$ or $C_6$ or $C_7$ or $C_8$ or $C_9$ or $C_{10}$ alkyl or substituted or unsubstituted aryl or arylalkyl; $R^2$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl; $R^3$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl; $R^4$ is hydrogen or halogen or substituted or unsubstituted $C_1$ or $C_2$ or $C_3$ or $C_4$ or $C_5$ or $C_6$ or $C_7$ or $C_5$ or $C_9$ or $C_{10}$ alkyl; $R^5$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl; and $R^6$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ alkyl.

In an exemplary embodiment, for a formula described herein, Y, Z, $R^2$, $R^3$, $R^4$, $R^5$, and $R^6$ are as described herein, $R^1$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^2$, $R^3$, $R^4$, $R^5$, and $R^6$ are as described herein, $R^1$ is methyl or ethyl. In an exemplary embodiment, for a formula described herein, Y, Z, $R^2$, $R^3$, $R^4$, $R^5$, and $R^6$ are as described herein, $R^1$ is n-propyl or isopropyl or n-butyl or t-butyl or isobutyl or sec-butyl. In an exemplary embodiment, for a formula described herein, Y, Z, $R^2$, $R^3$, $R^4$, $R^5$, and $R^6$ are as described herein, $R^1$ is cyclopropyl or cyclopropylmethyl or cyclobutyl or cyclohexyl. In an exemplary embodiment, for a formula described herein, Y, Z, $R^2$, $R^3$, $R^4$, $R^5$, and $R^6$ are as described herein, $R^1$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^2$, $R^3$, $R^4$, $R^5$, and $R^6$ are as described herein, $R^1$ is substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, for a formula described herein, Y, Z, $R^2$, $R^3$, $R^4$, $R^5$, and $R^6$ are as described herein, $R^1$ is substituted or unsubstituted $C_1$ or $C_2$ or $C_3$ or $C_4$ or $C_5$ or $C_6$ or $C_7$ or $C_8$ or $C_9$ or $C_{10}$ haloalkyl. In an exemplary embodiment, for a formula described herein, Y, Z, $R^2$, $R^3$, $R^4$, $R^5$, and $R^6$ are as described herein, $R^1$ is $C_1$ or $C_2$ or $C_3$ haloalkyl. In an exemplary embodiment, for a formula described herein, Y, Z, $R^2$, $R^3$, $R^4$, $R^5$, and $R^6$ are as described herein, $R^1$ is 2-fluoroethyl or 2,2-difluoroethyl or 2,2,2-trifluoroethyl or 2-chloroethyl or 3-chloropropyl. In an exemplary embodiment, for a formula described herein, Y, Z, $R^2$, $R^3$, $R^4$, $R^5$, and $R^6$ are as described herein, $R^1$ is $C_1$-$C_4$ alkyl substituted with NR$^{8a}$R$^{8b}$, wherein R$^{8a}$ and R$^{8b}$ are each independently substituted or unsubstituted $C_1$-$C_4$ alkyl. In an exemplary embodiment, for a formula described herein, Y, Z, $R^2$, $R^3$, $R^4$, $R^5$, and $R^6$ are as described herein, $R^1$ is $C_1$-$C_4$ alkyl substituted with N(CH$_3$)$_2$. In an exemplary embodiment, for a formula described herein, Y, Z, $R^2$, $R^3$, $R^4$, $R^5$, and $R^6$ are as described herein, $R^1$ is $C_1$-$C_4$ alkyl substituted with N(CH$_2$CH$_3$)$_2$. In an exemplary embodiment, for a formula described herein, Y, Z, $R^2$, $R^3$, $R^4$, $R^5$, and $R^6$ are as described herein, $R^1$ is alkyl substituted with substituted or unsubstituted heterocycloalkyl. In an exemplary embodiment, for a formula described herein, Y, Z, $R^2$, $R^3$, $R^4$, $R^5$, and $R^6$ are as described herein, $R^1$ is $C_1$-$C_4$ alkyl substituted with substituted pyrrolidinyl or substituted piperazinyl or substituted morpholinyl or substituted piperidinyl or substituted pyrrolidinyl. In an exemplary embodiment, for a formula described herein, Y, Z, $R^2$, $R^3$, $R^4$, $R^5$, and $R^6$ are as described herein, $R^1$ is $C_1$-$C_4$ alkyl substituted with unsubstituted pyrrolidinyl or unsubstituted piperazinyl or unsubstituted morpholinyl or unsubstituted piperidinyl or unsubstituted pyrrolidinyl. In an exemplary embodiment, for a formula described herein, Y, Z, $R^2$, $R^3$, $R^4$, $R^5$, and $R^6$ are as described herein, $R^1$ is alkyl substituted with substituted or unsubstituted $C_3$-$C_7$ cycloalkyl. In an exemplary embodiment, for a formula described herein, Y, Z, $R^2$, $R^3$, $R^4$, $R^5$, and $R^6$ are as described herein, $R^1$ is substituted or unsubstituted aryl. In an exemplary embodiment, for a formula described herein, Y, Z, $R^2$, $R^3$, $R^4$, $R^5$, and $R^6$ are as described herein, $R^1$ is phenyl. In an exemplary embodiment, for a formula described herein, Y, Z, $R^2$, $R^3$, $R^4$, $R^5$, and $R^6$ are as described herein, $R^1$ is substituted or unsubstituted arylalkyl. In an exemplary embodiment, for a formula described herein, Y, Z, $R^2$, $R^3$, $R^4$, $R^5$, and $R^6$ are as described herein, $R^1$ is benzyl. In an exemplary embodiment, for a formula described herein, Y, Z, $R^2$, $R^3$, $R^4$, $R^5$, and $R^6$ are as described herein, $R^1$ is substituted or unsubstituted $C_1$ or $C_2$ or $C_3$ or $C_4$ or $C_5$ or $C_6$ or $C_7$ or C or $C_9$ or $C_{10}$ heteroalkyl. In an exemplary embodiment, for a formula described herein, Y, Z, $R^2$, $R^3$, $R^4$, $R^5$, and $R^6$ are as described herein, $R^1$ is —$CH_2$—$CH_2$—O—$CH_3$ or —$CH_2$—$CH_2$—N($CH_3$)—$CH_3$ or —$CH_2$—$CH_2$—$CH_2$—N ($CH_3$)—$CH_3$. In an exemplary embodiment, for a formula described herein, Y, Z, $R^2$, $R^3$, $R^4$, $R^5$, and $R^6$ are as described herein, $R^1$ is unsubstituted $C_1$ or $C_2$ or $C_3$ heteroalkyl. In an exemplary embodiment, for a formula described herein, Y, Z, $R^2$, $R^3$, $R^4$, $R^5$, and $R^6$ are as described herein, $R^1$ is substituted or unsubstituted $C_3$ or $C_4$ or $C_5$ or $C_6$ or $C_7$ or $C_8$ heterocycloalkyl. In an exemplary embodiment, for a formula described herein, Y, Z, $R^2$, $R^3$, $R^4$, $R^5$, and $R^6$ are as described herein, $R^1$ is substituted or unsubstituted oxetanyl. In an exemplary embodiment, for a formula described herein, Y, Z, $R^2$, $R^3$, $R^4$, $R^5$, and $R^6$ are as described herein, $R^1$ is substituted or unsubstituted tetrahydropyranyl. In an exemplary embodiment, for a formula described herein, Y, Z, $R^2$, $R^3$, $R^4$, $R^5$, and $R^6$ are as described herein, $R^1$ is substituted or unsubstituted azetidinyl. In an exemplary embodiment, for a formula described herein, Y, Z, $R^2$, $R^3$, $R^4$, $R^5$, and $R^6$ are as described herein, $R^1$ is substituted or unsubstituted methylazetidinyl or substituted or unsubstituted ethylazetidinyl. In an exemplary embodiment, for a formula described herein, Y, Z, $R^2$, $R^3$, $R^4$, $R^5$, and $R^6$ are as described herein, $R^1$ is substituted or unsubstituted piperidinyl. In an exemplary embodiment, for a formula described herein, Y, Z, $R^2$, $R^3$, $R^4$, $R^5$, and $R^6$ are as described herein, $R^1$ is substituted or unsubstituted methylpiperidinyl or substituted or unsubstituted ethylpiperidinyl. In an exemplary embodiment, for a formula described herein, Y, Z, $R^2$, $R^3$, $R^4$, $R^5$, and $R^6$ are as described herein, $R^1$ is 2-(4-methylpiperazin-1-yl)ethyl or 3-(4-methylpiperazin-1-yl)propyl or 2-morpholinoethyl or 3-morpholinopropyl or 1-methylazetidin-3-yl or 1-ethylazetidin-3-yl or 1-isopropylazetidin-3-yl or 1-methylpiperidin-4-yl or 1-ethylpiperidin-4-yl or 1-isopropylpiperidin-4-yl. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is substituted or unsubstituted $C_1$ or $C_2$ or $C_3$ or $C_4$ or $C_5$ or $C_6$ alkyl, and m is 4 or 5 or 6. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is substituted or unsubstituted $C_1$ or $C_2$ or $C_3$ or $C_4$ or $C_5$ or $C_6$ alkyl, and m is 1 or 2 or 3. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is substituted or unsubstituted $C_1$ or $C_2$ or $C_3$, and m is 1 or 2 or 3 or 4 or 5 or 6. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is substituted or unsubstituted $C_4$ or $C_5$ or $C_6$, and m is 1 or 2 or 3 or 4 or 5 or 6. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is substituted or unsubstituted $C_1$ or $C_2$ or $C_3$, and m is 1 or 2 or 3. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is methyl, and m is 1 or 2 or 3. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is ethyl, and m is 1 or 2 or 3. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is methyl, and m is 2. In an exemplary embodiment, for a formula described herein, Y, Z, $R^2$, $R^3$, $R^4$, $R^5$, and $R^6$ are as described herein, $R^1$ is —$(CH_2)_m OR^{1a}$, wherein $R^{1a}$ is ethyl, and m is 2.

In an exemplary embodiment, for a formula described herein, Y, Z, $R^1$, $R^3$, $R^4$, $R^5$, and $R^6$ are as described herein, $R^2$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^3$, $R^4$, $R^5$, and $R^6$ are as described herein, $R^2$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^3$, $R^4$, $R^5$, and $R^6$ are as described herein, $R^2$ is $CH_3$. In an exemplary embodiment, for a formula described herein, Y, Z, $R^1$, $R^3$, $R^4$, $R^5$, and $R^6$ are as described herein, $R^2$ is H. In an exemplary embodiment, for a formula described herein, Y, Z, $R^1$, $R^3$, $R^4$, $R^5$, and $R^6$ are as described herein, $R^2$ is halogen. In an exemplary embodiment, for a formula described herein, Y, Z, $R^1$, $R^3$, $R^4$, $R^5$, and $R^6$ are as described herein, $R^2$ is fluorine or chlorine. In an exemplary embodiment, for a formula described herein, Y, Z, $R^1$, $R^3$, $R^4$, $R^5$, and $R^6$ are as described herein, $R^2$ is chlorine.

In an exemplary embodiment, for a formula described herein, Y, Z, $R^1$, $R^2$, $R^4$, $R^5$, and $R^6$ are as described herein, $R^3$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, for a formula described herein, Y, Z, $R^1$, $R^2$, $R^4$, $R^5$, and $R^6$ are as described herein, $R^3$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^4$, $R^5$, and $R^6$ are as described herein, $R^3$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^4$, $R^5$, and $R^6$ are as described herein, $R^3$ is $CH_3$. In an exemplary embodiment, for a formula described herein, Y, Z, $R^1$, $R^2$, $R^4$, $R^5$, and $R^6$ are as described herein, $R^3$ is unsubstituted $C_1$ or $C_2$ or $C_3$ heteroalkyl. In an exemplary embodiment, for a formula described herein, Y, Z, $R^1$, $R^2$, $R^3$, $R^4$, $R^5$, and $R^6$ are as described herein, $R^3$ is $C_1$ or $C_2$ or $C_3$ alkoxy. In an exemplary embodiment, for a formula described herein, Y, Z, $R^1$, $R^2$, $R^4$, $R^5$, and $R^6$ are as described herein, $R^3$ is —$OCH_3$. In an exemplary embodiment, for a formula described herein, Y, Z, $R^1$, $R^2$, $R^4$, $R^5$, and $R^6$ are as described herein, $R^3$ is $C_1$ or $C_2$ or $C_3$ haloalkyl. In an exemplary embodiment, for a formula described herein, Y, Z, $R^1$, $R^2$, $R^3$, $R^4$, $R^5$, and $R^6$ are as described herein, $R^3$ is $CF_3$. In an exemplary embodiment, for a formula described herein, Y, Z, $R^1$, $R^2$, $R^4$, $R^5$, and $R^6$ are as described herein, $R^3$ is H. In an exemplary embodiment, for a formula described herein, Y, Z, $R^1$, $R^2$, $R^4$, $R^5$, and $R^6$ are as described herein, $R^3$ is halogen. In an exemplary embodiment, for a formula described herein, Y, Z, $R^1$, $R^2$, $R^3$, $R^4$, $R^5$, and $R^6$ are as described herein, $R^3$ is fluorine or chlorine. In an exemplary embodiment, for a formula described herein, Y, Z, $R^1$, $R^2$, $R^4$, $R^5$, and $R^6$ are as described herein, $R^3$ is fluorine.

In an exemplary embodiment, for a formula described herein, Y, Z, $R^1$, $R^2$, $R^3$, $R^5$, and $R^6$ are as described herein, $R^4$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, for a formula described herein, Y, Z, $R^1$, $R^2$, $R^3$, $R^5$, and $R^6$ are as described herein, $R^4$ is halogen. In an exemplary embodiment, for a formula described herein, Y, Z, $R^1$, $R^2$, $R^3$, $R^5$, and $R^6$ are as described herein, $R^4$ is fluorine or chlorine. In an exemplary embodiment, for a formula described herein, Y, Z, $R^1$, $R^2$, $R^3$, $R^5$, and $R^6$ are as described herein, $R^4$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, $R^5$, and $R^6$ are as described herein, $R^4$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, $R^5$, and $R^6$ are as described herein, $R^4$ is $CH_3$. In an exemplary embodiment, for a formula described herein, Y, Z, $R^1$, $R^2$, $R^3$, $R^5$, and $R^6$ are as described herein, $R^4$ is unsubstituted $C_1$ or $C_2$ or $C_3$ or heteroalkyl. In an exemplary embodiment, for a formula described herein, Y, Z, $R^1$, $R^2$, $R^3$, $R^5$, and $R^6$ are as described herein, $R^4$ is $C_1$ or $C_2$ or $C_3$ alkoxy. In an exemplary embodiment, for a formula described herein, Y, Z, $R^1$, $R^2$, $R^3$, $R^5$, and $R^6$ are as described herein, $R^4$ is —$OCH_3$. In an exemplary embodiment, for a formula described herein, Y, Z, $R^1$, $R^2$, $R^3$, $R^5$, and $R^6$ are as described herein, $R^4$ is $C_1$ or $C_2$ or $C_3$ haloalkyl. In an exemplary embodiment, for a formula described herein, Y, Z, $R^1$, $R^2$, $R^3$, $R^5$, and $R^6$ are as described herein, $R^4$ is $CF_3$. In an exemplary embodiment, for a formula described herein, Y, Z, $R^1$, $R^2$, $R^3$, $R^5$, and $R^6$ are as described herein, $R^4$ is hydrogen.

In an exemplary embodiment, for a formula described herein, Y, Z, $R^1$, $R^2$, $R^5$, and $R^6$ are as described herein, $R^3$ is halogen and $R^4$ is halogen. In an exemplary embodiment, for a formula described herein, for a formula described herein, Y, Z, $R^1$, $R^2$, $R^5$, and $R^6$ are as described herein, $R^3$ is halogen and $R^4$ is fluorine or chlorine. In an exemplary embodiment, for a formula described herein, Y, Z, $R^1$, $R^2$, $R^5$, and $R^6$ are as described herein, $R^4$ is halogen and $R^3$ is unsubstituted $C_1$ or $C_2$ or $C_3$ or heteroalkyl. In an exemplary embodiment, for a formula described herein, Y, Z, $R^1$, $R^2$, $R^5$, and $R^6$ are as described herein, $R^3$ is halogen and $R^4$ is $C_1$ or $C_2$ or $C_3$ alkoxy. In an exemplary embodiment, for a formula described herein, Y, Z, $R^1$, $R^2$, $R^5$, and $R^6$ are as described herein, $R^3$ is fluorine or chlorine and $R^4$ is —$OCH_3$. In an exemplary embodiment, for a formula described herein, Y, Z, $R^1$, $R^2$, $R^5$, and $R^6$ are as described herein, $R^4$ is hydrogen and $R^3$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^5$, and $R^6$ are as described herein, $R^3$ is hydrogen and $R^4$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl.

In an exemplary embodiment, for formula (VIII) or (IX) or (X) or (XI) or (XII) or (XIII) or (XIV) or (XV), Y, Z, $R^1$, $R^2$, $R^5$, and $R^6$ are as described herein, $R^3$ is F or Cl or $CH_3$ or $OCH_3$ and $R^4$ is F or Cl or $CH_3$ or $OCH_3$. In an exemplary embodiment, for formula (VIII) or (IX) or (X) or (XI) or (XII) or (XIII) or (XIV) or (XV), Y, Z, $R^1$, $R^2$, $R^5$, and $R^6$ are as described herein, $R^3$ is F and $R^4$ is F or Cl or $CH_3$ or $OCH_3$. In an exemplary embodiment, for formula (VIII) or (IX) or (X) or (XI) or (XII) or (XIII) or (XIV) or (XV), Y, Z, $R^1$, $R^2$, $R^5$, and $R^6$ are as described herein, $R^3$ is $CH_3$ and $R^4$ is F or Cl or $CH_3$ or $OCH_3$. In an exemplary embodiment, for formula (VIII) or (IX) or (X) or (XI) or (XII) or (XIII) or (XIV) or (XV), Y, Z, $R^1$, $R^2$, $R^5$, and $R^6$ are as described herein, $R^3$ is $OCH_3$ and $R^4$ is F. In an exemplary embodiment, for formula (Ia) or (VIIIb) or (Xb) or (XIIb) or (XIVb) or (XVIb), Y, Z, $R^1$, $R^2$, $R^5$, and $R^6$ are as described herein, $R^3$ is F and $R^4$ is $OCH_3$. In an exemplary embodiment, for formula (Ia) or (VIIIb) or (Xb) or (XIIb) or (XIVb) or (XVIb), Y, Z, $R^1$, $R^2$, $R^5$, and $R^6$ are as described herein, $R^3$ is $OCH_3$ and $R^4$ is F.

In an exemplary embodiment, for a formula described herein, Y, Z, $R^1$, $R^2$, $R^3$, $R^4$, and $R^6$ are as described herein, $R^5$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, for a formula described herein, Y, Z, $R^1$, $R^2$, $R^3$, $R^4$, and $R^6$ are as described herein, $R^5$ is halogen. In an exemplary embodiment, for a formula described herein, Y, Z, $R^1$, $R^2$, $R^3$, $R^4$, and $R^6$ are as described herein, $R^5$ is fluorine or chlorine or bromine. In an exemplary embodiment, for a formula described herein, Y, Z, $R^1$, $R^2$, $R^3$, $R^4$, and $R^6$ are as described herein, $R^5$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, $R^4$, and $R^6$ are as described herein, $R^5$ is unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, $R^4$, and $R^6$ are as described herein, $R^5$ is $CH_3$. In an exemplary embodiment, for a formula described herein, Y, Z, $R^1$, $R^2$, $R^3$, $R^4$, and $R^6$ are as described herein, $R^5$ is unsubstituted $C_1$ or $C_2$ or $C_3$ or heteroalkyl. In an exemplary embodiment, for a formula described herein, Y, Z, $R^1$, $R^2$, $R^3$, $R^4$, and $R^6$ are as described herein, $R^5$ is $C_1$ or $C_2$ or $C_3$ alkoxy. In an exemplary embodiment, for a formula described herein, Y, Z, $R^1$, $R^2$, $R^3$, $R^4$, and $R^6$ are as described herein, $R^5$ is —$OCH_3$. In an exemplary embodiment, for a formula described herein, Y, Z, $R^1$, $R^2$, $R^3$, $R^4$, and $R^6$ are as described herein, $R^5$ is $C_1$ or $C_2$ or $C_3$ haloalkyl. In an exemplary embodiment, for a formula described herein, Y, Z, $R^1$, $R^2$, $R^3$, $R^4$, and $R^6$ are as described herein, $R^5$ is $CF_3$. In an exemplary embodiment, for a formula described herein, Y, Z, $R^1$, $R^2$, $R^3$, $R^4$, and $R^6$ are as described herein, $R^5$ is hydrogen.

In an exemplary embodiment, for a formula described herein, Y, Z, $R^1$, $R^2$, $R^3$, $R^4$, and $R^5$ are as described herein, $R^6$ is hydrogen or halogen or substituted or unsubstituted $C_1$ or $C_2$ or $C_3$ or $C_4$ or $C_5$ or $C_6$ or $C_7$ or $C_8$ or $C_9$ or $C_{10}$ haloalkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl. In an exemplary embodiment, for a formula described herein, Y, Z, $R^1$, $R^2$, $R^3$, $R^4$, and $R^5$ are as described herein, $R^6$ is halogen. In an exemplary embodiment, for a formula described herein, Y, Z, $R^1$, $R^2$, $R^3$, $R^4$, and $R^5$ are as described herein, $R^6$ is fluorine or chlorine or bromine. In an exemplary embodiment, for a formula described herein, Y, Z, $R^1$, $R^2$, $R^3$, $R^4$, and $R^5$ are as described herein, $R^6$ is substituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, $R^4$, and $R^5$ are as described herein, $R^6$ is unsubstituted $C_1$ or $C_2$ or $C_3$ or $C_4$ or $C_5$ or $C_6$ or $C_7$ or $C_5$ or $C_9$ or $C_{10}$ alkyl. In an exemplary embodiment, for a formula described herein, Y, Z, $R^1$, $R^2$, $R^3$, $R^4$, and $R^5$ are as described herein, $R^6$ is $CH_3$. In an exemplary embodiment, for a formula described herein, Y, Z, $R^1$, $R^2$, $R^3$, $R^4$, and $R^5$ are as described herein, $R^6$ is $C_1$ or $C_2$ or $C_3$ heteroalkyl. In an exemplary embodiment, for a formula described herein, Y, Z, $R^1$, $R^2$, $R^3$, $R^4$, and $R^5$ are as described herein, $R^6$ is $C_1$ or $C_2$ or $C_3$ alkoxy. In an exemplary embodiment, for a formula described herein, Y, Z, $R^1$, $R^2$, $R^3$, $R^4$, and $R^5$ are as described herein, $R^6$ is —$OCH_3$. In an exemplary embodiment, for a formula described herein, Y, Z, $R^1$, $R^2$, $R^3$, $R^4$, and $R^5$ are as described herein, $R^6$ is unsubstituted $C_1$ or $C_2$ or $C_3$ haloalkyl. In an exemplary embodiment, for a formula described herein, Y, Z, $R^1$, $R^2$, $R^3$, $R^4$, and $R^5$ are as described herein, $R^6$ is $CF_3$. In an exemplary embodiment, for a formula described herein, Y, Z, $R^1$, $R^2$, $R^3$, $R^4$, $R^5$, and $R^6$ are as described herein, $R^6$ is hydrogen.

In an exemplary embodiment, for a formula described herein, Y, Z, $R^1$, $R^2$, $R^3$, and $R^4$ are as described herein, $R^5$ is halogen and $R^6$ is halogen. In an exemplary embodiment, for a formula described herein, Y, Z, $R^1$, $R^2$, $R^3$, $R^4$, $R^5$, and $R^6$ are as described herein, $R^5$ is halogen and $R^6$ is fluorine or chlorine. In an exemplary embodiment, for a formula described herein, Y, Z, $R^1$, $R^2$, $R^3$, and $R^4$ are as described herein, $R^5$ is hydrogen and $R^6$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl. In an exemplary embodiment, for a formula described herein, Y, Z, $R^1$, $R^2$, $R^3$, and $R^4$ are as described herein, $R^6$ is hydrogen and $R^5$ is halogen or unsubstituted $C_1$ or $C_2$ or $C_3$ haloalkyl or $C_1$ or $C_2$ or $C_3$ alkoxy or unsubstituted $C_1$ or $C_2$ or $C_3$ or $C_4$ or $C_5$ or $C_6$ or $C_7$ or $C_8$ or $C_9$ or $C_{10}$ alkyl.

In another aspect, the invention provides a compound, or a salt or a hydrate or a solvate thereof, having a structure according to the following formula:

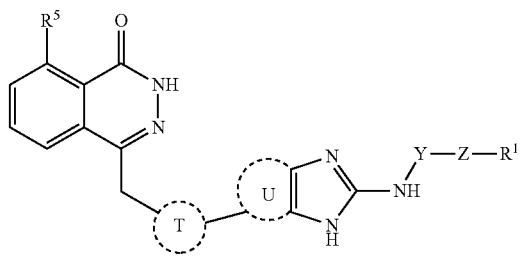

wherein $R^5$ is F or $CH_3$.

In another aspect, the invention provides a compound, or a salt or a hydrate or a solvate thereof, having a structure according to the following formula:

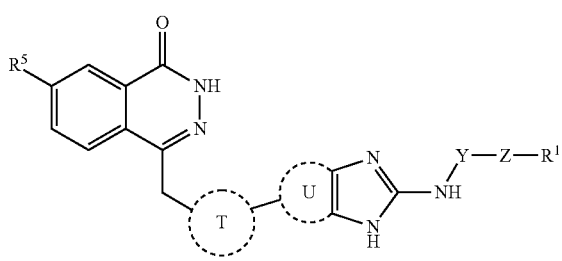

wherein $R^5$ is F or Cl or $CH_3$ or $CF_3$ or $OCH_3$.

In another aspect, the invention provides a compound, or a salt or a hydrate or a solvate thereof, having a structure according to the following formula:

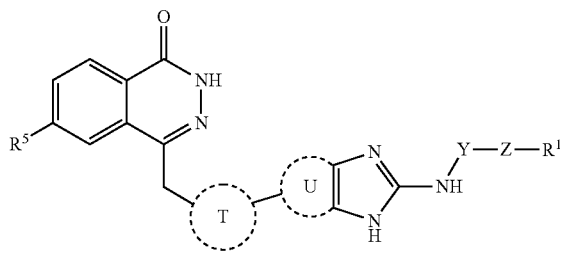

wherein $R^5$ is F or Cl or $CH_3$ or $CF_3$ or $OCH_3$ or $OCF_3$.

In another aspect, the invention provides a compound, or a salt or a hydrate or a solvate thereof, having a structure according to the following formula:

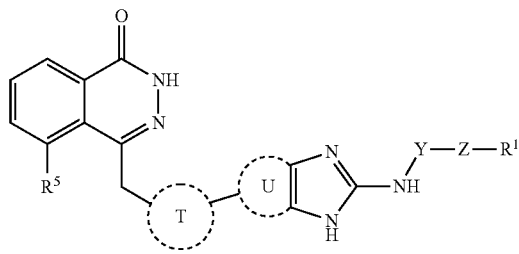

wherein $R^5$ is F or Cl or $CH_3$ or $CF_3$ or $OCH_3$.

In another aspect, the invention provides a compound, or a salt or a hydrate or a solvate thereof, having a structure according to the following formula:

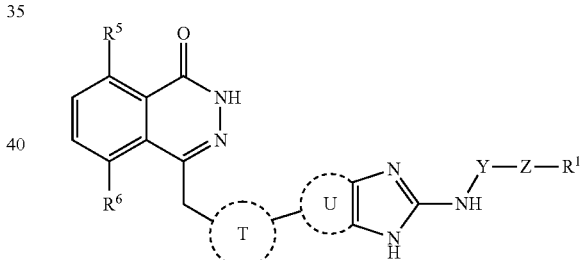

wherein $R^5$ is F and $R^6$ is F

In another aspect, the invention provides a compound, or a salt or a hydrate or a solvate thereof, having a structure according to the following formula:

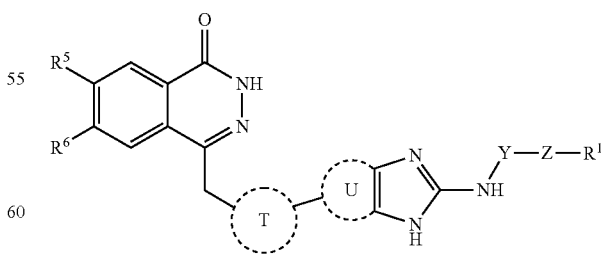

wherein $R^5$ is F and $R^6$ is F or $R^5$ is $OCH_3$ and $R^6$ is $OCH_3$.

In another aspect, the invention provides a compound, or a salt or a hydrate or a solvate thereof, having a structure according to the following formula:

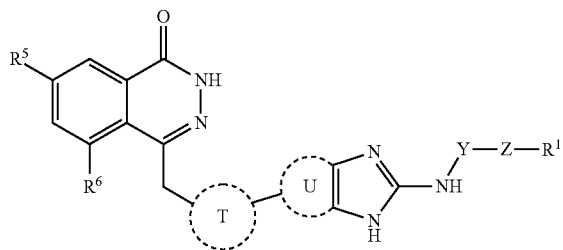

wherein $R^5$ is F and $R^6$ is F or $R^5$ is OCH$_3$ and $R^6$ is OCH$_3$.

In another aspect, the invention provides a compound, or a salt or a hydrate or a solvate thereof, having a structure according to the following formula:

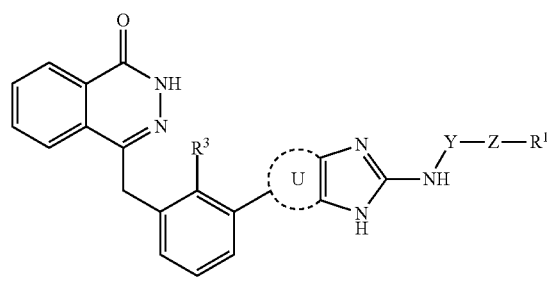

wherein $R^3$ is as described herein.

In another aspect, the invention provides a compound, or a salt or a hydrate or a solvate thereof, having a structure according to formula (XXV):

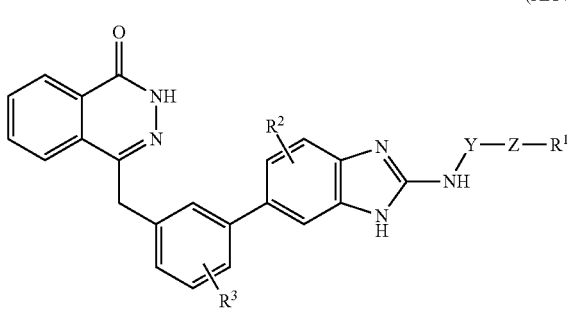
(XXV)

wherein Y, Z, $R^1$, $R^2$, and $R^3$ are as described herein.

In another aspect, the invention provides a compound, or a salt or a hydrate or a solvate thereof, having a structure according to formula (XXVI):

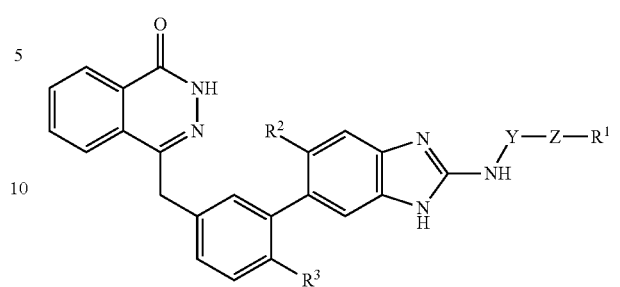
(XXVI)

wherein Y, Z, $R^1$, $R^2$, and $R^3$ are as described herein.

In another aspect, the invention provides a compound, or a salt or a hydrate or a solvate thereof, having a structure according to formula (XXVII):

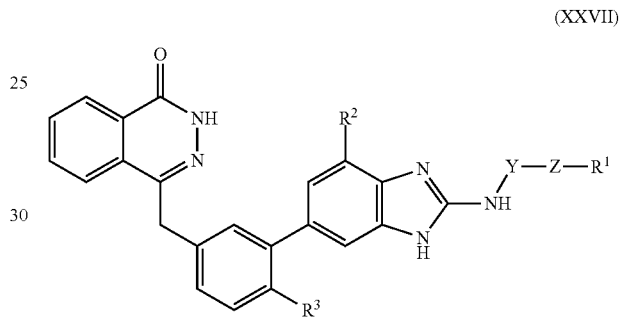
(XXVII)

wherein Y, Z, $R^1$, $R^2$, and $R^3$ are as described herein.

In another aspect, the invention provides a compound, or a salt or a hydrate or a solvate thereof, having a structure according to formula (XXVIII):

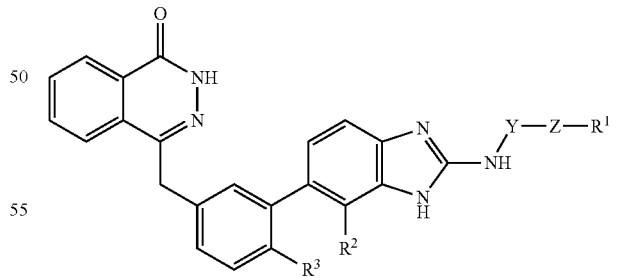
(XXVIII)

wherein Y, Z, $R^1$, $R^2$, and $R^3$ are as described herein.

In another aspect, the invention provides a compound, or a salt or a hydrate or a solvate thereof, having a structure according to formula (XXIX):

(XXIX)

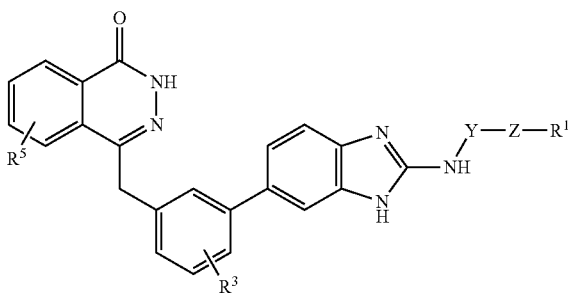

wherein Y, Z, R¹, R³, and R⁵ are as described herein. In an exemplary embodiment, the compound is according to formula (XXIX), wherein Y is C(O), Z is O or NH, R¹ is ethyl, R³ is F, and R⁵ is as described herein. In an exemplary embodiment, the compound is according to formula (XXIX), wherein Y is C(O), Z is O or NH, R¹ is methyl, R³ is F, and R⁵ is as described herein.

In another aspect, the invention provides a compound, or a salt or a hydrate or a solvate thereof, having a structure according to formula (XXX):

(XXX)

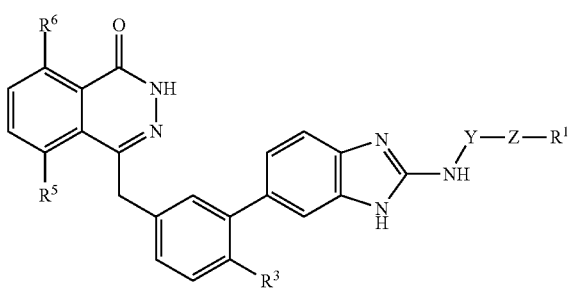

wherein Y, Z, R¹, R³, R⁵, and R⁶ are as described herein. In an exemplary embodiment, the compound is according to formula (XXX), wherein Y is C(O), Z is O or NH, R¹ is ethyl, R³ is F, and R⁵ and R⁶ are as described herein. In an exemplary embodiment, the compound is according to formula (XXX), wherein Y is C(O), Z is O or NH, R¹ is methyl, R³ is F, and R⁵ and R⁶ are as described herein.

In another aspect, the invention provides a compound, or a salt or a hydrate or a solvate thereof, having a structure according to formula (XXXI):

(XXXI)

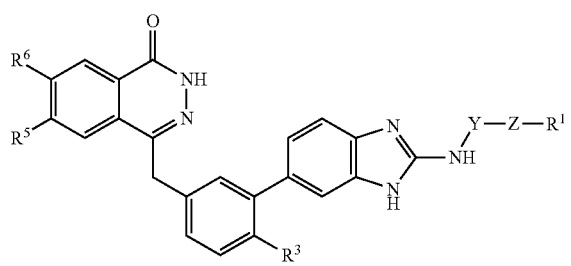

wherein Y, Z, R¹, R³, R⁵, and R⁶ are as described herein. In an exemplary embodiment, the compound is according to formula (XXXI), wherein Y is C(O), Z is O or NH, R¹ is ethyl, R³ is F, and R⁵ and R⁶ are as described herein. In an exemplary embodiment, the compound is according to formula (XXXI), wherein Y is C(O), Z is O or NH, R¹ is methyl, R³ is F, and R⁵ and R⁶ are as described herein.

In another aspect, the invention provides a compound, or a salt or a hydrate or a solvate thereof, having a structure according to formula (XXXII):

(XXXII)

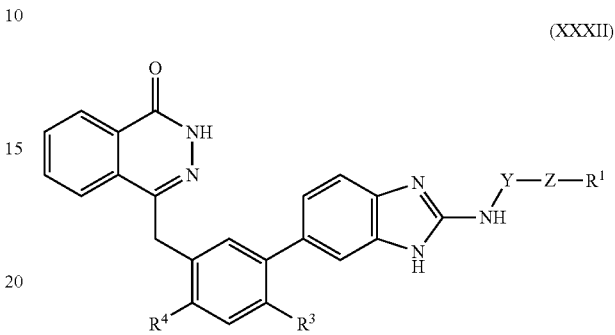

wherein Y, Z, R¹, R³, and R⁴ are as described herein.

In another aspect, the invention provides a compound, or a salt or a hydrate or a solvate thereof, having a structure according to formula (XXXIII):

(XXXIII)

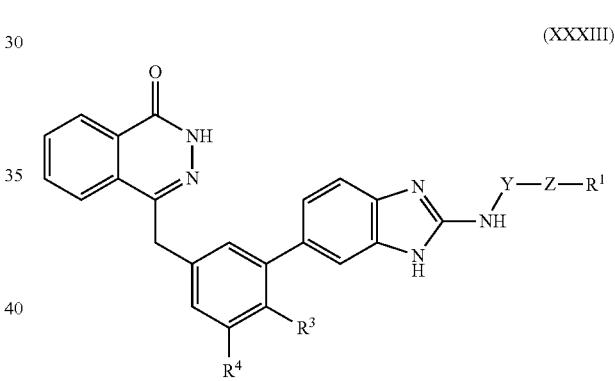

wherein Y, Z, R¹, R³, and R⁴ are as described herein.

In another aspect, the invention provides a compound, or a salt or a hydrate or a solvate thereof, having a structure according to formula (XXXIV):

(XXXIV)

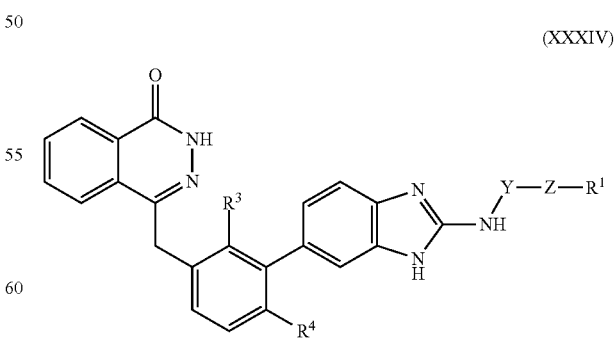

wherein Y, Z, R¹, R³, and R⁴ are as described herein.

In another aspect, the invention provides a compound, or a salt or a hydrate or a solvate thereof, having a structure according to formula (XXXV):

(XXXV)

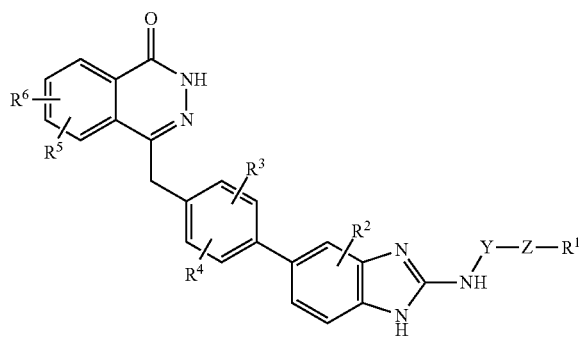

wherein Y, Z, $R^1$, $R^2$, $R^3$, $R^4$, $R^5$, and $R^6$ are as described herein.

In another aspect, the invention provides a compound, or a salt or a hydrate or a solvate thereof, having a structure according to formula (XXXVI):

(XXXVI)

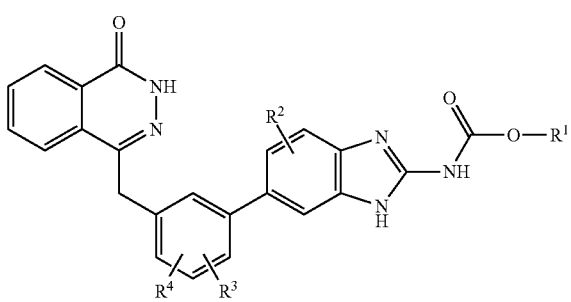

wherein $R^1$, $R^2$, $R^3$, and $R^4$ are as described herein. In an exemplary embodiment, the compound is according to formula (XXXVI), wherein $R^1$, $R^2$, and $R^3$ are as described herein, and $R^4$ is H. In an exemplary embodiment, the compound is according to formula (XXXVI), wherein $R^1$ and $R^2$ are as described herein, $R^3$ is H and $R^4$ is H. In an exemplary embodiment, the compound is according to formula (XXXVI), wherein $R^1$ and $R^2$ are as described herein, $R^3$ is F and $R^4$ is H. In an exemplary embodiment, the compound is according to formula (XXXVI), wherein $R^1$ and $R^2$ are as described herein, $R^3$ is Cl and $R^4$ is H. In an exemplary embodiment, the compound is according to formula (XXXVI), wherein $R^1$ and $R^2$ are as described herein, $R^3$ is $C_1$ or $C_2$ or $C_3$ alkyl and $R^4$ is H. In an exemplary embodiment, the compound is according to formula (XXXVI), wherein $R^1$ and $R^2$ are as described herein, $R^3$ is $C_1$ or $C_2$ or $C_3$ alkoxy and $R^4$ is H. In an exemplary embodiment, the compound is according to formula (XXXVI), wherein $R^1$ and $R^2$ are as described herein, $R^3$ is halogen-substituted $C_1$ or $C_2$ or $C_3$ alkoxy and $R^4$ is H. In an exemplary embodiment, the compound is according to formula (XXXVI), wherein $R^1$ is as described herein, $R^2$ is H, $R^3$ is H, and $R^4$ is H. In an exemplary embodiment, the compound is according to formula (XXXVI), wherein $R^1$ and $R^3$ are as described herein, $R^2$ is H and $R^4$ is H. In an exemplary embodiment, the compound is according to formula (XXXVI), wherein $R^2$, $R^3$, and $R^4$ are as described herein, and $R^1$ is methyl. In an exemplary embodiment, the compound is according to formula (XXXVI), wherein $R^2$ and $R^3$ are as described herein, $R^1$ is methyl, and $R^4$ is H. In an exemplary embodiment, the compound is according to formula (XXXVI), wherein $R^2$ is as described herein, $R^1$ is methyl, $R^3$ is H, and $R^4$ is H. In an exemplary embodiment, the compound is according to formula (XXXVI), wherein $R^3$ is as described herein, $R^1$ is methyl, $R^2$ is H, and $R^4$ is H. In an exemplary embodiment, the compound is according to formula (XXXVI), wherein $R^3$ is methyl, $R^1$ is methyl, $R^2$ is H, and $R^4$ is H. In an exemplary embodiment, the compound is according to formula (XXXVI), wherein $R^3$ is methoxy, $R^1$ is methyl, $R^2$ is H, and $R^4$ is H. In an exemplary embodiment, the compound is according to formula (XXXVI), wherein $R^3$ is F, $R^1$ is methyl, $R^2$ is F, and $R^4$ is H. In an exemplary embodiment, the compound is according to formula (XXXVI), wherein $R^3$ is $OCHF_2$, $R^1$ is methyl, $R^2$ is H, and $R^4$ is H. In an exemplary embodiment, the compound is according to formula (XXXVI), wherein $R^3$ is methoxy, $R^1$ is methyl, $R^2$ is H, and $R^4$ is H. In an exemplary embodiment, the compound is according to formula (XXXVI), wherein $R^3$ is ethoxy, $R^1$ is methyl, $R^2$ is H, and $R^4$ is H. In an exemplary embodiment, the compound is according to formula (XXXVI), wherein $R^3$ is $OCF_3$, $R^1$ is methyl, $R^2$ is H, and $R^4$ is H. In an exemplary embodiment, the compound is according to formula (XXXVI), wherein $R^3$ is Cl, $R^1$ is methyl, $R^2$ is H, and $R^4$ is H. In an exemplary embodiment, the compound is according to formula (XXXVI), wherein $R^3$ is F, $R^1$ is methyl, $R^2$ is H, and $R^4$ is F. In an exemplary embodiment, the compound is according to formula (XXXVI), wherein $R^2$, $R^3$, and $R^4$ are as described herein, and $R^1$ is ethyl. In an exemplary embodiment, the compound is according to formula (XXXVI), wherein $R^2$ and $R^3$ are as described herein, $R^1$ is ethyl, and $R^4$ is H. In an exemplary embodiment, the compound is according to formula (XXXVI), wherein $R^2$ is as described herein, $R^1$ is ethyl, $R^3$ is H, and $R^4$ is H. In an exemplary embodiment, the compound is according to formula (XXXVI), wherein $R^3$ is as described herein, $R^1$ is ethyl, $R^2$ is H, and $R^4$ is H. In an exemplary embodiment, the compound is according to formula (XXXVI), wherein $R^3$ is methyl, $R^1$ is ethyl, $R^2$ is H, and $R^4$ is H. In an exemplary embodiment, the compound is according to formula (XXXVI), wherein $R^3$ is methoxy, $R^1$ is ethyl, $R^2$ is H, and $R^4$ is H. In an exemplary embodiment, the compound is according to formula (XXXVI), wherein $R^3$ is F, $R^1$ is ethyl, $R^2$ is F, and $R^4$ is H. In an exemplary embodiment, the compound is according to formula (XXXVI), wherein $R^3$ is $OCHF_2$, $R^1$ is ethyl, $R^2$ is H, and $R^4$ is H. In an exemplary embodiment, the compound is according to formula (XXXVI), wherein $R^3$ is methoxy, $R^1$ is ethyl, $R^2$ is H, and $R^4$ is H. In an exemplary embodiment, the compound is according to formula (XXXVI), wherein $R^3$ is ethoxy, $R^1$ is ethyl, $R^2$ is H, and $R^4$ is H. In an exemplary embodiment, the compound is according to formula (XXXVI), wherein $R^3$ is $OCF_3$, $R^1$ is ethyl, $R^2$ is H, and $R^4$ is H. In an exemplary embodiment, the compound is according to formula (XXXVI), wherein $R^3$ is Cl, $R^1$ is ethyl, $R^2$ is H, and $R^4$ is H. In an exemplary embodiment, the compound is according to formula (XXXVI), wherein $R^3$ is F, $R^1$ is ethyl, $R^2$ is H, and $R^4$ is F.

In another aspect, the invention provides a compound, or a salt or a hydrate or a solvate thereof, having a structure according to formula (XXXVII):

(XXXVII)

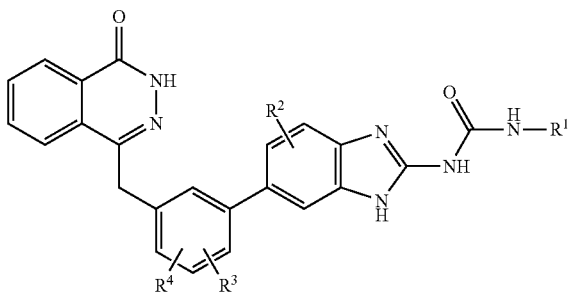

wherein $R^1$, $R^2$, $R^3$, and $R^4$ are as described herein. In an exemplary embodiment, the compound is according to formula (XXXVII), wherein $R^1$, $R^2$, and $R^3$ are as described herein, and $R^4$ is H. In an exemplary embodiment, the compound is according to formula (XXXVII), wherein $R^1$ and $R^2$ are as described herein, $R^3$ is H and $R^4$ is H. In an exemplary embodiment, the compound is according to formula (XXXVII), wherein $R^1$ is as described herein, $R^2$ is H, $R^3$ is H, and $R^4$ is H. In an exemplary embodiment, the compound is according to formula (XXXVII), wherein $R^1$ and $R^3$ are as described herein, $R^2$ is H and $R^4$ is H. In an exemplary embodiment, the compound is according to formula (XXXVII), wherein $R^2$, $R^3$, and $R^4$ are as described herein, and $R^1$ is methyl. In an exemplary embodiment, the compound is according to formula (XXXVII), wherein $R^2$, $R^3$, and $R^4$ are as described herein, and $R^1$ is methyl. In an exemplary embodiment, the compound is according to formula (XXXVII), wherein $R^2$ and $R^3$ are as described herein, $R^1$ is methyl, and $R^4$ is H. In an exemplary embodiment, the compound is according to formula (XXXVII), wherein $R^2$ is as described herein, $R^1$ is methyl, $R^3$ is H, and $R^4$ is H. In an exemplary embodiment, the compound is according to formula (XXXVII), wherein $R^3$ is as described herein, $R^1$ is methyl, $R^2$ is H, and $R^4$ is H. In an exemplary embodiment, the compound is according to formula (XXXVII), wherein $R^3$ is methyl, $R^1$ is methyl, $R^2$ is H, and $R^4$ is H. In an exemplary embodiment, the compound is according to formula (XXXVII), wherein $R^3$ is methoxy, $R^1$ is methyl, $R^2$ is H, and $R^4$ is H. In an exemplary embodiment, the compound is according to formula (XXXVII), wherein $R^3$ is F, $R^1$ is methyl, $R^2$ is F, and $R^4$ is H. In an exemplary embodiment, the compound is according to formula (XXXVII), wherein $R^3$ is $OCHF_2$, $R^1$ is methyl, $R^2$ is H, and $R^4$ is H. In an exemplary embodiment, the compound is according to formula (XXXVII), wherein $R^3$ is methoxy, $R^1$ is methyl, $R^2$ is H, and $R^4$ is H. In an exemplary embodiment, the compound is according to formula (XXXVII), wherein $R^3$ is ethoxy, $R^1$ is methyl, $R^2$ is H, and $R^4$ is H. In an exemplary embodiment, the compound is according to formula (XXXVII), wherein $R^3$ is $OCF_3$, $R^1$ is methyl, $R^2$ is H, and $R^4$ is H. In an exemplary embodiment, the compound is according to formula (XXXVII), wherein $R^3$ is Cl, $R^1$ is methyl, $R^2$ is H, and $R^4$ is H. In an exemplary embodiment, the compound is according to formula (XXXVII), wherein $R^3$ is F, $R^1$ is methyl, $R^2$ is H, and $R^4$ is F. In an exemplary embodiment, the compound is according to formula (XXXVII), wherein $R^2$, $R^3$, and $R^4$ are as described herein, and $R^1$ is ethyl. In an exemplary embodiment, the compound is according to formula (XXXVII), wherein $R^2$ and $R^3$ are as described herein, $R^1$ is ethyl, and $R^4$ is H. In an exemplary embodiment, the compound is according to formula (XXXVII), wherein $R^2$ is as described herein, $R^1$ is ethyl, $R^3$ is H, and $R^4$ is H. In an exemplary embodiment, the compound is according to formula (XXXVII), wherein $R^3$ is as described herein, $R^1$ is ethyl, $R^2$ is H, and $R^4$ is H. In an exemplary embodiment, the compound is according to formula (XXXVII), wherein $R^3$ is methyl, $R^1$ is ethyl, $R^2$ is H, and $R^4$ is H. In an exemplary embodiment, the compound is according to formula (XXXVII), wherein $R^3$ is methoxy, $R^1$ is ethyl, $R^2$ is H, and $R^4$ is H. In an exemplary embodiment, the compound is according to formula (XXXVII), wherein $R^3$ is F, $R^1$ is ethyl, $R^2$ is F, and $R^4$ is H. In an exemplary embodiment, the compound is according to formula (XXXVII), wherein $R^3$ is $OCHF_2$, $R^1$ is ethyl, $R^2$ is H, and $R^4$ is H. In an exemplary embodiment, the compound is according to formula (XXXVII), wherein $R^3$ is methoxy, $R^1$ is ethyl, $R^2$ is H, and $R^4$ is H. In an exemplary embodiment, the compound is according to formula (XXXVII), wherein $R^3$ is ethoxy, $R^1$ is ethyl, $R^2$ is H, and $R^4$ is H. In an exemplary embodiment, the compound is according to formula (XXXVII), wherein $R^3$ is $OCF_3$, $R^1$ is ethyl, $R^2$ is H, and $R^4$ is H. In an exemplary embodiment, the compound is according to formula (XXXVII), wherein $R^3$ is Cl, $R^1$ is ethyl, $R^2$ is H, and $R^4$ is H. In an exemplary embodiment, the compound is according to formula (XXXVII), wherein $R^3$ is F, $R^1$ is ethyl, $R^2$ is H, and $R^4$ is F.

In another aspect, the invention provides a compound, or a salt or a hydrate or a solvate thereof, having a structure according to formula (XXXVIII):

(XXXVIII)

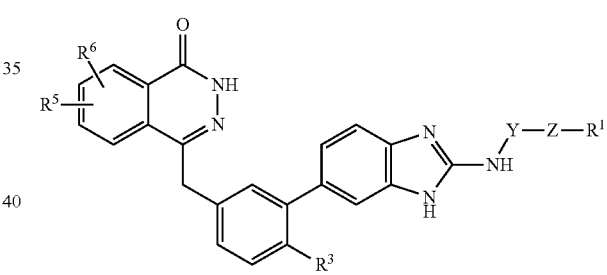

wherein Y, Z, $R^1$, $R^3$, $R^5$, and $R^6$ are as described herein. In an exemplary embodiment, the compound is according to formula (XXXVIII), wherein Y is C(O), Z is O or NH, $R^1$ is ethyl, $R^3$ is F, and $R^5$ and $R^6$ are as described herein. In an exemplary embodiment, the compound is according to formula (XXXVIII), wherein Y is C(O), Z is O or NH, $R^1$ is methyl, $R^3$ is F, and $R^5$ and $R^6$ are as described herein. In an exemplary embodiment, the compound is according to formula (XXXVIII), wherein Y is C(O), Z is O or NH, $R^3$ is F, and $R^1$, $R^5$ and $R^6$ are as described herein.

In an exemplary embodiment, the compound is according to a formula described herein, wherein this structure

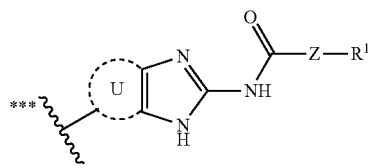

is selected from the group in the following table

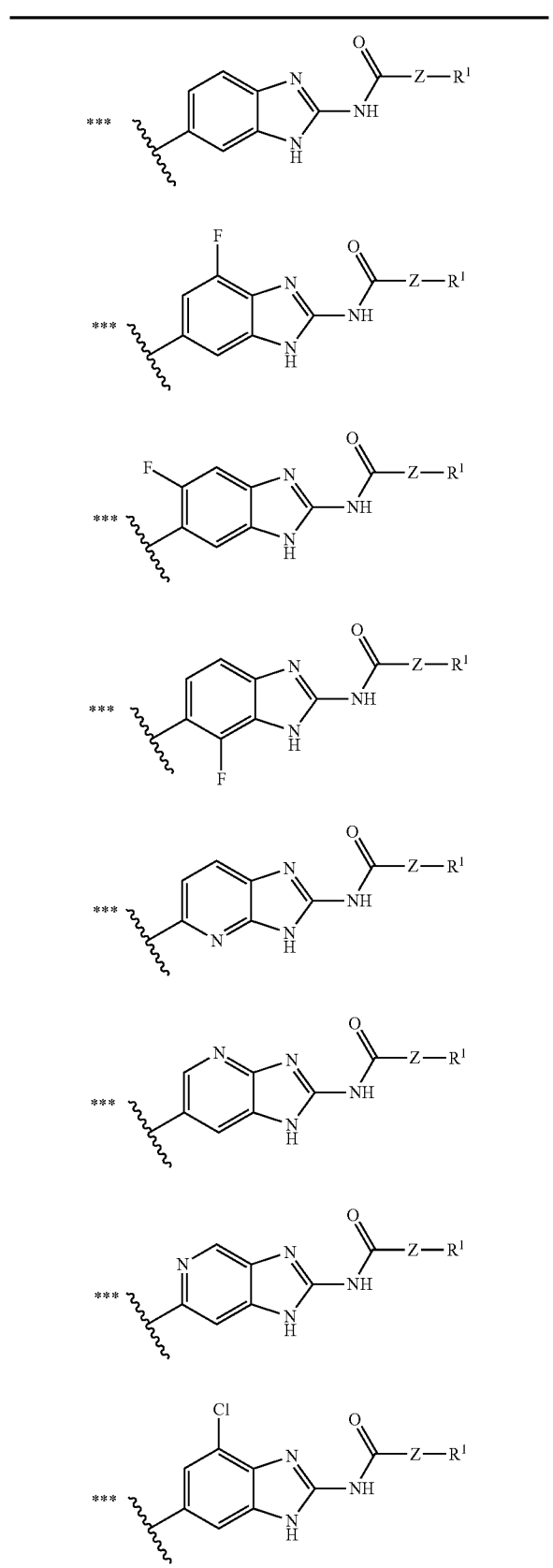

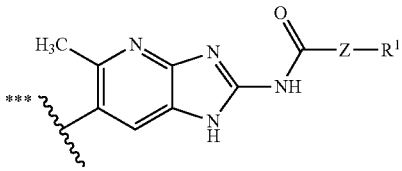

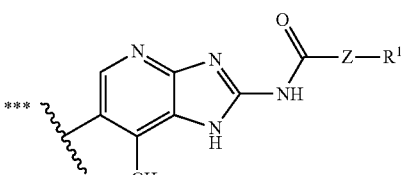

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

III.b) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent. In an exemplary embodiment, the combination comprises a compound described herein or a pharmaceutically acceptable salt thereof together with at least one additional therapeutic agent. In an exemplary embodiment, the additional therapeutic agent is a compound of the invention. In an exemplary embodiment, the combination comprises: a) a compound of the invention and b) a first additional therapeutic agent. In an exemplary embodiment, the combination comprises: a) a compound of the invention; b) a first additional therapeutic agent; and c) a second additional therapeutic agent. In an exemplary embodiment, the combination comprises: a) a compound of the invention; b) a first additional therapeutic agent; c) a second additional therapeutic agent; and d) a third additional therapeutic agent. In an exemplary embodiment, the combination comprises: a) a compound of the invention according to a formula provided herein and b) a first additional therapeutic agent. In an exemplary embodiment, the combination comprises: a) a compound of the invention according to a formula provided herein; b) a first additional therapeutic agent; and c) a second additional therapeutic agent.

In an exemplary embodiment, an additional therapeutic agent is a chemotherapeutic and/or radiation treatment. In an exemplary embodiment, an additional therapeutic agent is radiation treatment. In an exemplary embodiment, an additional therapeutic agent is an antitumor agent. In an exemplary embodiment, an additional therapeutic agent is an antitumor alkylating agent, an antitumor antimetabolite, an antitumor antibiotic, a plant-derived antitumor agent, an antitumor organoplatinum compound, an antitumor camptothecin derivative, an antitumor tyrosine kinase inhibitor, a checkpoint inhibitor, a monoclonal antibody, an angiogenesis inhibitor, an immunotherapy, an interferon, or a biological response modifier, or a pharmaceutically acceptable salt thereof.

When a compound of the invention is used in combination with at least one additional therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician.

In an exemplary embodiment, the additional therapeutic agent is useful in treating cancer. In an exemplary embodiment, the additional therapeutic agent is cisplatin. In an exemplary embodiment, the additional therapeutic agent is paclitaxel.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

Compounds described herein can be converted into hydrates and solvates by methods similar to those described herein.

IV. Methods of Inhibiting PARP and/or Tubulin

The compounds of the invention inhibit one or more proteins, and said one or more proteins are PARP and/or tubulin, and therefore have the potential to treat diseases in which these proteins are associated. The compounds of the invention inhibit tubulin, and therefore have the potential to treat diseases in which tubulin is associated. The compounds of the invention inhibit PARP, and therefore have the potential to treat diseases in which PARP is associated. In an exemplary embodiment, the PARP is PARP1. In an exemplary embodiment, the PARP is PARP2. In an exemplary embodiment, the compounds of the invention inhibit one or more proteins, and said one or more proteins are PARP1 and/or PARP2 and/or tubulin, and therefore have the potential to treat diseases in which these proteins are associated.

In a further aspect, the invention provides a method of inhibiting PARP and/or tubulin, said method comprising: contacting said PARP and/or tubulin with an effective amount of a compound of the invention, thereby inhibiting said PARP and/or tubulin. In a further aspect, the invention provides a method of inhibiting PARP, said method comprising: contacting said PARP with an effective amount of a compound of the invention, thereby inhibiting said PARP. In a further aspect, the invention provides a method of inhibiting tubulin, said method comprising: contacting said tubulin with an effective amount of a compound of the invention, thereby inhibiting said tubulin. In a further aspect, the invention provides a method of inhibiting PARP1 and/or PARP2 and/or tubulin, said method comprising: contacting said PARP1 and/or PARP2 and/or tubulin with an effective amount of a compound of the invention, thereby inhibiting said PARP1 and/or PARP2 and/or tubulin. In an exemplary embodiment, the one or more proteins is one protein which is PARP1. In an exemplary embodiment, the one or more proteins is one protein which is PARP2. In an exemplary embodiment, the one or more proteins is one protein which is tubulin. In an exemplary embodiment, the one or more proteins are two proteins which are PARP1 and tubulin. In an exemplary embodiment, the one or more proteins are two proteins which are PARP2 and tubulin. In an exemplary embodiment, the one or more proteins are two proteins which are PARP1 and PARP2. In an exemplary embodiment, the invention provides a method of inhibiting PARP1 and/or PARP2 and/or tubulin, comprising: contacting said PARP1 and/or PARP2 and/or tubulin with an effective amount of the compound of the invention, thereby inhibiting said PARP1 and/or PARP2 and/or tubulin.

V. Methods of Treating Disease

The compounds of the invention exhibit potency against disease, such as cancer, and therefore have the potential to achieve therapeutic efficacy in the animals described herein.

In an exemplary embodiment, the invention provides a method of treating a disease. The method includes administering to the animal a therapeutically effective amount of the compound of the invention, sufficient to treat the disease. In an exemplary embodiment, the invention provides a method of treating a disease in an animal comprising administering to the animal a therapeutically effective amount of the compound of the invention, wherein the animal is in need of treatment, sufficient to treat the disease. In another aspect, the invention provides a method of treating a disease in an animal comprising administering to the animal a therapeutically effective amount of the compound of the invention, wherein the animal is not otherwise in need of treatment with the compound of the invention, sufficient to treat the disease. In an exemplary embodiment, the disease is a tumor. In an exemplary embodiment, the disease is a tumor, and the tumor is benign, or non-cancerous. In an exemplary embodiment, the disease is a tumor, and the tumor is malignant, or cancerous. In an exemplary embodiment, the disease is a tumor, and the tumor is benign (non-cancerous). In an exemplary embodiment, the disease is cancer. In an exemplary embodiment, the disease is cancer. In an exemplary embodiment, the term "cancer" defines any malignant cancerous growth. In an exemplary embodiment, the disease is a sarcoma, adrenal cortical cancer, anal cancer, aplastic anemia, bile duct cancer, bladder cancer, bone cancer, bone metastasis, a central nervous system (CNS) cancer, a peripheral nervous system (PNS) cancer, Castleman's Disease, cervical cancer, colon cancer, rectum cancer, endometrial cancer, esophagus cancer, Ewing's family of tumors (e.g. Ewing's sarcoma), eye cancer, gallbladder cancer, a gastrointestinal carcinoid tumor, a gastrointestinal stromal tumor, gestational trophoblastic disease, hairy cell leukemia, Hodgkin's disease, kidney cancer, laryngeal cancer, a hypopharyngeal cancer, acute lymphocytic leukemia, acute myeloid leukemia, children's leukemia, chronic lymphocytic leukemia, chronic myeloid leukemia, liver cancer, lung cancer, a lung carcinoid tumor, malignant mesothelioma, multiple myeloma, myelodysplastic syndrome, myeloproliferative disorders, a nasal cavity cancer, a paranasal cancer, nasopharyngeal cancer, neuroblastoma, an oral cavity cancer, an oropharyngeal cancer, osteosarcoma, ovarian cancer, pancreatic cancer, penile cancer, pituitary tumor, prostate cancer, retinoblastoma, rhabdomyosarcoma, salivary gland cancer, an adult soft tissue cancer, melanoma skin cancer, non-melanoma skin cancer, stomach cancer, testicular cancer, thymus cancer, thyroid cancer, uterine cancer (e.g. uterine sarcoma), vaginal cancer, vulvar cancer, or Waldenstrom's macroglobulinemia.

In an exemplary embodiment, the disease is a cancer of the blood, such as leukemia, cancer of the skin, such as melanoma, cancer of the colon, cancer of the lung, cancer of the ovary, cancer of the uterus, cancer of the breast, cancer of the prostate, cancer of the pancreas. In an exemplary embodiment, the disease is a cancer of the central nervous system, or a cancer of the renal system. In an exemplary embodiment, the disease is a soft tissue cancer. In an exemplary embodiment, the disease is multiple myeloma. In an exemplary embodiment, the cancer is ovarian cancer. In an exemplary embodiment, the cancer is uterine cancer. In an exemplary embodiment, the cancer is pancreatic cancer. In an exemplary embodiment, the cancer is lung cancer. In an exemplary embodiment, the cancer is brain cancer. In an exemplary embodiment, the cancer is skin cancer. In some embodiments, the cancer is colon cancer. In an exemplary embodiment, the cancer is derived from cancer stem cells.

In an exemplary embodiment, the cancer is breast cancer. In an exemplary embodiment, the breast cancer is negative for one or more of Estrogen Receptor (ER), Progesterone Receptor (PR), or Human Epidermal Growth Factor Receptor 2 (HER2). In an exemplary embodiment, the breast cancer is negative for one or more of ER, PR or HER2; and wherein the breast cancer is positive for one or more of ER, PR or HER2. In an exemplary embodiment, the breast cancer is negative for two of ER, PR or HER2. In an exemplary embodiment, the breast cancer is ER negative and PR-negative.

In an exemplary embodiment, the breast cancer is ER-negative and HER2-negative. In an exemplary embodiment, the breast cancer is PR-negative and HER2-negative. In an exemplary embodiment, the breast cancer is an ER-negative breast cancer. In an exemplary embodiment, the breast cancer is an HER2-negative breast cancer.

In an exemplary embodiment, a compound of the invention treats a disease in an animal, by inhibiting tubulin polymerization and/or PARP activity. The present invention thus provides a method for treating a disease by inhibiting either or both tubulin polymerization and PARP activity comprising the step of administering compounds of the invention to a patient in need thereof.

In an exemplary embodiment, a compound of the invention is used at an early stage of a disease, or before early onset, or after significant progression, including metastasis in case of cancer. The term "treatment" or "treating" applied to tumor can refer to a reduction of the burden in a patient, such as a reduction in cell proliferation rate, a destruction of diseased proliferative cells, a reduction of tumor mass or tumor size, a delaying of tumor progression, or a complete tumor suppression.

In an exemplary embodiment, a compound of the invention can be used in treatment of cancers deficient in Homologous Recombination (HR) dependent DNA double strand repair (DSB), which consist or comprise one or more cancer cells which have a reduced or abrogated ability to repair DNA DSBs through that pathway.

In an exemplary embodiment, a compound of the invention can be used in any disease state for which either or both tubulin polymerisation and PARP play a role.

In an exemplary embodiment, the disease is a bacterial infection. In an exemplary embodiment, the disease is a bacterial ulcer infection. In an exemplary embodiment, the disease is a viral infection. In an exemplary embodiment, the disease is a herpes simplex infection. In an exemplary embodiment, the disease is an Acquired Immune Deficiency Syndrome (AIDS) infection. In an exemplary embodiment, the disease is a protozoal infection. In an exemplary embodiment, the disease is a flagellated parasite infection. In an exemplary embodiment, the disease is a Chagas' disease. In an exemplary embodiment, the disease is Leishmania.

In an exemplary embodiment, the disease is vascular neointimal hyperplasia.

In an exemplary embodiment, the invention provides a use of a compound of a invention in the manufacture of a medicament for the treatment of a disease described herein.

In an exemplary embodiment, a compound of the invention may be dosed at intervals of minutes, hours, days, weeks, months or years or continuously over any one of these periods. Suitable dosage amounts and dosing regimens can be determined by the attending physician and may depend on the particular condition being treated, the severity of the condition as well as the general age, health and weight of the subject.

In an exemplary embodiment, a compound of the invention may be administered in a single dose or a series of doses.

In another exemplary embodiment, the animal is a eukaryote. In another exemplary embodiment, the animal is a vertebrate animal. In another exemplary embodiment, the animal is a mammal. In another exemplary embodiment, the animal is a rodent. In another exemplary embodiment, the animal is a mouse. In another exemplary embodiment, the animal is a horse. In another exemplary embodiment, the animal is a primate or a simian. In another exemplary embodiment, the animal is a monkey or an ape. In another exemplary embodiment, the animal is a human or a farm animal or a companion animal. In another exemplary embodiment, the animal is a human. In another exemplary embodiment, the animal is a goat or pig or sheep or horse or cow or bull. In another exemplary embodiment, the animal is a cat. In another exemplary embodiment, the animal is a dog. In another exemplary embodiment, the animal is a rabbit.

The compounds of the invention may be administered to a subject by any convenient route of administration, whether systemically/peripherally or at the site of desired action, including but not limited to oral e.g. tablets, chewable tablets or capsules); topical (e.g. transdermal, intranasal, ocular, buccal, and sublingual); pulmonary (e.g. inhalation or insufflation therapy using, e.g. an aerosol, e.g. through mouth or nose); rectal; vaginal, parenteral, for example, by injection, including subcutaneous, intradermal, intramuscular, intravenous, intraarterial, intracardiac, intrathecal, intraspinal, intreacapsular, subcupsular, intraorbital, intraperitoneal, intratracheal, subcuticular, intraarticular, subarachnoid, and intrasternal; by implant of a depot, for example, subcutaneously or intramuscularly.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another exemplary embodiment, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of infected cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain infected cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Sigma-Aldrich in Sure-Seal bottles and used as received. All solvents may be purified using standard methods known to those skilled in the art, unless otherwise indicated. The reactions set forth below were run generally at ambient temperature, unless otherwise indicated. The reaction vessels were fitted with rubber septa for introduction of substrates and reagents via syringe. Analytical thin layer chromatography (TLC) was performed using glass-backed silica gel pre-coated plates (Analtech TLC Uniplates™ with fluorescent indicator) and eluted with appropriate solvent ratios (v/v). Reactions were assayed by TLC or LC/MS, and terminated as judged by the consumption of starting material. Visualization of the TLC plates was done with UV light (254 nm wavelength) or with an appropriate TLC visualizing solvent, such as basic aqueous KMnO4 solution, ninhydrin, cerium molybdate, or phosphomolybdic acid, activated with heat. Flash column chromatography (W. C. Still et al., J. Org. Chem., 43, 1978, 2923-2925) was performed using Biotage Isolera Prime automated flash purification system (220 and 254 nm wavelength) with ZIP Sphere-spherical Silica or KP Silica cartridges or various preparative HPLC systems. The compound structures in the examples below were confirmed by one or more of the following methods: proton magnetic resonance spectroscopy, mass spectrometry, and melting point. Proton magnetic resonance (1HNMR) spectra were recorded using an NMR spectrometers operating at 300, 400 or 500 MHz field strength. Chemical shifts are reported in the form of delta (δ) values given in parts per million (ppm) relative to an internal standard, such as tetramethylsilane (TMS). Alternatively, 1HNMR spectra were referenced to signals from residual protons in deuterated solvents as follows: CDCl$_3$=7.25 ppm; DMSO-d$_6$=2.49 ppm; CD$_3$OD=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectrometric (MS) data were obtained using a mass spectrometer with APCI or ESI ionization.

Starting materials used were either available from commercial sources or prepared according to literature procedures and had experimental data in accordance with those reported.

Synthesis of Compounds of the Invention

Scheme 1 depicts the general synthetic routes for compounds of the invention and is not intended to be limiting. Specific examples are described subsequently to this general synthetic description. In the generalizations below, specific reaction conditions or details, for example, added reagents, catalysts, solvents, reaction temperature, and the like are not described. The general routes depicted in conjunction with the specific examples provided contain sufficient information to allow one of ordinary skill in the art to synthesize compounds of the invention.

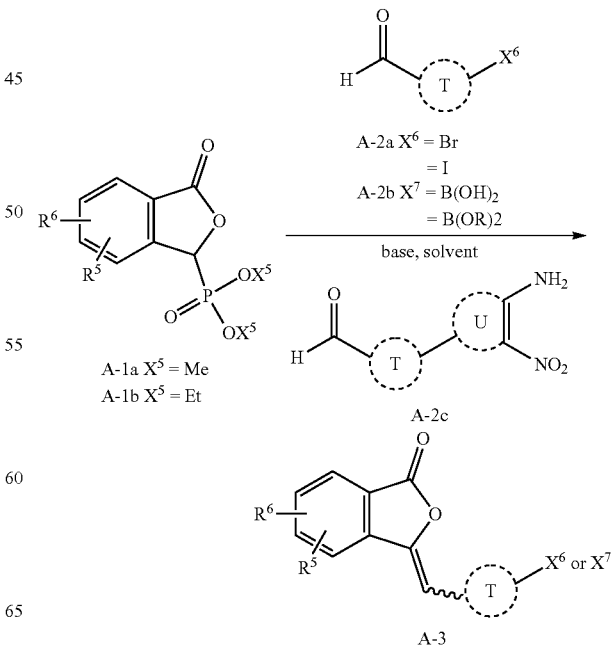

SCHEME A

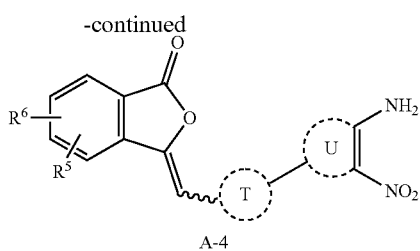

A-4

A number of methods may be available for the synthesis of compounds represented by formula A-3 and A-4; most of them involve the cyclization of ortho-substituted arylaldehydes, followed by C-3 alkylation, condensation of 3-bromo-pthalides with aldehydes, the Wittig-Horner reaction of phthalide-3-phosphonate esters (A-1) with aldehydes (A-2) or reacting phthalic anhydrides with phenylacetic acids. (SCHEME A).

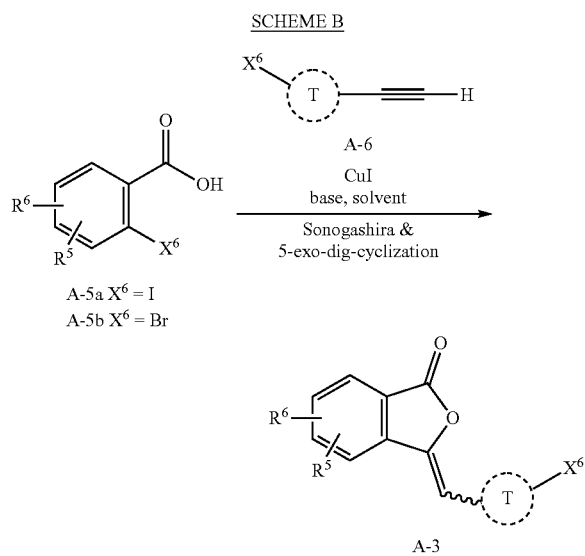

One of the most attractive methods for the synthesis of 3-isobenzofurane-1-ones (A-3) is a copper (I) mediated tandem Sonogashira coupling and intramolecular 5-exo-dig cyclization reaction. For example, reaction of 2-iodobenzoic acid (A-5a) and phenyl acetylenes (A-6) in the presence of a copper catalyst (copper(I) bromide, copper(I) iodide) and organic (trimethylamine, Hunig's base) or inorganic (potassium carbonate, cesium carbonate) bases in an appropriate solvent (dimethyl sulfoxide, N,N-dimethyl formamide) afford A-3 in excellent yield. 2-Bromobenzoic acid (A-5b) and terminal alkyne (A-6) may also be used in similar fashion. Electron withdrawing groups such as halogens and/or a pyridyl ring in combination with the carboxylic acid moiety in the A-5 component increase the reactivity of the C-Halogen bond producing phthalides in good yields. Electron-donating groups (methyl, methoxy, tert-butyl) in both, the benzoic acid and the alkyne components decrease the reactivity of the alkyne moiety as well as the reactivity of the C-Halogen bond, resulting in lower yields (SCHEME B.).

LITERATURE

1. Synthesis of dimethyl phthalide-3-phosphonates and their use in the regiospecific synthesis of 3-ylidenephthalides; Elio Napolitano, Guido Spinelli, Rita Fiaschi, Antonio Marsili; Synthesis, 1985, 38-40.
2. Regioselective One-Pot Synthesis of Isocoumarins and Phthalides from 2-Iodobenzoic acids and Alkynes by Temperature Control; Manian Rajesh Kumar, Francis Mariaraj Irudayanathan, Joong Ho Moon, and Sunwoo Lee; Adv. Synth. Catal., 2013, 355, 3221-3230.
3. Pd-free Sonogashira coupling: one pot synthesis of phthalide via domino Sonogashira coupling and 5-exo-dig cyclization; Shubhendu Dhara, Raju Singha, Munmun Ghosh, Atiur Ahmed, Yasin Nuree, Anuvab Das and Jayanta K. Ray; RSC Adv., 2014, 4, 42604-42607.

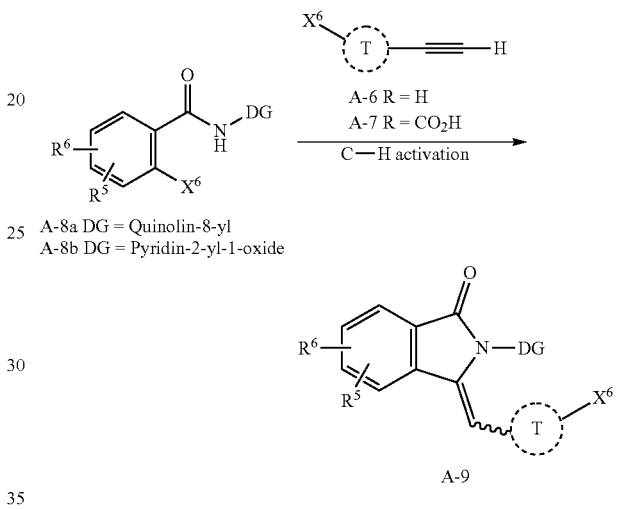

For the synthesis of the 3-benzylidene-isoindolin-1-one scaffold, represented by formula A-9, a highly efficient copper-mediated tandem oxidative C(sp2)-H/C(sp)-H cross-coupling and intramolecular annulation reaction of arenes with terminal alkynes (A-6) has been developed. In this oxidative coupling process, copper(II)acetate acts as both the promoter and the terminal oxidant, and 8-aminoquinoline as a directing auxiliary (A-8a). This synthetic method tolerates a wide range of substrates and functional groups, proceeds with high chemo-, regio-, and stereoselectivity; it is a simple, readily available, inexpensive reaction system. Isoindolin-1-ones may also be straightforwardly synthesized from terminal alkynes (A-6) and 8-aminoquinoline benzamides (A-8a) utilizing cobalt(II) catalytic system or form substituted 2-aminopyridine 1-oxide amides (A-8b) using nickel(II) catalyst in tandem C(sp2)-H alkynylation-annulation reactions. An extension of the above reaction utilizes optionally substituted alkynyl carboxylic acids (A-7) in copper-catalyzed tandem decarboxylative cross-coupling-cyclization reactions with various substituted aromatic amides (A-8a), bearing electron-withdrawing or electron-donating groups (SCHEME C.).

LITERATURE

1. Copper-Mediated Tandem Oxidative C(sp2)-H/C(sp)-H Alkynylation and Annulation of Arenes with Terminal Alkynes; Jiaxing Dong, Fei Wang, and Jingsong You; Org. Lett., 2014, 16, 2884-2887.
2. The facile construction of the phthalazin-1(2H)-one scaffold via copper-mediated C—H(sp2)/C—H(sp) coupling under mild conditions; Wei Zhu, Bao Wang, Shengbin Zhou and Hong Liu; Beilstein J. Org. Chem., 2015, 11, 1624-1631.
3. Cobalt-Catalyzed Cyclization of Aliphatic Amides and Terminal Alkynes with Silver-Cocatalyst; Jitan Zhang, Hui Chen, Cong Lin, Zhanxiang Liu, Chen Wang and Yuhong Zhang; J. Am. Chem. Soc., 2015, 137, 12990-12996.
4. Ni(II)—Catalyzed C(sp2)-H Alkynylation/Annulation with Terminal Alkynes under an Oxygen Atmosphere: A One-Pot Approach to 3-Methyleneisoindolin-1-one; Xin-Xiang Zheng, Cong Du, Xue-Mei Zhao, Xinju Zhu, Jian-Feng Suo, Xin-Qi Hao, Jun-Long Niu and Mao-Ping Song; J. Org. Chem., 2016, 81, 4002-4011.
5. Copper(II)/Silver(I)-Catalyzed Sequential Alkynylation and Annulation of Aliphatic Amides with Alkynyl Carboxylic Acids: Efficient Synthesis of Pyrrolidones; Jitan Zhang, Danyang Li, Hui Chen, Binjie Wang, Zhanxiang Liu, and Yuhong Zhang; Adv. Synth. Catal., 2016, 358, 792-807.

Substituted 4-benzylphthalazin-1(2H)-ones, formula A-10 and A11, may be conveniently synthesized from 3-benzylidene-3H-isobenzofurane-1-ones (A-3 or A-4) or from 3-benzylidene-isoindolin-1-ones (A-9) under hydrazinolysis condition (SCHEME D.).

LITERATURE

1. The opening of the lactonic ring of derivatives of phthalide by hydrazine; Teppemma, T.; Recueil des Travaux Chimiques des Pays-Bas et de la Belgique, 1923, 42, 30-68.
2. Derivatives of 3-fluorofluorene by the Pschorr synthesis; Suzuki, Kazuo, Weisburger, Elizabeth K., Weisburger, John H; Journal of Organic Chemistry, 1961, 26, 2239-2242.
3. The facile construction of the phthalazin-1(2H)-one scaffold via copper-mediated C—H(sp2)/C—H(sp) coupling under mild conditions; Wei Zhu, Bao Wang, Shengbin Zhou and Hong Liu; Beilstein J. Org. Chem., 2015, 11, 1624-1631.

SCHEME D

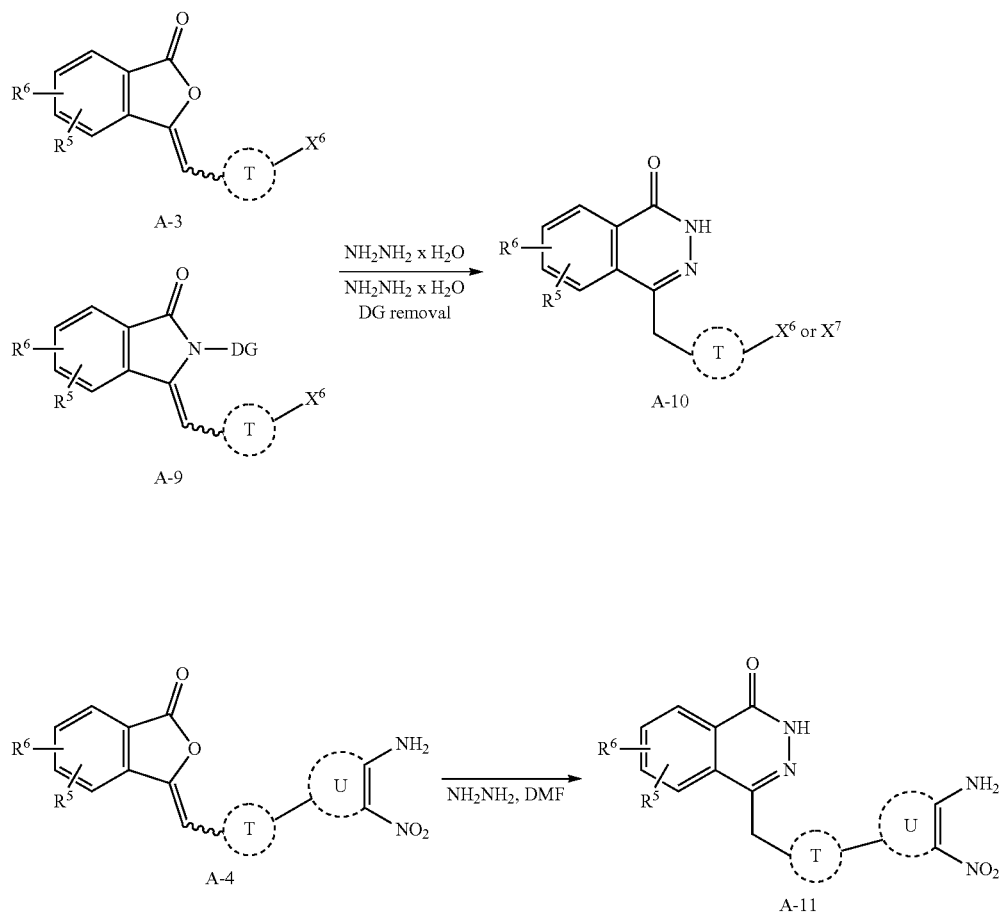

SCHEME E

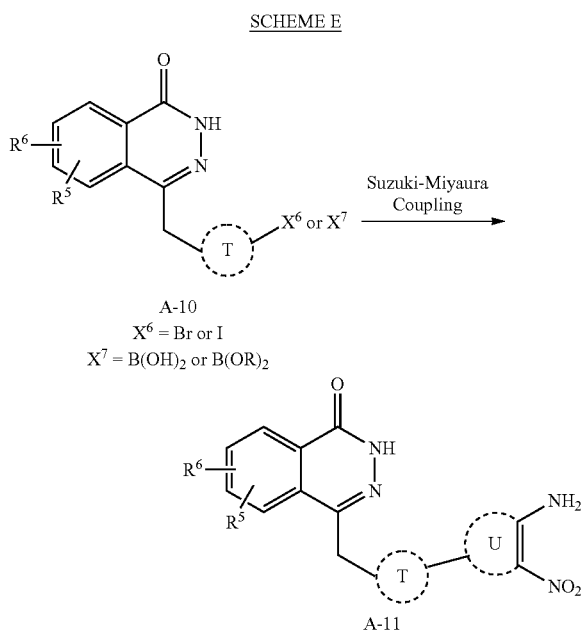

A-10
$X^6$ = Br or I
$X^7$ = B(OH)$_2$ or B(OR)$_2$

A-11

Compounds, represented by formula A-11 may also be prepared from an adequately functionalized A-10 in palladium-mediated cross coupling reactions. The heterocyclic ring can be installed directly or may be formed from an appropriate precursor, for example from 2-nitroaniline. Reduction of the 2-nitroaniline intermediate may be carried out under a range of conditions, for example catalytic hydrogenation or hydrogen transfer may be employed using palladium on carbon, platinum oxide or Raney nickel catalysts. Alternatively, iron metal or tin(II) chloride may also be used as effective reducing agents. Conversion of the resulting phenylenediamine to benzimidazole can be achieved in one step, for example treating the appropriate phenylenediamine with 1,3-bis(methoxycarbonyl)-2-methyl-2-thiopseudourea in acetic acid with heating. Alternatively, the conversion may be carried out by treating the phenylenediamine intermediate with a substituted isothiocyanate, followed by heating it in the presence of an appropriate carbodiimide. To introduce other carbamates, ureas or amides at the benzimidazole 2-position the thiopseudourea reagent of choice may be straightforwardly prepared. Alternatively, the appropriate 2-amino-benzimidazole intermediate may also be conveniently functionalized.

Intermediate 1

4-(3-bromo-4-fluorobenzyl)phthalazin-1(2H)-one
(I-1.1.)

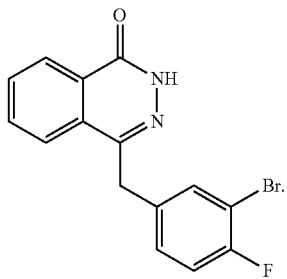

I-1.1

Method A

STEP 1. To a solution of dimethyl 3-oxo-1,3-dihydroisobenzofuran-1-ylphosphonate (1a) (3.70 g, 15.30 mmol) and 3-bromo-4-fluorobenzaldehyde (2a) (3.10 g, 15.30 mmol) in tetrahydrofuran (35 mL) a solution of trimethylamine (2.2 mL, 15.80 mmol) in tetrahydrofuran (5 mL) was added dropwise at 0° C. and the reaction mixture was stirred at room temperature overnight. The solvent was concentrated and the residue was partitioned with ethyl acetate (200 mL) and 2M aqueous hydrochloric acid (100 mL). The organic layer was separated, washed with water (2×100 mL) and brine (2×100 mL), dried over anhydrous sodium sulfate and concentrated. The resulting crude solid was crystallized from ethyl acetate-hexanes to give (Z)-3-(3-bromo-4-fluorobenzylidene) isobenzofuran-1(3H)-one as withe solid (3a) (3.9 g, 80%). (TLC 10% ethyl acetate in hexanes, Rf.: 0.65). MS (EI) for $C_{15}H_8BrFO_2$: 319 [M+H].

STEP 2. To a suspension of 3-(3-bromo-4-fluorobenzylidene)isobenzofuran-1(3H)-one (3a) (3.80 g, 11.90 mmol) in a mixture of water (45 mL) and tetrahydrofuran (15 mL) 10N aqueous sodium hydroxide (5.4 mL, 53.55 mmol) was added and the reaction mixture was heated to reflux and stirred until the solid went into solution (approximately 1 hour). Upon cooling it to room temperature hydrazine monohydrate (64-65 wt %, 9.0 mL, 119.0 mmol) was added to the reaction mixture and it was stirred at 90° C. overnight (some precipitate has formed). It was cooled in ice water followed by the addition of concentrated hydrochloric acid to adjust the pH 4-5 (more precipitate formed). The mixture was diluted with ethyl acetate (500 mL) and the organic layer was separated. The aqueous phase was partitioned with an additional amount of ethyl acetate (300 mL) and separated. The combined organic phase was washed with water (350 mL) and brine (2×300 mL), dried over anhydrous sodium sulfate and concentrated. Upon removing the solvent (~⅔ volume) a white solid product has precipitated; it was collected by filtration washed with hexanes and dried in vacuo to give 4-(3-bromo-4-fluorobenzyl)phthalazin-1(2H)-one (I-1.1) (3.6 g, 92%). (TLC 30% ethyl acetate in hexanes, Rf.: 0.50). 1H NMR (300 MHz, $d_6$-DMSO): 12.57 (s, 1H), 8.26 (d, 1H), 8.02 (d, 1H), 7.89 (m, 2H), 7.56 (m, 1H), 7.23 (m, 2H), 4.35 (s, 2H). MS (EI) for $C_{15}H_{10}BrFN_2O$: 333 [M+H].

Intermediate I-1.2. 4-(3-Bromobenzyl)phthalazin-1(2H)-one was prepared using 3-bromo benzaldehyde in step 1. MS (EI) for $C_{15}H_{11}BrN_2O$ 315 [M+H].

Intermediate I-1.3. 4-(3-Bromo-4-chlorobenzyl)phthalazin-1 (2H)-one was prepared using 3-bromo-4-fluorobenzaldehyde in step 1. MS (EI) for $C_{15}H_{10}BrClN_2O$: 350 [M+H].

Intermediate I-1.4. 4-(3-Bromo-4-methylbenzyl)phthalazin-1 (2H)-one was prepared using 3-bromo-4-methylbenzaldehyde in step 1. MS (EI) for $C_{16}H_{13}BrN_2O$: 330 [M+H].

Intermediate I-1.5. 4-(3-Bromo-4-(trifluoromethyl)benzyl)phthalazin-1(2H)-one was prepared using 3-bromo-4-(trifluoromethyl)benzaldehyde in step 1. MS (EI) for $C_{16}H_{10}BrF_3N_2O$: 383 [M+H].

Intermediate I-1.6. 4-(3-Bromo-4-(trifluoromethoxy)benzyl)phthalazin-1(2H)-one was prepared using 3-bromo-4-trifluoromethoxylbenzaldehyde in step 1. MS (EI) for $C_{16}H_{10}BrF_3N_2O_2$: 400 [M+H].

Intermediate I-1.7. 4-(3-Bromo-4-methoxybenzyl)phthalazin-1(2H)-one was prepared using 3-bromo-4-methoxylbenzaldehyde in step 1. MS (EI) for $C_{16}H_{13}BrN_2O_2$: 356 [M+H].

Intermediate I-1.8. 4-(3-Vromo-4-ethoxybenzyl)phthalazin-1(2H)-one was prepared using 3-bromo-4-ethoxylbenzaldehyde in step 1. MS (EI) for $C_{17}H_{15}BrN_2O_2$: 360 [M+H].

Intermediate I-1.9. 4-(3-Bromo-4-(2-methoxyethoxy) benzyl)phthalazin-1(2H)-one was prepared using 3-bromo-4-(2-methoxyethoxy)benzaldehyde in step 1. MS (EI) for $C_{18}H_{17}BrN_2O_3$: 390 [M+H].

Intermediate I-1.10. 4-(3-Bromo-4-(difluoromethoxy) benzyl)phthalazin-1(2H)-one was prepared using 3-bromo-4-diflouromethoxyethoxybenzaldehyde (R-1.1.) in step 1. MS (EI) for $C_{16}H_{11}BrF_2N_2O_2$: 382 [M+H].

Intermediate I-1.11. 4-(3-Bromo-5-fluorobenzyl)phthalazin-1(2H)-one was prepared using 3-bromo-5-flourobenzaldehyde in step 1. MS (EI) for $C_{15}H_{10}BrFN_2O$: 334 [M+H].

Intermediate I-1.12. 4-(5-bromo-2-fluorobenzyl)phthalazin-1(2H)-one was prepared using 5-bromo-2-flourobenzaldehyde in step 1. MS (EI) for $C_{15}H_{10}BrFN_2O$: 334 [M+H].

Intermediate I-1.13. 4-(3-Bromo-2-fluorobenzyl)phthalazin-1(2H)-one was prepared using 3-bromo-2-flourobenzaldehyde in step 1. MS (EI) for $C_{15}H_{10}BrFN_2O$: 334 [M+H].

Intermediate I-1.14. 4-(5-Bromo-2,4-difluorobenzyl) phthalazin-(2H)-one was prepared using 5-bromo-2,4-difluorobenzaldehyde in step 1. MS (EI) for $C_{15}H_9BrF_2N_2O$: 352 [M+H].

Intermediate I-1.16. 4-(3-Bromo-5-methoxybenzyl) phthalazin-1(2H)-one was prepared using 3-bromo-5-methoxybenzaldehyde in step 1. MS (EI) for $C_{16}H_{13}BrN_2O_2$: 346 [M+H].

Intermediate I-1.17. 4-(5-Bromo-2-methoxybenzyl) phthalazin-1 (2H)-one was prepared using 5-bromo-2-methoxybenzaldehyde in step 1. MS (EI) for $C_{16}H_{13}BrN_2O_2$: 346 [M+H].

Intermediate I-1.18. 4-(3-bromo-2-methoxybenzyl)phthalazin-1 (2H)-one was prepared using 3-bromo-2-methoxybenzaldehyde in step 1. MS (EI) for $C_{16}H_{13}BrN_2O_2$: 346 [M+H].

Intermediate I-1.19. 4-(3-Bromo-4,5-dimethoxybenzyl) phthalazin-1(2H)-one was prepared using 5-bromo-4,5-dimethoxybenzaldehyde in step 1. MS (EI) for $C_{17}H_{15}BrN_2O_3$: 376 [M+H].

Intermediate I-1.20. 4-(5-Bromo-2,4-dimethoxybenzyl) phthalazin-1(2H)-one was prepared using 5-bromo-2,4-dimethoxybenzaldehyde in step 1. MS (EI) for $C_{17}H_{15}BrN_2O_3$: 376 [M+H].

Intermediate I-1.21. 4-(5-Bromo-4-fluoro-2-methoxybenzyl)phthalazin-1(2H)-one was prepared using 5-bromo-4-fluoro-2-methoxybenzaldehyde (R-2. 1.) in step 1. MS (EI) for $C_{16}H_{12}BrFN_2O_2$: 364 [M+H].

Intermediate I-1.22. 4-(5-Bromo-2-fluoro-4-methoxybenzyl)phthalazin-1(2H)-one was prepared using 5-bromo-2-fluoro-4-methoxybenzaldehyde (R-2.2.) in step 1. MS (EI) for $C_{16}H_{12}BrFN_2O_2$: 364 [M+H].

Intermediate I-1.38. 4-((5-Bromofuran-2-yl)methyl) phthalazin-1(2H)-one was prepared using 5-bromofuran-2-carbaldehyde in step 1. MS (EI) for $C_{13}H_9BrN_2O_2$: 306 [M+H].

Intermediate I-1.49. 4-(4-Bromo-3-fluorobenzyl)phthalazin-1(2H)-one was prepared using 4-bromo-3-fluorobenzaldehyde in step 1. MS (EI) for $C_{15}H_{10}BrN_2O$: 333 [M+H].

Method B

STEP 1. To a suspension of 2-iodobenzoic acid (1b) (2.50 g, 10.00 mol), 2-bromo-4-ethynyl-1-fluorobenzene (2b, R-2.1.) (2.20 g, 11.00 mmol) and cesium-carbonate (6.52 g, 20.00 mmol) in dimethyl sulfoxide (10 mL) was added cooper(I) iodide (0.19 g, 1.00 mmol) and the reaction mixture was stirred at room temperature for 18 hours. It was partitioned with ethyl acetate (300 mL) and water (50 mL). The organic layer was separated and washed with water (50 mL), 1M aqueous hydrochloric acid (50 mL) and brine (2×100 mL), dried over anhydrous sodium sulfate and concentrated. The resulting crude product was purified by gradient silica gel flash chromatography (0-50% ethyl acetate in hexanes) to give (Z)-3-(3-bromo-4-fluorobenzylidene)-isobenzofuran-1(3H)-one (3a) (2.83 g, 88%). MS (EI) for $C_{15}H_8BrFO_2$: 319 [M+H].

STEP 2. To a suspension of (Z)-3-(3-bromo-4-fluorobenzylidene)-isobenzofuran-1(3H)-one (3a) (2.80 g, 8.77 mmol) in water (45 mL) was added sodium hydroxide (3.95 mL, 39.47 mmol, 10N aqueous solution) and the reaction mixture was heated to 90° C. for 1 hour then cooled to 50° C., followed by the addition of hydrazine hydrate (11.7 mL, 87.70 mmol, 24-25% aqueous solution) and stirred at 90° C. for 18 hours. It was cooled to room temperature and the pH was adjusted to 4 by the addition of concentrated aqueous hydrochloric acid. The crude mixture was partitioned with ethyl acetate (500 mL) and the organic layer was separated, washed with water (2×100 mL) and brine (200 mL), dried over anhydrous sodium sulfate and concentrated. The precipitated white solid was collected by filtration to give 4-(3-bromo-4-fluorobenzyl)phthalazin-1(2H)-one (I-1.1.) (2.08 g, 71%). MS (EI) for $C_{15}H_{10}BrFN_2O$: 333 [M+H].

Intermediate I-1.23. 4-(3-Bromo-4-fluorobenzyl)-8-fluorophthalazin-1(2H)-one was prepared using 2-fluoro-6-iodobenzoic acid in step 1. MS (EI) for $C_{15}H_9BrF_2N_2O$: 352 [M+H].

Intermediate I-1.24. 4-(3-Bromo-4-fluorobenzyl)-7-fluorophthalazin-1(2H)-one is prepared using 5-fluoro-2-iodobenzoic acid in step 1. MS (EI) for $C_{15}H_9BrF_2N_2O$: 352 [M+H].

Intermediate I-1.25. 4-(3-Bromo-4-fluorobenzyl)-6-fluorophthalazin-1(2H)-one was prepared using 4-fluoro-2-iodobenzoic acid in step 1. 1H NMR (300 MHz, $d_6$-DMSO): 12.57 (s, 1H), 8.24 (d, 1H), 7.96 (m, 1H), 7.78 (m, 1H), 7.56 (m, 1H), 7.26 (m, 1H), 7.18 (m, 1H), 4.35 (s, 2H). MS (EI) for $C_{15}H_9BrF_2N_2O$: 352 [M+H].

Intermediate I-1.26. 4-(3-Bromo-4-fluorobenzyl)-5-fluorophthalazin-1(2H)-one was prepared using 3-fluoro-2-iodobenzoic acid in step 1. MS (EI) for $C_{15}H_9BrF_2N_2O$: 352 [M+H].

Intermediate I-1.28. 4-(3-Bromo-4-fluorobenzyl)-6,7-difluorophthalazin-1(2H)-one is prepared using 4,5-difluoro-2-iodobenzoic acid in step 1. MS (EI) for $C_{15}H_8BrF_3N_2O$: 370 [M+H].

Intermediate I-1.36. 4-(3-Bromo-4-fluorobenzyl)-6,7-dimethoxyphthalazin-1(2H)-one was prepared using 2-bromo-4,5-dimethoxybenzoic acid in step 1. 1H NMR (300 MHz, $d_6$-DMSO): 12.56 (s, 1H), 7.58 (s. 1H), 7.55 (m, 1H), 7.42, (s, 1H), 7.23 (m, 2H), 4.28 (s, 2H) 3.94 (s, 3H), 3.93 (s, 3H). MS (EI) for $C_{17}H_{14}BrFN_2O_3$: 394 [M+H}.

Method C

STEP 1. To a solution of N-(quinolin-8-yl)benzamide (1c, R-3.1.) (1.24 g, 5.00 mmol) 2-bromo-4-ethynyl-1-fluorobenzene (2b) (R-2.1.) (2.00 g, 10.00 mmol) and potassium-carbonate (1.40 g, 10.00 mmol) in N,N-dimethylformamide (20 mL) was added cooper(II) acetate (0.91 g, 5.00 mmol) and the reaction mixture was stirred at 80° C. for 18 hours under oxygen atmosphere. The reaction mixture was cooed to room temperature, diluted with dichloromethane (250 mL) and filtered through a pad of Celite. The organic layer was washed with water (2×50 mL) and brine (2×100 mL), dried over anhydrous sodium sulfate and concentrated. The resulting crude product was purified by gradient silica gel flash chromatography (0-5% methanol in dichloromethane) to give (Z)-3-(3-bromo-4-fluorobenzylidene)-2-(quinolin-8-yl)isoindolin-1-one (3b) (1.74 g, 78%). MS (EI) for $C_{24}H_{14}BrFN_2O$: 446 [M+H].

STEP 2. To a suspension of 3-(3-bromo-4-fluorobenzylidene)-2-(quinolin-8-yl)isoindolin-1-one (3b) (1.74 g, 3.90 mmol) in a mixture of water (25 mL) and ethanol (15 mL) 10N aqueous sodium hydroxide (3.90 mL, 39.0 mmol) was added and the reaction mixture was heated to reflux for 1 hour. Upon cooling it to room temperature hydrazine monohydrate (64-65 wt %, 3.0 mL, 39.0 mmol) was added to the reaction mixture and it was stirred at 90° C. overnight. Upon cooling in ice water, the pH was adjusted to 4-5 by the addition of concentrated aqueous hydrochloric acid and it was partitioned with ethyl acetate (250 mL). The organic layer was separated and washed with water (2×100 mL) and brine (100 mL), dried over anhydrous sodium sulfate and concentrated. Upon removing the solvent the product has precipitated; it was collected by filtration washed with hexanes and dried in vacuo to give 4-(3-bromo-4-fluorobenzyl) phthalazin-1(2H)-one (I-1.1) (1.2 g, 94%). MS (EI) for $C_{15}H_{10}BrFN_2O$: 333 [M+H].

Intermediate I-1.27. 4-(3-Bromo-4-fluorobenzyl)-5,8-difluorophthalazin-1(2H)-one was prepared using 2,5-difluoro-N-(quinolin-8-yl)benzamide (R-3.2.) in step 1. MS (EI) for $C_{15}H_8BrF_3N_2O$: 370 [M+H].

Intermediate I-1.29. 4-(3-Bromo-4-fluorobenzyl)-8-methylphthalazin-1(2H)-one is prepared using 2-methyl-N-(quinolin-8-yl)benzamide (R-3.3.) in step 1. MS (EI) for $C_{16}H_{12}BrFN_2O$: 348 [M+H].

Intermediate I-1.30. 4-(3-Bromo-4-fluorobenzyl)-7-methylphthalazin-1(2H)-one was prepared using 3-methyl-N-(quinolin-8-yl)benzamide (R-3.4.) in step 1. 1H NMR (300 MHz, $d_6$-DMSO): 12.52 (s, 1H), 8.16 (s, 1H), 7.78 (d, 1H), 7.64 (d, 1H), 7.57 (m, 1H), 7.22 (m, 2H), 4.28 (s, 2H), 2.43 (s, 3H). MS (EI) for $C_{16}H_{12}BrFN_2O$: 348 [M+H].

Intermediate I-1.31. 4-(3-bromo-4-fluorobenzyl)-6-methylphthalazin-1(2H)-one was prepared using 4-methyl-N-(quinolin-8-yl)benzamide (R-3.5.) in step 1. 1H NMR (300 MHz, $d_6$-DMSO): 12.51 (s, 1H), 8.14 (d, 1H), 7.76 (s, 1H), 7.62 (d, 1H), 7.57 (m, 1H), 7.22 (m, 2H), 4.28 (s, 2H), 2.45 (s, 3H). MS (EI) for $C_{16}H_{12}BrFN_2O$: 348 [M+H].

Intermediate I-1.32. 4-(3-Bromo-4-fluorobenzyl)-6-chlorophthalazin-1(2H)-one is prepared using 4-methyl-N-(quinolin-8-yl)benzamide (R-3.6.) in step 1. MS (EI) for $C_{15}H_9BrClFN_2O$: 368 [M+H].

Intermediate I-1.33. 4-(3-Bromo-4-fluorobenzyl)-6-(trifluoromethyl)phthalazin-1(2H)-one is prepared using N-(quinolin-8-yl)-4-(trifluoromethyl)benzamide (R-3.7.) in step 1. MS (EI) for $C_{16}H_9BrF_4N_2O$: [M+H]402.

Intermediate I-1.34. 4-(3-Bromo-4-fluorobenzyl)-6-methoxyphthalazin-1(2H)-one is prepared using 4-methoxy-N-(quinolin-8-yl)benzamide (R-3.8.) in step 1. MS (EI) for $C_{16}H_{12}BrFN_2O_2$: [M+H] 364.

Intermediate I-1.35. 4-(3-Bromo-4-fluorobenzyl)-6-(trifluoromethoxy) phthalazin-1(2H)-one is prepared using N-(quinolin-8-yl)-4-(trifluoromethoxy) benzamide (R-3.9.) in step 1. MS (EI) for $C_{16}H_9BrF_4N_2O_2$: [M+H] 418.

Intermediate I-1.37. 4-(3-Bromo-4-fluorobenzyl)-5,7-dimethoxyphthalazin-1(2H)-one is prepared using 3,5-dimethoxy-N-(quinolin-8-yl)benzamide (R-3.10.) in step 1. MS (EI) for $C_{17}H_{14}BrFN_2O_3$: 394.

Intermediate 2

4-(4-fluoro-3-(4,4,5,5-tetramethyl-1,3,2-dioxaborolan-2-yl)benzyl)phthalazin-1(2H)-one (I-2.1.)

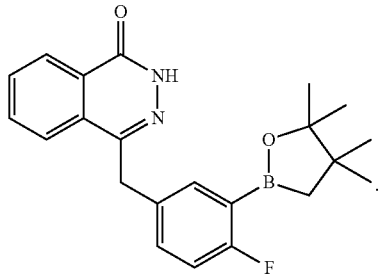

I-2.1

A solution of 4-(3-bromo-4-fluorobenzyl) phthalazin-1 (2H)-one (I-1.1.) (0.33 g, 1.00 mmol), bis (pinacolato) diboron (0.28 g, 1.10 mmol), potassium acetate (0.30 g, 3.00 mmol) and dichloro[1,1'-bis(diphenylphosphino)ferrocene] palladium(II) dichloromethane adduct (37 mg, 0.05 mmol) in dimethyl sulfoxide (3.0 mL) was heated to 80° C. for three hours. Upon cooling the reaction mixture to room temperature, it was diluted with ethyl acetate (100 mL) and filtered through a pad of Celite. The filtrate was partitioned with 1M aqueous hydrochloric acid (50 ml). The organic layer was separated and washed with brine (2×50 mL), dried over anhydrous sodium sulfate and concentrated. The resulting crude was purified by gradient silica gel flash chromatography (0-50% ethyl acetate in hexanes) to give 4-(4-fluoro-3-(4,4,5,5-tetramethyl-1,3,2-dioxaborolan-2-yl)benzyl) phthalazin-1 (2H)-one (I-2.1.) (0.33 g, 87%). (TLC 30% ethyl acetate in hexanes). MS (EI) for $C_{21}H_{22}BFN_2O_3$: 381 [M+H].

Intermediate 3

4-((4'-amino-6-fluoro-3'-nitro-[1,1'-biphenyl]-3-yl)methyl)phthalazin-1(2H)-one (I-3.1.)

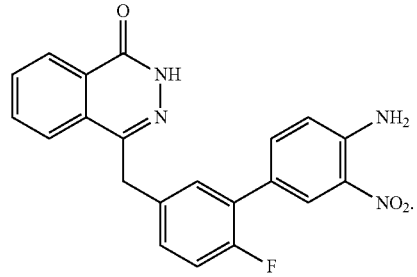

I-3.1

Method A.

A solution of 4-(3-bromo-4-fluorobenzyl) phthalazin-1 (2H)-one (I-1.1.) (0.33 g, 1.00 mmol), 2-nitro-4-(4,4,5,5-tetramethyl-1,3,2-dioxaborolan-2-yl)aniline (0.26 g, 1.00 mmol) and potassium carbonate (0.41 g, 3.00 mmol) in a mixture of 1,4-dioxane (4.5 mL) and water (0.5 mL) was degassed by repeatedly evacuating the reaction wessel then bubbling nitrogen gas through the solution, followed by the addition of dichloro[1,1'-bis(diphenylphosphino)ferrocene] palladium (II) dichloromethane adduct (41 mg, 0.05 mmol) and stirring the reaction mixture at 98° C. for 18 hours. It was cooled to room temperature and partitioned with ethyl acetate (100 mL) and 1M aqueous hydrochloric acid (50 ml). The organic layer was washed with 1M aqueous hydrochloric acid (2×50 ml) and brine (2×50 mL), dried over anhydrous sodium sulfate and concentrated. The resulting crude was purified by gradient silica gel flash chromatography (5-75% ethyl acetate in hexanes) to give 4-((3'-amino-6-fluoro-4'-nitro-[1,1'-biphenyl]-3-yl)methyl) phthalazin-1(2H)-one (I-3.1.) (0.26 g, 67%). (TLC 50% ethyl acetate in hexanes). 1H NMR (300 MHz, $d_6$-DMSO): 12.56 (s, 1H), 8.26 (d, 1H), 8.12 (s, 1H), 8.02 (d, 1H), 7.92 (t, 1H), 7.86 (t, 1H), 7.60 (m, 4H), 7.26 (m, 2H), 7.10 (d, 1H), 4.35 (s, 2H). MS (EI) for $C_{21}H_{15}FN_4O_3$: 391 [M+H].

Intermediate I-3.2. 4-((4'-Amino-3'-nitro-[1,1'-biphenyl]-3-yl)methyl)phthalazin-1(2H)-one was prepared using 4-(3-bromobenzyl)phthalazin-1(2H)-one (I-1.2.). MS (EI) for $C_{21}H_{16}N_4O_3$: 373 [M+H].

Intermediate I-3.3. 4-((4'-Amino-6-chloro-3'-nitro-[1,1'-biphenyl]-3-yl)methyl)phthalazin-1(2H)-one was prepared using 4-(3-bromo-4-chlorobenzyl)phthalazin-1(2H)-one (I-1.3.). MS (EI) for $C_{21}H_{15}ClN_4O_3$: 407 [M+H].

Intermediate I-3.4. 4-((4'-Amino-6-methyl-3'-nitro-[1,1'-biphenyl]-3-yl)methyl)phthalazin-1(2H)-one was prepared using 4-(3-bromo-4-methylbenzyl)phthalazin-1(2H)-one (I-1.4.). MS (EI) for $C_{22}H_{18}N_4O_3$: 387 [M+H].

Intermediate I-3.5. 4-((3'-Amino-4'-nitro-6-(trifluoromethyl)-[1,1'-biphenyl]-3-yl)methyl)phthalazin-1(2H)-one was prepared using 4-(3-bromo-4-(trifluoromethyl)benzyl) phthalazin-1(2H)-one (I-1.5.). MS (EI) for $C_{22}H_{15}F_3N_4O_3$: 441 [M+H].

Intermediate I-3.6. 4-((4'-Amino-3'-nitro-6-(trifluoromethoxy)-[1,1'-biphenyl]-3-yl)methyl) phthalazin-1(2H)-one was prepared using 4-(3-bromo-4-(trifluoromethoxy)benzyl)phthalazin-1(2H)-one (I-1.6.). MS (EI) for $C_{22}H_{15}F_3N_4O_4$: 457 [M+H].

Intermediate I-3.7. 4-((4'-Amino-6-methoxy-3'-nitro-[1,1'-biphenyl]-3-yl)methyl)phthalazin-1 (2H)-one was prepared using 4-(3-bromo-4-methoxybenzyl)phthalazin-1(2H)-one (I-1.7.). 1H NMR (300 MHz, $d_6$-DMSO): 12.55 (s, 1H), 8.26 (d, 1H), 8.04 (s, 1H), 8.02 (d, 1H), 7.88 (t, 1H), 7.85 (t, 1H), 7.56 (d, 1H), 7.46 (m, 2H), 7.32 (s, 1H), 7.20 (d, 1H), 7.05 (m, 2H), 4.28 (s, 2H), 3.72 (s, 3H). MS (EI) for $C_{22}H_{18}N_4O_4$: 403.

Intermediate I-3.8. 4-((4'-Amino-6-ethoxy-3'-nitro-[1,1'-biphenyl]-3-yl)methyl)phthalazin-1(2H)-one was prepared using 4-(3-bromo-4-ethoxybenzyl)phthalazin-1(2H)-one (I-1.8.). MS (EI) for $C_{23}H_{20}N_4O_4$: 417 [M+H].

Intermediate I-3.9. 4-((4'-Amino-6-(2-methoxyethoxy)-3'-nitro-[1,1'-biphenyl]-3-yl)methyl) phthalazin-1 (2H)-one was prepared using 4-(3-bromo-4-(2-methoxyethoxy)benzyl)phthalazin-1(2H)-one (I-1.9.). MS (EI) for $C_{24}H_{22}N_4O_5$: 47 [M+H].

Intermediate I-3.10. 4-((4'-Amino-6-(difluoromethoxy)-3'-nitro-[1,1'-biphenyl]-3-yl)methyl) phthalazin-1(2H)-one was prepared using 4-(3-bromo-4-(difluoromethoxy)benzyl) phthalazin-1(2H)-one (I-1.10.). MS (EI) for $C_{22}H_{16}F_2N_4O_4$: 439 [M+H].

Intermediate I-3.11. 4-((4'-Amino-5-fluoro-3'-nitro-[1,1'-biphenyl]-3-yl)methyl)phthalazin-1(2H)-one was prepared using 4-(3-bromo-5-fluorobenzyl)phthalazin-1(2H)-one (I-1.11.). MS (EI) for $C_{21}H_{15}FN_4O_3$: 391 [M+H].

Intermediate I-3.12. 4-((4'-Amino-4-fluoro-3'-nitro-[1,1'-biphenyl]-3-yl)methyl)phthalazin-1(2H)-one was prepared using 4-(5-bromo-2-fluorobenzyl)phthalazin-1(2H)-one (I-1.12.). MS (EI) for $C_{21}H_{15}FN_4O_3$: 391 [M+H].

Intermediate I-3.13. 4-((4'-Amino-2-fluoro-3'-nitro-[1,1'-biphenyl]-3-yl)methyl)phthalazin-1(2H)-one was prepared using 4-(3-bromo-2-fluorobenzyl)phthalazin-1(2H)-one (I-1.13.). MS (EI) for $C_{21}H_{15}FN_4O_3$: 391 [M+H].

Intermediate I-3.14. 4-((4'-Amino-4,6-difluoro-3'-nitro-[1,1'-biphenyl]-3-yl)methyl)phthalazin-1(2H)-one was prepared using 4-(5-bromo-2,4-difluorobenzyl)phthalazin-1 (2H)-one (I-1.14.). MS (EI) for $C_{21}H_{14}F_2N_4O_3$: 409 [M+H].

Intermediate I-3.16. 4-((4'-Amino-5-methoxy-3'-nitro-[1,1'-biphenyl]-3-yl)methyl)phthalazin-1(2H)-one was prepared using 4-(3-bromo-5-methoxybenzyl)phthalazin-1(2H)-one (I-1.16.). MS (EI) for $C_{22}H_{18}N_4O_4$: 403 [M+H].

Intermediate I-3.17. 4-((4'-Amino-4-methoxy-3'-nitro-[1,1'-biphenyl]-3-yl)methyl)phthalazin-1(2H)-one was prepared using 4-(5-bromo-2-methoxybenzyl)phthalazin-1(2H)-one (I-1.17.). MS (EI) for $C_{22}H_{18}N_4O_4$: 403 [M+H].

Intermediate I-3.18. 4-((4'-Amino-2-methoxy-3'-nitro-[1,1'-biphenyl]-3-yl)methyl)phthalazin-1(2H)-one was prepared using 4-(3-bromo-2-methoxybenzyl)phthalazin-1(2H)-one (I-1.18.). MS (EI) for $C_{22}H_{18}N_4O_4$: 403 [M+H].

Intermediate I-3.19. 4-((4'-Amino-5,6-dimethoxy-3'-nitro-[1,1'-biphenyl]-3-yl)methyl)phthalazin-1(2H)-one was prepared using 4-(3-bromo-4,5-dimethoxybenzyl)phthalazin-1(2H)-one (I-1.19.). MS (EI) for $C_{23}H_{20}N_4O_5$: 433 [M+H].

Intermediate I-3.20. 4-((4'-Amino-4,6-dimethoxy-3'-nitro-[1,1'-biphenyl]-3-yl)methyl)phthalazin-1(2H)-one was prepared using 4-(5-bromo-2,4-dimethoxybenzyl)phthalazin-1(2H)-one (I-1.20.). MS (EI) for $C_{23}H_{20}N_4O_5$: 433 [M+H].

Intermediate I-3.21. 4-((4'-Amino-6-fluoro-4-methoxy-3'-nitro-[1,1'-biphenyl]-3-yl)methyl) phthalazin-1(2H)-one was prepared using 4-(5-bromo-4-fluoro-2-methoxybenzyl) phthalazin-1(2H)-one (I-1.21.). MS (EI) for $C_{22}H_{17}FN_4O_4$: 421 [M+H].

Intermediate I-3.22. 4-((4'-Amino-4-fluoro-6-methoxy-3'-nitro-[1,1'-biphenyl]-3-yl)methyl) phthalazin-1(2H)-one was prepared using 4-(5-bromo-2-fluoro-4-methoxybenzyl) phthalazin-1(2H)-one (I-1.22.). MS (EI) for $C_{22}H_{17}FN_4O_4$: 421 [M+H].

Intermediate I-3.23. 4-((4'-Amino-6-fluoro-3'-nitro-[1,1'-biphenyl]-3-yl)methyl)-8-fluorophthalazin-1 (2H)-one was be prepared using 4-(3-bromo-4-fluorobenzyl)-8-fluorophthalazin-1(2H)-one (I-1.23.). MS (EI) for $C_{21}H_{14}F_2N_4O_3$: 409 [M+H].

Intermediate I-3.24. 4-((4'-Amino-6-fluoro-3'-nitro-[1,1'-biphenyl]-3-yl)methyl)-7-fluorophthalazin-1 (2H)-one is prepared using 4-(3-bromo-4-fluorobenzyl)-7-fluorophthalazin-1(21H)-one (I-1.24.). MS (EI) for $C_{21}H_{14}F_2N_4O_3$: 409 [M+H].

Intermediate I-3.25. 4-((4'-amino-6-fluoro-3'-nitro-[1,1'-biphenyl]-3-yl)methyl)-6-fluorophthalazin-1 (2H)-one was prepared using 4-(3-bromo-4-fluorobenzyl)-6-fluorophthalazin-1(2H)-one (I-1.25.). MS (EI) for $C_{21}H_{14}F_2N_4O_3$: 409 [M+H].

Intermediate I-3.26. 4-((4'-Amino-6-fluoro-3'-nitro-[1,1'-biphenyl]-3-yl)methyl)-5-fluorophthalazin-1 (2H)-one was prepared using 4-(3-bromo-4-fluorobenzyl)-5-fluorophthalazin-1(2H)-one (I-1.26.). MS (EI) for $C_{21}H_{14}F_2N_4O_3$: 409 [M+H].

Intermediate I-3.27. 4-((4'-Amino-6-fluoro-3'-nitro-[1,1'-biphenyl]-3-yl)methyl)-5,8-difluoro-phthalazin-1 (2H)-one was prepared using 4-(3-bromo-4-fluorobenzyl)-5,8-difluorophthalazin-1(2H)-one (I-1.27.). MS (EI) for $C_{21}H_{13}F_3N_4O_3$: 427 [M+H].

Intermediate I-3.28. 4-((4'-Amino-6-fluoro-3'-nitro-[1,1'-biphenyl]-3-yl)methyl)-6,7-difluoro-phthalazin-1 (2H)-one is prepared using 4-(3-bromo-4-fluorobenzyl)-6,7-difluorophthalazin-1(2H)-one (I-1.28.). MS (EI) for $C_{21}H_{13}F_3N_4O_3$: 427 [M+H].

Intermediate I-3.29. 4-((4'-Amino-6-fluoro-3'-nitro-[1,1'-biphenyl]-3-yl)methyl)-8-methylphthalazin-1(2H)-one was prepared using 4-(3-bromo-4-fluorobenzyl)-8-methylphthalazin-1(2H)-one (I-1.29.). MS (EI) for $C_{22}H_{17}FN_4O_3$: 405 [M+H].

Intermediate I-3.30. 4-((4'-Amino-6-fluoro-3'-nitro-[1,1'-biphenyl]-3-yl)methyl)-7-methylphthalazin-1(2H)-one was prepared using 4-(3-bromo-4-fluorobenzyl)-7-methylphthalazin-1(2H)-one (I-1.30.). MS (EI) for $C_{22}H_{17}FN_4O_3$: 405 [M+H].

Intermediate I-3.31. 4-((4'-Amino-6-fluoro-3'-nitro-[1,1'-biphenyl]-3-yl)methyl)-6-methylphthalazin-1(2H)-one was prepared using 4-(3-bromo-4-fluorobenzyl)-6-methylphthalazin-1(2H)-one (I-1.31.). MS (EI) for $C_{22}H_{17}FN_4O_3$: 405 [M+H].

Intermediate I-3.32. 4-((4'-Amino-6-fluoro-3'-nitro-[1,1'-biphenyl]-3-yl)methyl)-6-chlorophthalazin-1(2H)-one is prepared using 4-(3-bromo-4-fluorobenzyl)-6-chlorophthalazin-1(2H)-one (I-1.32.). MS (EI) for $C_{21}H_{14}ClFN_4O_3$: 425 [M+H}.

Intermediate I-3.33. 4-((4'-Amino-6-fluoro-3'-nitro-[1,1'-biphenyl]-3-yl)methyl)-6-(trifluoro-methyl)phthalazin-1 (2H)-one is prepared using 4-(3-bromo-4-fluorobenzyl)-6-(trifluoromethyl) phthalazin-1(2H)-one (I-1.33.). MS (EI) for $C_{22}H_{14}F_4N_4O_3$: 459 [M+H].

Intermediate I-3.34. 4-((4'-Amino-6-fluoro-3'-nitro-[1,1'-biphenyl]-3-yl)methyl)-6-methoxy-phthalazin-1 (2H)-one is prepared using 4-(3-bromo-4-fluorobenzyl)-6-methoxyphthalazin-1(2H)-one (I-1.33.). MS (EI) for $C_{22}H_{17}FN_4O_4$: 421 [M+H].

Intermediate I-3.35. 4-((4'-Amino-6-fluoro-3'-nitro-[1,1'-biphenyl]-3-yl)methyl)-6-(trifluoro-methoxy)phthalazin-1 (2H)-one is prepared using 4-(3-bromo-4-fluorobenzyl)-6-(trifluoro-methoxy)phthalazin-1(2H)-one (I-1.35.). MS (EI) for $C_{22}H_{14}F_4N_4O_4$: 475 [M+H].

Intermediate I-3.36. 4-((4'-Amino-6-fluoro-3'-nitro-[1,1'-biphenyl]-3-yl)methyl)-6,7-dimethoxy-phthalazin-1(2H)-one one was prepared using 4-(3-bromo-4-fluorobenzyl)-6,7-dimethoxyphthalazin-1(2H)-one (I-1.36.). MS (EI) for $C_{23}H_{19}FN_4O_5$: 451 [M+H].

Intermediate I-3.37. 4-((4'-Amino-6-fluoro-3'-nitro-[1,1'-biphenyl]-3-yl)methyl)-5,7-dimethoxy-phthalazin-1(2H)-one is prepared using 4-(3-bromo-4-fluorobenzyl)-5,7-dimethoxyphthalazin-1(2H)-one (I-1.37.). MS (EI) for $C_{23}H_{19}FN_4O_5$: 451 [M+H].

Intermediate I-3.38. 4-((5-(4-Amino-3-nitrophenyl)furan-2-yl)methyl)phthalazin-1(2H)-one was prepared using 4-((5-bromofuran-2-yl)methyl)phthalazin-1(2H)-one (I-1.38.). MS (EI) for $C_{19}H_{14}N_4O_4$: 363 [M+H].

Intermediate I-3.49. 4-((4'-Amino-2-fluoro-3'-nitro-[1,1'-biphenyl]-4-yl)methyl)phthalazin-1(2H)-one was prepared using 4-(4-bromo-3-fluorobenzyl)phthalazin-1(2H)-one (I-1.49.). MS (EI) for $C_{21}H_{15}FN_4O_3$: 391 [M+H].

Method B

A solution of 4-(4-fluoro-3-(4,4,5,5-tetramethyl-1,3,2-dioxaborolan-2-yl)benzyl)phthalazin-1(2H)-one (I-2.1.) (0.38 g, 1.00 mmol), 4-bromo-2-nitroaniline (0.22 g, 100 mmol) and potassium carbonate (0.41 g, 3.00 mmol) in a mixture of 1,4-dioxane (4.5 mL) and water (0.5 mL) was purged with nitrogen gas for 20 minutes, followed by the addition of dichloro[1,1'-bis(diphenylphosphino) ferrocene]palladium (II) dichloromethane adduct (41 mg, 0.05 mmol) and the reaction mixture was stirred at 98° C. for 18 hours. Upon cooling it to room temperature it was diluted with ethyl acetate (50 mL) and the mixture was filtered through a pad of Celite, then washed with an additional portion of ethyl acetate (50 mL). The combined phases were washed with 1M aqueous hydrochloric acid (2×50 ml) and brine (2×50 mL), dried over anhydrous sodium sulfate and concentrated. The resulting crude was purified by gradient silica gel flash chromatography (5-75% ethyl acetate in hexanes) to give 4-((3'-amino-6-fluoro-4'-nitro-[1,1'-biphenyl]-3-yl)methyl) phthalazin-1(2H)-one (1-3.1.) (0.28 g, 73%). 1H NMR (300 MHz, $d_6$-DMSO): 12.56 (s, 1H), 8.26 (d, 1H), 8.12 (s, 1H), 8.02 (d, 1H), 7.92 (t, 1H), 7.86 (t, 1H), 7.60 (m, 4H), 7.26 (m, 2H), 7.10 (d, 1H), 4.35 (s, 2H). MS (EI) for $C_{21}H_{15}FN_4O_3$: 391 [M+H].

Intermediate I-3.40. 4-((4'-Amino-3',6-difluoro-5'-nitro-[1,1'-biphenyl]-3-yl)methyl)phthalazin-1 (2H)-one was prepared using 4-bromo-2-fluoro-6-nitroaniline MS (EI) for $C_{21}H_{14}F_2N_4O_3$: 409 [M+H].

Intermediate I-3.41. 4-((4'-Amino-2',6-difluoro-5'-nitro-[1,1'-biphenyl]-3-yl)methyl)phthalazin-1 (2H)-one was prepared using 4-bromo-3-fluoro-2-nitroaniline MS (EI) for $C_{21}H_{14}F_2N_4O_3$: 409 [M+H].

Intermediate I-3.42. 4-((4'-Amino-2',6-difluoro-3'-nitro-[1,1'-biphenyl]-3-yl)methyl)phthalazin-1(2H)-one was prepared using 4-bromo-5-fluoro-2-nitroaniline MS (EI) for $C_{21}H_{14}F_2N_4O_3$: 409 [M+H].

Intermediate I-3.44. 4-(3-(6-Amino-5-nitropyridin-2-yl)-4-fluorobenzyl)phthalazin-1 (2H)-one was prepared using 6-bromo-3-nitropyridin-2-amine MS (EI) for $C_{20}H_{14}FN_5O_3$: 392 [M+H].

Intermediate I-3.45. 4-(3-(6-Amino-5-nitropyridin-3-yl)-4-fluorobenzyl)phthalazin-1 (2H)-one is prepared using 5-bromo-3-nitropyridin-2-amine MS (EI) for $C_{20}H_{14}FN_5O_3$: 392 [M+H].

Intermediate I-3.46. 4-(3-(4-Amino-5-nitropyridin-2-yl)-4-fluorobenzyl)phthalazin-1 (2H)-one is prepared using 2-bromo-5-nitropyridin-4-amine MS (EI) for $C_{20}H_{14}FN_5O_3$: 392 [M+H].

Intermediate I-3.47. 4-(3-(6-Amino-2-methyl-5-nitropyridin-3-yl)-4-fluorobenzyl)phthalazin-1 (2H)-one was prepared using 5-bromo-6-methyl-3-nitropyridin-2-amine MS (EI) for $C_{21}H_{16}FN_5O_3$: 406 [M+H].

Intermediate I-3.48. 4-(3-(6-Amino-4-methyl-5-nitropyridin-3-yl)-4-fluorobenzyl)phthalazin-1 (2H)-one is prepared using 5-bromo-4-methyl-3-nitropyridin-2-amine MS (EI) for $C_{21}H_{16}FN_5O_3$: 406 [M+H].

Method C

STEP 1. To a solution of 4'-amino-6-fluoro-3'-nitro-[1,1'-biphenyl]-3-carbaldehyde (4, R-4.1.) (2.08 g, 8.0 mmol) ad dimethyl 3-oxo-1,3-dihydroisobenzofuran-1-ylphosphonate (1a) (3.70 g, 16.0 mmol) in tetrahydrofuran (50 mL) trimethylamine (11.2 mL, 80.0 mmol) was added dropwise and the reaction mixture was heated to reflux for 18 hours under nitrogen atmosphere. Upon cooling it to room temperature, the solvent was concentrated and the residue was partitioned with ethyl acetate (300 mL) and 2M aqueous hydrochloric acid (100 mL). The organic layer was separated, washed with 2M aqueous hydrochloric acid (2×100 mL), brine (150 mL), 1M aqueous sodium hydroxide (2×100 mL), brine (150 mL), 1M aqueous hydrochloric acid (100 mL) and bine (150 mL), dried over anhydrous sodium sulfate and the solvent was concentrated. The resulting crude solid was triturated with ethyl acetate and the solid was collected by filtration to give (E/Z)-3-((4'-amino-6-fluoro-3'-nitro-[1,1'-biphenyl]-3-yl)methylene)isobenzofuran-1(3H)-one (5) (2.65 g, 88%) as a brown solid. A portion of the crude product was recrystallized from ethyl acetate to give (Z)-3-((4'-amino-6-fluoro-3'-nitro-[1,1'-biphenyl]-3-yl)methylene)isobenzofuran-1 (3H)-one. 1H NMR (300 MHz, $d_6$-DMSO): 8.18 (s, 1H), 8.10 (d, 1H), 7.95 (d, 1H), 7.88 (m, 3H), 7.70 (s, 3H), 7.67 (t, 1H), 7.42 (dd, 1H), 7.21 (d, 1H), 7.07 (s, 1H). MS (EI) for $C_{21}H_{13}FN_2O_4$: 377 [M+H].

STEP 2. To a suspension of (E/Z)-3-((4'-amino-6-fluoro-3'-nitro-[1,1'-biphenyl]-3-yl)methylene) isobenzofuran-1 (3H)-one (5) (1.14 g, 3.00 mmol) in N,N-dimethylformamide (10 mL) N-methylmorpholine (0.70 mL, 6.00 mmol) was added, followed by the addition of a 1M solution of hydrazine in tetrahydrofuran (3.75 mL, 3.75 mmol). The reaction mixture was heated to 75° C. for 18 hours. It was cooled to room temperature and partitioned with ethyl acetate (250 mL) and 2M aqueous hydrochloric acid (100 mL). The organic layer was separated and washed with 2M aqueous hydrochloric acid[4] (100 mL) and brine (2×150 mL), dried over anhydrous sodium sulfate and the solvent was concentrated. The resulting crude was triturated with ethanol and the yellow solid was collected by filtration washed with 10% ethyl acetate in hexanes and air dried to give 4-((4'-amino-6-fluoro-3'-nitro-[1,1'-biphenyl]-3-yl)methyl) phthalazin-1(2H)-one (I-3.1.) (1.05 g, 89%). MS (EI) for $C_{21}H_{15}FN_4O_3$: 391 [M+H].

Intermediate I-3.15. 4-((4'-Amino-5,6-difluoro-3'-nitro-[1,1'-biphenyl]-3-yl)methyl)phthalazin-1(2H)-one was prepared using 4'-amino-6-fluoro-3'-nitro-[1,1'-biphenyl]-3-carbaldehyde (R-4.2.) in step 1. MS (EI) for $C_{21}H_{14}F_2N_4O_3$: 408 [M+H].

Intermediate I-3.39. 4-((4-(4-Amino-3-nitrophenyl)furan-2-yl)methyl)phthalazin-1(2H)-one was prepared using 4-(4-amino-3-nitrophenyl)furan-2-carbaldehyde (R-4.3.) in step 1. MS (EI) for $C_{19}H_{14}N_4O_4$: 363 [M+H].

Intermediate 4

4-((3',4'-diamino-5'-chloro-6-fluoro-[1,1'-biphenyl]-3-yl)methyl)phthalazin-1(2H)-one (I-4.1.)

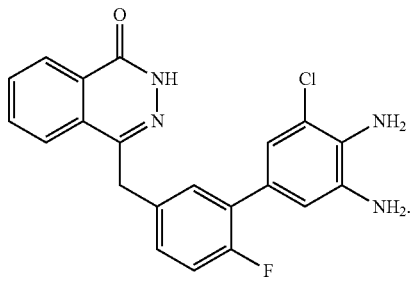

I-4.1

STEP 1 To a solution of 4-((3'-amino-6-fluoro-4'-nitro-[1,1'-biphenyl]-3-yl)methyl) phthalazin-1(2H)-one (I-2.1.) (0.54 g, 1.38 mmol) in N,N-dimethylformamid (10 mL) was added N-chlorosuccinimide (0.18 g, 1.38 mmol) in one portion. The reaction mixture was stirred at room temperature for 18 hours. The mixture was partitioned with ethyl acetate (100 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (5-50% ethyl acetate in hexanes) to give 4-((4'-amino-3'-chloro-6-fluoro-5'-nitro-[1,1'-biphenyl]-3-yl)methyl)phthalazin-1 (2H)-one (6) (0.55 g, 93%). 1H NMR (300 MHz, $d_6$-DMSO): 12.57 (s, 1H), 8.27 (d, 1H), 8.12 (s, 1H), 8.02 (d, 1H), 7.90-7.86 (m, 2H), 7.58 (m, 4H), 7.26 (s, 1H), 7.10 (d, 1H), 4.34 (s, 2H). MS (EI) for $C_{21}H_{14}ClFN_4O_3$: 426 [M+H].

STEP 2. A suspension of 4-((4'-amino-3'-chloro-6-fluoro-5'-nitro-[1,1'-biphenyl]-3-yl)methyl) phthalazin-1(2H)-one (6) (0.33 g, 0.78 mmol), ammonium formate (0.98 g, 15.54 mmol) and iron metal powder (0.43 g, 7.70 mmol) in a mixture of tetrahydrofuran (25 mL) and water (5 mL) was heated to 70° C. for 18 hours. It was cooled to room temperature and the solid was removed by filtering the reaction mixture through a pad of Celite. The residue was partitioned with ethyl acetate (250 mL) and saturated aqueous sodium bicarbonate (100 ml). The organic layer was separated, washed with saturated aqueous sodium bicarbonate (50 ml), brine (2×100 mL), dried over anhydrous sodium sulfate and concentrated. The resulting crude was purified by gradient silica gel flash chromatography (10-80% ethyl acetate in hexanes) to give 4-((4',5'-diamino-2'-chloro-6-fluoro-[1,1'-biphenyl]-3-yl)methyl)phthalazin-1(2H)-one (I-4.1.) (0.17 g, 56%). The crude product was used without further purification. MS (EI) for $C_{21}H_{16}ClFN_4O$: 395 [M+H].

Intermediate 5

4-((3'4'-diamino-6-fluoro-[1,1'-biphenyl]-3-yl)methyl)phthalazin-1(2H)-one (I-5.1.)

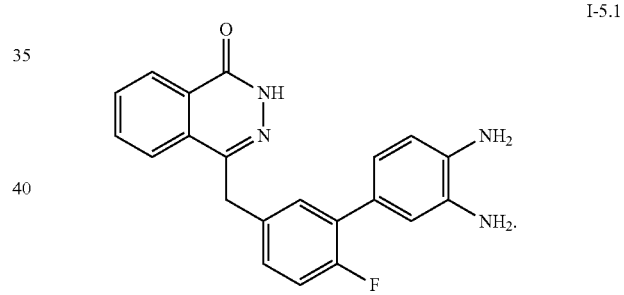

I-5.1

To a suspension of 4-((3'-amino-6-fluoro-4'-nitro-[1,1'-biphenyl]-3-yl)methyl) phthalazin-1(2H)-one (I-3.1.) (0.25 g, 0.64 mmol) and ammonium formate (0.81 g, 12.80 mmol) in methanol (25 mL) palladium on activated carbon (0.1 g, 10 wt % loading on wet support, Degussa type) was added and the reaction mixture was stirred at 62° C. for 18 hours. It was cooled to room temperature and the catalyst was removed filtering the reaction mixture through a pad of Celite; the solvent was concentrated, the residue was partitioned with ethyl acetate (100 mL) and saturated aqueous sodium bicarbonate (50 ml). The organic layer was separated, washed with saturated aqueous sodium bicarbonate (2×25 ml) and brine (2×100 mL), dried over anhydrous sodium sulfate and concentrated to give 4-((3',4'-diamino-6-fluoro-[1,1'-biphenyl]-3-yl)methyl)phthalazin-1(2H)-one (I-5.1.) as light brown solid (0.22 g, 96%). The crude product was used without further purification. MS (EI) for $C_{21}H_{17}FN_4O$: 361 [M+H].

Intermediate I-5.2. 4-((3',4'-Diamino-[1,1'-biphenyl]-3-yl)methyl)phthalazin-1(2H)-one was prepared using 4-((4'-amino-3'-nitro-[1,1'-biphenyl]-3-yl)methyl)phthalazin-1 (2H)-one (I-3.2.). MS (EI) for $C_{21}H_{18}N_4O$: 343 [M+H].

Intermediate I-5.3. 4-((3',4'-Diamino-6-chloro-[1,1'-biphenyl]-3-yl)methyl)phthalazin-1(2H)-one was prepared using 4-((4'-amino-6-chloro-3'-nitro-[1,1'-biphenyl]-3-yl)methyl)phthalazin-1(2H)-one (1-3.3.). MS (EI) for $C_{21}H_{17}ClN_4O$: 377 [M+H].

Intermediate I-5.4. 4-((3',4'-Diamino-6-methyl-[1,1'-biphenyl]-3-yl)methyl)phthalazin-1(2H)-one was prepared using 4-((4'-amino-6-methyl-3'-nitro-[1,1'-biphenyl]-3-yl)methyl)phthalazin-1 (2H)-one (1-3.4.). MS (EI) for $C_{22}H_{20}N_4O$: 357 [M+H].

Intermediate I-5.5. 4-((3',4'-Diamino-6-(trifluoromethyl)-[1,1'-biphenyl]-3-yl)methyl)phthalazin-1(2H)-one was prepared using 4-((3'-amino-4'-nitro-6-(trifluoromethyl)-[1,1'-biphenyl]-3-yl)methyl)phthalazin-1(2H)-one (1-3.5.). MS (EI) for $C_{22}H_{17}F_3N_4O$: 410 [M+H].

Intermediate I-5.6. 4-((3',4'-Diamino-6-(trifluoromethoxy)-[1,1'-biphenyl]-3-yl)methyl)phthalazin-1 (2H)-one was prepared using 4-((4'-amino-3'-nitro-6-(trifluoromethoxy)-[1,1'-biphenyl]-3-yl)methyl)phthalazin-1 (2H)-one (1-3.6.). MS (EI) for $C_{22}H_{17}F_3N_4O_2$: 427 [M+H].

Intermediate I-5.7. 4-((3',4'-Diamino-6-methoxy-[1,1'-biphenyl]-3-yl)methyl)phthalazin-1(2H)-one was prepared using 4-((4'-amino-6-methoxy-3'-nitro-[1,1'-biphenyl]-3-yl)methyl)phthalazin-1(2H)-one (1-3.7.). MS (EI) for $C_{22}H_{20}N_4O_2$: 372 [M+H].

Intermediate I-5.8. 4-((3',4'-Diamino-6-ethoxy-[1,1'-biphenyl]-3-yl)methyl)phthalazin-1(2H)-one was prepared using 4-((4'-amino-6-ethoxy-3'-nitro-[1,1'-biphenyl]-3-yl)methyl)phthalazin-1(2H)-one (1-3.8.). MS (EI) for $C_{23}H_{22}N_4O_2$: 387 [M+H].

Intermediate I-5.9. 4-((3',4'-Diamino-6-(2-methoxyethoxy)-[1,1'-biphenyl]-3-yl)methyl)phthalazin-1 (2H)-one was prepared using 4-((4'-amino-6-(2-methoxyethoxy)-3'-nitro-[1,1'-biphenyl]-3-yl)methyl) phthalazin-1 (2H)-one (1-3.9.). MS (EI) for $C_{24}H_{24}N_4O_3$: 417 [M+H].

Intermediate I-5.10. 4-((3',4'-Diamino-6-(difluoromethoxy)-[1,1'-biphenyl]-3-yl)methyl)phthalazin-1(2H)-one was prepared using 4-((4'-amino-6-(difluoromethoxy)-3'-nitro-[1,1'-biphenyl]-3-yl)methyl) phthalazin-1 (2H)-one (I-3.10.). MS (EI) for $C_{22}H_{18}F_2N_4O_2$: 409 [M+H].

Intermediate I-5.11. 4-((3',4'-Diamino-5-fluoro-[1,1'-biphenyl]-3-yl)methyl)phthalazin-1(2H)-one was prepared using 4-((4'-amino-5-fluoro-3'-nitro-[1,1'-biphenyl]-3-yl)methyl)phthalazin-1(2H)-one (1-3.11.). MS (EI) for $C_{21}H_{17}FN_4O$: 361 [M+H].

Intermediate I-5.12. 4-((3',4'-Diamino-4-fluoro-[1,1'-biphenyl]-3-yl)methyl)phthalazin-1(2H)-one was prepared using 4-((4'-amino-4-fluoro-3'-nitro-[1,1'-biphenyl]-3-yl)methyl)phthalazin-1(2H)-one (1-3.12.). MS (EI) for $C_{21}H_{17}FN_4O$: 361 [M+H].

Intermediate I-5.13. 4-((3',4'-Diamino-2-fluoro-[1,1'-biphenyl]-3-yl)methyl)phthalazin-1(2H)-one was prepared using 4-((4'-amino-2-fluoro-3'-nitro-[1,1'-biphenyl]-3-yl)methyl)phthalazin-1(2H)-one (1-3.13.). MS (EI) for $C_{21}H_{17}FN_4O$: 361 [M+H].

Intermediate I-5.14. 4-((3',4'-Diamino-4,6-difluoro-[1,1'-biphenyl]-3-yl)methyl)phthalazin-1(2H)-one was prepared using 4-((4'-amino-4,6-difluoro-3'-nitro-[1,1'-biphenyl]-3-yl)methyl) phthalazin-1(2H)-one (1-3.14.). MS (EI) for $C_{21}H_{16}F_2N_4O$: 379 [M+H].

Intermediate I-5.15. 4-((3',4'-Diamino-5,6-difluoro-[1,1'-biphenyl]-3-yl)methyl)phthalazin-1 (2H)-one was prepared using 4-((4'-amino-5,6-difluoro-3'-nitro-[1,1'-biphenyl]-3-yl)methyl) phthalazin-1(2H)-one (1-3.15.). MS (EI) for $C_{21}H_{16}F_2N_4O$: 379 [M+H].

Intermediate I-5.16. 4-((3',4'-Diamino-5-methoxy-[1,1'-biphenyl]-3-yl)methyl)phthalazin-1(2H)-one was prepared using 4-((4'-amino-5-methoxy-3'-nitro-[1,1'-biphenyl]-3-yl)methyl)phthalazin-1(2H)-one (1-3.16.). MS (EI) for $C_{22}H_{20}N_4O_2$: 373 [M+H].

Intermediate I-5.17. 4-((3',4'-Diamino-4-methoxy-[1,1'-biphenyl]-3-yl)methyl)phthalazin-1(2H)-one was prepared using 4-((4'-amino-4-methoxy-3'-nitro-[1,1'-biphenyl]-3-yl)methyl)phthalazin-1(2H)-one (1-3.17.). MS (EI) for $C_{22}H_{20}N_4O_2$: 373 [M+H].

Intermediate I-5.18. 4-((3',4'-Diamino-2-methoxy-[1,1'-biphenyl]-3-yl)methyl)phthalazin-1(2H)-one was prepared using 4-((4'-amino-2-methoxy-3'-nitro-[1,1'-biphenyl]-3-yl)methyl)phthalazin-1(2H)-one (1-3.18.). MS (EI) for $C_{22}H_{20}N_4O_2$: 373 [M+H].

Intermediate I-5.19. 4-((3',4'-Diamino-5,6-dimethoxy-[1,1'-biphenyl]-3-yl)methyl)phthalazin-1(2H)-one was prepared using 4-((4'-amino-5,6-dimethoxy-3'-nitro-[1,1'-biphenyl]-3-yl)methyl) phthalazin-1(2H)-one (1-3.19.). MS (EI) for $C_{23}H_{22}N_4O_3$: 403 [M+H].

Intermediate I-5.20. 4-((3',4'-Diamino-4,6-dimethoxy-[1,1'-biphenyl]-3-yl)methyl)phthalazin-1(2H)-one was prepared using 4-((4'-amino-4,6-dimethoxy-3'-nitro-[1,1'-biphenyl]-3-yl)methyl) phthalazin-1(2H)-one (1-3.20.). MS (EI) for $C_{23}H_{22}N_4O_3$: 403 [M+H].

Intermediate I-5.21. 4-((3',4'-Diamino-6-fluoro-4-methoxy-[1,1'-biphenyl]-3-yl)methyl)phthalazin-1(2H)-one was prepared using 4-((4'-amino-6-fluoro-4-methoxy-3'-nitro-[1,1'-biphenyl]-3-yl)methyl) phthalazin-1(2H)-one (1-3.21.). MS (EI) for $C_{22}H_{19}FN_4O_2$: 391 [M+H].

Intermediate I-5.22. 4-((3',4'-Diamino-4-fluoro-6-methoxy-[1,1'-biphenyl]-3-yl)methyl)phthalazin-1(2H)-one was prepared using 4-((4'-amino-4-fluoro-6-methoxy-3'-nitro-[1,1'-biphenyl]-3-yl)methyl)phthalazin-1(2H)-one (1-3.22.). MS (EI) for $C_{22}H_{19}FN_4O_2$: 391 [M+H].

Intermediate I-5.23. 4-((3',4'-Diamino-6-fluoro-[1,1'-biphenyl]-3-yl)methyl)-8-fluorophthalazin-1(2H)-one was prepared using 4-((4'-amino-6-fluoro-3'-nitro-[1,1'-biphenyl]-3-yl)methyl)-8-fluorophthalazin-1(2H)-one (1-3.23.). MS (EI) for $C_{21}H_{16}F_2N_4O$: 379 [M+H].

Intermediate I-5.24. 4-((3',4'-Diamino-6-fluoro-[1,1'-biphenyl]-3-yl)methyl)-7-fluorophthalazin-1(2H)-one is prepared using 4-((4'-amino-6-fluoro-3'-nitro-[1,1'-biphenyl]-3-yl)methyl)-7-fluorophthalazin-1(2H)-one (1-3.24.). MS (EI) for $C_{21}H_{16}F_2N_4O$: 379 [M+H].

Intermediate I-5.25. 4-((3',4'-Diamino-6-fluoro-[1,1'-biphenyl]-3-yl)methyl)-6-fluorophthalazin-1(2H)-one was prepared using 4-((4'-amino-6-fluoro-3'-nitro-[1,1'-biphenyl]-3-yl)methyl)-6-fluorophthalazin-1(2H)-one (1-3.25.). MS (EI) for $C_{21}H_{16}F_2N_4O$: 379 [M+H].

Intermediate I-5.26. 4-((3',4'-Diamino-6-fluoro-[1,1'-biphenyl]-3-yl)methyl)-5-fluorophthalazin-1 (2H)-one was prepared using 4-((4'-amino-6-fluoro-3'-nitro-[1,1'-biphenyl]-3-yl)methyl)-5-fluorophthalazin-1 (2H)-one (1-3.26.). MS (EI) for $C_{21}H_{16}F_2N_4O$: 379 [M+H].

Intermediate I-5.27. 4-((3',4'-Diamino-6-fluoro-[1,1'-biphenyl]-3-yl)methyl)-5,8-difluorophthalazin-1(2H)-one was prepared using 4-((4'-amino-6-fluoro-3'-nitro-[1,1'-biphenyl]-3-yl)methyl)-5,8-difluorophthalazin-1(2H)-one (1-3.27.). MS (EI) for $C_{21}H_{15}F_3N_4O$: 397 [M+H].

Intermediate I-5.28. 4-((3',4'-Diamino-6-fluoro-[1,1'-biphenyl]-3-yl)methyl)-6,7-difluorophthalazin-1(2H)-one is prepared using 4-((4'-amino-6-fluoro-3'-nitro-[1,1'-biphenyl]-3-yl)methyl)-6,7-difluorophthalazin-1(2H)-one (1-3.28.). MS (EI) for $C_{21}H_{15}F_3N_4O$: 397 [M+H].

Intermediate I-5.29. 4-((3',4'-Diamino-6-fluoro-[1,1'-biphenyl]-3-yl)methyl)-8-methylphthalazin-1(2H)-one was prepared using 4-((4'-amino-6-fluoro-3'-nitro-[1,1'-biphe- Intermediate I-5.29. ...nyl]-3-yl)methyl)-8-methylphthalazin-1(2H)-one (1-3.29.). MS (EI) for $C_{22}H_{19}FN_4O$: 375 [M+H].

Intermediate I-5.30. 4-((3',4'-Diamino-6-fluoro-[1,1'-biphenyl]-3-yl)methyl)-7-methylphthalazin-1(2H)-one was prepared using 4-((4'-amino-6-fluoro-3'-nitro-[1,1'-biphenyl]-3-yl)methyl)-7-methylphthalazin-1(2H)-one (1-3.30.). MS (EI) for $C_{22}H_{19}FN_4O$: 375 [M+H].

Intermediate I-5.31. 4-((3',4'-Diamino-6-fluoro-[1,1'-biphenyl]-3-yl)methyl)-6-methylphthalazin-1(2H)-one was prepared using 4-((4'-amino-6-fluoro-3'-nitro-[1,1'-biphenyl]-3-yl)methyl)-6-methylphthalazin-1(2H)-one (1-3.31.). MS (EI) for $C_{22}H_{19}FN_4O$: 375 [M+H].

Intermediate I-5.32. 6-Chloro-4-((3',4'-diamino-6-fluoro-[1,1'-biphenyl]-3-yl)methyl)phthalazin-1(2H)-one can is using 4-((4'-amino-6-fluoro-3'-nitro-[1,1'-biphenyl]-3-yl)methyl)-6-chloro-phthalazin-1(2H)-one (1-3.32.). MS (EI) for $C_{21}H_{16}ClFN_4O$: 395 [M+H].

Intermediate I-5.33. 4-((3',4'-Diamino-6-fluoro-[1,1'-biphenyl]-3-yl)methyl)-6-(trifluoromethyl) phthalazin-1(2H)-one was prepared using 4-((4'-amino-6-fluoro-3'-nitro-[1,1'-biphenyl]-3-yl)methyl)-6-(trifluoromethyl)phthalazin-1(2H)-one (I-3.33.). MS (EI) for $C_{22}H_{16}F_4N_4O$: 429 [M+H].

Intermediate I-5.34. 4-((3',4'-Diamino-6-fluoro-[1,1'-biphenyl]-3-yl)methyl)-6-methoxy-phthalazin-1(2H)-one is prepared using 4-((4'-amino-6-fluoro-3'-nitro-[1,1'-biphenyl]-3-yl)methyl)-6-methoxyphthalazin-1(2H)-one (1-3.34.). MS (EI) for $C_{22}H_{19}FN_4O_2$: 391 [M+H].

Intermediate I-5.35. 4-((3',4'-Diamino-6-fluoro-[1,1'-biphenyl]-3-yl)methyl)-6-(trifluoromethoxy) phthalazin-1(2H)-one was prepared using 4-((4'-amino-6-fluoro-3'-nitro-[1,1'-biphenyl]-3-yl)methyl)-6-(trifluoromethoxy) phthalazin-1(2H)-one (I-3.35.). MS (EI) for $C_{22}H_{16}F_4N_4O_2$: 445 [M+H].

Intermediate I-5.36. 4-((3',4'-Diamino-6-fluoro-[1,1'-biphenyl]-3-yl)methyl)-6,7-dimethoxyphthalazin-1(2H)-one was prepared using 4-((4'-amino-6-fluoro-3'-nitro-[1,1'-biphenyl]-3-yl)methyl)-6,7-dimethoxyphthalazin-1 (2H)-one (1-3.36.). MS (EI) for $C_{23}H_{21}FN_4O_3$: 421.

Intermediate I-5.37. 4-((3',4'-Diamino-6-fluoro-[1,1'-biphenyl]-3-yl)methyl)-5,7-dimethoxy-phthalazin-1(2H)-one is prepared using 4-((4'-amino-6-fluoro-3'-nitro-[1,1'-biphenyl]-3-yl) methyl)-5,7-dimethoxyphthalazin-1(2H)-one (1-3.37.). MS (EI) for $C_{23}H_{21}FN_4O_3$: 421.

Intermediate I-5.38. 4-((5-(3,4-Diaminophenyl)furan-2-yl)methyl)phthalazin-1(2H)-one was prepared using 4-((5-(4-amino-3-nitrophenyl)furan-2-yl)methyl)phthalazin-1(2H)-one (I-3.38.). MS (EI) for $C_{19}H_{16}N_4O_2$: 333 [M+H].

Intermediate I-5.39. 4-((4-(3,4-Diaminophenyl)furan-2-yl)methyl)phthalazin-1 (2H)-one was prepared using 4-((4-(4-amino-3-nitrophenyl)furan-2-yl)methyl)phthalazin-1(2H)-one (I-3.39.). MS (EI) for $C_{19}H_{16}N_4O_2$: 333 [M+H].

Intermediate I-5.40. 4-((3',4'-Diamino-5',6-difluoro-[1,1'-biphenyl]-3-yl)methyl)phthalazin-1(2H)-one was prepared using 4-((4'-amino-3',6-difluoro-5'-nitro-[1,1'-biphenyl]-3-yl)methyl) phthalazin-1(2H)-one (1-3.40.). MS (EI) for $C_{21}H_{16}F_2N_4O$: 379 [M+H].

Intermediate I-5.41. 4-((4',5'-Diamino-2',6-difluoro-[1,1'-biphenyl]-3-yl)methyl)phthalazin-1(2H)-one was prepared using 4-((4'-amino-2',6-difluoro-5'-nitro-[1,1'-biphenyl]-3-yl)methyl) phthalazin-1(2H)-one (1-3.56.). MS (EI) for $C_{21}H_{16}F_2N_4O$: 379 [M+H].

Intermediate I-5.42. 4-((3',4'-Diamino-2',6-difluoro-[1,1'-biphenyl]-3-yl)methyl)phthalazin-1(2H)-one was prepared using 4-((4'-amino-2',6-difluoro-3'-nitro-[1,1'-biphenyl]-3-yl)methyl) phthalazin-1(2H)-one (1-3.42.). MS (EI) for $C_{21}H_{16}F_2N_4O$: 379 [M+H].

Intermediate I-5.44. 4-(3-(5,6-Diaminopyridin-2-yl)-4-fluorobenzyl)phthalazin-1(2H)-one was prepared using 4-(3-(6-amino-5-nitropyridin-2-yl)-4-fluorobenzyl)phthalazin-1(2H)-one (1-3.59.). MS (EI) for $C_{20}H_{16}FN_5O$: 362 [M+H].

Intermediate I-5.45. 4-(3-(5,6-Diaminopyridin-3-yl)-4-fluorobenzyl)phthalazin-1 (2H)-one is prepared using 4-(3-(6-amino-5-nitropyridin-3-yl)-4-fluorobenzyl)phthalazin-1(2H)-one (1-3.45.). MS (EI) for $C_{20}H_{16}FN_5O$: 362 [M+H].

Intermediate I-5.46. 4-(3-(4,5-Diaminopyridin-2-yl)-4-fluorobenzyl)phthalazin-1 (2H)-one is prepared using 4-(3-(4-amino-5-nitropyridin-2-yl)-4-fluorobenzyl)phthalazin-1(2H)-one (1-3.61.). MS (EI) for $C_{20}H_{16}FN_5O$: 362 [M+H].

Intermediate I-5.47. 4-(3-(5,6-Diamino-2-methylpyridin-3-yl)-4-fluorobenzyl)phthalazin-1 (2H)-one was prepared using 4-(3-(6-amino-2-methyl-5-nitropyridin-3-yl)-4-fluorobenzyl)phthalazin-1(2H)-one (1-3.47.). MS (EI) for $C_{21}H_{18}FN_5O$: 376 [M+H].

Intermediate I-5.48. 4-(3-(5,6-Diamino-4-methylpyridin-3-yl)-4-fluorobenzyl)phthalazin-1 (2H)-one is prepared using 4-(3-(6-amino-4-methyl-5-nitropyridin-3-yl)-4-fluorobenzyl) phthalazin-1(2H)-one (1-3.48.). MS (EI) for $C_{21}H_{18}FN_5O$: 376 [M+H].

Intermediate I-5.49. 4-((3',4'-Diamino-2-fluoro-[1,1'-biphenyl]-4-yl)methyl)phthalazin-1(2H)-one was prepared using 4-((4'-amino-2-fluoro-3'-nitro-[1,1'-biphenyl]-4-yl)methyl)phthalazin-1(2H)-one (1-3.49.). MS (EI) for $C_{21}H_{17}FN_4O$: 361 [M+H].

Example 1

Example 1.1. Methyl (5-{2-fluoro-5-[(4-oxo-3,4-dihydrophthalazin-1-yl)methyl]phenyl}-1H-benzimidazol-2-yl)carbamate

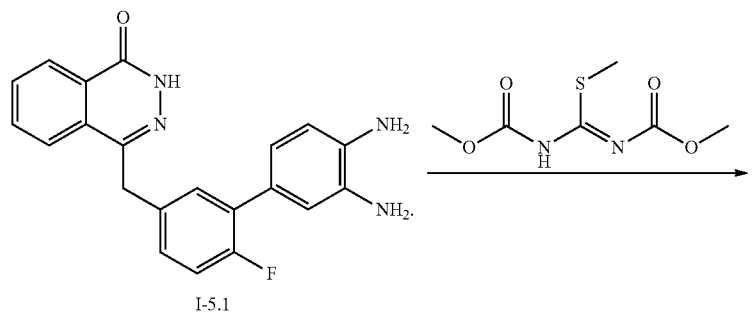

I-5.1

-continued

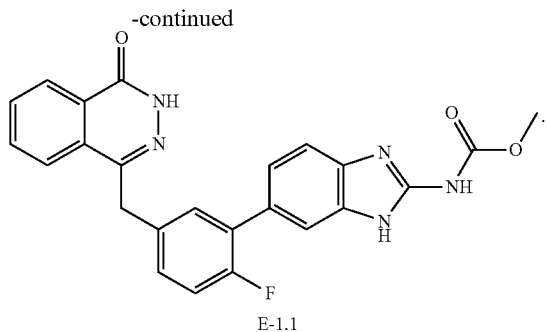

E-1.1

A solution of 4-((3',4'-diamino-6-fluoro-[1,1'-biphenyl]-3-yl)methyl)phthalazin-1(2H)-one (I-5.1.) (0.36 g, 1.00 mmol) and 1,3-bis(methoxycarbonyl)-2-methyl-2-thiopseudourea (0.21 g, 1.00 mmol) in acetic acid (5.0 mL) was stirred at 98° C. for 18 hours. After cooling the reaction mixture to room temperature it was diluted with water (5 mL) and the pH was adjusted to 8 by the addition of 10N aqueous sodium hydroxide (8.6 mL), and then partitioned with ethyl acetate (100 mL). The organic layer was separated, washed with saturated aqueous sodium bicarbonate (50 ml), brine (50 mL), dried over anhydrous sodium sulfate and concentrated. The resulting crude was purified by gradient silica gel flash chromatography (5-20% 7N ammonia in methanol in ethyl acetate) to give methyl (5-(2-fluoro-5-((4-oxo-3,4-dihydrophthalazin-1-yl)methyl)phenyl)-H-benzimidazol-2-yl)carbamate (E-1.1.) (0.25 g, 57%). 1H-NMR (300 MHz, $d_6$-DMSO): 12.58 (s, 1H), 11.82 (br s, 2H), 8.26 (d, 1H), 8.04 (d, 1H), 7.90 (t, 1H), 7.80 (t, 1H), 7.54-7.46 (m, 2H), 7.44 (d, 1H), 7.26 (m, 1H), 7.20 (m, 2H), 4.34 (s, 2H), 3.80 (s, 3H). MS (EI) for $C_{24}H_{18}FN_5O_3$: 444 [M+H].

Example E-1.2

Methyl (5-(3-((4-oxo-3,4-dihydrophthalazin-1-yl)methyl) phenyl)-1H-benzoimidazol-2-yl)carbamate was prepared using 4-((3',4'-diamino-[1,1'-biphenyl]-3-yl)methyl)phthalazin-1(2H)-one) (I-5.2.). 1H-NMR (300 MHz, $d_6$-DMSO): 12.58 (s, 1H), 8.25 (d, 1H), 8.02 (d, 1H), 7.88 (t, 1H), 7.81 (t, 1H), 7.57 (m, 2H), 7.43 (m, 2H), 7.29 (m, 2H), 7.20 (m, 1H), 4.35 (s, 2H), 3.77 (s, 3H). MS (EI) for $C_{24}H_{19}N_5O_3$: 426 [M+H].

Example E-1.3

Methyl (5-(2-chloro-5-((4-oxo-3,4-dihydrophthalazin-1-yl)methyl)phenyl)-1H-benzoimidazol-2-yl)carbamate was prepared using 4-((3',4'-diamino-6-chloro-[1,1'-biphenyl]-3-yl)methyl)phthalazin-1 (2H)-one (I-5.3.). 1H-NMR (300 MHz, $d_6$-DMSO): 12.60 (s, 1H), 8.26 (d, 1H), 8.04 (d, 1H), 7.92 (t, 1H), 7.82 (t, 1H), 7.49 (m, 2H), 7.45 (d, 1H), 7.26-7.18 (m, 3H), 4.36 (s, 2H), 3.78 (s, 3H). MS (EI) for $C_{24}H_{18}ClN_5O_3$: 460 [M+H].

Example E-1.4

Methyl (5-(2-methyl-5-((4-oxo-3,4-dihydrophthalazin-1-yl)methyl)phenyl)-1H-benzoimidazol-2-yl)carbamate was prepared using 4-((3',4'-diamino-6-methyl-[1,1'-biphenyl]-3-yl)methyl)phthalazin-1(2H)-one (I-5.4.). 1H-NMR (300 MHz, $d_6$-DMSO): 12.58 (s, 1H), 8.26 (d, 1H), 8.02 (d, 1H), 7.89 (t, 1H), 7.82 (t, 1H), 7.45 (s, 1H), 7.42 (d, 1H), 7.26-7.22 (m, 2H), 7.12 (d, 1H), 7.04 (d, 1H), 4.28 (s, 2H), 3.78 (s, 3H), 2.42 (s, 3H). MS (EI) for $C_{25}H_{21}N_5O_3$: 440 [M+H].

Example E-1.5

Methyl (5-(5-((4-oxo-3,4-dihydrophthalazin-1-yl) methyl)-2-(trifluoromethyl) phenyl)-1H-benzoimidazol-2-yl)carbamate was prepared using 4-((3',4'-diamino-6-(trifluoro-methyl)-[1,1'-biphenyl]-3-yl)methyl)phthalazin-1 (2H)-one (I-5.5). 1H-NMR (300 MHz, $d_6$-DMSO): 12.60 (s, 1H), 8.26 (d, 1H), 8.04 (d, 1H), 7.92 (t, 1H), 7.82 (t, 1H), 7.50 (m, 2H), 7.47 (d, 1H), 7.26-7.18 (m, 3H), 4.35 (s, 2H), 3.78 (s, 3H). MS (EI) for $C_{25}H_{18}F_3N_5O_3$: 494 [M+H].

Example E-1.6

Methyl (5-(5-((4-oxo-3,4-dihydrophthalazin-1-yl) methyl)-2-(trifluoromethoxy) phenyl)-1H-benzoimidazol-2-yl)carbamate carbamate was prepared using 4-((3',4'-diamino-6-(trifluoromethoxy)-[1,1'-biphenyl]-3-yl)methyl) phthalazin-1(2H)-one (I-5.6.). 1H-NMR (300 MHz, $d_6$-DMSO): 12.58 (s, 1H), 8.25 (d, 1H), 8.03 (d, 1H), 7.89 (t, 1H), 7.83 (t, 1H), 7.45 (s, 1H), 7.36 (d, 1H), 7.26 (s, 1H), 7.22 (d, 1H), 7.10 (d, 1H), 6.98 (d, 1H), 4.28 (s, 2H), 3.78 (s, 3H). MS (EI) for $C_{25}H_{18}F_3N_5O_4$: 510 [M+H].

Example E-1.7

Methyl (5-(2-methoxy-5-((4-oxo-3,4-dihydrophthalazin-1-yl)methyl)phenyl)-1H-benzoimidazol-2-yl)carbamate was prepared using 4-((3',4'-diamino-6-methoxy-[1,1'-biphenyl]-3-yl)methyl)phthalazin-1(2H)-one (I-5.7.). 1H-NMR (300 MHz, $d_6$-DMSO): 12.56 (s, 1H), (d, 1H), 8.03 (d, 1H), 7.88 (t, 1H), 7.82 (t, 1H), 7.44 (s, 1H), 7.39 (d, 1H), 7.26 (s, 1H), 7.24 (d, 1H), 7.06 (d, 1H), 6.96 (d, 1H), 4.28 (s, 2H), 3.80 (s, 3H). MS (EI) for $C_{25}H_{21}N_5O_4$: 456 [M+H].

Example E-1.8

Methyl (5-(2-ethoxy-5-((4-oxo-3,4-dihydrophthalazin-1-yl)methyl)phenyl)-1H-benzoimidazol-2-yl)carbamate was prepared using 4-((3',4'-diamino-6-ethoxy-[1,1'-biphenyl]-3-yl)methyl)phthalazin-1(2H)-one (I-5.8.). 1H-NMR (300 MHz, $d_6$-DMSO): 12.57 (s, 1H), 8.26 (d, 1H), 8.04 (d, 1H), 7.89 (t, 1H), 7.82 (t, 1H), 7.43 (s, 1H), 7.37 (d, 1H), 7.26 (s, 1H), 7.22 (d, 1H), 7.10 (d, 1H), 6.98 (d, 1H), 4.63 (q, 2H), 4.28 (s, 2H), 3.79 (s, 3H), 1.58 (t, 3H). MS (EI) for $C_{26}H_{23}N_5O_4$: 470 [M+H].

Example E-1.9

Methyl (5-(2-(2-methoxyethoxy)-5-((4-oxo-3,4-dihydrophthalazin-1-yl)methyl)phenyl)-1H-benzoimidazol-2-yl)carbamate was prepared using 4-((3',4'-diamino-6-(2-methoxyethoxy)-[1,1'-biphenyl]-3-yl)methyl)phthalazin-1(2H)-one (I-5.9.). 1H-NMR (300 MHz, $d_6$-DMSO): 12.56 (s, 1H), 8.25 (d, 1H), 8.02 (d, 1H), 7.88 (t, 1H), 7.82 (t, 1H), 7.43 (s, 1H), 7.40 (d, 1H), 7.28 (s, 1H), 7.22 (d, 1H), 7.11 (d, 1H), 6.96 (d, 1H), 4.30 (m, 2H), 4.28 (s, 2H), 3.80 (s, 3H), 3.60 (m, 2H), 3.78 (s, 3H). MS (EI) for $C_{27}H_{25}N_5O_5$: 500 [M+H].

Example E-1.10

Methyl (5-(2-(difluoromethoxy)-5-((4-oxo-3,4-dihydrophthalazin-1-yl)methyl)phenyl)-1H-benzoimidazol-2-yl)carbamate was prepared using 4-((3',4'-diamino-6-(difluoromethoxy)-[1,1'-biphenyl]-3-yl)methyl)phthalazin-1(2H)-one (I-5.10.). 1H-NMR (300 MHz, $d_6$-DMSO): 12.58 (s, 1H), 8.26 (d, 1H), 8.03 (d, 1H), 7.90 (t, 1H), 7.82 (t, 1H), 7.43 (m, 2H), 7.41 (d, 1H), 7.26 (m, 1H), 7.22-7.12 (m, 3H), 4.35 (s, 2H), 3.78 (s, 3H). MS (EI) for $C_{25}H_{19}F_2N_5O_4$: 492 [M+H].

Example E-1.11

Methyl (5-(3-fluoro-5-((4-oxo-3,4-dihydrophthalazin-1-yl)methyl)phenyl)-1H-benzoimidazol-2-yl)carbamate was prepared using 4-((3',4'-diamino-5-fluoro-[1,1'-biphenyl]-3-yl)methyl)phthalazin-1(2H)-one (I-5.11.). 1H-NMR (300 MHz, $d_6$-DMSO): 12.60 (s, 1H), 8.24 (d, 1H), 8.04 (d, 1H), 7.90 (t, 1H), 7.82 (t, 1H), 7.62 (s, 1H), 7.47-7.42 (m, 2H), 7.31 (d, 1H), 7.26 (dd, 1H), 7.07 (d, 1H), 4.38 (s, 2H), 3.78 (s, 3H). MS (EI) for $C_{24}H_{18}FN_5O_3$: 444 [M+H].

Example E-1.12

Methyl (5-(4-fluoro-3-((4-oxo-3,4-dihydrophthalazin-1-yl)methyl)phenyl)-1H-benzoimidazol-2-yl)carbamate was prepared using 4-((3',4'-diamino-4-fluoro-[1,1'-biphenyl]-3-yl)methyl)phthalazin-1(2H)-one (I-5.12.). 1H-NMR (300 MHz, $d_6$-DMSO): 12.59 (s, 1H), 8.26 (d, 1H), 8.04 (d, 1H), 7.90 (t, 1H), 7.82 (t, 1H), 7.48 (m, 2H), 7.45 (d, 1H), 7.30 (m, 1H), 7.21 (m, 2H), 4.35 (s, 2H), 3.79 (s, 3H). MS (EI) for $C_{24}H_{18}FN_5O_3$: 444 [M+H].

Example E-1.13

Methyl (5-(2-fluoro-3-((4-oxo-3,4-dihydrophthalazin-1-yl)methyl)phenyl)-1H-benzoimidazol-2-yl)carbamate was prepared using 4-((3',4'-diamino-2-fluoro-[1,1'-biphenyl]-3-yl)methyl)phthalazin-1(2H)-one (I-5.13.). 1H-NMR (300 MHz, $d_6$-DMSO): 12.59 (s, 1H), 8.26 (d, 1H), 8.04 (d, 1H), 7.90 (t, 1H), 7.82 (t, 1H), 7.52 (s, 1H), 7.45 (m, 2H), 7.22 (m, 3H), 4.36 (s, 2H), 3.78 (s, 3H). MS (EI) for $C_{24}H_{18}FN_5O_3$: 444 [M+H].

Example E-1.14

Methyl (5-(2,4-difluoro-5-((4-oxo-3,4-dihydrophthalazin-1-yl)methyl)phenyl)-1H-benzoimidazol-2-yl)carbamate was prepared using 4-((3',4'-diamino-4,6-difluoro-[1,1'-biphenyl]-3-yl)methyl)phthalazin-1(2H)-one (I-5.14.) 1H-NMR (300 MHz, $d_6$-DMSO): 12.60 (s, 1H), 8.26 (d, 1H), 8.04 (d, 1H), 7.90 (t, 1H), 7.82 (t, 1H), 7.48 (m, 2H), 7.45 (d, 1H), 7.21 (d, 1H), 6.84 (m, 1H), 4.35 (s, 2H), 3.78 (s, 3H). MS (EI) for $C_{24}H_{17}F_2N_5O_3$: 462 [M+H].

Example E-1.15

Methyl (5-(2,3-difluoro-5-((4-oxo-3,4-dihydrophthalazin-1-yl)methyl)phenyl)-1H-benzoimidazol-2-yl)carbamate was prepared using 4-((3',4'-diamino-5,6-difluoro-[1,1'-biphenyl]-3-yl)methyl)phthalazin-1(2H)-one (I-5.15.). 1H-NMR (300 MHz, $d_6$-DMSO): 12.59 (s, 1H), 8.25 (d, 1H), 8.04 (d, 1H), 7.92 (t, 1H), 7.83 (t, 1H), 7.49 (m, 3H), 7.23 (d, 1H), 7.08 (m, 1H), 4.35 (s, 2H), 3.78 (s, 3H). MS (EI) for $C_{24}H_{17}F_2N_5O_3$: 462 [M+H].

Example E-1.16

Methyl (5-(3-methoxy-5-((4-oxo-3,4-dihydrophthalazin-1-yl)methyl)phenyl)-1H-benzoimidazol-2-yl)carbamate was prepared using 4-((3',4'-diamino-5-methoxy-[1,1'-biphenyl]-3-yl)methyl)phthalazin-1(2H)-one (I-5.16.). 1H-NMR (300 MHz, $d_6$-DMSO): 12.56 (s, 1H), 8.24 (d, 1H), 8.03 (d, 1H), 7.89 (t, 1H), 7.82 (t, 1H), 7.43 (s, 1H), 7.36 (d, 1H), 7.21 (d, 1H), 7.20 (s, 1H), 7.18 (s, 1H), 6.98 (d, 1H), 4.28 (s, 2H), 3.76 (3H), 3.70 (s, 3H). MS (EI) for $C_{25}H_{21}N_5O_4$: 456 [M+H].

Example E-1.17

Methyl (5-(4-methoxy-3-((4-oxo-3,4-dihydrophthalazin-1-yl)methyl)phenyl)-1H-benzoimidazol-2-yl)carbamate was prepared using 4-((3',4'-diamino-4-methoxy-[1,1'-biphenyl]-3-yl)methyl)phthalazin-1(2H)-one (I-5.17.). 1H-NMR (300 MHz, $d_6$-DMSO): 12.56 (s, 1H), 8.2 (d, 1H), 8.02 (d, 1H), 7.88 (t, 1H), 7.82 (t, 1H), 7.44 (s, 1H), 7.38 (d, 1H), 7.26 (s, 1H), 7.19-7.12 (m, 2H), 6.98 (d, 1H), 4.28 (s, 2H), 3.78 (s, 3H), 3.64 (s, 3H). MS (EI) for $C_{25}H_{21}N_5O_4$: 456 [M+H].

Example E-1.18

Methyl (5-(2-methoxy-3-((4-oxo-3,4-dihydrophthalazin-1-yl)methyl)phenyl)-H-benzoimidazol-2-yl)carbamate was prepared using 4-((3',4'-diamino-2-methoxy-[1,1'-biphenyl]-3-yl)methyl)phthalazin-1(2H)-one (I-5.18.). 1H-NMR (300 MHz, $d_6$-DMSO): 12.57 (s, 1H), 8.25 (d, 1H), 8.02 (d, 1H), 7.88 (t, 1H), 7.82, (t, 1H), 7.56 (s, 1H), 7.42 (d, 1H), 7.23 (m, 2H), 7.08 (m, 2H), 4.36 (s, 2H), 3.70 (s, 3H), 3.30 (s, 3H). MS (EI) for $C_{25}H_{21}N_5O_4$: 456 [M+H].

Example E-1.19

Methyl (5-(2,3-dimethoxy-5-((4-oxo-3,4-dihydrophthalazin-1-yl)methyl)phenyl)-1H-benzoimidazol-2-yl)carbamate was prepared using 4-((3',4'-diamino-5,6-dimethoxy-[1,1'-biphenyl]-3-yl)methyl)phthalazin-1(2H)-one (I-5.1.). 1H-NMR (300 MHz, $d_6$-DMSO): 12.56 (s, 1H), 8.24 (d, 1H), 8.02 (d, 1H), 7.88 (t, 1H), 7.82, (t, 1H), 7.44 (s, 1H), 7.38 (d, 1H), 7.22 (s, 1H), 6.98 (d, 1H), 6.88 (s, 1H), 4.28 (s, 2H), 3.78 (s, 3H), 3.70 (s, 6H). MS (EI) for $C_{26}H_{23}N_5O_5$: 486 [M+H].

Example E-1.20

Methyl (5-(2,4-dimethoxy-5-((4-oxo-3,4-dihydrophthalazin-1-yl)methyl) phenyl)-1H-benzoimidazol-2-yl)carbamate was prepared using 4-((3',4'-diamino-4,6-dimethoxy-[1,1'-biphenyl]-3-yl)methyl)phthalazin-1(2H)-one (I-5.20.).

1H-NMR (300 MHz, d$_6$-DMSO): 12.56 (s, 1H), 8.24 (d, 1H), 8.03 (d, 1H), 7.88 (t, 1H), 7.82, (t, 1H), 7.44 (s, 1H), 7.37 (d, 1H), 7.27 (s, 1H), 6.98 (d, 1H), 6.68 (s, 1H), 4.28 (s, 2H), 3.77 (s, 3H), 3.70 (s, 3H), 3.68 (s, 3H). MS (EI) for C$_{26}$H$_{23}$N$_5$O$_5$: 486 [M+H].

Example E-1.21

Methyl (5-(2-fluoro-4-methoxy-5-((4-oxo-3,4-dihydrophthalazin-1-yl)methyl) phenyl)-1H-benzoimidazol-2-yl)carbamate was prepared using 4-((3',4'-diamino-6-fluoro-4-methoxy-[1,1'-biphenyl]-3-yl)methyl)phthalazin-1(2H)-one (I-5.21.). 1H-NMR (300 MHz, d$_6$-DMSO): 12.58 (s, 1H), 8.26 (d, 1H), 8.04 (d, 1H), 7.88 (t, 1H), 7.82, (t, 1H), 7.52 (s, 1H), 7.48 (m, 2H), 7.24 (m, 1H), 7.21 (d, 1H), 4.35 (s, 2H), 3.80 (s, 3H), 3.68 (s, 3H). MS (EI) for C$_{25}$H$_{20}$FN$_5$O$_4$: 474 [M+H].

Example E-1.22

Methyl (5-(4-fluoro-2-methoxy-5-((4-oxo-3,4-dihydrophthalazin-1-yl)methyl) phenyl)-1H-benzoimidazol-2-yl)carbamate was prepared using 4-((3',4'-diamino-4-fluoro-6-methoxy-[1,1'-biphenyl]-3-yl)methyl)phthalazin-1(2H)-one can (I-5.22.). MS (EI) for C$_{25}$H$_{20}$FN$_5$O$_4$: 474 [M+H].

Example E-1.23

Methyl (5-(2-fluoro-5-((5-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-8-fluorophthalazin-1(2H)-one (I-5.23.). MS (EI) for C$_{24}$H$_{17}$F$_2$N$_5$O$_3$: 462 [M+H].

Example E-1.24

Methyl (5-(2-fluoro-5-((6-fluoro-4-oxo-3,4-dihydrophthalazin-1-yl)methyl) phenyl)-1H-benzoimidazol-2-yl)carbamate is prepared using 4-((3',4'-diamino-6-fluoro-[1,1'-biphenyl]-3-yl)methyl)-7-fluorophthalazin-1(2H)-one (I-5.24.). MS (EI) for C$_{24}$H$_{17}$F$_2$N$_5$O$_3$: 462 [M+H].

Example E-1.25

Methyl (5-(2-fluoro-5-((7-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-6-fluorophthalazin-1(2H)-one (I-5.25.). MS (EI) for C$_{24}$H$_{17}$F$_2$N$_5$O$_3$: 462 [M+H].

Example E-1.26

Methyl (5-(2-fluoro-5-((8-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-5-fluorophthalazin-1(2H)-one (I-5.26.). MS (EI) for C$_{24}$H$_{17}$F$_2$N$_5$O$_3$: 462 [M+H].

Example E-1.27

Methyl (5-(5-((5,8-difluoro-4-oxo-3,4-dihydrophthalazin-1-yl)methyl)-2-fluorophenyl)-1H-benzoimidazol-2-yl)carbamate is prepared using 4-((3',4'-diamino-6-fluoro-[1,1'-biphenyl]-3-yl)methyl)-5,8-difluorophthalazin-1(2H)-one (I-5.27.). MS (EI) for C$_{24}$H$_{16}$F$_3$N$_5$O$_3$: 480 [M+H].

Example E-1.28

Methyl (5-(5-((6,7-difluoro-4-oxo-3,4-dihydrophthalazin-1-yl)methyl)-2-fluorophenyl)-1H-benzoimidazol-2-yl)carbamate is prepared using 4-((3',4'-diamino-6-fluoro-[1,1'-biphenyl]-3-yl)methyl)-6,7-difluorophthalazin-1(2H)-one (I-5.28.). MS (EI) for C$_{24}$H$_{16}$F$_3$N$_5$O$_3$: 480 [M+H].

Example E-1.29

Methyl (5-(2-fluoro-5-((5-methyl-4-oxo-3,4-dihydrophthalazin-1-yl)methyl) phenyl)-1H-benzoimidazol-2-yl)carbamate is prepared using 4-((3',4'-diamino-6-fluoro-[1,1'-biphenyl]-3-yl)methyl)-8-methylphthalazin-1(2H)-one (I-5.29.). MS (EI) for C$_{25}$H$_{20}$FN$_5$O$_3$: 458 [M+H].

Example E-1.30

Methyl (5-(2-fluoro-5-((6-methyl-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-7-methylphthalazin-1(2H)-one (I-5.30.). 1H NMR (300 MHz, d$_6$-DMSO): 12.47 (s, 1H), 8.13 (s, 1H), 7.88 (d, 0.5H), 7.86 (s, 1H), 7.68 (d, 0.5H), 7.48 (m, 2H), 7.44 (d, 1H), 7.27 (m, 1H), 7.21 (m, 2H), 4.30 (s, 2H), 3.76 (s, 3H), 2.46 (s, 3H). MS (EI) for C$_{25}$H$_{20}$FN$_5$O$_3$: 458 [M+H].

Example E-1.31

Methyl (5-(2-fluoro-5-((7-methyl-4-oxo-3,4-dihydrophthalazin-1-yl)methyl) phenyl)-1H-benzoimidazol-2-yl)carbamate is prepared using 4-((3',4'-diamino-6-fluoro-[1,1'-biphenyl]-3-yl)methyl)-6-methylphthalazin-1(2H)-one (I-5.31.). 1H NMR (300 MHz, d$_6$-DMSO): 12.47 (s, 1H), 8.14 (d, 1H), 7.73 (s, 1H), 7.60 (d, 1H), 7.48 (m, 2H), 7.45 (d, 1H), 7.26 (m, 1H), 7.19 (m, 2H), 4.29 (s, 2H), 3.76 (s, 3H), 2.45 (s, 3H). MS (EI) for C$_{25}$H$_{20}$FN$_5$O$_3$: 458 [M+H].

Example E-1.32

Methyl (5-(5-((7-chloro-4-oxo-3,4-dihydrophthalazin-1-yl)methyl)-2-fluorophenyl)-1H-benzoimidazol-2-yl)carbamate is prepared using 6-chloro-4-((3',4'-diamino-6-fluoro-[1,1'-biphenyl]-3-yl)methyl)phthalazin-1(2H)-one (I-5.32.). MS (EI) for C$_{24}$H$_{17}$ClFN$_5$O$_3$: 478 [M+H].

Example E-1.33

Methyl (5-(2-fluoro-5-((4-oxo-7-(trifluoromethyl)-3,4-dihydrophthalazin-1-yl)methyl)phenyl)-H-benzoimidazol-2-yl)carbamate is prepared using 4-((3',4'-diamino-6-fluoro-[1,1'-biphenyl]-3-yl)methyl)-6-(trifluoromethyl)phthalazin-1(2H)-one (I-5.33.). MS (EI) for C$_{25}$H$_{17}$F$_4$N$_5$O$_3$: 512 [M+H].

Example E-1.34

Methyl (5-(2-fluoro-5-((7-methoxy-4-oxo-3,4-dihydrophthalazin-1-yl)methyl)phenyl)-H-benzoimidazol-2-yl) carbamate is prepared using 4-((3',4'-diamino-6-fluoro-[1,1'-biphenyl]-3-yl)methyl)-6-methoxyphthalazin-1(2H)-one (I-5.34.). MS (EI) for C$_{25}$H$_{20}$FN$_5$O$_4$: 474 [M+H].

Example E-1.35

Methyl (5-(2-fluoro-5-((4-oxo-7-(trifluoromethoxy)-3,4-dihydrophthalazin-1-yl)methyl)phenyl)-H-benzoimidazol-2-yl)carbamate is prepared using 4-((3',4'-diamino-6-fluoro-

[1,1'-biphenyl]-3-yl)methyl)-6-(trifluoromethoxy) phthalazin-1(2H)-one (I-5.35.). MS (EI) for $C_{25}H_{17}F_4N_5O_4$: 528 [M+H].

Example E-1.36

Methyl (5-(5-((6,7-dimethoxy-4-oxo-3,4-dihydrophthalazin-1-yl)methyl)-2-fluorophenyl)-1H-benzoimidazol-2-yl)carbamate was prepared using 4-((3',4'-diamino-6-fluoro-[1,1'-biphenyl]-3-yl)methyl)-6,7-dimethoxyphthalazin-1 (2H)-one (I-5.36.). 1H NMR (300 MHz, $d_6$-DMSO): 12.54 (s, 1H), 7.58 (s. 1H), 7.56-7.43 (m, 3H), 7.44, (s, 1H), 7.27 (m, 1H), 7.21 (m, 2H), 4.28 (s, 2H), 3.94 (s, 6H), 3.78 (s, 3H). MS (EI) for $C_{26}H_{22}FN_5O_5$: 504 [M+H].

Example E-1.37

Methyl (5-(5-((6,8-dimethoxy-4-oxo-3,4-dihydrophthalazin-1-yl)methyl)-2-fluorophenyl)-1H-benzoimidazol-2-yl)carbamate is prepared using 4-((3',4'-diamino-6-fluoro-[1,1'-biphenyl]-3-yl)methyl)-5,7-dimethoxyphthalazin-1 (2H)-one (I-5.37.). MS (EI) for $C_{26}H_{22}FN_5O_5$: 504 [M+H].

Example E-1.538

Methyl (6-(5-((4-oxo-3,4-dihydrophthalazin-1-yl)methyl) furan-2-yl)-1H-benzoimidazol-2-yl)carbamate carbamate was prepared using 4-((5-(3,4-diaminophenyl)furan-2-yl) methyl)phthalazin-1(2H)-one (I-5.38.). 1H NMR (300 MHz, $d_6$-DMSO): 12.59 (s, 1H), 8.25 (d, 1H), 8.04 (d, 1H), 7.89 (t, 1H), 7.81 (t, 1H), 7.52 (s, 1H), 7.44 (d, 1H), 7.18 (d 1H), 6.64 (d, 1H), 6.30 (d, 1H), 4.38 (s, 2H), 3.76 (s, 3H). MS (EI) for $C_{22}H_{17}N_5O_4$: 416 [M+H].

Example E-1.39

Methyl (6-(5-((4-oxo-3,4-dihydrophthalazin-1-yl)methyl) furan-3-yl)-1H-benzoimidazol-2-yl)carbamate is prepared using 4-((4-(3,4-diaminophenyl)furan-2-yl)methyl)phthalazin-1(2H)-one (I-5.39.). MS (EI) for $C_{22}H_{17}N_5O_4$: 416 [M+H].

Example E-1.40

Methyl (7-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-5',6-difluoro-[1,1'-biphenyl]-3-yl)methyl)phthalazin-1(2H)-one (I-5.40.). 1H-NMR (300 MHz, $d_6$-DMSO): 12.62 (s, 1H), 12.20 (s, 1H), 11.50 (s, 1H), 8.25 (d, 1H), 8.04 (d, 1H), 7.88 (t, 1H), 7.84 (t, 1H), 7.54 (d, 1H), 7.44 (s, 1H), 7.27 (m, 1H), 7.23 (q, 1H), 7.08 (d, 1H), 4.36 (s, 2H), 3.78 (s, 3H). MS (EI) for $C_{24}H_{17}F_2N_5O_3$: 462 [M+H].

Example E-1.41

Methyl (6-fluoro-5-(2-fluoro-5-((4-oxo-3,4-dihydrophthalazin-1-yl)methyl)phenyl)-1H-benzoimidazol-2-yl)carbamate was prepared using 4-((4',5'-diamino-2',6-difluoro-[1,1'-biphenyl]-3-yl)methyl)phthalazin-1(2H)-one (I-5.41.). 1H-NMR (300 MHz, $d_6$-DMSO): 12.58 (s, 1H), 8.24 (d, 1H), 8.02 (d, 1H), 7.89 (t, 1H), 7.82 (t, 1H), 7.41 (d, 1H), 7.33 (m, 2H), 7.24 (m, 2H), 7.21 (t, 1H), 4.34 (s, 2H), 3.75 (s, 3H). MS (EI) for $C_{24}H_{17}F_2N_5O_3$: 462 [M+H].

Example E-1.42

Methyl (4-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-2',6-difluoro-[1,1'-biphenyl]-3-yl)methyl)phthalazin-1(2H)-one (I-5.42.). 1H-NMR (300 MHz, $d_6$-DMSO): 12.57 (s, 1H), 8.23 (d, 1H), 8.02 (d, 1H), 7.88 (t, 1H), 7.80 (t, 1H), 7.41 (dd, 1H), 7.32 (m, 2H), 7.20 (t, 1H), 7.00 (t, 1H), 4.34 (s, 2H), 3.76 (s, 3H). MS (EI) for $C_{24}H_{17}F_2N_5O_3$: 462 [M+H].

Example E-1.43

Methyl (7-chloro-5-(2-fluoro-5-((4-oxo-3,4-dihydrophthalazin-1-yl)methyl)phenyl)-1H-benzoimidazol-2-yl)carbamate was prepared using 4-((4',5'-diamino-2'-chloro-6-fluoro-[1,1'-biphenyl]-3-yl)methyl)phthalazin-1(2H)-one (1-4.1.). MS (EI) for $C_{24}H_{17}ClFN_5O_3$: 478 [M+H].

Example E-1.44

Methyl (5-(2-fluoro-5-((4-oxo-3,4-dihydrophthalazin-1-yl)methyl)phenyl)-1H-imidazo[4,5-b]pyridin-2-yl)carbamate was prepared using 4-(3-(5,6-diaminopyridin-2-yl)-4-fluorobenzyl)phthalazin-1(2H)-one (I-5.44.). 1H-NMR (300 MHz, $d_6$-DMSO): 12.59 (s, 1H), 8.23 (d, 1H), 8.01 (d, 1H), 7.84 (m, 1H), 7.80 (m, 3H), 7.47 (d, 1H), 7.36 (m, 1H), 7.22 (dd, 1H), 4.36 (s, 2H), 3.76 (s, 3H). MS (EI) for $C_{23}H_{17}FN_6O_3$: 445 [M+H].

Example E-1.45

Methyl (6-(2-fluoro-5-((4-oxo-3,4-dihydrophthalazin-1-yl)methyl)phenyl)-3H-imidazo[4,5-b]pyridin-2-yl)carbamate carbamate is prepared using 4-(3-(5,6-diaminopyridin-3-yl)-4-fluorobenzyl)phthalazin-1 (2H)-one (I-5.45.). MS (EI) for $C_{23}H_{17}FN_6O_3$: 445 [M+H].

Example E-1.46

Methyl (6-(2-fluoro-5-((4-oxo-3,4-dihydrophthalazin-1-yl)methyl)phenyl)-3H-imidazo[4,5-c]pyridin-2-yl)carbamate is prepared using 4-(3-(4,5-diaminopyridin-2-yl)-4-fluorobenzyl)phthalazin-1(2H)-one (I-5.46.). MS (EI) for $C_{23}H_{17}FN_6O_3$: 445 [M+H].

Example E-1.47

Methyl (6-(2-fluoro-5-((4-oxo-3,4-dihydrophthalazin-1-yl)methyl)phenyl)-5-methyl-3H-imidazo[4,5-b]pyridin-2-yl)carbamate was prepared using 4-(3-(5,6-diamino-2-methylpyridin-3-yl)-4-fluorobenzyl)phthalazin-1(2H)-one (I-5.47.). 1H-NMR (300 MHz, $d_6$-DMSO): 12.58 (s, 1H), 8.25 (d, 1H), 8.01 (d, 1H), 7.88 (t, 1H), 7.84 (m, 1H), 7.45 (s, 1H), 7.34 (m, 2H), 7.23 (t, 1H), 4.34 (s, 2H), 3.74 (s, 3H), 2.24 (s, 3H). MS (EI) for $C_{24}H_{19}FN_6O_3$: 459 [M+H].

Example E-1.48

Methyl (6-(2-fluoro-5-((4-oxo-3,4-dihydrophthalazin-1-yl)methyl)phenyl)-7-methyl-3H-imidazo[4,5-b]pyridin-2-yl)carbamate is prepared using 4-(3-(5,6-diamino-4-methylpyridin-3-yl)-4-fluorobenzyl)phthalazin-1(2H)-one (I-5.48.). MS (EI) for $C_{24}H_{19}FN_6O_3$: 459 [M+H].

Example E-1.49

Methyl (6-(2-fluoro-4-((4-oxo-3,4-dihydrophthalazin-1-yl)methyl)phenyl)-1H-benzoimidazol-2-yl)carbamate was prepared using 4-((3',4'-diamino-2-fluoro-[1,1'-biphenyl]-4-yl)methyl)phthalazin-1(2H)-one (I-5.49.). 1H-NMR (300

MHz, d$_6$-DMSO): 12.59 (s, 1H), 8.26 (d, 1H), 8.02 (d, 1H), 7.88 (t, 1H), 7.83 (t, 1H), 7.49 (s, 1H), 7.41 (m, 2H), 7.28-7.16 (m, 3H), 4.35 (s, 2H), 3.78 (s, 3H). MS (EI) for C$_{24}$H$_{18}$FN$_5$O$_3$:444 [M+H].

Example 2

Example 2.1. Ethyl (5-{2-fluoro-5-[(4-oxo-3,4-dihydrophthalazin-1-yl)methyl]phenyl}-1H-benzimidazol-2-yl) carbamate

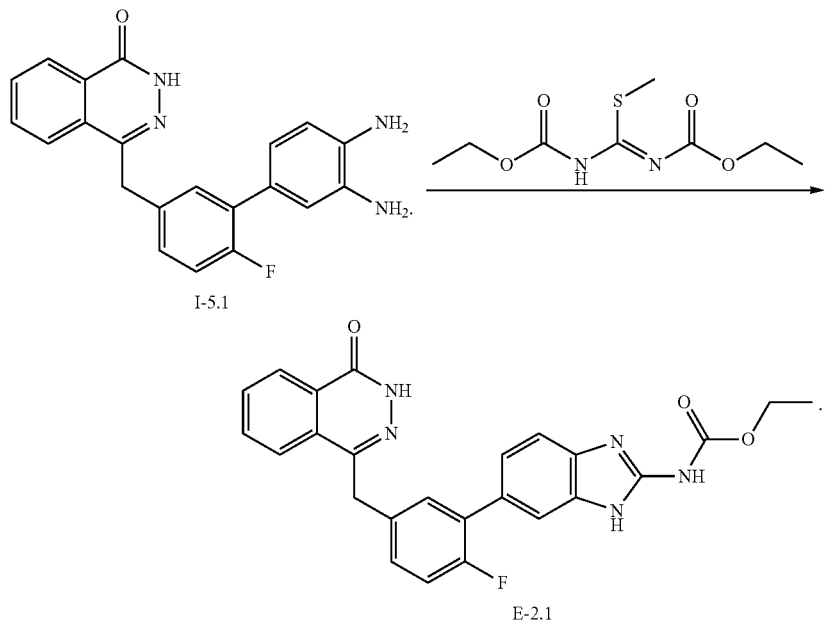

A solution of 4-((3',4'-diamino-6-fluoro-[1,1'-biphenyl]-3-yl)methyl)phthalazin-1(2H)-one (I-5.1.) (0.36 g, 1.00 mmol) and 1,3-bis(ethoxycarbonyl)-2-methyl-2-thiopseudourea (R-5.1.) (0.23 g, 1.00 mmol) in acetic acid (5.0 mL) was stirred at 98° C. for 18 hours. After cooling it to room temperature it was diluted with water (5 mL) and the pH was adjusted to 8 by the addition of 10N aqueous sodium hydroxide (8.6 mL). The white precipitate was collected by filtration, washed with water and dried in vacuo. The crude product was triturated with a mixture of ethyl acetate (45 mL) and ethanol (5 mL). The white solid was collected by filtration to give ethyl (5-{2-fluoro-5-[(4-oxo-3,4-dihydrophthalazin-1-yl)methyl]phenyl}-1H-benzimidazol-2-yl) carbamate (E-2.1.) (0.35 g, 76%). 1H-NMR (300 MHz, d$_6$-DMSO): 12.59 (s, 1H), 11.77 (br s, 2H), 8.26 (d, 1H), 8.04 (d, 1H), 7.92 (t, 1H), 7.82 (t, 1H), 7.50 (s, 1H), 7.49 (m, 1H), 7.45 (d, 1H), 7.27 (m, 1H), 7.21 (d, 1H), 7.20 (t, 1H), 4.35 (s, 2H), 4.22 (q, 2H), 1.28 (t, 3H). 13C-NMR (d$_6$-DMSO): 159.47, 159.39, 156.23, 154.31, 148.08, 145.24, 134.58, 134.53, 133.52, 131.52, 131.16, 129.24, 129.16, 129.07, 128.76, 127.91, 127.76, 126.06, 125.62, 122.02, 116.25, 115.94, 61.32, 36.74, 14.41. MS (EI) for C$_{25}$H$_{20}$FN$_5$O$_3$: 458 [M+H].

Example E-2.2

Ethyl (5-(3-((4-oxo-3,4-dihydrophthalazin-1-yl)methyl)phenyl)-1H-benzoimidazol-2-yl)carbamate was prepared using 4-((3',4'-diamino-[1,1'-biphenyl]-3-yl)methyl)phthalazin-1(2H)-one) (I-5.2.). 1H-NMR (300 MHz, d$_6$-DMSO): 12.57 (s, 1H), 11.58 (s, 2H), 8.24 (d, 1H), 8.01 (d, 1H), 7.88 (t, 1H), 7.80 (t, 1H), 7.58 (m, 2H), 7.42 (m, 2H), 7.30 (m, 2H), 7.20 (m, 1H), 4.36 (s, 2H), 4.21 (q, 2H), 1.26 (t, 3H). MS (EI) for C$_{25}$H$_{21}$N$_5$O$_3$: 440 [M+H].

Example E-2.3

Ethyl (5-(2-chloro-5-((4-oxo-3,4-dihydrophthalazin-1-yl)methyl)phenyl)-1H-benzoimidazol-2-yl)carbamate was prepared using 4-((3',4'-diamino-6-chloro-[1,1'-biphenyl]-3-yl)methyl)phthalazin-1 (2H)-one (I-5.3.). 1H-NMR (300 MHz, d$_6$-DMSO): 12.60 (s, 1H), 8.25 (d, 1H), 8.04 (d, 1H), 7.93 (t, 1H), 7.83 (t, 1H), 7.50 (m, 2H), 7.46 (d, 1H), 7.26-7.18 (m, 3H), 4.35 (s, 2H), 4.22 (q, 2H), 1.28 (t, 3H). MS (EI) for C$_{25}$H$_{20}$ClN$_5$O$_3$: 474 [M+H].

Example E-2.4

Ethyl (5-(2-methyl-5-((4-oxo-3,4-dihydrophthalazin-1-yl)methyl)phenyl)-1H-benzoimidazol-2-yl)carbamate was prepared using 4-((3',4'-diamino-6-methyl-[1,1'-biphenyl]-3-yl)methyl)phthalazin-1 (2H)-one (I-5.4.). 1H-NMR (300 MHz, d$_6$-DMSO): 12.56 (s, 1H), 8.24 (d, 1H), 8.02 (d, 1H), 7.88 (t, 1H), 7.82 (t, 1H), 7.45 (s, 1H), 7.41 (d, 1H), 7.26-7.22 (m, 2H), 7.12 (d, 1H), 7.04 (d, 1H), 4.27 (s, 2H), 4.22 (q, 2H), 2.45 (s, 3H), 1.28 (t, 3H). MS (EI) for C$_{26}$H$_{23}$N$_5$O$_3$: 454 [M+H].

Example E-2.5

Ethyl (5-(5-((4-oxo-3,4-dihydrophthalazin-1-yl)methyl)-2-(trifluoromethyl) phenyl)-1H-benzoimidazol-2-yl)carbamate was prepared using 4-((3',4'-diamino-6-(trifluoromethyl)-[1,1'-biphenyl]-3-yl)methyl)phthalazin-1(2H)-one (I-5.5.). 1H-NMR (300 MHz, d$_6$-DMSO): 12.60 (s, 1H), 8.26 (d, 1H), 8.04 (d, 1H), 7.93 (t, 1H), 7.82 (t, 1H), 7.50 (m, 2H), 7.47 (d, 1H), 7.26-7.18 (m, 3H), 4.35 (s, 2H), 4.21 (q, 2H), 1.28 (t, 3H). MS (EI) for C$_{26}$H$_{20}$F$_3$N$_5$O$_3$: 507 [M+H].

Example E-2.6

Ethyl (5-(5-((4-oxo-3,4-dihydrophthalazin-1-yl)methyl)-2-(trifluoromethoxy)phenyl)-1H-benzoimidazol-2-yl)carbamate was prepared using 4-((3',4'-diamino-6-(trifluoromethoxy)-[1,1'-biphenyl]-3-yl)methyl)phthalazin-1(2H)-one (I-5.6.). 1H-NMR (300 MHz, $d_6$-DMSO): 12.57 (s, 1H), 8.24 (d, 1H), 8.02 (d, 1H), 7.89 (t, 1H), 7.83 (t, 1H), 7.44 (s, 1H), 7.37 (d, 1H), 7.26 (s, 1H), 7.22 (d, 1H), 7.10 (d, 1H), 6.98 (d, 1H), 4.28 (s, 2H), 4.21 (q, 2H), 1.28 (t, 3H). MS (EI) for $C_{26}H_{20}F_3N_5O_4$: 524 [M+H].

Example E-2.7

Ethyl (5-(2-methoxy-5-((4-oxo-3,4-dihydrophthalazin-1-yl)methyl)phenyl)-1H-benzoimidazol-2-yl)carbamate was prepared using 4-((3',4'-diamino-6-methoxy-[1,1'-biphenyl]-3-yl)methyl)phthalazin-1(2H)-one (I-5.7.). 1H-NMR (300 MHz, $d_6$-DMSO): 12.56 (s, 1H), 11.55 (br s, 2H), 8.24 (d, 1H), 8.02 (d, 1H), 7.88 (t, 1H), 7.83 (t, 1H), 7.44 (s, 1H), 7.38 (d, 1H), 7.27 (s, 1H), 7.23 (d, 1H), 7.09 (d, 1H), 6.98 (d, 1H), 4.28 (s, 2H), 4.22 (q, 2H), 3.70 (s, 3H), 1.27 (t, 3H). 13C-NMR ($d_6$-DMSO): 159.39, 154.77, 145.57, 133.45, 131.43, 130.87, 130.79, 130.17, 129.17, 127.91, 126.02, 125.77, 111.88, 61.16, 59.77, 55.51, 36.78, 20.78, 14.43, 14.09. MS (EI) for $C_{26}H_{23}N_5O_4$: 470 [M+H].

Example E-2.8

Ethyl (5-(2-ethoxy-5-((4-oxo-3,4-dihydrophthalazin-1-yl)methyl)phenyl)-1H-benzoimidazol-2-yl)carbamate was prepared using 4-((3',4'-diamino-6-ethoxy-[1,1'-biphenyl]-3-yl)methyl)phthalazin-1(2H)-one (I-5.8.). 1H-NMR (300 MHz, $d_6$-DMSO): 12.56 (s, 1H), 11.55 (br s, 1H), 8.24 (d, 1H), 8.03 (d, 1H), 7.89 (t, 1H), 7.82 (t, 1H), 7.43 (s, 1H), 7.37 (d, 1H), 7.26 (s, 1H), 7.22 (d, 1H), 7.10 (d, 1H), 6.98 (d, 1H), 4.63 (q, 2H), 4.28 (s, 2H), 4.22 (q, 2H), 1.58 (t, 3H), 1.28 (t, 3H). MS (EI) for $C_{27}H_{25}N_5O_4$: 484 [M+H].

Example E-2.9

Ethyl (5-(2-(2-methoxyethoxy)-5-((4-oxo-3,4-dihydrophthalazin-1-yl)methyl)phenyl)-1H-benzoimidazol-2-yl)carbamate was prepared using 4-((3',4'-diamino-6-(2-methoxyethoxy)-[1,1'-biphenyl]-3-yl)methyl)phthalazin-1(2H)-one (I-5.9.). 1H-NMR (300 MHz, $d_6$-DMSO): 12.56 (s, 1H), 8.24 (d, 1H), 8.02 (d, 1H), 7.88 (t, 1H), 7.82 (t, 1H), 7.44 (s, 1H), 7.38 (d, 1H), 7.27 (s, 1H), 7.23 (d, 1H), 7.12 (d, 1H), 6.97 (d, 1H), 4.30 (m, 2H), 4.28 (s, 2H), 4.20 (q, 2H), 3.60 (m, 2H), 3.30 (s, 3H), 1.26 (s, 3H). MS (EI) for $C_{28}H_{27}N_5O_5$: 514 [M+H].

Example E-2.10

Ethyl (5-(2-(difluoromethoxy)-5-((4-oxo-3,4-dihydrophthalazin-1-yl)methyl)phenyl)-1H-benzoimidazol-2-yl)carbamate was prepared using 4-((3',4'-diamino-6-(difluoromethoxy)-[1,1'-biphenyl]-3-yl)methyl)phthalazin-1(2H)-one (I-5.10.). 1H-NMR (300 MHz, $d_6$-DMSO): 12.58 (s, 1H), 8.25 (d, 1H), 8.04 (d, 1H), 7.89 (t, 1H), 7.82 (t, 1H), 7.44 (m, 2H), 7.42 (s, 1H), 7.26 (m, 1.5H), 7.20-7.11 (m, 2.5H), 4.35 (s, 2H), 4.22 (q, 2H), 1.26 (t, 3H). MS (EI) for $C_{26}H_{21}F_2N_5O_4$: 506 [M+H].

Example E-2.11

Ethyl (5-(3-fluoro-5-((4-oxo-3,4-dihydrophthalazin-1-yl)methyl)phenyl)-1H-benzoimidazol-2-yl)carbamate was prepared using 4-((3',4'-diamino-5-fluoro-[1,1'-biphenyl]-3-yl)methyl)phthalazin-1(2H)-one (I-5.11.). 1H-NMR (300 MHz, $d_6$-DMSO): 12.58 (s, 1H), 11.63 (br s, 2H), 8.25 (d, 1H), 8.03 (d, 1H), 7.90 (t, 1H), 7.82 (t, 1H), 7.62 (s, 1H), 7.46 (s, 1H), 7.43 (d, 1H), 7.32 (d, 1H), 7.27 (dd, 1H), 7.06 (d, 1H), 4.38 (s, 2H), 4.23 (q, 2H), 1.26 (t, 3H). MS (EI) for $C_{25}H_{20}FN_5O_3$: 458 [M+H].

Example E-2.12

Ethyl (5-(4-fluoro-3-((4-oxo-3,4-dihydrophthalazin-1-yl)methyl)phenyl)-1H-benzoimidazol-2-yl)carbamate was prepared using 4-((3',4'-diamino-4-fluoro-[1,1'-biphenyl]-3-yl)methyl)phthalazin-1(2H)-one (I-5.12.). 1H-NMR (300 MHz, $d_6$-DMSO): 12.59 (s, 1H), 8.25 (d, 1H), 8.03 (d, 1H), 7.91 (t, 1H), 7.82 (t, 1H), 7.48 (m, 2H), 7.46 (d, 1H), 7.30 (m, 1H), 7.20 (m, 2H), 4.35 (s, 2H), 4.21 (q, 2H), 1.28 (t, 3H). MS (EI) for $C_{25}H_{20}FN_5O_3$: 458 [M+H].

Example E-2.13

Ethyl (5-(2-fluoro-3-((4-oxo-3,4-dihydrophthalazin-1-yl)methyl)phenyl)-1H-benzoimidazol-2-yl)carbamate was prepared using 4-((3',4'-diamino-2-fluoro-[1,1'-biphenyl]-3-yl)methyl)phthalazin-1(2H)-one (I-5.13.). 1H-NMR (300 MHz, $d_6$-DMSO): 12.59 (s, 1H), 8.26 (d, 1H), 8.04 (d, 1H), 7.92 (t, 1H), 7.83 (t, 1H), 7.52 (s, 1H), 7.46 (m, 2H), 7.24 (m, 3H), 4.35 (s, 2H), 4.21 (q, 2H), 1.28 (t, 3H). MS (EI) for $C_{25}H_{20}FN_5O_3$: 458 [M+H].

Example E-2.14

Ethyl (5-(2,4-difluoro-5-((4-oxo-3,4-dihydrophthalazin-1-yl)methyl)phenyl)-1H-benzoimidazol-2-yl)carbamate was prepared using 4-((3',4'-diamino-4,6-difluoro-[1,1'-biphenyl]-3-yl)methyl)phthalazin-1 (2H)-one (I-5.14.). 1H-NMR (300 MHz, $d_6$-DMSO): 12.59 (s, 1H), 8.26 (d, 1H), 8.03 (d, 1H), 7.91 (t, 1H), 7.82 (t, 1H), 7.48 (m, 2H), 7.44 (d, 1H), 7.22 (d, 1H), 6.84 (m, 1H), 4.34 (s, 2H), 4.22 (q, 2H), 1.28 (t, 3H). MS (EI) for $C_{25}H_{19}F_2N_5O_3$: 476 [M+H].

Example E-2.15

Ethyl (5-(2,3-difluoro-5-((4-oxo-3,4-dihydrophthalazin-1-yl)methyl)phenyl)-1H-benzoimidazol-2-yl)carbamate was prepared using 4-((3',4'-diamino-5,6-difluoro-[1,1'-biphenyl]-3-yl)methyl)phthalazin-1(2H)-one (I-5.15.). 1H-NMR (300 MHz, $d_6$-DMSO): 12.59 (s, 1H), 8.26 (d, 1H), 8.04 (d, 1H), 7.92 (t, 1H), 7.82 (t, 1H), 7.48 (m, 3H), 7.24 (d, 1H), 7.08 (m, 1H), 4.35 (s, 2H), 4.22 (q, 2H), 1.28 (t, 3H). MS (EI) for $C_{25}H_{19}F_2N_5O_3$: 476 [M+H].

Example E-2.16

Ethyl (5-(3-methoxy-5-((4-oxo-3,4-dihydrophthalazin-1-yl)methyl)phenyl)-1H-benzoimidazol-2-yl)carbamate was prepared using 4-((3',4'-diamino-5-methoxy-[1,1'-biphenyl]-3-yl)methyl)phthalazin-1(2H)-one (I-5.16.). 1H-NMR (300 MHz, $d_6$-DMSO): 12.56 (s, 1H), 8.24 (d, 1H), 8.02 (d, 1H), 7.88 (t, 1H), 7.82 (t, 1H), 7.43 (s, 1H), 7.36 (d, 1H), 7.23 (d, 1H), 7.20 (s, 1H), 7.16 (s, 1H), 6.98 (d, 1H), 4.28 (s, 2H), 4.22, (q, 2H), 3.72 (s, 3H), 1.27 (t, 3H). MS (EI) for $C_{26}H_{23}N_5O_4$: 470 [M+H].

Example E-2.17

Ethyl (5-(4-methoxy-3-((4-oxo-3,4-dihydrophthalazin-1-yl)methyl)phenyl)-1H-benzoimidazol-2-yl)carbamate was prepared using 4-((3',4'-diamino-4-methoxy-[1,1'-biphenyl]-3-yl)methyl)phthalazin-1(2H)-one (I-5.17.). 1H-NMR (300 MHz, $d_6$-DMSO): 12.56 (s, 1H), 8.24 (d, 1H), 8.02 (d, 1H), 7.88 (t, 1H), 7.83 (t, 1H), 7.44 (s, 1H), 7.38 (d, 1H), 7.27 (s, 1H), 7.19-7.12 (m, 2H), 7.00 (d, 1H), 4.28 (s, 2H), 4.22, (q, 2H), 3.64 (s, 3H), 1.27 (t, 3H). MS (EI) for $C_{26}H_{23}N_5O_4$: 470 [M+H].

Example E-2.18

Ethyl (5-(2-methoxy-3-((4-oxo-3,4-dihydrophthalazin-1-yl)methyl)phenyl)-1H-benzoimidazol-2-yl)carbamate was prepared using 4-((3',4'-diamino-2-methoxy-[1,1'-biphenyl]-3-yl)methyl)phthalazin-1(2H)-one (I-5.18.). 1H-NMR (300 MHz, $d_6$-DMSO): 12.53 (s, 1H), 8.27 (d, 1H), 8.03 (d, 1H), 7.94 (t, 1H), 7.86, (t, 1H), 7.58 (s, 1H), 7.44 (d, 1H), 7.24 (m, 2H), 7.08 (m, 2H), 4.36 (s, 2H), 4.22, (q, 2H), 3.30 (s, 3H), 1.28 (t, 3H). MS (EI) for $C_{26}H_{23}N_5O_4$: 470 [M+H].

Example E-2.19

Ethyl (5-(2,3-dimethoxy-5-((4-oxo-3,4-dihydrophthalazin-1-yl)methyl)phenyl)-1H-benzoimidazol-2-yl)carbamate was prepared using 4-((3',4'-diamino-5,6-dimethoxy-[1,1'-biphenyl]-3-yl)methyl)phthalazin-1(2H)-one (I-5.19.). 1H-NMR (300 MHz, $d_6$-DMSO): 12.56 (s, 1H), 8.24 (d, 1H), 8.03 (d, 1H), 7.87 (t, 1H), 7.82, (t, 1H), 7.44 (s, 1H), 7.37 (d, 1H), 7.22 (s, 1H), 6.98 (d, 1H), 6.88 (s, 1H), 4.28 (s, 2H), 4.22, (q, 2H), 3.70 (s, 6H), 1.27 (t, 3H). MS (EI) for $C_{27}H_{25}N_5O_5$: 500 [M+H].

Example E-2.20

Ethyl (5-(2,4-dimethoxy-5-((4-oxo-3,4-dihydrophthalazin-1-yl)methyl)phenyl)-1H-benzoimidazol-2-yl)carbamate was prepared using 4-((3',4'-diamino-4,6-dimethoxy-[1,1'-biphenyl]-3-yl)methyl)phthalazin-1(2H)-one (I-5.20.). 1H-NMR (300 MHz, $d_6$-DMSO): 12.56 (s, 1H), 8.24 (d, 1H), 8.03 (d, 1H), 7.87 (t, 1H), 7.82, (t, 1H), 7.44 (s, 1H), 7.38 (d, 1H), 7.28 (s, 1H), 6.98 (d, 1H), 6.68 (s, 1H), 4.28 (s, 2H), 4.22, (q, 2H), 3.70 (s, 3H), 3.68 (s, 3H), 1.27 (t, 3H). MS (EI) for $C_{27}H_{25}N_5O_5$: 500 [M+H].

Example E-2.21

Ethyl (5-(2-fluoro-4-methoxy-5-((4-oxo-3,4-dihydrophthalazin-1-yl)methyl) phenyl)-1H-benzoimidazol-2-yl)carbamate was prepared using 4-((3',4'-diamino-6-fluoro-4-methoxy-[1,1'-biphenyl]-3-yl)methyl)phthalazin-1(2H)-one (I-5.21.). 1H-NMR (300 MHz, $d_6$-DMSO): 12.58 (s, 1H), 8.26 (d, 1H), 8.04 (d, 1H), 7.90 (t, 1H), 7.82, (t, 1H), 7.52 (s, 1H), 7.49 (m, 2H), 7.24 (m, 1H), 7.22 (d, 1H), 4.35 (s, 2H), 4.21 (q, 2H), 3.68 (s, 3H), 1.28 (t, 3H). MS (EI) for $C_{26}H_{22}FN_5O_4$: 488 [M+H].

Example E-2.22

Ethyl (5-(4-fluoro-2-methoxy-5-((4-oxo-3,4-dihydrophthalazin-1-yl)methyl) phenyl)-1H-benzoimidazol-2-yl)carbamate was prepared using 4-((3',4'-diamino-4-fluoro-6-methoxy-[1,1'-biphenyl]-3-yl)methyl)phthalazin-1(2H)-one can (I-5.22.). MS (EI) for $C_{26}H_{22}FN_5O_4$: 488 [M+H].

Example E-2.23

Ethyl (5-(2-fluoro-5-((5-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-8-fluorophthalazin-1(2H)-one (I-5.23.). MS (EI) for $C_{25}H_{19}F_2N_5O_3$: 476 [M+H]

Example E-2.24

Ethyl (5-(2-fluoro-5-((6-fluoro-4-oxo-3,4-dihydrophthalazin-1-yl)methyl) phenyl)-1H-benzoimidazol-2-yl)carbamate is prepared using 4-((3',4'-diamino-6-fluoro-[1,1'-biphenyl]-3-yl)methyl)-7-fluorophthalazin-1(2H)-one (I-5.24.). MS (EI) for $C_{25}H_{19}F_2N_5O_3$: 476 [M+H].

Example E-2.25

Ethyl (5-(2-fluoro-5-((7-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-6-fluorophthalazin-1(2H)-one (I-5.25.). 1H NMR (300 MHz, $d_6$-DMSO): 12.56 (s, 1H), 8.24 (d, 1H), 7.96 (m, 1H), 7.78 (m, 1H), 7.52-7.47 (m, 2H), 7.45 (d, 1H), 7.27 (m, 1H), 7.20 (m, 2H), 4.36 (s, 2H), 4.20 (q, 2H), 1.27 (t, 3H). MS (EI) for $C_{25}H_{19}F_2N_5O_3$: 476 [M+H].

Example E-2.26

Ethyl (5-(2-fluoro-5-((8-fluoro-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-5-fluorophthalazin-1(2H)-one (I-5.26.). MS (EI) for $C_{25}H_{19}F_2N_5O_3$: 476 [M+H].

Example E-2.27

Ethyl (5-(5-((5,8-difluoro-4-oxo-3,4-dihydrophthalazin-1-yl)methyl)-2-fluorophenyl)-1H-benzoimidazol-2-yl)carbamate was prepared using 4-((3',4'-diamino-6-fluoro-[1,1'-biphenyl]-3-yl)methyl)-5,8-difluorophthalazin-1(2H)-one (I-5.27.). MS (EI) for $C_{25}H_{18}F_3N_5O_3$: 494 [M+H].

Example E-2.28

Ethyl (5-(5-((6,7-difluoro-4-oxo-3,4-dihydrophthalazin-1-yl)methyl)-2-fluorophenyl)-1H-benzoimidazol-2-yl)carbamate is prepared using 4-((3',4'-diamino-6-fluoro-[1,1'-biphenyl]-3-yl)methyl)-6,7-difluorophthalazin-1(2H)-one (I-5.28.). MS (EI) for $C_{25}H_{18}F_3N_5O_3$: 494 [M+H].

Example E-2.29

Ethyl (5-(2-fluoro-5-((5-methyl-4-oxo-3,4-dihydrophthalazin-1-yl)methyl) phenyl)-1H-benzoimidazol-2-yl)carbamate is prepared using 4-((3',4'-diamino-6-fluoro-[1,1'-biphenyl]-3-yl)methyl)-8-methylphthalazin-1(2H)-one (I-5.29.). MS (EI) for $C_{26}H_{22}FN_5O_3$: 472 [M+H].

Example E-2.30

Ethyl (5-(2-fluoro-5-((6-methyl-4-oxo-3,4-dihydrophthalazin-1-yl)methyl) phenyl)-1H-benzoimidazol-2-yl)carbamate was prepared using 4-((3',4'-diamino-6-fluoro-[1,1'-biphenyl]-3-yl)methyl)-7-methylphthalazin-1(2H)-one (I-5.30.). 1H NMR (300 MHz, $d_6$-DMSO): 12.46 (s, 1H), 11.56 (br s, 2H), 8.12 (s, 1H), 7.90 (d, 0.5H), 7.86 (s, 1H), 7.65 (d, 0.5H), 7.48 (m, 2H), 7.46 (d, 1H), 7.26 (m, 1H), 7.22

(m, 2H), 4.31 (s, 2H), 4.21 (q, 2H), 2.46 (s, 3H), 1.27 (t, 3H). MS (EI) for $C_{26}H_{22}FN_5O_3$: 472 [M+H].

Example E-2.31

Ethyl (5-(2-fluoro-5-((7-methyl-4-oxo-3,4-dihydrophthalazin-1-yl)methyl)phenyl)-1H-benzoimidazol-2-yl)carbamate was prepared using 4-((3',4'-diamino-6-fluoro-[1,1'-biphenyl]-3-yl)methyl)-6-methylphthalazin-1(2H)-one (I-5.31.). 1H NMR (300 MHz, $d_6$-DMSO): 12.46 (s, 1H), 11.58 (br s, 2H), 8.13 (d, 1H), 7.74 (s, 1H), 7.60 (d, 1H), 7.48 (m, 2H), 7.46 (d, 1H), 7.26 (m, 1H), 7.20 (m, 2H), 4.30 (s, 2H), 4.22 (q, 2H), 2.45 (s, 3H), 1.26 (t, 3H). MS (EI) for $C_{26}H_{22}FN_5O_3$: 472 [M+H]. MS (EI) for $C_{26}H_{22}FN_5O_3$: 472 [M+H].

Example E-2.32

Ethyl (5-(5-((7-chloro-4-oxo-3,4-dihydrophthalazin-1-yl)methyl)-2-fluorophenyl)-1H-benzoimidazol-2-yl)carbamate is prepared using 6-chloro-4-((3',4'-diamino-6-fluoro-[1,1'-biphenyl]-3-yl)methyl)phthalazin-1 (2H)-one can (I-5.32.). MS (EI) for $C_{25}H_{19}ClFN_5O_3$: 492 [M+H].

Example E-2.33

Ethyl (5-(2-fluoro-5-((4-oxo-7-(trifluoromethyl)-3,4-dihydrophthalazin-1-yl)methyl)phenyl)-H-benzoimidazol-2-yl)carbamate is prepared using 4-((3',4'-diamino-6-fluoro-[1,1'-biphenyl]-3-yl)methyl)-6-(trifluoromethyl)phthalazin-1(2H)-one (I-5.33.). MS (EI) for $C_{26}H_{19}F_4N_5O_3$: 526 [M+H].

Example E-2.34

Ethyl (5-(2-fluoro-5-((7-methoxy-4-oxo-3,4-dihydrophthalazin-1-yl)methyl)phenyl)-1H-benzoimidazol-2-yl)carbamate is prepared using 4-((3',4'-diamino-6-fluoro-[1,1'-biphenyl]-3-yl)methyl)-6-methoxyphthalazin-1(2H)-one (I-5.34.). MS (EI) for $C_{26}H_{22}FN_5O_4$: 488 [M+H].

Example E-2.35

Ethyl (5-(2-fluoro-5-((4-oxo-7-(trifluoromethoxy)-3,4-dihydrophthalazin-1-yl)methyl)phenyl)-1H-benzoimidazol-2-yl)carbamate was prepared using 4-((3',4'-diamino-6-fluoro-[1,1'-biphenyl]-3-yl)methyl)-6-(trifluoromethoxy)phthalazin-1(2H)-one (I-5.35.). MS (EI) for $C_{26}H_{19}F_4N_5O_4$: 542 [M+H].

Example E-2.36

Ethyl (5-(5-(((6,7-dimethoxy-4-oxo-3,4-dihydrophthalazin-1-yl)methyl)-2-fluorophenyl)-1H-benzoimidazol-2-yl)carbamate was prepared using 4-((3',4'-diamino-6-fluoro-[1,1'-biphenyl]-3-yl)methyl)-6,7-dimethoxyphthalazin-1(2H)-one (I-5.36.). 1H NMR (300 MHz, $d_6$-DMSO): 12.56 (s, 1H), 7.57 (s. 1H), 7.54-7.44 (m, 3H), 7.43, (s, 1H), 7.27 (m, 1H), 7.20 (m, 2H), 4.28 (s, 2H), 4.22 (q, 2H), 3.94 (s, 6H), 1.28 (t, 3H). MS (EI) for $C_{27}H_{24}FN_5O_5$: 518 [M+H].

Example E-2.37

Ethyl (5-(5-(((6,8-dimethoxy-4-oxo-3,4-dihydrophthalazin-1-yl)methyl)-2-fluorophenyl)-1H-benzoimidazol-2-yl)carbamate is prepared using 4-((3',4'-diamino-6-fluoro-[1,1'-biphenyl]-3-yl)methyl)-5,7-dimethoxyphthalazin-1(2H)-one (I-5.37.). MS (EI) for $C_{27}H_{24}FN_5O_5$: 518 [M+H].

Example E-2.38

Ethyl (6-(5-((4-oxo-3,4-dihydrophthalazin-1-yl)methyl)furan-2-yl)-1H-benzoimidazol-2-yl)carbamate was prepared using 4-((5-(3,4-diaminophenyl)furan-2-yl)methyl)phthalazin-1(2H)-one (I-5.38.). 1H NMR (300 MHz, $d_6$-DMSO): 12.59 (s, 1H), 11.63 (br s, 2H), 8.26 (d, 1H), 8.04 (d, 1H), 7.90 (t, 1H), 7.82 (t, 1H), 7.54 (s, 1H), 7.43 (d, 1H), 7.20 (d 1H), 6.65 (d, 1H), 6.30 (d, 1H), 4.39 (s, 2H), 4.22 (q, 2H), 1.26 (t, 3H). MS (EI) for $C_{23}H_{19}N_5O_4$: 430 [M+H].

Example E-2.39

Ethyl (6-(5-((4-oxo-3,4-dihydrophthalazin-1-yl)methyl)furan-3-yl)-1H-benzoimidazol-2-yl)carbamate was prepared using 4-((4-(3,4-diaminophenyl)furan-2-yl)methyl)phthalazin-1(2H)-one (I-5.39.). MS (EI) for $C_{23}H_{19}N_5O_4$: 430 [M+H].

Example E-2.40

Ethyl (7-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-5',6-difluoro-[1,1'-biphenyl]-3-yl)methyl)phthalazin-1(2H)-one (I-5.40.). 1H-NMR (300 MHz, $d_6$-DMSO): 12.61 (s, 1H), 12.20 (s, 1H), 11.44 (s, 1H), 8.25 (d, 1H), 8.04 (d, 1H), 7.90 (t, 1H), 7.84 (t, 1H), 7.54 (d, 1H), 7.43 (s, 1H), 7.30 (m, 1H), 7.24 (q, 1H), 7.08 (d, 1H), 4.36 (s, 2H), 4.24 (q, 2H), 1.28 (t, 3H). MS (EI) for $C_{25}H_{19}F_2N_5O_3$: 476 [M+H].

Example E-2.41

Ethyl (6-fluoro-5-(2-fluoro-5-((4-oxo-3,4-dihydrophthalazin-1-yl)methyl)phenyl)-1H-benzoimidazol-2-yl)carbamate was prepared using 4-((4',5'-diamino-2',6-difluoro-[1,1'-biphenyl]-3-yl)methyl)phthalazin-1(2H)-one (I-5.41.). 1H-NMR (300 MHz, $d_6$-DMSO): 12.58 (s, 1H), 11.97 (s, 1H), 11.35 (s, 1H), 8.24 (d, 1H), 8.02 (d, 1H), 7.89 (t, 1H), 7.81 (t, 1H), 7.41 (m, 1H), 7.32 (m, 2H), 7.24 (d, 1H), 7.20 (t, 1H), 4.34 (s, 2H), 4.23 (q, 2H), 1.26 (t, 3H). MS (EI) for $C_{25}H_{19}F_2N_5O_3$: 476 [M+H].

Example E-2.42

Ethyl (4-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-2',6-difluoro-[1,1'-biphenyl]-3-yl)methyl)phthalazin-1(2H)-one (I-5.42.). 1H-NMR (300 MHz, $d_6$-DMSO): 12.61 (s, 1H), 12.20 (s, 1H), 11.42 (s, 1H), 8.25 (d, 1H), 8.04 (d, 1H), 7.91 (t, 1H), 7.88 (t, 1H), 7.43 (d, 1H), 7.30 (m, 2H), 7.20 (t, 1H), 7.00 (t, 1H), 4.35 (s, 2H), 4.23 (q, 2H), 1.28 (t, 3H). MS (EI) for $C_25H_{19}F_2N_5O_3$: 476 [M+H].

Example E-2.58

Ethyl (7-chloro-5-(2-fluoro-5-((4-oxo-3,4-dihydrophthalazin-1-yl)methyl)phenyl)-1H-benzoimidazol-2-yl)carbamate was prepared using 4-((4',5'-diamino-2'-chloro-6-fluoro-[1,1'-biphenyl]-3-yl)methyl)phthalazin-1(2H)-one (1-4.1.). $^1$H-NMR (300 MHz, $d_6$-DMSO): 12.62 (s, 1H), 12.19 (s, 1H), 11.41 (s, 1H), 8.24 (d, 1H), 8.03 (d, 1H), 7.94-7.83 (m, 2H), 7.44 (d, 1H), 7.32 (m, 2H), 7.21 (t, 1H), 6.98 (t, 1H), 4.35 (m, 2H), 4.24 (q, 2H), 1.26 (t, 3H). MS (EI) for $C_{25}H_{19}ClFN_5O_3$: 492 [M+H].

Example E-2.44

Ethyl (5-(2-fluoro-5-((4-oxo-3,4-dihydrophthalazin-1-yl)methyl)phenyl)-1H-imidazo[4,5-b]pyridin-2-yl)carbamate was prepared using 4-(3-(5,6-diaminopyridin-2-yl)-4-fluorobenzyl)phthalazin-1(2H)-one (I-5.44.). 1H-NMR (300 MHz, $d_6$-DMSO): 12.59 (s, 1H), 12 01 (br s, 1H), 11.68 (br s, 1H), 8.24 (d, 1H), 8.11 (d, 1H), 7.83 (m, 1H), 7.82-7.78 (m, 3H), 7.46 (d, 1H), 7.38 (m, 1H), 7.21 (dd, 1H), 4.34 (s, 2H), 4.23 (q, 2H), 1.28 (t, 3H). MS (EI) for $C^{24}H_{19}FN_6O_3$: 459 [M+H].

Example E-2.45

Ethyl (6-(2-fluoro-5-((4-oxo-3,4-dihydrophthalazin-1-yl)methyl)phenyl)-3H-imidazo[4,5-b]pyridin-2-yl)carbamate is prepared using 4-(3-(5,6-diaminopyridin-3-yl)-4-fluorobenzyl)phthalazin-1(2H)-one (I-5.45.). MS (EI) for $C_{24}H_{19}FN_6O_3$: 459 [M+H].

Example E-2.46

Ethyl (6-(2-fluoro-5-((4-oxo-3,4-dihydrophthalazin-1-yl)methyl)phenyl)-3H-imidazo[4,5-c]pyridin-2-yl)carbamate is prepared using 4-(3-(4,5-diaminopyridin-2-yl)-4-fluorobenzyl)phthalazin-1(2H)-one can (I-5.46.). MS (EI) for $C_{24}H_{19}FN_6O_3$: 459 [M+H].

Example E-2.47

Ethyl (6-(2-fluoro-5-((4-oxo-3,4-dihydrophthalazin-1-yl)methyl)phenyl)-5-methyl-3H-imidazo[4,5-b]pyridin-2-yl)carbamate was prepared using 4-(3-(5,6-diamino-2-methylpyridin-3-yl)-4-fluorobenzyl)phthalazin-1(2H)-one (I-5.47.). 1H-NMR (300 MHz, $d_6$-DMSO): 12.58 (s, 1H), 11.92 (br s, 1H), 11.46 (br s, 1H), 8.21 (d, 1H), 8.01 (d, 1H), 7.87 (t, 1H), 7.82 (m, 1H), 7.44 (s, 1H), 7.34 (m, 2H), 7.22 (t, 1H), 4.34 (s, 2H), 4.20 (q, 2H), 2.24 (s, 3H), 1.28 (t, 3H). MS (EI) for $C_{25}H_{21}FN_6O_3$: 473 [M+H].

Example E-2.48

Ethyl (6-(2-fluoro-5-((4-oxo-3,4-dihydrophthalazin-1-yl)methyl)phenyl)-7-methyl-3H-imidazo[4,5-b]pyridin-2-yl)carbamate is prepared using 4-(3-(5,6-diamino-4-methylpyridin-3-yl)-4-fluorobenzyl)phthalazin-1(2H)-one (I-5.48.). MS (EI) for $C_{25}H_{21}FN_6O_3$: 473 [M+H].

Example E-2.49

Ethyl (6-(2-fluoro-4-((4-oxo-3,4-dihydrophthalazin-1-yl)methyl)phenyl)-1H-benzoimidazol-2-yl)carbamate was prepared using 4-((3',4'-diamino-2-fluoro-[1,1'-biphenyl]-4-yl)methyl)phthalazin-1(2H)-one (I-5.49.). 1H-NMR (300 MHz, $d_6$-DMSO): 12.59 (s, 1H), 8.26 (d, 1H), 8.01 (d, 1H), 7.88 (t, 1H), 7.82 (t, 1H), 7.50 (s, 1H), 7.42 (m, 2H), 7.26 (t, 1H), 7.17 (m, 2H), 4.35 (s, 2H), 4.19 (q, 2H), 1.26 (t, 3H). MS (EI) for $C_{25}H_{20}FN_5O_3$: 458 [M+H].

Example 3

Example 3.1. 2-Methoxyethyl (5-(2-fluoro-5-((4-oxo-3,4-dihydrophthalazin-1-yl)methyl) phenyl)-1H-benzoimidazol-2-yl)carbamate

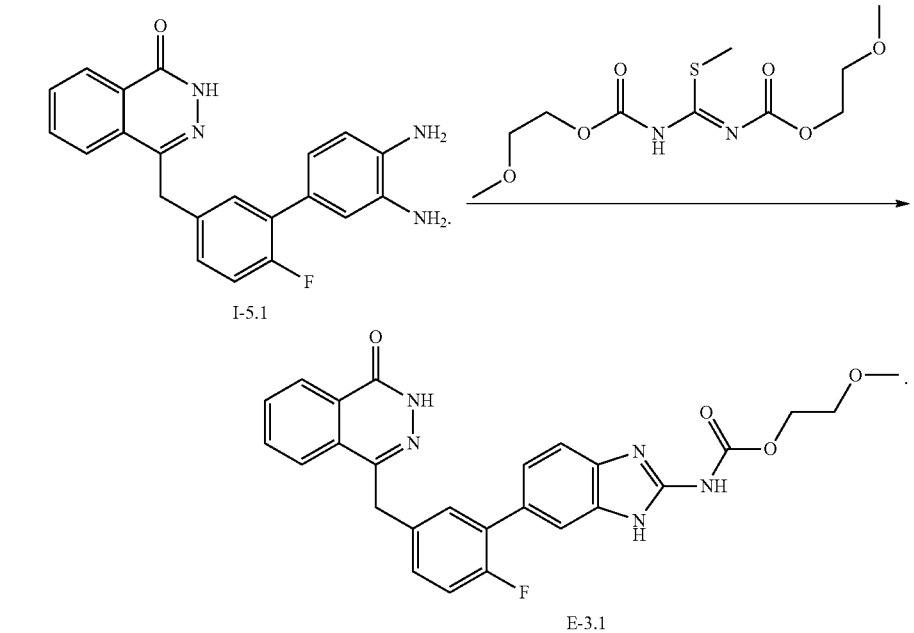

A solution of 4-((3',4'-diamino-6-fluoro-[1,1'-biphenyl]-3-yl)methyl)phthalazin-1(2H)-one (I-5.1.) (0.18 g, 0.50 mmol) and 1,3-bis(methoxyethoxycarbonyl)-2-methyl-2-thiopseudourea (R-5.2.) (0.15 g, 0.50 mmol) in acetic acid (3.0 mL) was stirred at 98° C. for 18 hours. After cooling the reaction mixture to room temperature it was diluted with water (5 mL) and the pH was adjusted to 8 by the addition of 10N aqueous sodium hydroxide (5.2 mL) and the residue was partitioned with ethyl acetate (100 mL). The organic layer was separated, washed with saturated aqueous sodium bicarbonate (2×25 mL) and brine (2×50 mL), dried over anhydrous sodium sulfate and concentrated. The resulting crude was purified by gradient silica gel flash chromatography (5-20% 7N ammonia in methanol in ethyl acetate) to give 2-methoxyethyl (5-(2-fluoro-5-((4-oxo-3,4-dihydrophthalazin-1-yl)methyl)phenyl)-1H-benzoimidazol-2-yl)carbamate (E-3.1.) (0.18 g, 68%). 1H NMR (300 MHz, d$_6$-DMSO): 12.60 (s, 1H), 8.26 (d, 1H), 8.04 (d, 1H), 7.93 (t, 1H), 7.82 (t, 1H), 4.51-7.47 (m, 2H), 7.44 (d, 1H), 7.28 (m, 1H), 7.21-7.18 (m, 2H), 4.35 (s, 2H), 4.30 (m, 2H), 3.59 (m, 2H), 3.24 (s, 3H). MS (EI) for $C_{26}H_{22}FN_5O_4$: 488 [M+H].

Example E-3.2

2-Methoxyethyl (7-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-5',6-difluoro-[1,1'-biphenyl]-3-yl)methyl)phthalazin-1(2H)-one (I-5.55.). 1H-NMR (300 MHz, d$_6$-DMSO): 12.62 (s, 1H), 8.23 (d, 1H), 8.02 (d, 1H), 7.90 (t, 1H), 7.80 (t, 1H), 7.51 (d, 1H), 7.29 (s, 1H), 7.22 (m, 1H), 7.16 (q, 1H), 6.88 (d, 1H), 4.33 (s, 2H), 4.14 (m, 2H), 3.53 (m, 2H), 3.23 (s, 3H). MS (EI) for $C_{26}H_{21}F_2N_5O_4$: 506 [M+H].

Example E-3.3

2-Methoxyethyl (6-fluoro-5-(2-fluoro-5-((4-oxo-3,4-dihydrophthalazin-1-yl)methyl)phenyl)-1H-benzoimidazol-2-yl)carbamate was prepared using 4-((4',5'-diamino-2',6-difluoro-[1,1'-biphenyl]-3-yl)methyl)phthalazin-1(2H)-one (I-5.56.). 1H-NMR (300 MHz, d$_6$-DMSO): 12.58 (s, 1H), 8.24 (d, 1H), 8.02 (d, 1H), 7.91 (t, 1H), 7.81 (t, 1H), 7.38 (d, 1H), 7.34 (m, 2H), 7.24 (d, 1H), 7.20 (t, 1H), 4.34 (s, 2H), 4.30 (m, 2H), 3.58 (m, 2H), 3.26 (s, 3H). MS (EI) for $C_{26}H_{21}F_2N_5O_4$: 506 [M+H].

Example E-3.4

2-Methoxyethyl (4-fluoro-5-(2-fluoro-5-((4-oxo-3,4-dihydrophthalazin-1-yl)methyl)phenyl)-1H-benzoimidazol-2-yl)carbamate was prepared using 4-((3',4'-diamino-2',6-difluoro-[1,1'-biphenyl]-3-yl)methyl)phthalazin-1(2H)-one (I-5.57.). 1H-NMR (300 MHz, d$_6$-DMSO): 12.56 (s, 1H), 8.23 (d, 1H), 8.02 (d, 1H), 7.89 (t, 1H), 7.81 (t, 1H), 7.41 (d, 1H), 7.34 (m, 2H), 7.20 (t, 1H), 7.00 (t, 1H), 4.33 (s, 2H), 4.30 (m, 2H), 3.60 m, (2H), 3.23 (s, 3H). MS (EI) for $C_{26}H_{21}F_2N_5O_4$: 506 [M+H].

Example 4

Intermediate 6

4-(3-(2-amino-1H-benzoimidazol-6-yl)-4-fluorobenzyl)phthalazin-1(2H)-one (I-6.)

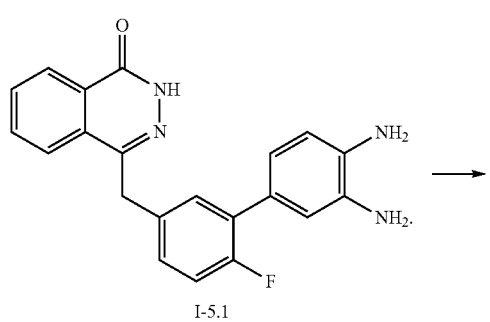

I-5.1

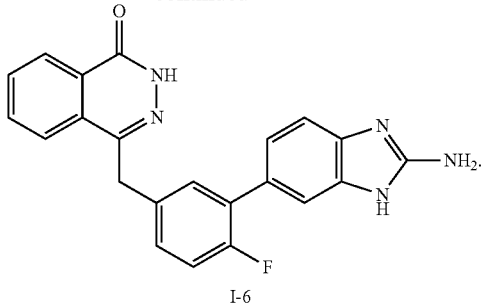

I-6

A solution of 4-((3',4'-diamino-6-fluoro-[1,1'-biphenyl]-3-yl)methyl)phthalazin-1(2H)-one (I-.5.1.) (0.54 g, 1.50 mmol) and cyanogen bromide (0.24 g, 2.25 mmol) in a mixture of ethanol-acetonitrile-water (2:1:1) (20 mL) was heated to 76° C. for five hours. The reaction mixture was cooled to room temperature and partitioned with ethyl acetate (200 mL). The organic layer was separated, washed with saturated aqueous sodium bicarbonate (2×50 mL) and brine (100 mL), dried over anhydrous sodium sulfate and concentrated to give 4-(3-(2amino-1H-benzoimidazol-6-yl)-4-fluorobenzyl)phthalazin-1(2H)-one (I-6.). MS (EI) for $C_{22}H_{16}FN_5O$: 386 [M+H].

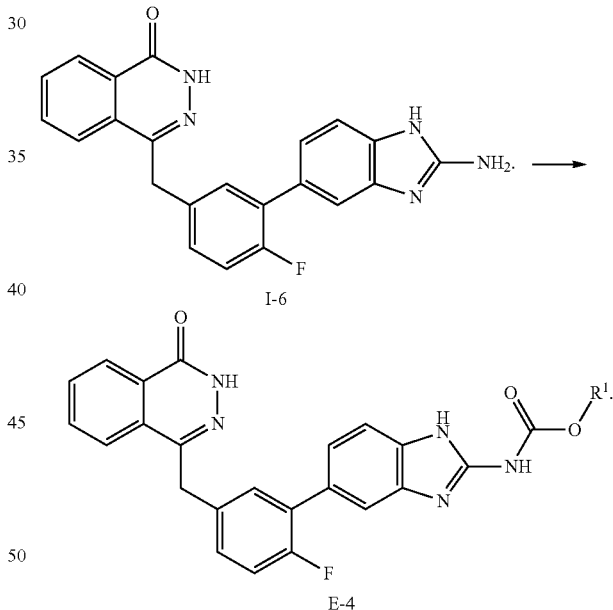

General Synthesis of Carbamate-Library (E-4.).

To solution of 4-(3-(2-amino-1H-benzoimidazol-6-yl)-4-fluorobenzyl)phthalazin-1(2H)-one (I-6.) (0.040 mg, 0.1 mmol) in anhydrous tetrahydrofuran (1.0 ml) 1,1'-carbonyldiimidazole (0.021 g, 0.13 mmol) was added and the reaction mixture was stirred at 50° C. for eight hours, followed by the addition of alcohol (1.0 mmol, 10 eq.) and the reaction mixture was heated to 75° C. for four hours. The mixture was cooled to room temperature and purified by preparative reverse phase HPLC chromatography (acetonitrile-water with 0.1% trifluoroacetic acid). The desired product was collected, by concentrating the solvent to give title carbamate.

Example E-4.1

Propyl (5-(2-fluoro-5-((4-oxo-3,4-dihydrophthalazin-1-yl)methyl)phenyl)-1H-benzoimidazol-2-yl)carbamate was prepared using 1-propanol. MS (EI) for $C_{26}H_{22}FN_5O_3$: 472 [M+H].

Example E-4.2

2-Fluoroethyl (5-(2-fluoro-5-((4-oxo-3,4-dihydrophthalazin-1-yl)methyl) phenyl)-1H-benzoimidazol-2-yl)carbamate was prepared using 2-fluoroethan-1-ol. MS (EI) for $C_{25}H_{19}F_2N_5O_3$: 476 [M+H].

Example E-4.3

2,2-Difluoroethyl (5-(2-fluoro-5-((4-oxo-3,4-dihydrophthalazin-1-yl)methyl) phenyl)-1H-benzoimidazol-2-yl)carbamate was prepared using 2,2-difluoroethan-1-ol. MS (EI) for $C_{25}H_{18}F_3N_5O_3$: 494 [M+H].

Example E-4.4

2,2,2-Trifluoroethyl (5-(2-fluoro-5-((4-oxo-3,4-dihydrophthalazin-1-yl)methyl) phenyl)-1H-benzoimidazol-2-yl)carbamate was prepared using 2,2,2-trifluoroethan-1-ol. MS (EI) for $C_{25}H_{17}F_4N_5O_3$: 512 [M+H].

Example E-4.5

Isopropyl (5-(2-fluoro-5-((4-oxo-3,4-dihydrophthalazin-1-yl)methyl)phenyl)-1H-benzoimidazol-2-yl)carbamate was prepared using 2-propanol. MS (EI) for $C_{26}H_{22}FN_5O_3$: 472 [M+H].

Example E-4.6 sec-Butyl (5-(2-fluoro-5-((4-oxo-3,4-dihydrophthalazin-1-yl)methyl)phenyl)-1H-benzoimidazol-2-yl)carbamate was prepared using 2-butanol. MS (EI) for $C_{27}H_{24}FN_5O_3$: 486 [M+H].

Example E-4.7

Cyclopropyl (5-(2-fluoro-5-((4-oxo-3,4-dihydrophthalazin-1-yl)methyl)phenyl)-1H-benzoimidazol-2-yl)carbamate was prepared using cyclopropanol. MS (EI) for $C_{26}H_{20}FN_5O_3$: 470 [M+H].

Example E-4.8

Cyclobutyl (5-(2-fluoro-5-((4-oxo-3,4-dihydrophthalazin-1-yl)methyl)phenyl)-1H-benzoimidazol-2-yl)carbamate was prepared using cyclobutanol. MS (EI) for $C_{27}H_{22}FN_5O_3$: 484 [M+H].

Example E-4.9

Cyclopentyl (5-(2-fluoro-5-((4-oxo-3,4-dihydrophthalazin-1-yl)methyl)phenyl)-1H-benzoimidazol-2-yl)carbamate was prepared using cyclopentanol. MS (EI) for $C_{28}H_{24}FN_5O_3$: 498 [M+H].

Example E-4.10

Cyclohexyl (5-(2-fluoro-5-((4-oxo-3,4-dihydrophthalazin-1-yl)methyl)phenyl)-1H-benzoimidazol-2-yl)carbamate was prepared using cyclohexanol. MS (EI) for $C_{29}H_{26}FN_5O_3$: 512 [M+H].

Example E-4.11

Oxetan-3-yl (5-(2-fluoro-5-((4-oxo-3,4-dihydrophthalazin-1-yl)methyl)phenyl)-1H-benzoimidazol-2-yl)carbamate was prepared using oxetan-3-ol. MS (EI) for $C_{26}H_{20}FN_5O_4$: 486 [M+H].

Example E-4.12

Tetrahydro-2H-pyran-4-yl (5-(2-fluoro-5-((4-oxo-3,4-dihydrophthalazin-1-yl)methyl)phenyl)-1H-benzoimidazol-2-yl)carbamate was prepared using tetrahydro-2H-pyran-4-ol. MS (EI) for $C_{28}H_{24}FN_5O_4$: 514 [M+H].

Example E-4.13

1-Methylazetidin-3-yl (5-(2-fluoro-5-((4-oxo-3,4-dihydrophthalazin-1-yl)methyl)phenyl)-1H-benzoimidazol-2-yl) carbamate was prepared using 1-methylazetidin-3-ol. MS (EI) for $C_{27}H_{23}FN_6O_3$: 499 [M+H].

Example E-4.14

1-Methylpiperidin-4-yl (5-(2-fluoro-5-((4-oxo-3,4-dihydrophthalazin-1-yl)methyl)phenyl)-1H-benzoimidazol-2-yl) carbamate was prepared using 1-methylpiperidin-4-ol. MS (EI) for $C_{29}H_{27}FN_6O_3$: 527 [M+H].

Example E-4.15

2-(Dimethylamino)ethyl (5-(2-fluoro-5-((4-oxo-3,4-dihydrophthalazin-1-yl)methyl)phenyl)-1H-benzoimidazol-2-yl) carbamate was prepared using 2-(dimethylamino) ethan-1-ol. MS (EI) for $C_{27}H_{25}FN_6O_3$: 501 [M+H].

Example E-4.16

2-(Diethylamino)ethyl (5-(2-fluoro-5-((4-oxo-3,4-dihydrophthalazin-1-yl)methyl)phenyl)-1H-benzoimidazol-2-yl) carbamate was prepared using 2-(diethylamino)ethan-1-ol. MS (EI) for $C_{29}H_{29}FN_6O_3$: 529 [M+H].

Example E-4.17

2-(Pyrrolidin-1-yl)ethyl (5-(2-fluoro-5-((4-oxo-3,4-dihydrophthalazin-1-yl)methyl)phenyl)-1H-benzoimidazol-2-yl) carbamate was prepared using 2-(pyrrolidin-1-yl)ethan-1-ol. MS (EI) for $C_{29}H_{27}FN_6O_3$: 527 [M+H].

Example E-4.18

2-(4-Methylpiperazin-1-yl)ethyl (5-(2-fluoro-5-((4-oxo-3,4-dihydrophthalazin-1-yl)methyl)phenyl)-1H-benzo[d]imidazol-2-yl)carbamate was prepared using 2-(4-methylpiperazin-1-yl)ethan-1-ol. MS (EI) for $C_{30}H_{30}FN_7O_3$: 556 [M+H].

Example E-4.19

2-Morpholinoethyl (5-(2-fluoro-5-((4-oxo-3,4-dihydrophthalazin-1-yl)methyl)phenyl)-1H-benzoimidazol-2-yl)

carbamate was prepared using 2-morpholinoethan-1-ol. MS (EI) for $C_{29}H_{27}FN_6O_4$: 543 [M+H].

Example E-4.20

2-(1-Methylpiperidin-4-yl)ethyl (5-(2-fluoro-5-((4-oxo-3,4-dihydrophthalazin-1-yl)methyl)phenyl)-1H-benzoimidazol-2-yl)carbamate was prepared using 2-(1-methylpiperidin-4-yl)ethan-1-ol. MS (EI) for $C_{31}H_{31}FN_6O_3$: 555 [M+H].

Example E-4.21

3-(Dimethylamino)propyl (5-(2-fluoro-5-((4-oxo-3,4-dihydrophthalazin-1-yl)methyl)phenyl)-1H-benzoimidazol-2-yl)carbamate was prepared using 3-(dimethylamino)propan-1-ol. MS (EI) for $C_{28}H_{27}FN_6O_3$: 515 [M+H].

Example E-4.22

Phenyl (5-(2-fluoro-5-((4-oxo-3,4-dihydrophthalazin-1-yl)methyl)phenyl)-1H-benzoimidazol-2-yl)carbamate was prepared using phenol. MS (EI) for $C_{29}H_{20}FN_5O_3$: 506 [M+H].

Example E-4.23

Benzyl (5-(2-fluoro-5-((4-oxo-3,4-dihydrophthalazin-1-yl)methyl)phenyl)-1H-benzoimidazol-2-yl)carbamate was prepared using phenylmethanol. MS (EI) for $C_{30}H_{22}FN_5O_3$: 520 [M+H].

Example 5

Example 5.1. 1-Ethyl-3-(5-(2-fluoro-5-((4-oxo-3,4-dihydrophthalazin-1-yl)methyl)phenyl)-1H-benzimidazol-2-yl)urea thioic acid methyl ester (R-5.3.) (0.23 g, 1.00 mmol) in acetic acid (5.0 mL) was stirred at 98° C. for 18 hours. After cooling the reaction mixture to room temperature it was diluted with water (5 mL) and the pH was adjusted to 8 by the addition of 10N aqueous sodium hydroxide (8.6 mL), and then partitioned with ethyl acetate (100 mL). The organic layer was separated, washed with saturated aqueous sodium bicarbonate (50 ml), brine (50 mL), dried over anhydrous sodium sulfate and concentrated. The resulting crude was purified by gradient silica gel flash chromatography (5-20% 7N ammonia in methanol in ethyl acetate) to give 1-ethyl-3-(5-(2-fluoro-5-((4-oxo-3,4-dihydrophthalazin-1-yl)methyl)phenyl)-1H-benzimidazol-2-yl)urea (E-5.1.) (0.30 g, 66%). 1H-NMR (300 MHz, $d_6$-DMSO): 12.58 (s, 1H), 11.64 (s, 1H), 10.04 (s, 1H), 8.25 (d, 1H), 8.02 (d, 1H), 7.90 (t, 1H), 7.82 (t, 1H), 7.43-7.43 (m, 3H), 7.27 (m, 1H), 7.22 (m, 2H), 4.35 (s, 2H), 3.18 (m, 2H), 1.06 (t, 3H). MS (EI) for $C_{25}H_{21}FN_6O_2$: 457 [M+H].

Example E-5.2

1-Ethyl-3-(5-(3-((4-oxo-3,4-dihydrophthalazin-1-yl)methyl)phenyl)-1H-benzoimidazol-2-yl)urea was prepared using 4-((3',4'-diamino-[1,1'-biphenyl]-3-yl)methyl) phthalazin-1(2H)-one) (I-5.2.). MS (EI) for $C_{25}H_{22}N_6O_2$: 439 [M+H].

Example E-5.3

1-(5-(2-Chloro-5-((4-oxo-3,4-dihydrophthalazin-1-yl)methyl)phenyl)-1H-benzoimidazol-2-yl)-3-ethylurea was prepared using 4-((3',4'-diamino-6-chloro-[1,1'-biphenyl]-3-yl)methyl)phthalazin-1 (2H)-one (I-5.3.). 1H-NMR (300 MHz, $d_6$-DMSO): 12.58 (s, 1H), 8.26 (d, 1H), 8.04 (d, 1H),

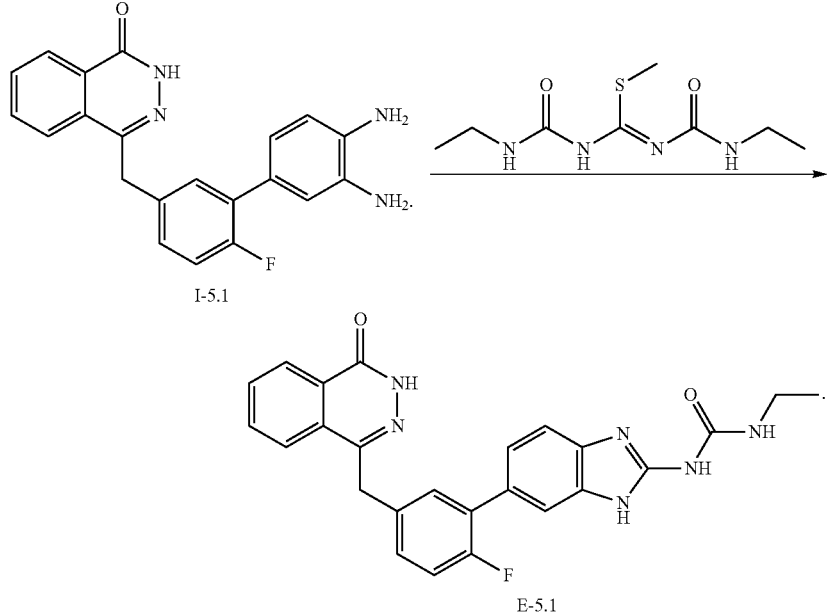

A solution of 4-((3',4'-diamino-6-fluoro-[1,1'-biphenyl]-3-yl)methyl)phthalazin-1(2H)-one (I-5.1.) (0.36 g, 1.00 mmol) and N,N'-bis[(ethylamino)-carbonyl] carbamimido 7.92 (t, 1H), 7.82 (t, 1H), 7.49 (m, 2H), 7.45 (d, 1H), 7.28-7.16 (m, 3H), 4.35 (s, 2H), (3.20 (m, 2H), 1.09 (t, 3H). MS (EI) for $C_{25}H_{21}ClN_6O_2$: 473 [M+H].

Example E-5.4

1-Ethyl-3-(5-(2-methyl-5-((4-oxo-3,4-dihydrophthalazin-1-yl)methyl)phenyl)-1H-benzoimidazol-2-yl)urea was prepared using 4-((3',4'-diamino-6-methyl-[1,1'-biphenyl]-3-yl)methyl)phthalazin-1(2H)-one (I-5.4.). 1H-NMR (300 MHz, $d_6$-DMSO): 12.56 (s, 1H), 8.25 (d, 1H), 8.02 (d, 1H), 7.89 (t, 1H), 7.83 (t, 1H), 7.44 (s, 1H), 7.41 (d, 1H), 7.27-7.22 (m, 2H), 7.12 (d, 1H), 7.03 (d, 1H), 4.28 (s, 2H), 3.19 (m, 2H), 2.43 (s, 3H), 1.08 (t, 3H). MS (EI) for $C_{26}H_{24}N_6O_2$: 453 [M+H].

Example E-5.5

1-Ethyl-3-(5-(5-((4-oxo-3,4-dihydrophthalazin-1-yl)methyl)-2-(trifluoromethyl) phenyl)-1H-benzoimidazol-2-yl)urea was prepared using 4-((3',4'-diamino-6-(trifluoromethyl)-[1,1'-biphenyl]-3-yl)methyl)phthalazin-1(2H)-one (I-5.5.). 1H-NMR (300 MHz, $d_6$-DMSO): 12.60 (s, 1H), 8.25 (d, 1H), 8.03 (d, 1H), 7.92 (t, 1H), 7.82 (t, 1H), 7.50 (m, 2H), 7.46 (d, 1H), 7.26-7.16 (m, 3H), 4.35 (s, 2H), 3.20 (m, 2H), 1.08 (t, 3H). MS (EI) for $C_{26}H_{21}F_3N_6O_2$: 506 [M+H].

Example E-5.6

1-Ethyl-3-(5-(5-((4-oxo-3,4-dihydrophthalazin-1-yl)methyl)-2-(trifluoromethoxy)phenyl)-1H-benzoimidazol-2-yl)urea was prepared using 4-((3',4'-diamino-6-(trifluoromethoxy)-[1,1'-biphenyl]-3-yl)methyl)phthalazin-1(2H)-one (I-5.6.). 1H-NMR (300 MHz, $d_6$-DMSO): 12.58 (s, 1H), 8.25 (d, 1H), 8.02 (d, 1H), 7.88 (t, 1H), 7.83 (t, 1H), 7.43 (s, 1H), 7.36 (d, 1H), 7.26 (s, 1H), 7.21 (d, 1H), 7.10 (d, 1H), 6.98 (d, 1H), 4.28 (s, 2H), 3.18 (m, 2H), 1.07 (t, 3H). MS (EI) for $C_{26}H_{21}F_3N_6O_3$: 523 [M+H].

Example E-5.7

1-Ethyl-3-(5-(2-methoxy-5-((4-oxo-3,4-dihydrophthalazin-1-yl)methyl)phenyl)-1H-benzoimidazol-2-yl)urea was prepared using 4-((3',4'-diamino-6-methoxy-[1,1'-biphenyl]-3-yl)methyl)phthalazin-1(2H)-one (I-5.7.). 1H-NMR (300 MHz, $d_6$-DMSO): 12.56 (s, 1H), 11.56 (s, 1H), 8.25 (d, 1H), 8.02 (d, 1H), 7.87 (t, 1H), 7.82 (t, 1H), 7.45 (s, 1H), 7.38 (d, 1H), 7.28 (s, 1H), 7.22 (d, 1H), 7.07 (d, 1H), 6.97 (d, 1H), 4.28 (s, 2H), 3.70 (s, 3H), 3.20 (m, 2H), 1.08 (t, 3H). MS (EI) for $C_{26}H_{24}N_6O_3$: 469 [M+H].

Example E-5.8

1-(5-(2-Ethoxy-5-((4-oxo-3,4-dihydrophthalazin-1-yl)methyl)phenyl)-1H-benzoimidazol-2-yl)-3-ethylurea was prepared using 4-((3',4'-diamino-6-ethoxy-[1,1'-biphenyl]-3-yl)methyl)phthalazin-1(2H)-one (I-5.8.). 1H-NMR (300 MHz, $d_6$-DMSO): 12.56 (s, 1H), 8.24 (d, 1H), 8.02 (d, 1H), 7.88 (t, 1H), 7.82 (t, 1H), 7.42 (s, 1H), 7.38 (d, 1H), 7.26 (s, 1H), 7.21 (d, 1H), 7.08 (d, 1H), 6.97 (d, 1H), 4.62 (q, 2H), 4.28 (s, 2H), 3.18 (m, 2H), 1.58 (t, 3H), 1.06 (t, 3H). MS (EI) for $C_{27}H_{26}N_6O_3$: 483 [M+H].

Example E-5.9

1-Ethyl-3-(5-(2-(2-methoxyethoxy)-5-((4-oxo-3,4-dihydrophthalazin-1-yl)methyl)phenyl)-1H-benzoimidazol-2-yl)urea was prepared using 4-((3',4'-diamino-6-(2-methoxyethoxy)-[1,1'-biphenyl]-3-yl)methyl)phthalazin-1(2H)-one (I-5.9.). MS (EI) for $C_{28}H_{28}N_6O_4$: 513 [M+H].

Example E-5.10

1-(5-(2-(Difluoromethoxy)-5-((4-oxo-3,4-dihydrophthalazin-1-yl)methyl)phenyl)-1H-benzoimidazol-2-yl)-3-ethylurea was prepared using 4-((3',4'-diamino-6-(difluoromethoxy)-[1,1'-biphenyl]-3-yl)methyl)phthalazin-1(2H)-one (I-5.10.). 1H-NMR (300 MHz, $d_6$-DMSO): 12.58 (s, 1H), 8.26 (d, 1H), 8.04 (d, 1H), 7.88 (t, 1H), 7.82 (t, 1H), 7.43 (m, 2H), 7.41 (s, 1H), 7.28 (m, 1H), 7.22-7.12 (m, 3H), 4.35 (s, 2H), 3.0 (m, 2H), 1.06 (t, 3H). MS (EI) for $C_{26}H_{22}F_2N_6O_3$: 505 [M+H].

Example E-5.11

1-Ethyl-3-(5-(3-fluoro-5-((4-oxo-3,4-dihydrophthalazin-1-yl)methyl)phenyl)-1H-benzoimidazol-2-yl)urea was prepared using 4-((3',4'-diamino-5-fluoro-[1,1'-biphenyl]-3-yl)methyl)phthalazin-1 (2H)-one (I-5.11.). 1H-NMR (300 MHz, $d_6$-DMSO): 12.60 (s, 1H), 8.26 (d, 1H), 8.04 (d, 1H), 7.90 (t, 1H), 7.82 (t, 1H), 7.50 (m, 2H), 7.44 (d, 1H), 7.24-7.19 (m, 3H), 4.35 (s, 2H), 3.18 (m, 2H), 1.06 (t, 3H). MS (EI) for $C_{25}H_{21}FN_6O_2$: 457 [M+H].

Example E-5.12

1-Ethyl-3-(5-(4-fluoro-3-((4-oxo-3,4-dihydrophthalazin-1-yl)methyl)phenyl)-1H-benzoimidazol-2-yl)urea was prepared using 4-((3',4'-diamino-4-fluoro-[1,1'-biphenyl]-3-yl)methyl)phthalazin-1 (2H)-one (I-5.12.). 1H-NMR (300 MHz, $d_6$-DMSO): 12.59 (s, 1H), 8.26 (d, 1H), 8.02 (d, 1H), 7.9 (t, 1H), 7.82 (t, 1H), 7.4 (m, 2H), 7.46 (d, 1H), 7.30 (m, 1H), 7.19 (m, 2H), 4.35 (s, 2H), 3.20 (m, 2H), 1.09 (t, 3H). MS (EI) for $C_{25}H_{21}FN_6O_2$: 457 [M+H].

Example E-5.13

1-Ethyl-3-(5-(2-fluoro-3-((4-oxo-3,4-dihydrophthalazin-1-yl)methyl)phenyl)-1H-benzoimidazol-2-yl)urea was prepared using 4-((3',4'-diamino-2-fluoro-[1,1'-biphenyl]-3-yl)methyl)phthalazin-1 (2H)-one (I-5.13.). 1H-NMR (300 MHz, $d_6$-DMSO): 12.59 (s, 1H), 8.26 (d, 1H), 8.04 (d, 1H), 7.91 (t, 1H), 7.82 (t, 1H), 7.51 (s, 1H), 7.44 (m, 2H), 7.26 (m, 3H), 4.35 (s, 2H),), 3.19 (m, 2H), 1.07 (t, 3H). MS (EI) for $C_{25}H_{21}FN_6O_2$: 457 [M+H].

Example E-5.14

1-(5-(2,4-Difluoro-5-((4-oxo-3,4-dihydrophthalazin-1-yl)methyl)phenyl)-1H-benzoimidazol-2-yl)-3-ethylurea was prepared using 4-((3',4'-diamino-4,6-difluoro-[1,1'-biphenyl]-3-yl)methyl)phthalazin-1 (2H)-one (I-5.14.). 1H-NMR (300 MHz, $d_6$-DMSO): 12.59 (s, 1H), 8.26 (d, 1H), 8.04 (d, 1H), 7.90 (t, 1H), 7.82 (t, 1H), 7.49 (m, 2H), 7.44 (d, 1H), 7.21 (d, 1H), 6.85 (m, 1H), 4.35 (s, 2H), 3.20 (m, 2H), 1.06 (t, 3H). MS (EI) for $C_{25}H_{20}F_2N_6O_2$: 475 [M+H].

Example E-5.15

1-(5-(2,3-Difluoro-5-((4-oxo-3,4-dihydrophthalazin-1-yl)methyl)phenyl)-1H-benzoimidazol-2-yl)-3-ethylurea was prepared using 4-((3',4'-diamino-5,6-difluoro-[1,1'-biphenyl]-3-yl)methyl)phthalazin-1 (2H)-one (I-5.15.). 1H-NMR (300 MHz, $d_6$-DMSO): 12.59 (s, 1H), 8.26 (d, 1H), 8.04 (d, 1H), 7.90 (t, 1H), 7.82 (t, 1H), 7.49 (m, 3H), 7.2 (d, 1H), 7.08 (m, 1H), 4.35 (s, 2H), 3.18 (m, 2H), 1.06 (t, 3H). MS (EI) for $C_{25}H_{20}F_2N_6O_2$: 475 [M+H].

Example E-5.16

1-Ethyl-3-(5-(3-methoxy-5-((4-oxo-3,4-dihydrophthalazin-1-yl)methyl) phenyl)-1H-benzoimidazol-2-yl)urea was prepared using 4-((3',4'-diamino-5-methoxy-[1,1'-biphenyl]-3-yl)methyl)phthalazin-1(2H)-one (I-5.16.). 1H-NMR (300 MHz, $d_6$-DMSO): 12.56 (s, 1H), 8.26 (d, 1H), 8.02 (d, 1H), 7.90 (t, 1H), 7.82 (t, 1H), 7.43 (s, 1H), 7.36 (d, 1H), 7.22 (d, 1H), 7.20 (s, 1H), 7.16 (s, 1H), 6.98 (d, 1H), 4.28 (s, 2H), 3.72 (s, 3H), 3.18 (m, 2H), 1.06 (t, 3H). MS (EI) for $C_{26}H_{24}N_6O_3$: 469 [M+H].

Example E-5.17

1-Ethyl-3-(5-(4-methoxy-3-((4-oxo-3,4-dihydrophthalazin-1-yl)methyl) phenyl)-1H-benzoimidazol-2-yl)urea was prepared using 4-((3',4'-diamino-4-methoxy-[1,1'-biphenyl]-3-yl)methyl)phthalazin-1(2H)-one (I-5.17.). MS (EI) for $C_{26}H_{24}N_6O_3$: 469 [M+H].

Example E-5.18

1-Ethyl-3-(5-(2-methoxy-3-((4-oxo-3,4-dihydrophthalazin-1-yl)methyl) phenyl)-1H-benzoimidazol-2-yl)urea was prepared using 4-((3',4'-diamino-2-methoxy-[1,1'-biphenyl]-3-yl)methyl)phthalazin-1(2H)-one (I-5.18.). MS (EI) for $C_{26}H_{24}N_6O_3$: 469 [M+H].

Example E-5.19

1-(5-(2,3-Dimethoxy-5-((4-oxo-3,4-dihydrophthalazin-1-yl)methyl)phenyl)-1H-benzoimidazol-2-yl)-3-ethylurea was prepared using 4-((3',4'-diamino-5,6-dimethoxy-[1,1'-biphenyl]-3-yl)methyl)phthalazin-1(2H)-one (I-5.19.). MS (EI) for $C_{27}H_{26}N_6O_4$: 499 [M+H].

Example E-5.20

1-(5-(2,4-Dimethoxy-5-((4-oxo-3,4-dihydrophthalazin-1-yl)methyl)phenyl)-1H-benzoimidazol-2-yl)-3-ethylurea was prepared using 4-((3',4'-diamino-4,6-dimethoxy-[1,1'-biphenyl]-3-yl)methyl)phthalazin-1(2H)-one (I-5.20.). 1H-NMR (300 MHz, $d_6$-DMSO): 12.56 (s, 1H), 8.24 (d, 1H), 8.02 (d, 1H), 7.89 (t, 1H), 7.81, (t, 1H), 7.45 (s, 1H), 7.38 (d, 1H), 7.28 (s, 1H), 6.97 (d, 1H), 6.68 (s, 1H), 4.28 (s, 2H), 3.70 (s, 3H), 3.68 (s, 3H), 3.18 (m, 2H), 1.06 (t, 3H). MS (EI) for Formula: $C_{27}H_{26}N_6O_4$: 499 [M+H].

Example E-5.21

1-Ethyl-3-(5-(2-fluoro-4-methoxy-5-((4-oxo-3,4-dihydrophthalazin-1-yl)methyl)phenyl)-1H-benzoimidazol-2-yl)urea was prepared using 4-((3',4'-diamino-6-fluoro-4-methoxy-[1,1'-biphenyl]-3-yl)methyl)phthalazin-1(2H)-one (I-5.21.). MS (EI) for $C_{26}H_{23}FN_6O_3$: 487 [M+H].

Example E-5.22

1-Ethyl-3-(5-(4-fluoro-2-methoxy-5-((4-oxo-3,4-dihydrophthalazin-1-yl)methyl)phenyl)-1H-benzoimidazol-2-yl)urea was prepared using 4-((3',4'-diamino-4-fluoro-6-methoxy-[1,1'-biphenyl]-3-yl)methyl)phthalazin-1(2H)-one can (I-5.22.). MS (EI) for $C_{26}H_{23}FN_6O_3$: 487 [M+H].

Example E-5.23

1-Ethyl-3-(5-(2-fluoro-5-((5-fluoro-4-oxo-3,4-dihydrophthalazin-1-yl)methyl)phenyl)-1H-benzoimidazol-2-yl)urea was prepared using 4-((3',4'-diamino-6-fluoro-[1,1'-biphenyl]-3-yl)methyl)-8-fluorophthalazin-1(2H)-one (I-5.23.). MS (EI) for $C_{25}H_{20}F_2N_6O_2$: 475 [M+H].

Example E-5.24

1-Ethyl-3-(5-(2-fluoro-5-((6-fluoro-4-oxo-3,4-dihydrophthalazin-1-yl)methyl)phenyl)-1H-benzoimidazol-2-yl)urea is prepared using 4-((3',4'-diamino-6-fluoro-[1,1'-biphenyl]-3-yl)methyl)-7-fluorophthalazin-1 (2H)-one (I-5.24.). MS (EI) for $C_{25}H_{20}F_2N_6O_2$: 475 [M+H].

Example E-5.25

1-Ethyl-3-(5-(2-fluoro-5-((7-fluoro-4-oxo-3,4-dihydrophthalazin-1-yl)methyl)phenyl)-1H-benzoimidazol-2-yl)urea was prepared using 4-((3',4'-diamino-6-fluoro-[1,1'-biphenyl]-3-yl)methyl)-6-fluorophthalazin-1(2H)-one (I-5.25.). MS (EI) for $C_{25}H_{20}F_2N_6O_2$: 475 [M+H].

Example E-5.26

1-Ethyl-3-(5-(2-fluoro-5-((8-fluoro-4-oxo-3,4-dihydrophthalazin-1-yl)methyl)phenyl)-1H-benzoimidazol-2-yl)urea was prepared using 4-((3',4'-diamino-6-fluoro-[1,1'-biphenyl]-3-yl)methyl)-5-fluorophthalazin-1(2H)-one (I-5.26.). MS (EI) for $C_{25}H_{20}F_2N_6O_2$: 475 [M+H].

Example E-5.27

1-(5-(5-((5,8-Difluoro-4-oxo-3,4-dihydrophthalazin-1-yl)methyl)-2-fluorophenyl)-1H-benzoimidazol-2-yl)-3-ethylurea is prepared using 4-((3',4'-diamino-6-fluoro-[1,1'-biphenyl]-3-yl)methyl)-5,8-difluorophthalazin-1(2H)-one (I-5.27.). MS (EI) for $C_{25}H_{19}F_3N_6O_2$: 493 [M+H].

Example E-5.28

1-(5-(5-((6,7-Difluoro-4-oxo-3,4-dihydrophthalazin-1-yl)methyl)-2-fluorophenyl)-1H-benzoimidazol-2-yl)-3-ethylurea is prepared using 4-((3',4'-diamino-6-fluoro-[1,1'-biphenyl]-3-yl)methyl)-6,7-difluorophthalazin-1(2H)-one (I-5.28.). MS (EI) for $C_{25}H_{19}F_3N_6O_2$: 493 [M+H].

Example E-5.29

1-Ethyl-3-(5-(2-fluoro-5-((5-methyl-4-oxo-3,4-dihydrophthalazin-1-yl)methyl)phenyl)-1H-benzoimidazol-2-yl)urea is prepared using 4-((3',4'-diamino-6-fluoro-[1,1'-biphenyl]-3-yl)methyl)-8-methylphthalazin-1 (2H)-one (I-5.29.). MS (EI) for $C_{26}H_{23}FN_6O_2$: 471 [M+H].

Example E-5.30

1-Ethyl-3-(5-(2-fluoro-5-((6-methyl-4-oxo-3,4-dihydrophthalazin-1-yl)methyl) phenyl)-1H-benzoimidazol-2-yl)urea was prepared using 4-((3',4'-diamino-6-fluoro-[1,1'-biphenyl]-3-yl)methyl)-7-methylphthalazin-1(2H)-one (I-5.30.). MS (EI) for $C_{26}H_{23}FN_6O_2$: 471[M+H].

Example E-5.31

1-Ethyl-3-(5-(2-fluoro-5-((7-methyl-4-oxo-3,4-dihydrophthalazin-1-yl)methyl) phenyl)-1H-benzoimidazol-2-yl)urea was prepared using 4-((3',4'-diamino-6-fluoro-[1,1'- biphenyl]-3-yl)methyl)-6-methylphthalazin-1(2H)-one (I-5.31.). MS (EI) for $C_{26}H_{23}FN_6O_2$: 471 [M+H].

Example E-5.32

1-(5-(5-((7-Chloro-4-oxo-3,4-dihydrophthalazin-1-yl)methyl)-2-fluorophenyl)-1H-benzoimidazol-2-yl)-3-ethylurea is prepared using 6-chloro-4-((3',4'-diamino-6-fluoro-[1,1'-biphenyl]-3-yl)methyl)phthalazin-1(2H)-one can (I-5.32.). MS (EI) for $C_{25}H_{20}ClFN_6O_2$: 491 [M+H].

Example E-5.33

1-Ethyl-3-(5-(2-fluoro-5-((4-oxo-7-(trifluoromethyl)-3,4-dihydrophthalazin-1-yl)methyl)phenyl)-1H-benzoimidazol-2-yl)urea is prepared using 4-((3',4'-diamino-6-fluoro-[1,1'-biphenyl]-3-yl)methyl)-6-(trifluoromethyl)phthalazin-1(2H)-one (I-5.33.). MS (EI) for $C_{26}H_{20}F_4N_6O_2$: 525 [M+H].

Example E-5.34

1-Ethyl-3-(5-(2-fluoro-5-((7-methoxy-4-oxo-3,4-dihydrophthalazin-1-yl)methyl)phenyl)-1H-benzoimidazol-2-yl)urea is prepared using 4-((3',4'-diamino-6-fluoro-[1,1'-biphenyl]-3-yl)methyl)-6-methoxyphthalazin-1(2H)-one (I-5.34.). MS (EI) for $C_{26}H_{23}FN_6O_3$: 487 [M+H].

Example E-5.35

1-Ethyl-3-(5-(2-fluoro-5-((4-oxo-7-(trifluoromethoxy)-3,4-dihydrophthalazin-1-yl)methyl)phenyl)-1H-benzoimidazol-2-yl)urea is prepared using 4-((3',4'-diamino-6-fluoro-[1,1'-biphenyl]-3-yl)methyl)-6-(trifluoromethoxy)phthalazin-1(2H)-one (I-5.35.). MS (EI) for $C_{26}H_{20}F_4N_6O_3$: 541 [M+H].

Example E-5.36

1-(5-(5-((6,7-Dimethoxy-4-oxo-3,4-dihydrophthalazin-1-yl)methyl)-2-fluorophenyl)-1H-benzoimidazol-2-yl)-3-ethylurea was prepared using 4-((3',4'-diamino-6-fluoro-[1,1'-biphenyl]-3-yl)methyl)-6,7-dimethoxyphthalazin-1(2H)-one (I-5.36.). MS (EI) for $C_{27}H_{25}FN_6O_4$: 517 [M+H].

Example E-5.37

1-(5-(5-((6,8-Dimethoxy-4-oxo-3,4-dihydrophthalazin-1-yl)methyl)-2-fluorophenyl)-1H-benzoimidazol-2-yl)-3-ethylurea is prepared using 4-((3',4'-diamino-6-fluoro-[1,1'-biphenyl]-3-yl)methyl)-5,7-dimethoxyphthalazin-1(2H)-one (I-5.37.). MS (EI) for $C_{27}H_{25}FN_6O_4$: 517 [M+H].

Example E-5.38

1-Ethyl-3-(6-(5-((4-oxo-3,4-dihydrophthalazin-1-yl)methyl)furan-2-yl)-1H-benzoimidazol-2-yl)urea was prepared using 4-((5-(3,4-diaminophenyl)furan-2-yl)methyl)phthalazin-1(2H)-one (I-5.38.). MS (EI) for $C_{23}H_{20}N_6O_3$: 429 [M+H].

Example E-5.39

Ethyl-3-(6-(5-((4-oxo-3,4-dihydrophthalazin-1-yl)methyl)furan-3-yl)-1H-benzoimidazol-2-yl)urea is prepared using 4-((4-(3,4-diaminophenyl)furan-2-yl)methyl)phthalazin-1(2H)-one (I-5.39.). MS (EI) for: $C_{23}H_{20}N_6O_3$: 429 [M+H].

Example E-5.40

1-Ethyl-3-(7-fluoro-5-(2-fluoro-5-((4-oxo-3,4-dihydrophthalazin-1-yl)methyl)phenyl)-1H-benzoimidazol-2-yl)urea was prepared using 4-((3',4'-diamino-5',6-difluoro-[1,1'-biphenyl]-3-yl)methyl)phthalazin-1(2H)-one (I-5.40.). 1H-NMR (300 MHz, $d_6$-DMSO): 12.58 (s, 1H), 8.24 (d, 1H), 8.02 (d, 1H), 7.88 (t, 1H), 7.82 (t, 1H), 7.52 (d, 1H), 7.36 (s, 1H), 7.26 (m, 1H), 7.18 (q, 1H), 7.00 (d, 1H), 4.33 (s, 2H), 3.18 (m, 2H), 1.09 (t, 3H). MS (EI) for $C_{25}H_{20}F_2N_6O_2$: 475 [M+H].

Example E-5.41

1-Ethyl-3-(6-fluoro-5-(2-fluoro-5-((4-oxo-3,4-dihydrophthalazin-1-yl)methyl)phenyl)-1H-benzoimidazol-2-yl)urea is prepared using 4-((4',5'-diamino-2',6-difluoro-[1,1'-biphenyl]-3-yl)methyl)phthalazin-1(2H)-one (I-5.41.). MS (EI) for $C_{25}H_{20}F_2N_6O_2$: 475 [M+H].

Example E-5.42

1-Ethyl-3-(4-fluoro-5-(2-fluoro-5-((4-oxo-3,4-dihydrophthalazin-1-yl)methyl)phenyl)-1H-benzoimidazol-2-yl)urea was prepared using 4-((3',4'-diamino-2',6-difluoro-[1,1'-biphenyl]-3-yl)methyl)phthalazin-1(2H)-one (I-5.42.). 1H-NMR (300 MHz, $d_6$-DMSO): 12.58 (s, 1H), 8.23 (d, 1H), 8.02 (d, 1H), 7.86 (t, 1H), 7.80 (t, 1H), 7.43 (d, 1H), 7.33 (m, 1H), 7.22 (d, 1H), 7.20 (t, 1H), 7.93 (t, 1H), 4.33 (s, 2H), 3.20 (m, 2H), 1.09 (t, 3H). MS (EI) for $C_{25}H_{20}F_2N_6O_2$: 475 [M+H].

Example E-5.43

1-(7-Chloro-5-(2-fluoro-5-((4-oxo-3,4-dihydrophthalazin-1-yl)methyl)phenyl)-1H-benzoimidazol-2-yl)-3-ethylurea is prepared using 4-((4',5'-diamino-2'-chloro-6-fluoro-[1,1'-biphenyl]-3-yl)methyl)phthalazin-1 (2H)-one (1-4.1.). MS (EI) for $C_{25}H_{20}ClFN_6O_2$: 491 [M+H].

Example E-5.44

1-Ethyl-3-(5-(2-fluoro-5-((4-oxo-3,4-dihydrophthalazin-1-yl)methyl)phenyl)-1H-imidazo[4,5-b]pyridin-2-yl)urea is prepared using 4-(3-(5,6-diaminopyridin-2-yl)-4-fluorobenzyl)phthalazin-1 (2H)-one (I-5.44.). MS (EI) for $C_{24}H_{20}FN_7O_2$: 458 [M+H].

Example E-5.45

1-Ethyl-3-(6-(2-fluoro-5-((4-oxo-3,4-dihydrophthalazin-1-yl)methyl)phenyl)-3H-imidazo[4,5-b]pyridin-2-yl)urea is prepared using 4-(3-(5,6-diaminopyridin-3-yl)-4-fluorobenzyl)phthalazin-1 (2H)-one (I-5.45.). MS (EI) for $C_{24}H_{20}FN_7O_2$: 458 [M+H].

Example E-5.46

1-Ethyl-3-(6-(2-fluoro-5-((4-oxo-3,4-dihydrophthalazin-1-yl)methyl)phenyl)-3H-imidazo[4,5-c]pyridin-2-yl)urea is prepared using 4-(3-(4,5-diaminopyridin-2-yl)-4-fluorobenzyl)phthalazin-1(2H)-one (I-5.46.). MS (EI) for $C_{24}H_{20}FN_7O_2$: 458 [M+H].

Example E-5.47

1-Ethyl-3-(6-(2-fluoro-5-((4-oxo-3,4-dihydrophthalazin-1-yl)methyl)phenyl)-5-methyl-3H-imidazo[4,5-b]pyridin-2- yl)urea is prepared using 4-(3-(5,6-diamino-2-methylpyridin-3-yl)-4-fluorobenzyl)phthalazin-1(2H)-one (I-5.47.). MS (EI) for $C_{25}H_{22}FN_7O_2$: 472 [M+H].

Example E-5.48

1-Ethyl-3-(5-(2-fluoro-5-((4-oxo-4,5-dihydrofuro[2,3-d]pyridazin-7-yl)methyl)phenyl)-1H-benzoimidazol-2-yl)urea is prepared using 4-(3-(5,6-diamino-4-methylpyridin-3-yl)-4-fluorobenzyl)phthalazin-1(2H)-one (I-5.48). MS (EI) for $C_{25}H_{22}FN_7O_2$: 472 [M+H].

Example E-5.49

1-Ethyl-3-(6-(2-fluoro-4-((4-oxo-3,4-dihydrophthalazin-1-yl)methyl)phenyl)-1H-benzo[d]imidazol-2-yl)urea was prepared using 4-((3',4'-diamino-2-fluoro-[1,1'-biphenyl]-4-yl)methyl)phthalazin-1(2H)-one (I-5.49). MS (EI) for $C_{25}H_{21}FN_6O_2$: 457 [M+H].

Example 6

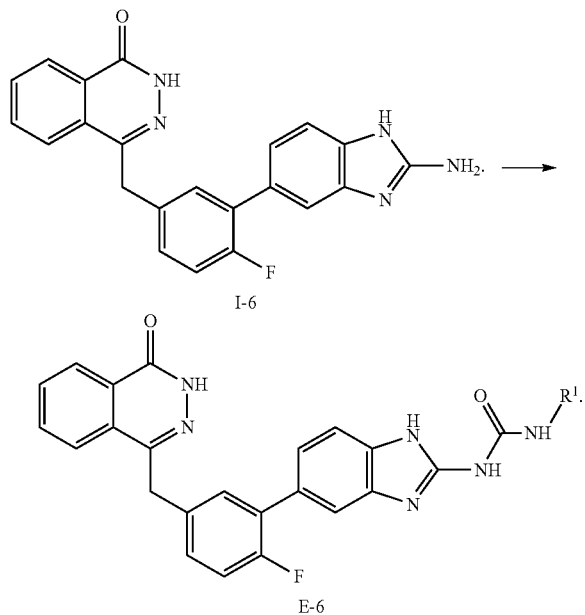

General Synthesis of Urea-Library (E-6.):

To solution of 4-(3-(2-amino-1H-benzoimidazol-6-yl)-4-fluorobenzyl)phthalazin-1(2H)-one (I-6.) (0.040 mg, 0.1 mmol) in anhydrous tetrahydrofuran (1.0 ml) 1,1'-carbonyl-diimidazole (0.021 g, 0.13 mmol) was added and the reaction mixture was stirred at 50° C. for eight hours, followed by the addition of amine (1.0 mmol, 10 eq.) and the reaction mixture was heated to 75° C. for four hours. It was cooled to room temperature and the residue was purified by preparative reverse phase HPLC chromatography (acetonitrile-water with 0.1% trifluoroacetic acid). The desired product was collected by concentrating the solvent to give title urea compound.

Example E-6.1

1-(5-(2-Fluoro-5-((4-oxo-3,4-dihydrophthalazin-1-yl)methyl)phenyl)-1H-benzoimidazol-2-yl)-3-propylurea was prepared from 1-aminopropane. MS (EI) for $C_{26}H_{23}FN_6O_2$: 471 [M+H].

Example E-6.2

1-(5-(2-Fluoro-5-((4-oxo-3,4-dihydrophthalazin-1-yl)methyl)phenyl)-1H-benzoimidazol-2-yl)-3-(2-fluoroethyl)urea was prepared using 2-fluoroethan-1-amine. MS (EI) for $C_{25}H_{20}F_2N_6O_2$: 475 [M+H].

Example E-6.3

1-(2,2-Difluoroethyl)-3-(5-(2-fluoro-5-((4-oxo-3,4-dihydrophthalazin-1-yl)methyl)phenyl)-1H-benzoimidazol-2-yl)urea was prepared using 2,2-difluoroethan-1-amine. MS (EI) for $C_{25}H_{19}F_3N_6O_2$: 493 [M+H].

Example E-6.4

1-(5-(2-Fluoro-5-((4-oxo-3,4-dihydrophthalazin-1-yl)methyl)phenyl)-1H-benzoimidazol-2-yl)-3-(2,2,2-trifluoroethyl)urea was prepared using 2,2,2-trifluoroethan-1-amine. MS (EI) for $C_{25}H_{18}F_4N_6O_2$: 511 [M+H].

Example E-6.5

1-(5-(2-Fluoro-5-((4-oxo-3,4-dihydrophthalazin-1-yl)methyl)phenyl)-1H-benzoimidazol-2-yl)-3-isopropylurea was prepared using 2-aminopropane. MS (EI) for $C_{26}H_{23}FN_6O_2$: 471 [M+H].

Example E-6.6

1-(sec-Butyl)-3-(5-(2-fluoro-5-((4-oxo-3,4-dihydrophthalazin-1-yl)methyl) phenyl)-1H-benzoimidazol-2-yl)urea was prepared using 2-aminobutane. MS (EI) for $C_{27}H_{25}FN_6O_2$: 485 M+H].

Example E-6.7

1-Cyclopropyl-3-(5-(2-fluoro-5-((4-oxo-3,4-dihydrophthalazin-1-yl)methyl) phenyl)-1H-benzoimidazol-2-yl)urea was prepared using cyclopropanamine. MS (EI) for $C_{26}H_{21}FN_6O_2$: 469 [M+H].

Example E-6.8

1-Cyclobutyl-3-(5-(2-fluoro-5-((4-oxo-3,4-dihydrophthalazin-1-yl)methyl) phenyl)-1H-benzoimidazol-2-yl)urea was prepared using cyclobutanamine. MS (EI) for $C_{27}H_{23}FN_6O_2$: 483 [M+H].

Example E-6.9

1-Cyclopentyl-3-(5-(2-fluoro-5-((4-oxo-3,4-dihydrophthalazin-1-yl)methyl) phenyl)-1H-benzoimidazol-2-yl)urea was prepared using cyclopentanamine. MS (EI) for $C_{28}H_{25}FN_6O_2$: 497 [M+H].

Example E-6.10

1-Cyclohexyl-3-(5-(2-fluoro-5-((4-oxo-3,4-dihydrophthalazin-1-yl)methyl) phenyl)-1H-benzoimidazol-2-yl)urea was prepared using cyclohexanamine. MS (EI) for $C_{29}H_{27}FN_6O_2$: 511 [M+H].

Example E-6.11

1-(5-(2-Fluoro-5-((4-oxo-3,4-dihydrophthalazin-1-yl)methyl)phenyl)-1H-benzoimidazol-2-yl)-3-(oxetan-3-yl) urea was prepared using 3-amino-oxetan. MS (EI) for $C_{26}H_{21}FN_6O_3$: 485 [M+H].

Example E-6.12

1-(5-(2-Fluoro-5-((4-oxo-3,4-dihydrophthalazin-1-yl)methyl)phenyl)-1H-benzoimidazol-2-yl)-3-(tetrahydro-2H-pyran-4-yl)urea was prepared using 4-amino-tetrahydro-2H-pyran. MS (EI) for $C_{28}H_{25}FN_6O_3$: 513 [M+H].

Example E-6.13

1-(5-(2-Fluoro-5-((4-oxo-3,4-dihydrophthalazin-1-yl)methyl)phenyl)-1H-benzoimidazol-2-yl)-3-(1-methylazetidin-3-yl)urea was prepared using 3-amino-1-methylazetidin. MS (EI) for $C_{27}H_{24}FN_7O_2$: 498 [M+H].

Example E-6.14

1-(5-(2-Fluoro-5-((4-oxo-3,4-dihydrophthalazin-1-yl)methyl)phenyl)-1H-benzoimidazol-2-yl)-3-(1-methylpiperidin-4-yl)urea was prepared using 4-amino-1-methylpiperidin. MS (EI) for $C_{29}H_{28}FN_7O_2$: 526 [M+H].

Example E-6.15

1-(2-(Dimethylamino)ethyl)-3-(5-(2-fluoro-5-((4-oxo-3,4-dihydrophthalazin-1-yl)methyl)phenyl)-1H-benzoimidazol-2-yl)urea was prepared using N,N-dimethylethylenediamine. MS (EI) for $C_{27}H_{26}FN_7O_2$: 500 [M+H].

Example E-6.16

1-(2-(Diethylamino)ethyl)-3-(5-(2-fluoro-5-((4-oxo-3,4-dihydrophthalazin-1-yl)methyl)phenyl)-1H-benzoimidazol-2-yl)urea was prepared using N,N-diethylethylenediamine. MS (EI) for $C_{29}H_{30}FN_7O_2$: 528 [M+H].

Example E-6.17

1-(5-(2-Fluoro-5-((4-oxo-3,4-dihydrophthalazin-1-yl)methyl)phenyl)-H-benzoimidazol-2-yl)-3-(2-(pyrrolidin-1-yl)ethyl)urea was prepared using 2-(pyrrolidin-1-yl)ethan-1-amine. MS (EI) for $C_{29}H_{28}FN_7O_2$: 526 [M+H].

Example E-6.18

1-(5-(2-Fluoro-5-((4-oxo-3,4-dihydrophthalazin-1-yl)methyl)phenyl)-1H-benzoimidazol-2-yl)-3-(2-(4-methylpiperazin-1-yl)ethyl)urea was prepared using 2-(4-methylpiperazin-1-yl)ethan-1-amine. MS (EI) for $C_{30}H_{31}FN_8O_2$: 555 [M+H].

Example E-6.19

1-(5-(2-Fluoro-5-((4-oxo-3,4-dihydrophthalazin-1-yl)methyl)phenyl)-1H-benzoimidazol-2-yl)-3-(2-morpholinoethyl)urea was prepared using 2-morpholinoethan-1-amine. MS (EI) for $C_{29}H_{28}FN_7O_3$: 542 [M+H].

Example E-6.20

1-(5-(2-Fluoro-5-((4-oxo-3,4-dihydrophthalazin-1-yl)methyl)phenyl)-1H-benzoimidazol-2-yl)-3-(2-(1-methylpiperidin-4-yl)ethyl)urea was prepared using 2-(1-methylpiperidin-4-yl)ethan-1-amine. MS (EI) for $C_{31}H_{32}FN_7O_2$: 554 [M+H].

Example E-6.21

1-(3-(Dimethylamino)propyl)-3-(5-(2-fluoro-5-((4-oxo-3,4-dihydrophthalazin-1-yl)methyl)phenyl)-1H-benzoimidazol-2-yl)urea was prepared using N,N-dimethylpropylenediamine. MS (EI) for $C_{28}H_{28}FN_7O_2$: 514 [M+H].

Example E-6.22

1-(5-(2-Fluoro-5-((4-oxo-3,4-dihydrophthalazin-1-yl)methyl)phenyl)-1H-benzoimidazol-2-yl)-3-phenylurea was prepared using aniline. MS (EI) for $C_{29}H_{21}FN_6O_2$: 505 [M+H].

Example E-6.23

1-Benzyl-3-(5-(2-fluoro-5-((4-oxo-3,4-dihydrophthalazin-1-yl)methyl)phenyl)-1H-benzoimidazol-2-yl)urea was prepared using phenylmethanamine. MS (EI) for $C_{30}H_{23}FN_6O_2$: 519 [M+H].

Example E-6.24

Methyl ((5-(2-fluoro-5-((4-oxo-3,4-dihydrophthalazin-1-yl)methyl)phenyl)-1H-benzoimidazol-2-yl)carbamoyl)glycinate was prepared using methyl glycinate. MS (EI) for $C_{26}H_{21}FN_6O_4$: 501 [M+H].

Example E-6.25

3-(5-(2-Fluoro-5-((4-oxo-3,4-dihydrophthalazin-1-yl)methyl)phenyl)-1H-benzoimidazol-2-yl)-1,1-dimethylurea was prepared using dimethylamine. MS (EI) for $C_{25}H_{21}FN_6O_2$: 457 [M+H].

Example E-6.26

1,1-Diethyl-3-(5-(2-fluoro-5-((4-oxo-3,4-dihydrophthalazin-1-yl)methyl)phenyl)-1H-benzoimidazol-2-yl)urea was prepared using diethylamine. MS (EI) for $C_{27}H_{25}FN_6O_2$: 485 [M+H].

Example 7

Example 7.1. N-(5-(2-fluoro-5-((4-oxo-3,4-dihydrophthalazin-1-yl)methyl)phenyl)-1H-benzimidazol-2-yl) Methanesulfonamide

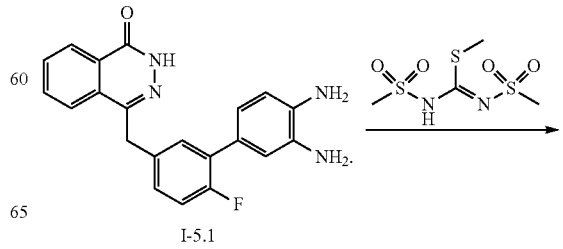

I-5.1

-continued

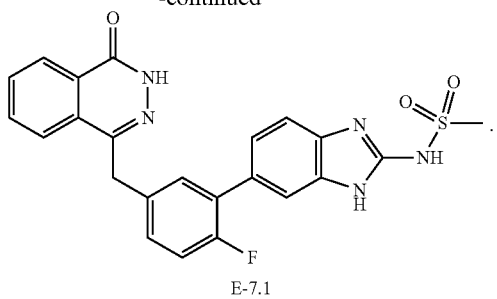

E-7.1

A solution of 4-((3',4'-diamino-6-fluoro-[1,1'-biphenyl]-3-yl)methyl)phthalazin-1(2H)-one (I-5.1.) (0.18 g, 0.50 mmol) and methyl-N,N'-bis(methylsulfonyl)carbamimidothioate (R.5.4.) (0.13 g, 0.50 mmol) in acetic acid (3.0 mL) was stirred at 98° C. for 18 hours. After cooling the reaction mixture to room temperature it was diluted with water (5 mL) and the pH was adjusted to 8 by the addition of 10N aqueous sodium hydroxide (5.2 mL), and then partitioned with ethyl acetate (100 mL), washed with brine (50 mL), dried over anhydrous sodium sulfate and concentrated. The resulting crude was purified by gradient silica gel flash chromatography (5-20% 7N ammonia in methanol in ethyl acetate) to give N-(5-(2-fluoro-5-((4-oxo-3,4-dihydrophthalazin-1-yl)methyl) phenyl)-1H-benzimidazol-2-yl) methanesulfonamide (E-7.1.) (0.17 g, 72%). 1H-NMR (300 MHz, $d_6$-DMSO): 12.58 (s, 1H), 12.27 (s, 1H), 8.26 (d, 1H), 8.04 (d, 1H), 7.90 (t, 1H), 7.82 (t, 1H), 7.55-752 (m, 3H), 7.23 (m, 2H), 7.20 (t, 1H), 4.36 (s, 2H), 3.32 (s, 3H). MS (EI) for $C_{23}H_{18}FN_5O_3S$: 464 [M+H].

Example 8

Example 8.1 Ethyl (5-{2-fluoro-5-[(4-oxo-3,4-dihydrophthalazin-1-yl)methyl]phenyl}-1H-benzimidazol-2-yl)carbamate A solution of 4-((3',4'-diamino-6-fluoro-[1,1'-biphenyl]-3-yl)methyl)phthalazin-1(2H)-one (I-5.1.) (0.18 g, 0.50 mmol) and methyl N,N'-bis[(propyl)carbonyl] imidothiocarbamate (R-5.5.) (0.12 g, 0.50 mmol) in acetic acid (3.0 mL) was stirred at 98° C. for 18 hours. After cooling the reaction mixture to room temperature it was diluted with water (5 mL) and the pH was adjusted to 8 by the addition of 10N aqueous sodium hydroxide (5.2 mL), and then partitioned with ethyl acetate (100 mL), washed with brine (50 mL), dried over anhydrous sodium sulfate and concentrated. The resulting crude was purified by gradient silica gel flash chromatography (5-20% 7N ammonia in methanol in ethyl acetate) to give N-(5-(2-fluoro-5-((4-oxo-3,4-dihydrophthalazin-1-yl)methyl)phenyl)-H-benzimidazol-2-yl)butyramide (E-8.1.) (0.09 g, 38%). 1H-NMR (300 MHz, $d_6$-DMSO): 12.60 (s, 1H), 11.82 (s, 2H), 8.26 (d, 1H), 8.04 (d, 1H), 7.88 (m, 2H), 7.46 (m, 3H), 7.26 (m, 3H), 4.32 (s, 2H), 3.40 (dd, 2H), 2.24 (m, 2H), 0.96 (t, 3H). MS (EI) for $C_{26}H_{22}FN_5O_2$: 456 [M+H].

REAGENT SYNTHESIS

Reagent R-1.1.
3-Bromo-4-(difluoromethoxy)benzaldehyde

To a mixture of 3-bromo-4-hydroxy-benzaldehyde (5.0 g, 24.88 mmol) and cesium carbonate (20.3 g, 62.20 mmol) in N,N-dimethylformamide (75 mL) was sodium chlorodifluoroacetate (7.6 g, 49.76 mmol) was added and the reaction mixture was stirred at 75° C. for 18 hours. It was partitioned with ethyl acetate (250 mL) and water (100 mL), the organic phase was washed with water (2×100 mL), 1M aqueous hydrochloric acid (2×150 mL) and brine (150 mL), dried over anhydrous sodium sulfate and concentrated. The resulting crude was purified by gradient silica gel flash chromatography (0-25% ethyl acetate in hexanes) to give 3-bromo-4-(difluoromethoxy) benzaldehyde (R-1.1.) (4.6 g, 74%). 1H-NMR (300 MHz, $d_6$-DMSO): 9.90 (s, 1H), 8.22 (d, 1H), 8.04 (dd, 1H), 7.56 (d, 1H), 7.44 (t, 1H). MS (EI) for $C_8H_5BrF_2O_2$: 234 [M+H].

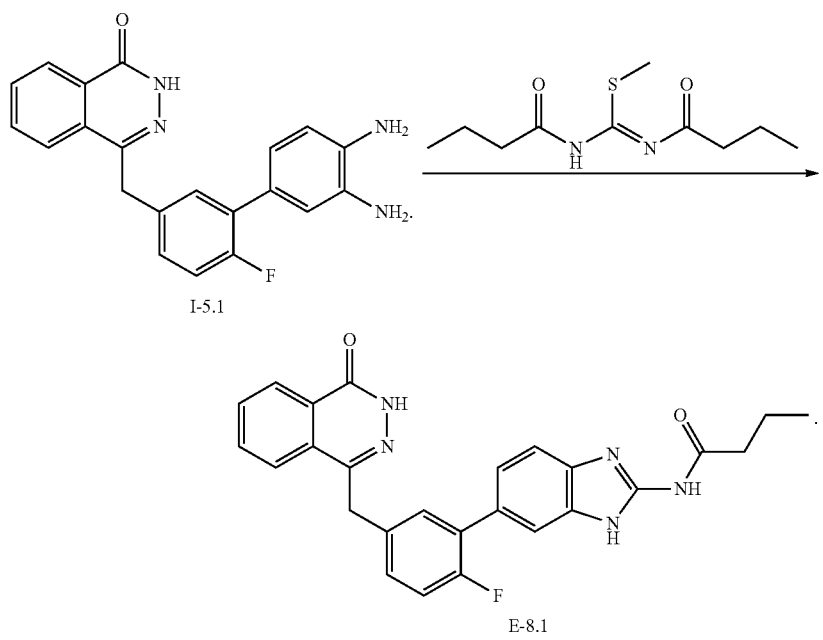

I-5.1

E-8.1

Reagent R-1.2.
5-Bromo-4-fluoro-2-methoxybenzaldehyde

To a solution of 4-fluoro-2-methoxybenzaldehyde (5.0 g, 32.45 mmol) in acetonitrile (100 mL) N-bromosuccinimide (7.22 g, 40.56 mmol) was added and the reaction mixture was stirred at 70° C. under an atmosphere of nitrogen for 18 hours. It was partitioned with ethyl acetate (350 mL) and water (100 mL), the organic phase was washed with 1M aqueous hydrochloric acid (2×150 mL) and brine (150 mL), dried over anhydrous sodium sulfate and concentrated. The resulting crude was purified by gradient silica gel flash chromatography (0-25% ethyl acetate in hexanes) to give 5-bromo-4-fluoro-2-methoxybenzaldehyde (R-1.2.) (7.1 g, 94%). 1H-NMR (300 MHz, $d_6$-DMSO): 10.28 (s, 1H), 7.98 (d, 1H), 6.86 (d, 1H), 3.90 (s, 3H). MS (EI) for $C_8H_6BrFO_2$: 234 [M+H].

Reagent R-1.3.
5-Bromo-2-fluoro-4-methoxybenzaldehyde

To a solution of 2-fluoro-4-methoxybenzaldehyde (5.0 g, 32.45 mmol) in methanol (50 mL) bromine (3.3 mL, 65.0 mmol)) was added dropwise at 0° C. and the reaction mixture was stirred for 18 hours. The mixture was partitioned with ethyl acetate (350 mL) and water (100 mL), the organic phase was washed with water (2×150 mL), 2M aqueous sodium hydrogen sulfite (2×150 mL and brine (150 mL), dried over anhydrous sodium sulfate and concentrated. The resulting crude was purified by gradient silica gel flash chromatography (0-25% ethyl acetate in hexanes) to give 5-bromo-2-fluoro-4-methoxybenzaldehyde (R-1.3.) (6.6 g, 87%). 1H-NMR (300 MHz, $d_6$-DMSO): 10.20 (s, 1H), 8.04 (d, 1H), 6.72 (d, 1H), 3.98 (s, 3H). MS (EI) for $C_8H_6BrFO_2$: 234 [M+H].

Reagent R-2.1. 2-Bromo-4-ethynyl-1-fluorobenzene

STEP 1. To a solution of 2-bromo-1-fluoro-4-iodobenzene (6.0 g, 20.0 mmol), ethynyl-trimethylsilane (4.20 mL, 30.0 mmol) and piperidine (3.0 mL, 30.0 mmol) in anhydrous tetrahydrofuran (100 mL) copper(I) iodide (0.38 g, 2.0 mmol) was added, followed by the addition of bis(triphenylphosphine)palladium(II) dichloride (0.70 g, 1.0 mmol) and the reaction mixture was stirred under an atmosphere of nitrogen for 18 hours. The mixture was diluted with ethyl acetate (250 mL) and filtered through a pad of Celite, washed with an additional portion of ethyl acetate (100 mL). The combined phases were washed with 1M aqueous hydrochloric acid (2×150 mL) and brine (150 mL), dried over anhydrous sodium sulfate and concentrated. The resulting crude was purified by gradient silica gel flash chromatography (0-20% ethyl acetate in hexanes) to give ((4-bromo-3-fluorophenyl)ethynyl)trimethylsilane (5.0 g, 92%).

STEP 2. To a solution of ((4-bromo-3-fluorophenyl)ethynyl)trimethylsilane (5.0 g, 18.40 mmol) in methanol (100 mL) was added potassium carbonate (7.64 g, 55.20 mmol) and the reaction mixture was stirred at room temperature for 5 hours. The solvent was removed and the residue was partitioned with ethyl acetate (250 mL) and water (100 mL). The organic phase was washed with water (100 mL), 0.5 M aqueous hydrochloric acid (100 mL) and brine (100 mL), dried over anhydrous sodium sulfate and concentrated. The resulting crude was purified by gradient silica gel flash chromatography (0-20% ethyl acetate in hexanes) to give 2-bromo-4-ethynyl-1-fluorobenzene (2b, R-2.1.) (3.40 g, 83%). 1H-NMR (300 MHz, $d_6$-DMSO): 7.78 (dd, 1H), 7.46 (m, 1H), 7.32 (d, 1H), 4.28 (1H). MS (EI) for $C_8H_4BrF$: 199 [M+H].

Reagent R-3.1. N-(Quinolin-8-yl)benzamide

To a solution of 8-aminoquinoline (1.44 g, 10.0 mmol) and trimethylamine (2.8 mL, 20.0 mmol) in anhydrous tetrahydrofuran (7 mL) was added a solution of benzoyl chloride (1.3 mL, 11.0 mmol) in tetrahydrofuran (5 mL) dropwise while maintain the temperature at 0° C. The reaction mixture was stirred for 18 hours at room temperature. It was partitioned with ethyl acetate (250 mL) and water (100 mL). The organic phase was washed with water (2×100 mL), and brine (100 mL), dried over anhydrous sodium sulfate and concentrated. The resulting crude was purified by gradient silica gel flash chromatography (0-80% ethyl acetate in hexanes) to give N-(quinolin-8-yl)benzamide (1c, R-3.1.) (2.4 g, 96%). 1H-NMR (300 MHz, $d_6$-DMSO): 10.70 (s, 1H), 9.01 (dd, 1H), 8.78 (dd, 1H), 8.48 (d, 1H), 8.12-8.06 (m, 2H), 7.78 (dd, 1H), 7.66 (m, 5H).). MS (EI) for $C_{16}H_{12}N_2O$: 249 [M+H].

Reagent R-3.2

2,5-Difluoro-N-(quinolin-8-yl)benzamide was prepared using 2,5-difluorobenzoyl chloride. MS (EI) for $C_{16}H_{10}F_2N_2O$: 285 [M+H].

Reagent R-3.3

2-Methyl-N-(quinolin-8-yl)benzamide is prepared using 2-methylbenzoyl chloride. MS (EI) for $C_{17}H_{14}N_2O$: 263 [M+H].

Reagent R-3.4

3-Methyl-N-(quinolin-8-yl)benzamide was prepared using 3-methylbenzoyl chloride. 1H NMR (300 MHz, $d_6$-DMSO): 10.65 (s, 1H), 9.02 (dd, 1H), 8.78 (dd, 1H), 8.48 (dd, 1H), 7.88 (d, 2H), 7.76 (dd, 1H), 7.72 (m, 2H), 7.60-7.48 (m, 2H), 2.48 (s, 3H). MS (EI) for $C_{17}H_{14}N_2O$: 263 [M+H].

Reagent R-3.5

4-Methyl-N-(quinolin-8-yl)benzamide was prepared using 4-methylbenzoyl chloride. 1H NMR (300 MHz, $d_6$-DMSO): 10.67 (s, 1H), 9.02 (dd, 1H), 8.79 (dd, 1H), 8.50 (dd, 1H), 8.00 (d, 2H), 7.76 (dd, 1H), 7.76-7.65 (m, 2H), 7.46 (d, 2H), 2.4 (s, 3H). MS (EI) for $C_{17}H_{14}N_2O$: 263 [M+H].

Reagent R-3.6

4-Chloro-N-(quinolin-8-yl)benzamide is prepared using 4-chlorobenzoyl chloride. MS (EI) for $C_{16}H_{11}ClN_2O$: 283 [M+H].

Reagent R-3.7

N-(Quinolin-8-yl)-4-(trifluoromethyl)benzamide is prepared using 4-(trifluoromethyl)benzoyl chloride. MS (EI) for $C_{17}H_{11}F_3N_2O$: 317 [M+H].

Reagent R-3.8

4-methoxy-N-(quinolin-8-yl)benzamide is prepared using 4-methoxybenzoyl chloride. MS (EI) for $C_{17}H_{14}N_2O_2$: 279 [M+H].

Reagent R-3.9

N-(quinolin-8-yl)-4-(trifluoromethoxy)benzamide is prepared using 4-(trifluoromethoxy)benzoyl chloride. MS (EI) for $C_{17}H_{11}F_3N_2O_2$: 233 [M+H].

Reagent R-3.10

3,5-dimethoxy-N-(quinolin-8-yl)benzamide is prepared using 3,5-dimethoxybenzoyl chloride. MS (EI) for $C_{18}H_{16}N_2O_3$: 309 [M+H].

Reagent 4.1. 4'-Amino-6-fluoro-3'-nitro-[1,1'-biphenyl]-3-carbaldehyde

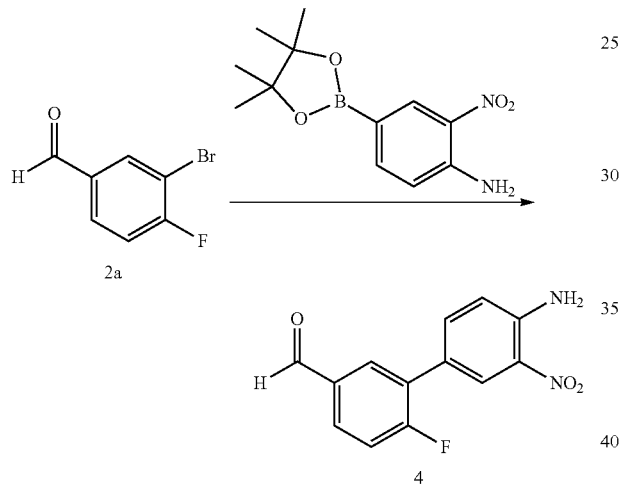

A mixture of 3-bromo-4-fluorobenzaldehyde (2a) (2.45 g, 12.0 mmol), 2-nitro-4-(4,4,5,5-tetramethyl-1,3,2-dioxaborolan-2-yl)aniline (3.20 g, 12.0 mmol in a mixture of 1,4-dioxane (32.5 mL) and a solution of potassium carbonate (5.0 g, 36.0 mmol) in water (7.5 mL) was heated to 98° C. and stirred until the reactants went into solution, then nitrogen gas was bubbled through the solution for approximately thirty minutes, followed by the addition of dichloro [1,1'-bis(diphenylphosphino)ferrocene]palladium (II) dichloromethane adduct (120 mg, 0.15 mmol). The reaction mixture was stirred under nitrogen atmosphere at 98° C. for 18 hours. It was cooled to room temperature and poured into water (250 mL). The precipitated product was collected by filtration and washed successively with water, and then air-dried for thirty minutes. The resulting crude material was dissolved in a mixture of ethyl acetate (300 mL) and tetrahydrofuran (150 mL) then anhydrous sodium sulfate (100 g) Celite (5 g) and silica gel (5 g) were added. The solution was left to age for twelve hours; then the solvent was concentrated. The precipitating solid was collected by filtration, washed with a solution of 10% ethyl acetate in hexanes and air dried for thirty minutes. The resulting crude was dissolved in hot tetrahydrofuran (200 mL) and treated with charcoal, filtered through a pad of Celite, and the solvent was concentrated. The precipitated product was collected by filtration and washed with heaxanes and air dried to give 4'-amino-6-fluoro-3'-nitro-[1,1'-biphenyl]-3-carbaldehyde (4, R-4.1.) (2.68 g, 86%) as an orange-brown solid. (TLC 30% ethyl acetate in hexanes, Rf.: 0.70). 1H NMR (300 MHz, $d_6$-DMSO): 10.03 (s, 1H), 8.22 (d, 1H), 8.12 (dd, 1H), 7.93 (m, 1H), 7.72-7.66 (m, 3H), 7.53 (dd, 1H), 7.14 (d, 1H). 13C NMR ($d_6$-DMSO): 191.76, 164.23, 160.84, 145.98, 135.77, 132.24, 127.39, 127.21, 125.36, 120.61, 119.74, 117.54, 117.23. MS (EI) for $C_{13}H_9FN_2O_3$: 261 [M+H].

Reagent R-4. 2. 4'-amino-5,6-difluoro-3'-nitro-[1,1'-biphenyl]-3-carbaldehyde A mixture of 3-bromo-4,5-difluorobenzaldehyde (0.66 g, 3.00 mmol) 2-nitro-4-(4,4,5,5-tetramethyl-1,3,2-dioxaborolan-2-yl)aniline (0.78 g, 3.00 mmol) and potassium carbonate (1.24 g, 9.00 mmol) in a mixture of 1,4-dioxane (12.5 mL) and water (2.5 mL) was purged with nitrogen gas and stirred 98° C. for 30 minutes followed by the addition of XPhos (Dicyclohexyl(2',4',6'-triisopropyl-[1,1'-biphenyl]2-yl)phosphine) (0.14 g, 0.3 mmol) and tetrakis(triphenylphosphine)palladium(O) (0.18 g, 0.15 mmol) and the stirring was continued for 18 hours. It was cooled to room temperature and partitioned with ethyl acetate (200 mL) and 1M aqueous hydrochloric acid (100 ml). The organic layer was separated and washed with 1M aqueous hydrochloric acid (100 ml) and brine (100 mL), dried over anhydrous sodium sulfate and concentrated. The resulting crude was purified by gradient silica gel flash chromatography (5-75% ethyl acetate in hexanes) to give 4'-amino-5,6-difluoro-3'-nitro-[1,1'-biphenyl]-3-carbaldehyde (R-4.2.) (0.26 g, 32%). MS (EI) for $C_{13}H_8F_2N_2O_3$: 279 [M+H].

Reagent R-4.3. 4-(4-amino-3-nitrophenyl)furan-2-carbaldehyde

A mixture of 4-bromofuran-2-carbaldehyde (0.52 g, 3.00 mmol) 2-nitro-4-(4,4,5,5-tetramethyl-1,3,2-dioxaborolan-2-yl)aniline (0.78 g, 3.00 mmol) and potassium carbonate (1.24 g, 9.00 mmol) in a mixture of 1,4-dioxane (12.5 mL) and water (2.5 mL) was purged with nitrogen gas and stirred 98° C. for 30 minutes followed by the addition of dichloro [1,1'-bis(diphenylphosphino)ferrocene] palladium (II) dichloromethane adduct (0.12 g, 0.15 mmol) and the stirring was continued for 18 hours. It was cooled to room temperature and partitioned with ethyl acetate (200 mL) and 1M aqueous hydrochloric acid (100 ml). The organic layer was separated and washed with 1M aqueous hydrochloric acid (100 ml) and brine (100 mL), dried over anhydrous sodium sulfate and concentrated. The resulting crude was purified by gradient silica gel flash chromatography (5-75% ethyl acetate in hexanes) to give 4-(4-amino-3-nitrophenyl)furan-2-carbaldehyde (R-4.3.) (0.40 g, 58%). MS (EI) for $C_{11}H_8N_2O_4$: 233 [M+H].

Reagent R-5.1. 1,3-Bis(ethoxycarbonyl)-2-methyl-2-thiopseudourea

STEP 1. To a suspension of 2-methyl-2-thiopseudourea hemi sulfate (4.56 g, 16.40 mmol) and sodium bicarbonate (6.90 g, 82.00 mmol) in a mixture of water (30 mL) and tetrahydrofuran (20 mL) was added dropwise a solution of ethyl chloroformate (3.30 mL, 34.40 mmol) in tetrahydrofuran (20 mL) at 0° C. in a course of two hours and was stirred overnight at room temperature. The solvent was concentrated, and the residue was partitioned with ethyl acetate (400 mL) and water (250 ml). The organic layer was washed with water (2×150 mL) and brine (2×250 mL), dried over anhydrous sodium sulfate and concentrated to give 1-ethoxycarbonyl-2-methyl-2-thiopseudourea (2.70 g). The resulting crude product was used without further purification.

STEP 2. To a solution of 1-ethoxycarbonyl-2-methyl-2-thiopseudourea (2.70 g, 16.40 mmol) and triethylamine (4.60 mL, 32.80 mmol) in tetrahydrofuran (30 mL) was added dropwise a solution of ethyl chloroformate (1.70 mL, 17.40 mmol) in tetrahydrofuran (20 mL) at 0° C. and was stirred overnight at room temperature. It was partitioned with ethyl acetate (400 mL) and 1M aqueous hydrochloric acid (150 ml). The organic layer was washed with 1M aqueous hydrochloric acid (2×150 mL) and brine (2×250 mL), dried over anhydrous sodium sulfate and concentrated. The resulting crude product was purified by gradient silica gel flash chromatography (hexane:ethyl acetate) to give 1,3-bis(ethoxycarbonyl)-2-methyl-2-thiopseudourea (R-5.1.) as an oil (solidifies to white solid upon standing) (3.65 g, 95%). 1H-NMR (300 MHz, $d_6$-DMSO): 11.13 (s, 1H), 4.10 (m, 4H), 2.28 (s, 3H), 1.22 (m, 6H). MS (EI) for $C_8H_{14}N_2O_4S$: 235 [M+H].

Reagent R-5.2

1,3-bis(methoxyethoxycarbonyl)-2-methyl-2-thiopseudourea was prepared using 2-methoxyethyl chloroformate. 1H-NMR (300 MHz, $d_6$-DMSO): 11.14 (s, 1H), 4.30 (m, 4H), 3.64 (m, 4H), 3.30 (s, 6H), 2.28 (s, 3H). MS (EI) for $C_{10}H_{18}N_2O_6S$: 295 [MH].

Reagent R-5.3

N,N'-bis[(ethylamino)-carbonyl] carbamimido thioic acid methyl ester was prepared using ethyl isocyanate. 1H-NMR (300 MHz, $d_6$-DMSO): 11.12 (s, 1H), 3.24 (q, 2H), 3.18 (q, 2H), 2.36 (s, 3H), 1.14 (m, 6H). MS (EI) for $C_8H_{16}N_4O_2S$: 233 [M+H].

Reagent R-5.4

Methyl-N,N-bis(methylsulfonyl)carbamimidothioate was prepared using methanesulfonyl chloride. 1H-NMR (300 MHz, $d_6$-DMSO): 11.16 (s, 1H), 2.48 (s, 3H), 2.86 (s, 3H), 2.98 (s, 3H). MS (EI) for $C_4H_{10}N_2O_4S_3$: 247 [M+H].

Reagent R-5.5

Methyl N,N'-bis[(propyl)carbonyl] imidothiocarbamate was prepared using butanoyl chloride. 1H-NMR (300 MHz, $d_6$-DMSO): 11.14 (s, 1H), 2.48 (s, 3H), 2.36 (m, 4H), 1.68 (m, 4H), 0.98 (m, 6H). MS [ESI] for $C_{10}H_{18}N_2O_2S$: 231 [M+H].

| Cmpd No. | Structure | Name |
|---|---|---|
| Example 1. | | |
| 1. | 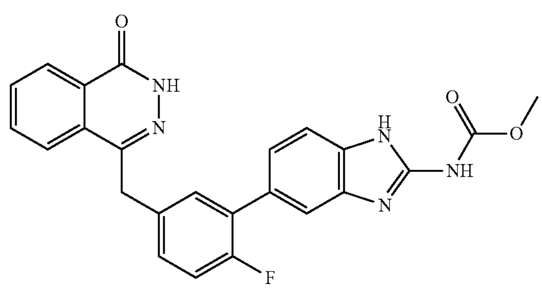 [SMILES: COC(=O)Nc1nc2cc(-c3cc(Cc4n[nH]c(=O)c5ccccc45)ccc3F)ccc2[nH]1] | Methyl (5-(2-fluoro-5-((4-oxo-3,4-dihydrophthalazin-1-yl)methyl)phenyl)-1H-benzoimidazol-2-yl)carbamate |
| 2. | 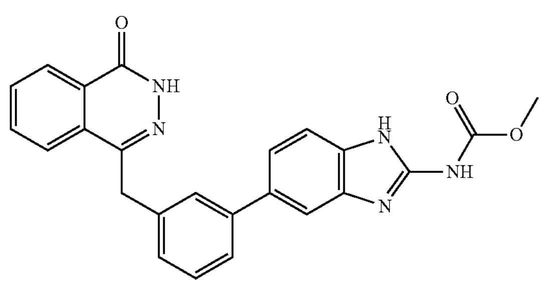 [SMILES: COC(=O)Nc1nc2cc(-c3cccc(Cc4n[nH]c(=O)c5ccccc45)c3)ccc2[nH]1] | Methyl (5-(3-((4-oxo-3,4-dihydrophthalazin-1-yl)methyl)phenyl)-1H-benzoimidazol-2-yl)carbamate |
| 3. | 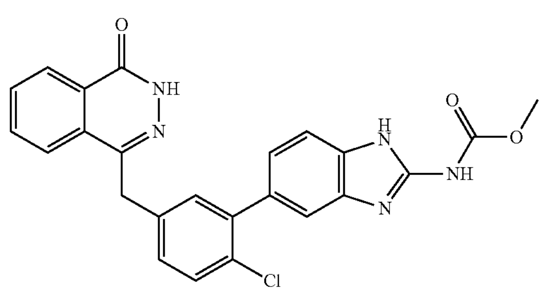 | Methyl (5-(2-chloro-5-((4-oxo-3,4-dihydrophthalazin-1-yl)methyl)phenyl)-1H-benzoimidazol-2-yl)carbamate |

| Cmpd No. | Structure | Name |
|---|---|---|
| 4. | 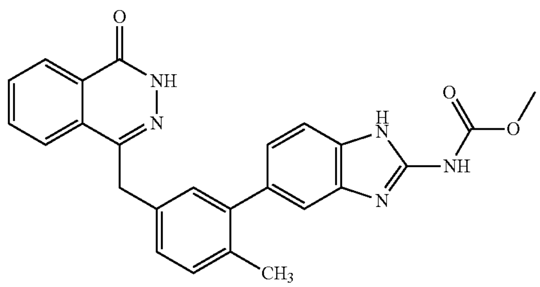 [SMILES: COC(=O)Nc1nc2cc(-c3cc(Cc4n[nH]c(=O)c5ccccc45)ccc3C)ccc2[nH]1] | Methyl (5-(2-methyl-5-((4-oxo-3,4-dihydrophthalazin-1-yl)methyl)phenyl)-1H-benzoimidazol-2-yl)carbamate |
| 5. | 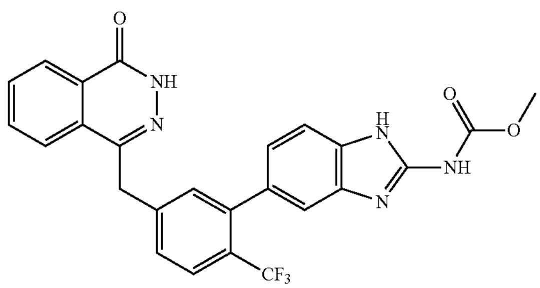 [SMILES: COC(=O)Nc1nc2cc(-c3cc(Cc4n[nH]c(=O)c5ccccc45)ccc3C(F)(F)F)ccc2[nH]1] | Methyl (5-(5-((4-oxo-3,4-dihydrophthalazin-1-yl)methyl)-2-(trifluoromethyl)phenyl)-1H-benzoimidazol-2-yl)carbamate |
| 6. | 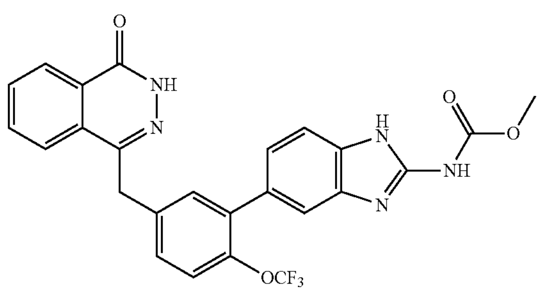 [SMILES: COC(=O)Nc1nc2cc(-c3cc(Cc4n[nH]c(=O)c5ccccc45)ccc3OC(F)(F)F)ccc2[nH]1] | Methyl (5-(5-((4-oxo-3,4-dihydrophthalazin-1-yl)methyl)-2-(trifluoromethoxy)phenyl)-1H-benzoimidazol-2-yl)carbamate |
| 7. | 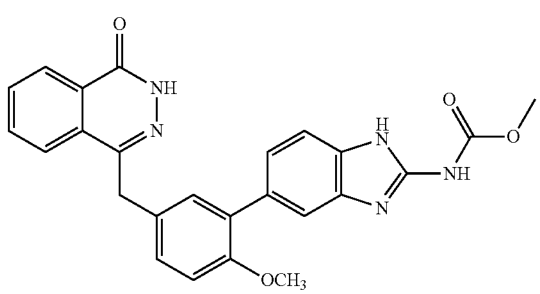 [SMILES: COC(=O)Nc1nc2cc(-c3cc(Cc4n[nH]c(=O)c5ccccc45)ccc3OC)ccc2[nH]1] | Methyl (5-(2-methoxy-5-((4-oxo-3,4-dihydrophthalazin-1-yl)methyl)phenyl)-1H-benzoimidazol-2-yl)carbamate |
| 8. | 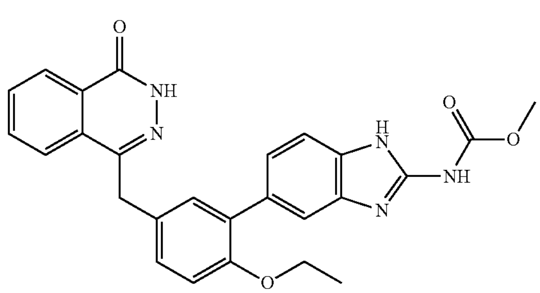 [SMILES: CCOc1ccc(Cc2n[nH]c(=O)c3ccccc23)cc1-c1ccc2[nH]c(NC(=O)OC)nc2c1] | Methyl (5-(2-ethoxy-5-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 9. | 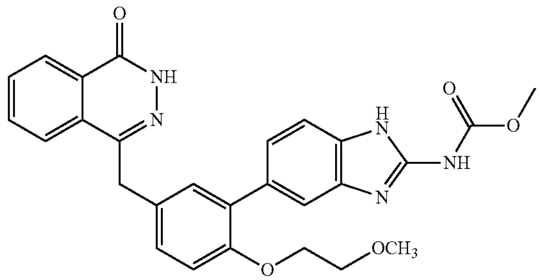 [SMILES: COCCOc1ccc(Cc2n[nH]c(=O)c3ccccc23)cc1-c1ccc2[nH]c(NC(=O)OC)nc2c1] | Methyl (5-(2-(2-methoxyethoxy)-5-((4-oxo-3,4-dihydrophthalazin-1-yl)methyl)phenyl)-1H-benzoimidazol-2-yl)carbamate |
| 10. | 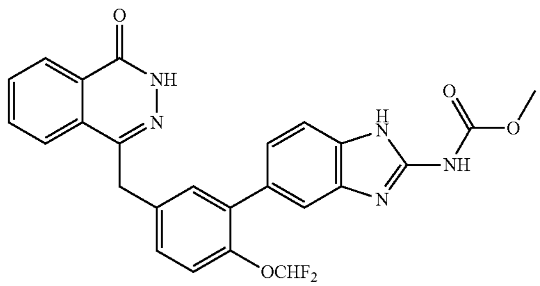 [SMILES: COC(=O)Nc1nc2cc(-c3cc(Cc4n[nH]c(=O)c5ccccc45)ccc3OC(F)F)ccc2[nH]1] | Methyl (5-(2-(difluoromethoxy)-5-((4-oxo-3,4-dihydrophthalazin-1-yl)methyl)phenyl)-1H-benzoimidazol-2-yl)carbamate |
| 11. | 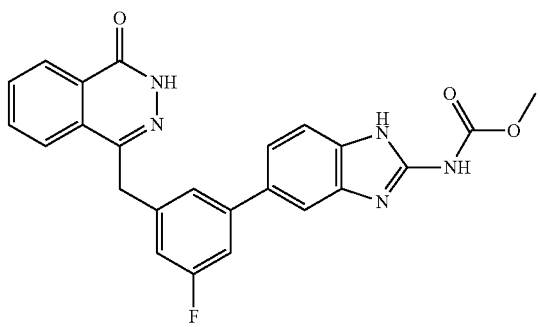 [SMILES: COC(=O)Nc1nc2cc(-c3cc(F)cc(Cc4n[nH]c(=O)c5ccccc45)c3)ccc2[nH]1] | Methyl (5-(3-fluoro-5-((4-oxo-3,4-dihydrophthalazin-1-yl)methyl)phenyl)-1H-benzoimidazol-2-yl)carbamate |
| 12. | 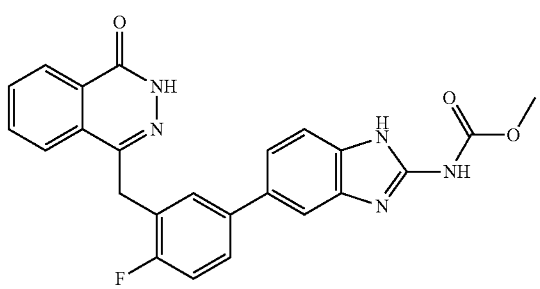 [SMILES: COC(=O)Nc1nc2cc(-c3ccc(F)c(Cc4n[nH]c(=O)c5ccccc45)c3)ccc2[nH]1] | Methyl (5-(4-fluoro-3-((4-oxo-3,4-dihydrophthalazin-1-yl)methyl)phenyl)-1H-benzoimidazol-2-yl)carbamate |
| 13. | 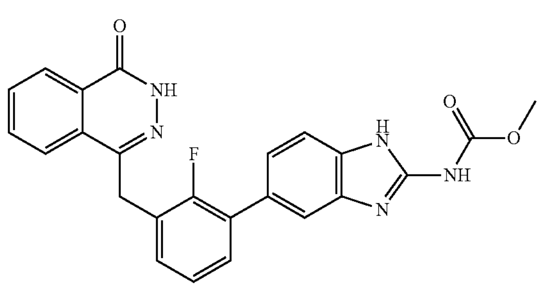 [SMILES: COC(=O)Nc1nc2cc(-c3cccc(Cc4n[nH]c(=O)c5ccccc45)c3F)ccc2[nH]1] | Methyl (5-(2-fluoro-3-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 14. | 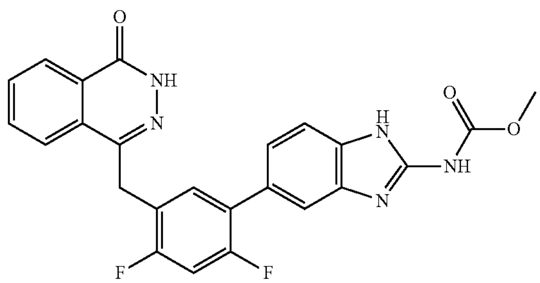 [SMILES: COC(=O)Nc1nc2cc(-c3cc(Cc4n[nH]c(=O)c5ccccc45)c(F)cc3F)ccc2[nH]1] | Methyl (5-(2,4-difluoro-5-((4-oxo-3,4-dihydrophthalazin-1-yl)methyl)phenyl)-1H-benzoimidazol-2-yl)carbamate |
| 15. | 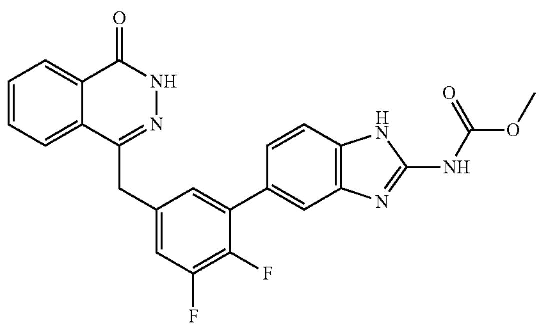 [SMILES: COC(=O)Nc1nc2cc(-c3cc(Cc4n[nH]c(=O)c5ccccc45)cc(F)c3F)ccc2[nH]1] | Methyl (5-(2,3-difluoro-5-((4-oxo-3,4-dihydrophthalazin-1-yl)methyl)phenyl)-1H-benzoimidazol-2-yl)carbamate |
| 16. | 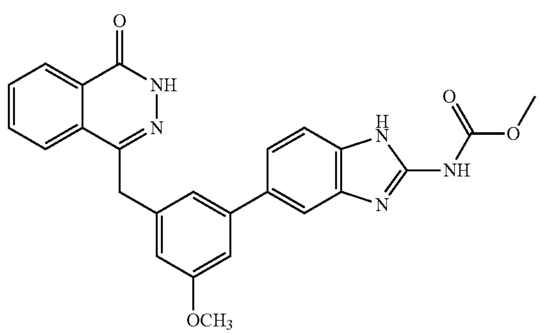 [SMILES: COC(=O)Nc1nc2cc(-c3cc(Cc4n[nH]c(=O)c5ccccc45)cc(OC)c3)ccc2[nH]1] | Methyl (5-(3-methoxy-5-((4-oxo-3,4-dihydroplithalazin-1-yl)methyl)phenyl)-1H-benzoimidazol-2-yl)carbamate |
| 17. | 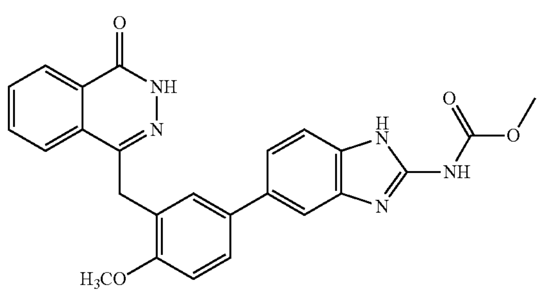 [SMILES: COC(=O)Nc1nc2cc(-c3ccc(OC)c(Cc4n[nH]c(=O)c5ccccc45)c3)ccc2[nH]1] | Methyl (5-(4-methoxy-3-((4-oxo-3,4-dihydrophthalazin-1-yl)methyl)phenyl)-1H-benzoimidazol-2-yl)carbamate |
| 18. | 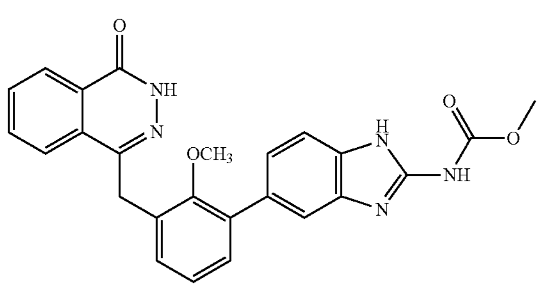 [SMILES: COC(=O)Nc1nc2cc(-c3cccc(Cc4n[nH]c(=O)c5ccccc45)c3OC)ccc2[nH]1] | Methyl (5-(2-methoxy-3-((4-oxo-3,4-dihydrophthalazin-1-yl)methyl)phenyl)-1H-benzoimidazol-2-yl)carbamate |

| Cmpd No. | Structure | Name |
|---|---|---|
| 19. | 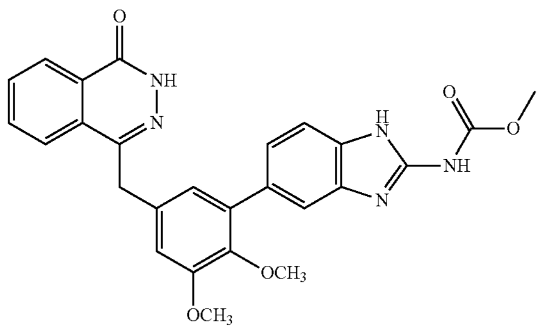 [SMILES: COC(=O)Nc1nc2cc(-c3cc(Cc4n[nH]c(=O)c5ccccc45)cc(OC)c3OC)ccc2[nH]1] | Methyl (5-(2,3-dimethoxy-5-((4-oxo-3,4-dihydrophthalazin-1-yl)methyl)phenyl)-1H-benzoimidazol-2-yl)carbamate |
| 20. | 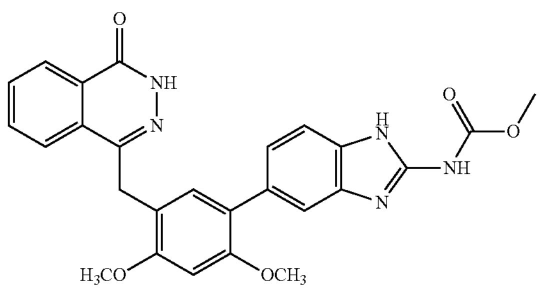 [SMILES: COC(=O)Nc1nc2cc(-c3cc(Cc4n[nH]c(=O)c5ccccc45)c(OC)cc3OC)ccc2[nH]1] | Methyl (5-(2,4-dimethoxy-5-((4-oxo-3,4-dihydrophthalazin-1-yl)methyl)phenyl)-1H-benzoimidazol-2-yl)carbamate |
| 21. | 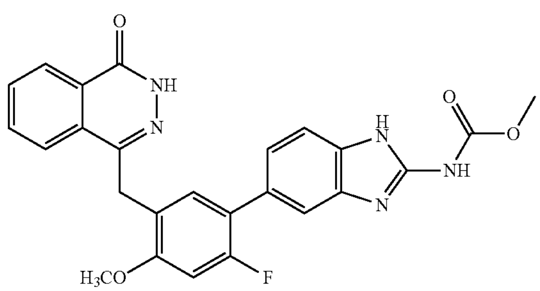 [SMILES: COC(=O)Nc1nc2cc(-c3cc(Cc4n[nH]c(=O)c5ccccc45)c(OC)cc3F)ccc2[nH]1] | Methyl (5-(2-fluoro-4-methoxy-5-((4-oxo-3,4-dihydrophthalazin-1-yl)methyl)phenyl)-1H-benzoimidazol-2-yl)carbamate |
| 22. | 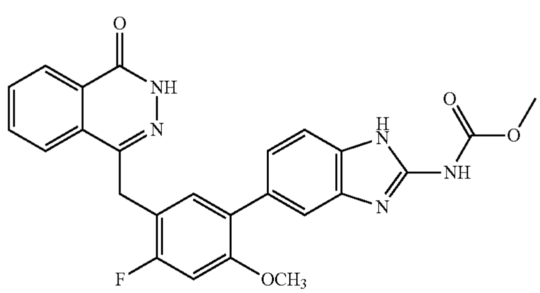 [SMILES: COC(=O)Nc1nc2cc(-c3cc(Cc4n[nH]c(=O)c5ccccc45)c(F)cc3OC)ccc2[nH]1] | Methyl (5-(4-fluoro-2-methoxy-5-((4-oxo-3,4-dihydrophthalazin-1-yl)methyl)phenyl)-1H-benzoimidazol-2-yl)carbamate |
| 23. | 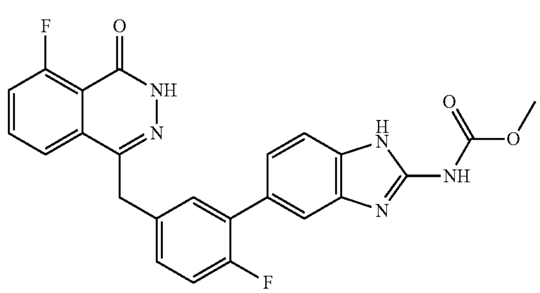 [SMILES: COC(=O)Nc1nc2cc(-c3cc(Cc4n[nH]c(=O)c5c(F)cccc45)ccc3F)ccc2[nH]1] | Methyl (5-(2-fluoro-5-((5-fluoro-4-oxo-3,4-dihydrophthalazin-1-yl)methyl)phenyl)-1H-benzoimidazol-2-yl)carbamate |

| Cmpd No. | Structure | Name |
|---|---|---|
| 24. | 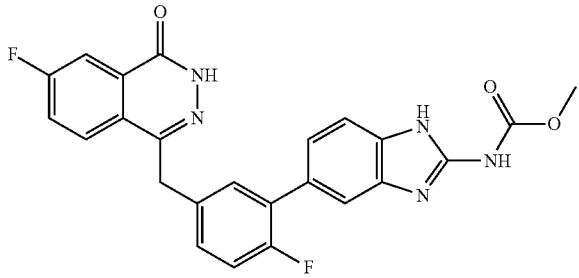 [SMILES: COC(=O)Nc1nc2cc(-c3cc(Cc4n[nH]c(=O)c5cc(F)ccc45)ccc3F)ccc2[nH]1] | Methyl (5-(2-fluoro-5-((6-fluoro-4-oxo-3,4-dihydrophthalazin-1-yl)methyl)phenyl)-1H-benzoimidazol-2-yl)carbamate |
| 25. | 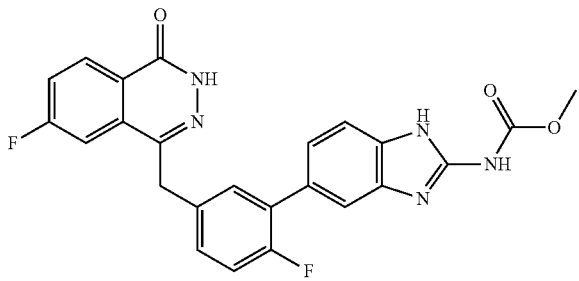 [SMILES: COC(=O)Nc1nc2cc(-c3cc(Cc4n[nH]c(=O)c5ccc(F)cc45)ccc3F)ccc2[nH]1] | Methyl (5-(2-fluoro-5-((7-fluoro-4-oxo-3,4-dihydrophthalazin-1-yl)methyl)phenyl)-1H-benzoimidazol-2-yl)carbamate |
| 26. | 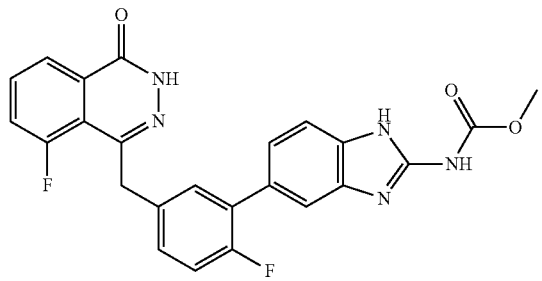 [SMILES: COC(=O)Nc1nc2cc(-c3cc(Cc4n[nH]c(=O)c5cccc(F)c45)ccc3F)ccc2[nH]1] | Methyl (5-(2-fluoro-5-((8-fluoro-4-oxo-3,4-dihydrophthalazin-1-yl)methyl)phenyl)-1H-benzoimidazol-2-yl)carbamate |
| 27. | 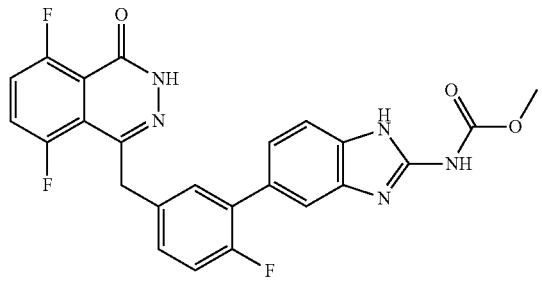 | Methyl (5-(5-((5,8-difluoro-4-oxo-3,4-dihydrophthalazin-1-yl)methyl)-2-fluorophenyl)-1H-benzoimidazol-2-yl)carbamate |
| 28. | 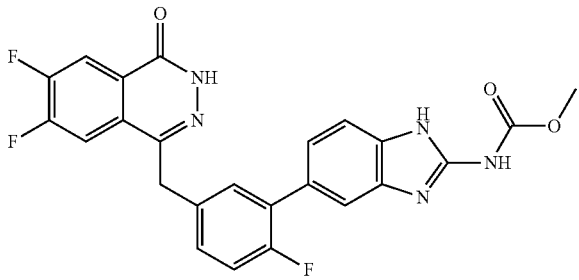 [SMILES: COC(=O)Nc1nc2cc(-c3cc(Cc4n[nH]c(=O)c5cc(F)c(F)cc45)ccc3F)ccc2[nH]1] | Methyl (5-(5-((6,7-difluoro-4-oxo-3,4-dihydrophthalazin-1-yl)methyl)-2-fluorophenyl)-1H-benzoimidazol-2-yl)carbamate |

-continued

| Cmpd No. | Structure | Name |
|---|---|---|
| 29. | 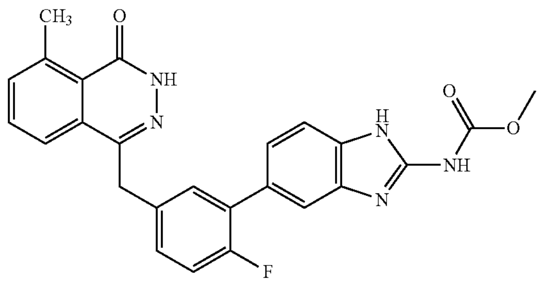 [SMILES: COC(=O)Nc1nc2cc(-c3cc(Cc4n[nH]c(=O)c5c(C)cccc45)ccc3F)ccc2[nH]1] | Methyl (5-(2-fluoro-5-((5-methyl-4-oxo-3,4-dihydrophthalazin-1-yl)methyl)phenyl)-1H-benzoimidazol-2-yl)carbamate |
| 30. | 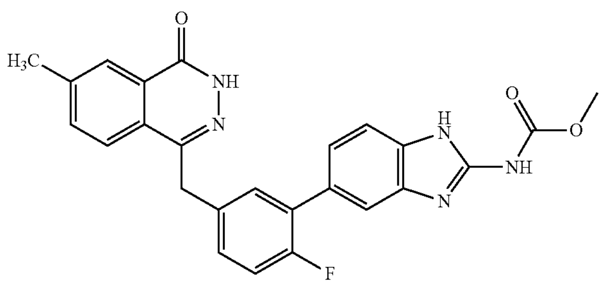 | Methyl (5-(2-fluoro-5-((6-methyl-4-oxo-3,4-dihydrophthalazin-1-yl)methyl)phenyl)-1H-benzoimidazol-2-yl)carbamate |
| 31. | 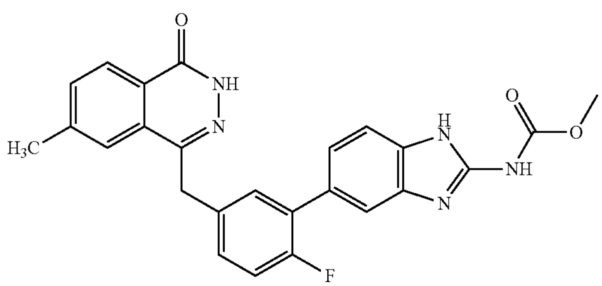 | Methyl (5-(2-fluoro-5-((7-methyl-4-oxo-3,4-dihydrophthalazin-1-yl)methyl)phenyl)-1H-benzoimidazol-2-yl)carbamate |
| 32. | 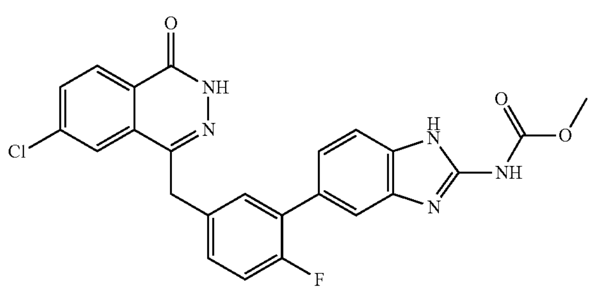 [SMILES: COC(=O)Nc1nc2cc(-c3cc(Cc4n[nH]c(=O)c5ccc(Cl)cc45)ccc3F)ccc2[nH]1] | Methyl (5-(5-((7-chloro-4-oxo-3,4-dihydrophthalazin-1-yl)methyl)-2-fluorophenyl)-1H-benzoimidazol-2-yl)carbamate |
| 33. | 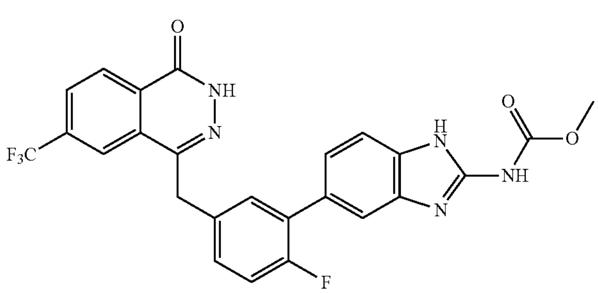 [SMILES: COC(=O)Nc1nc2cc(-c3cc(Cc4n[nH]c(=O)c5ccc(C(F)(F)F)cc45)ccc3F)ccc2[nH]1] | Methyl (5-(2-fluoro-5-((4-oxo-7-(trifluoromethyl)-3,4-dihydrophthalazin-1-yl)methyl)phenyl)-1H-benzoimidazol-2-yl)carbamate |

-continued

| Cmpd No. | Structure | Name |
|---|---|---|
| 34. | 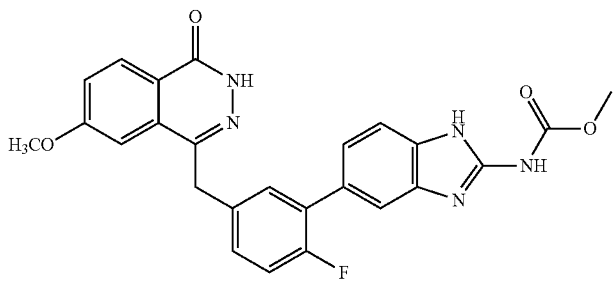 [SMILES: COC(=O)Nc1nc2cc(-c3cc(Cc4n[nH]c(=O)c5ccc(OC)cc45)ccc3F)ccc2[nH]1] | Methyl (5-(2-fluoro-5-((7-methoxy-4-oxo-3,4-dihydrophthalazin-1-yl)methyl)phenyl)-1H-benzoimidazol-2-yl)carbamate |
| 35. | 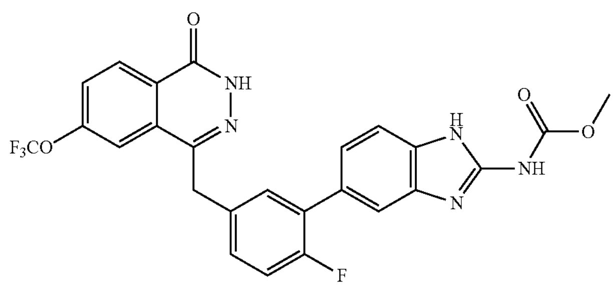 [SMILES: COC(=O)Nc1nc2cc(-c3cc(Cc4n[nH]c(=O)c5ccc(OC(F)(F)F)cc45)ccc3F)ccc2[nH]1] | Methyl (5-(2-fluoro-5-((4-oxo-7-(trifluoromethoxy)-3,4-dihydrophthalazin-1-yl)methyl)phenyl)-1H-benzoimidazol-2-yl)carbamate |
| 36. | 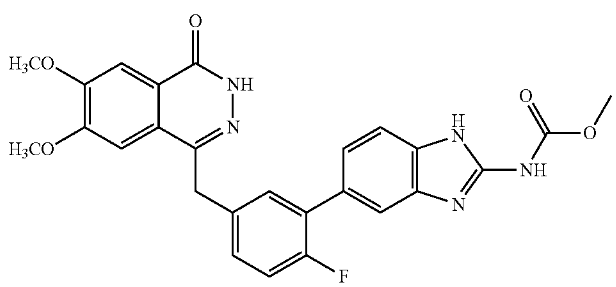 [SMILES: COC(=O)Nc1nc2cc(-c3cc(Cc4n[nH]c(=O)c5cc(OC)c(OC)cc45)ccc3F)ccc2[nH]1] | Methyl (5-(5-((6,7-dimethoxy-4-oxo-3,4-dihydrophthalazin-1-yl)methyl)-2-fluorophenyl)-1H-benzoimidazol-2-yl)carbamate |
| 37. | 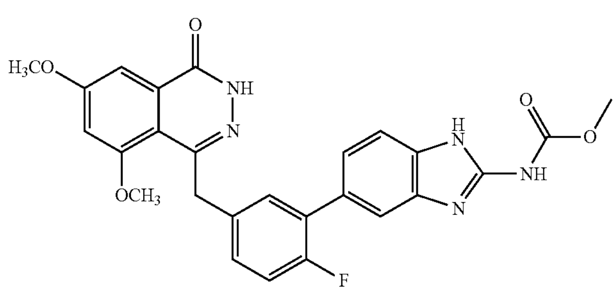 [SMILES: COC(=O)Nc1nc2cc(-c3cc(Cc4n[nH]c(=O)c5cc(OC)cc(OC)c45)ccc3F)ccc2[nH]1] | Methyl (5-(5-((6,8-dimethoxy-4-oxo-3,4-dihydrophthalazin-1-yl)methyl)-2-fluorophenyl)-1H-benzoimidazol-2-yl)carbamate |
| 38. | 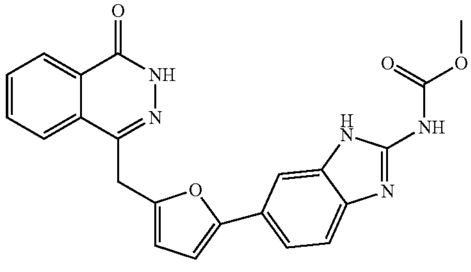 [SMILES: COC(=O)Nc1nc2ccc(-c3ccc(Cc4n[nH]c(=O)c5ccccc45)o3)cc2[nH]1] | Methyl (6-(5-((4-oxo-3,4-dihydrophthalazin-1-yl)methyl)furan-2-yl)-1H-benzoimidazol-2-yl)carbamate |

| Cmpd No. | Structure | Name |
|---|---|---|
| 39. | 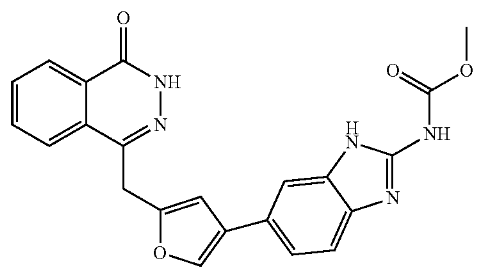 [SMILES: COC(=O)Nc1nc2ccc(-c3coc(Cc4n[nH]c(=O)c5ccccc45)c3)cc2[nH]1] | Methyl (6-(5-((4-oxo-3,4-dihydrophthalazin-1-yl)methyl)furan-3-yl)-1H-benzoimidazol-2-yl)carbamate |
| 40. | 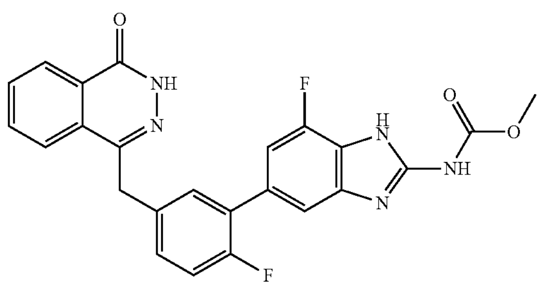 [SMILES: COC(=O)Nc1nc2cc(-c3cc(Cc4n[nH]c(=O)c5ccccc45)ccc3F)cc(F)c2[nH]1] | Methyl (7-fluoro-5-(2-fluoro-5-((4-oxo-3,4-dihydrophthalazin-1-yl)methyl)phenyl)-1H-benzoimidazol-2-yl)carbamate |
| 41. | 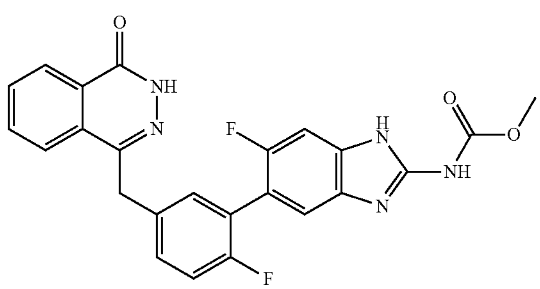 [SMILES: COC(=O)Nc1nc2cc(-c3cc(Cc4n[nH]c(=O)c5ccccc45)ccc3F)c(F)cc2[nH]1] | Methyl (6-fluoro-5-(2-fluoro-5-((4-oxo-3,4-dihydrophthalazin-1-yl)methyl)phenyl)-1H-benzoimidazol-2-yl)carbamate |
| 42. | 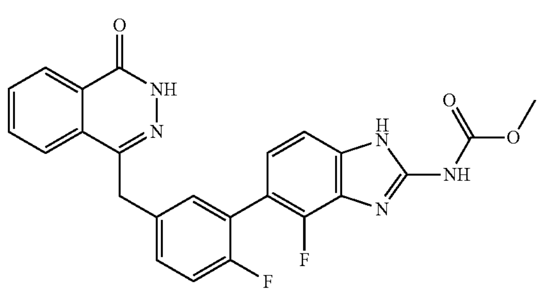 [SMILES: COC(=O)Nc1nc2c(F)c(-c3cc(Cc4n[nH]c(=O)c5ccccc45)ccc3F)ccc2[nH]1] | Methyl (4-fluoro-5-(2-fluoro-5-((4-oxo-3,4-dihydrophthalazin-1-yl)methyl)phenyl)-1H-benzoimidazol-2-yl)carbamate |
| 43. | 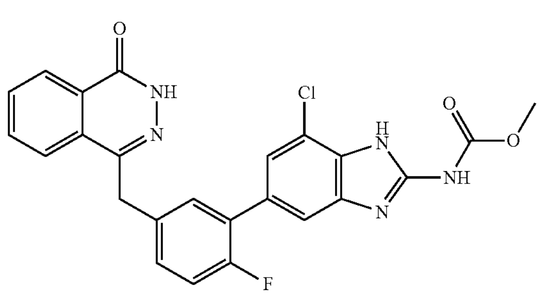 [SMILES: COC(=O)Nc1nc2cc(-c3cc(Cc4n[nH]c(=O)c5ccccc45)ccc3F)cc(Cl)c2[nH]1] | Methyl (7-chloro-5-(2-fluoro-5-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 44. | 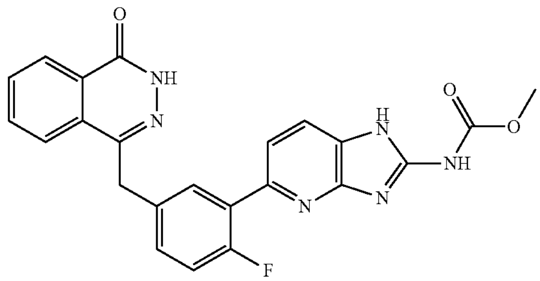 [SMILES: COC(=O)Nc1nc2nc(-c3cc(Cc4n[nH]c(=O)c5ccccc45)ccc3F)ccc2[nH]1] | Methyl (5-(2-fluoro-5-((4-oxo-3,4-dihydrophthalazin-1-yl)methyl)phenyl)-1H-imidazo[4,5-b]pyridin-2-yl)carbamate |
| 45. | 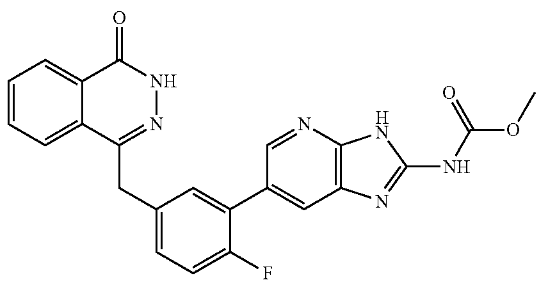 | Methyl (6-(2-fluoro-5-((4-oxo-3,4-dihydrophthalazin-1-yl)methyl)phenyl)-3H-imidazo[4,5-b]pyridin-2-yl)carbamate |
| 46. | 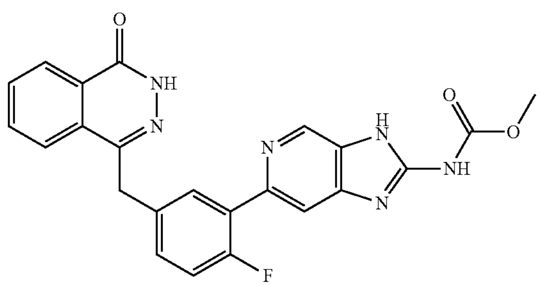 [SMILES: COC(=O)Nc1nc2cc(-c3cc(Cc4n[nH]c(=O)c5ccccc45)ccc3F)ncc2[nH]1] | Methyl (6-(2-fluoro-5-((4-oxo-3,4-dihydrophthalazin-1-yl)methyl)phenyl)-3H-imidazo[4,5-c]pyridin-2-yl)carbamate |
| 47. | 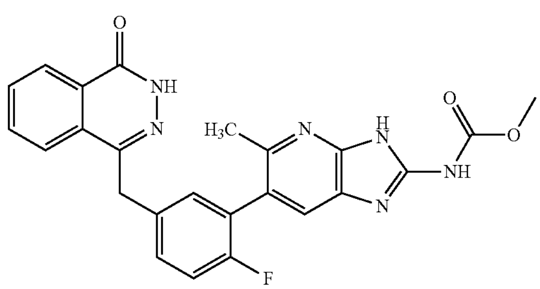 [SMILES: COC(=O)Nc1nc2cc(-c3cc(Cc4n[nH]c(=O)c5ccccc45)ccc3F)c(C)nc2[nH]1] | Methyl (6-(2-fluoro-5-((4-oxo-3,4-dihydrophthalazin-1-yl)methyl)phenyl)-5-methyl-3H-imidazo[4,5-b]pyridin-2-yl)carbamate |
| 48. | 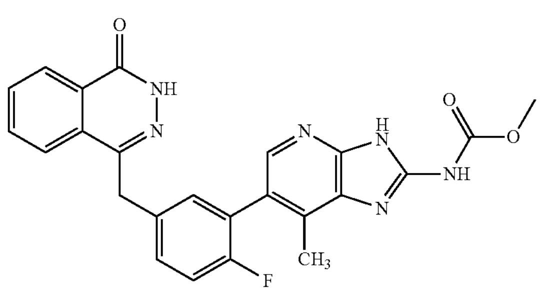 [SMILES: COC(=O)Nc1nc2c(C)c(-c3cc(Cc4n[nH]c(=O)c5ccccc45)ccc3F)cnc2[nH]1] | Methyl (6-(2-fluoro-5-((4-oxo-3,4-dihydrophthalazin-1-yl)methyl)phenyl)-7-methyl-3H-imidazo[4,5-b]pyridin-2-yl)carbamate |

| Cmpd No. | Structure | Name |
|---|---|---|
| 49. | 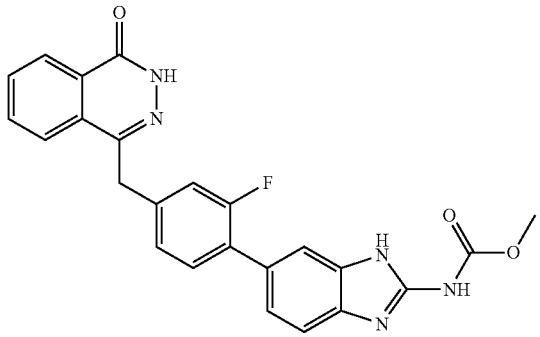 [SMILES: COC(=O)Nc1nc2ccc(-c3ccc(Cc4n[nH]c(=O)c5ccccc45)cc3F)cc2[nH]1] | Methyl (6-(2-fluoro-4-((4-oxo-3,4-dihydrophthalazin-1-yl)methyl)phenyl)-1H-benzoimidazol-2-yl)carbamate |

Example 2.

| | | |
|---|---|---|
| 1. | 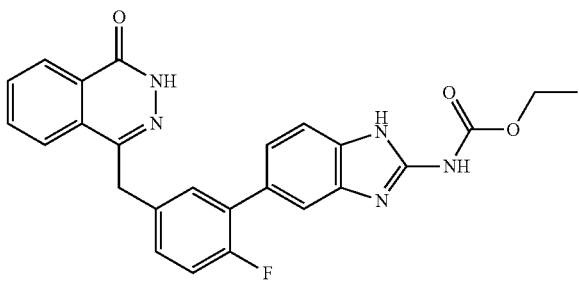 [SMILES: CCOC(=O)Nc1nc2cc(-c3cc(Cc4n[nH]c(=O)c5ccccc45)ccc3F)ccc2[nH]1] | Ethyl (5-(2-fluoro-5-((4-oxo-3,4-dihydrophthalazin-1-yl)methyl)phenyl)-1H-benzoimidazol-2-yl)carbamate |
| 2. | 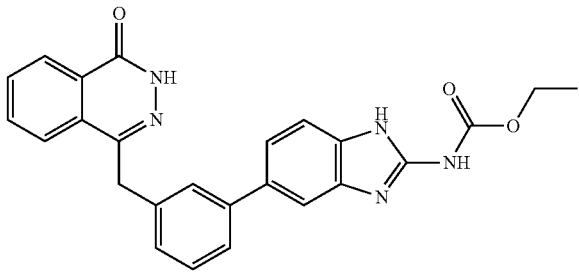 [SMILES: CCOC(=O)Nc1nc2cc(-c3cccc(Cc4n[nH]c(=O)c5ccccc45)c3)ccc2[nH]1] | Ethyl (5-(3-((4-oxo-3,4-dihydrophthalazin-1-yl)methyl)phenyl)-1H-benzoimidazol-2-yl)carbamate |
| 3. | 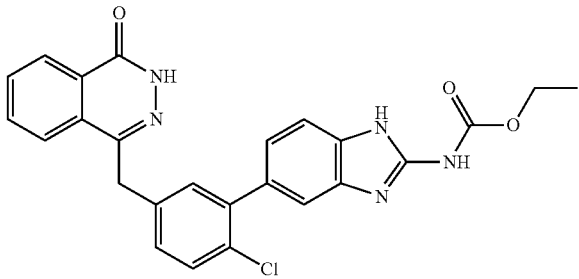 [SMILES: CCOC(=O)Nc1nc2cc(-c3cc(Cc4n[nH]c(=O)c5ccccc45)ccc3Cl)ccc2[nH]1] | Ethyl (5-(2-chloro-5-((4-oxo-3,4-dihydrophthalazin-1-yl)methyl)phenyl)-1H-benzoimidazol-2-yl)carbamate |
| 4. | 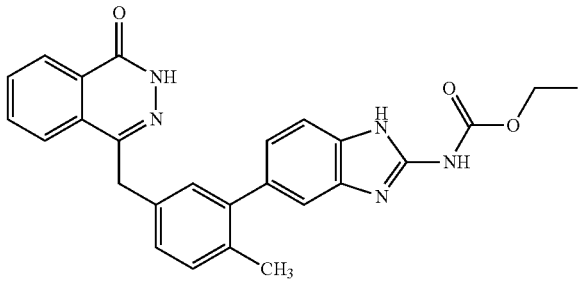 | Ethyl (5-(2-methyl-5-((4-oxo-3,4-dihydrophthalazin-1-yl)methyl)phenyl)-1H-benzoimidazol-2-yl)carbamate |

| Cmpd No. | Structure | Name |
|---|---|---|
| 5. | 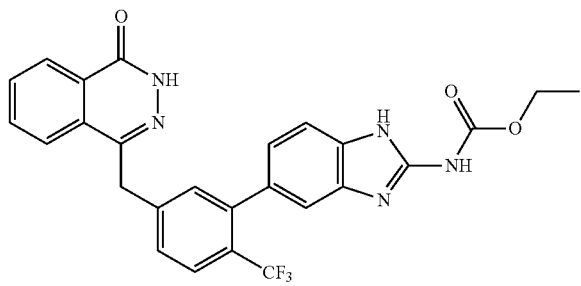 [SMILES: CCOC(=O)Nc1nc2cc(-c3cc(Cc4n[nH]c(=O)c5ccccc45)ccc3C(F)(F)F)ccc2[nH]1] | Ethyl (5-(5-((4-oxo-3,4-dihydrophthalazin-1-yl)methyl)-2-(trifluoromethyl)phenyl)-1H-benzoimidazol-2-yl)carbamate |
| 6. | 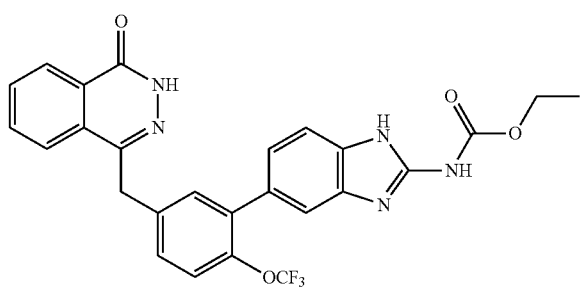 [SMILES: CCOC(=O)Nc1nc2cc(-c3cc(Cc4n[nH]c(=O)c5ccccc45)ccc3OC(F)(F)F)ccc2[nH]1] | Ethyl (5-(5-((4-oxo-3,4-dihydrophthalazin-1-yl)methyl)-2-(trifluoromethoxy)phenyl)-1H-benzoimidazol-2-yl)carbamate |
| 7. | 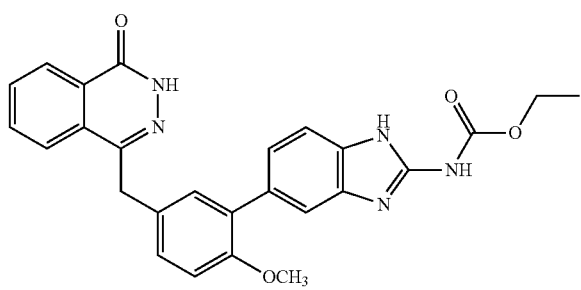 | Ethyl (5-(2-methoxy-5-((4-oxo-3,4-dihydrophthalazin-1-yl)methyl)phenyl)-1H-benzoimidazol-2-yl)carbamate |
| 8. | 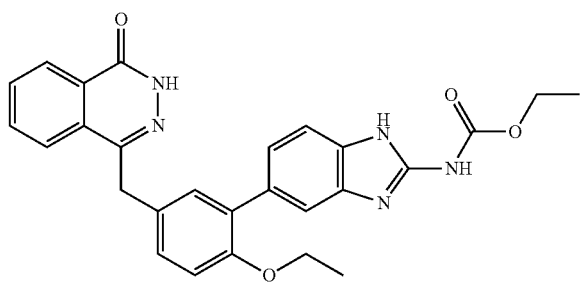 [SMILES: CCOC(=O)Nc1nc2cc(-c3cc(Cc4n[nH]c(=O)c5ccccc45)ccc3OCC)ccc2[nH]1] | Ethyl (5-(2-ethoxy-5-((4-oxo-3,4-dihydrophthalazin-1-yl)methyl)phenyl)-1H-benzoimidazol-2-yl)carbamate |
| 9. | 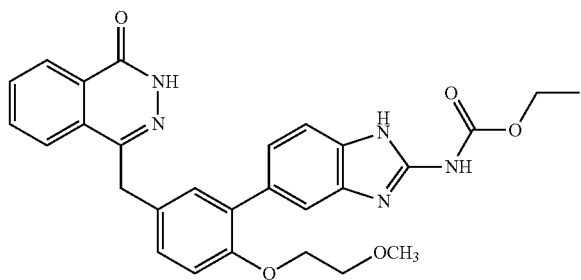 [SMILES: CCOC(=O)Nc1nc2cc(-c3cc(Cc4n[nH]c(=O)c5ccccc45)ccc3OCCOC)ccc2[nH]1] | Ethyl (5-(2-(2-methoxyethoxy)-5-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 10. | 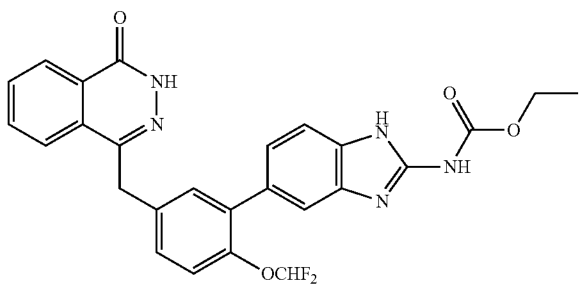 [SMILES: CCOC(=O)Nc1nc2cc(-c3cc(Cc4n[nH]c(=O)c5ccccc45)ccc3OC(F)F)ccc2[nH]1] | Ethyl (5-(2-(difluoromethoxy)-5-((4-oxo-3,4-dihydrophthalazin-1-yl)methyl)phenyl)-1H-benzoimidazol-2-yl)carbamate |
| 11. | 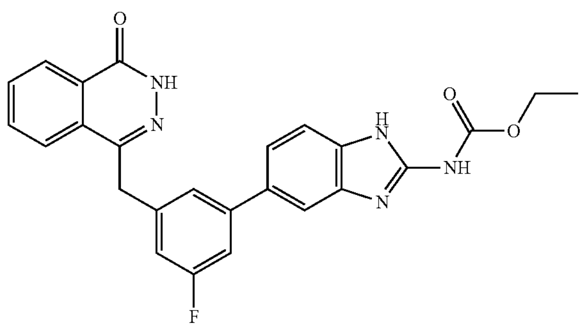 [SMILES: CCOC(=O)Nc1nc2cc(-c3cc(F)cc(Cc4n[nH]c(=O)c5ccccc45)c3)ccc2[nH]1] | Ethyl (5-(3-fluoro-5-((4-oxo-3,4-dihydrophthalazin-1-yl)methyl)phenyl)-1H-benzoimidazol-2-yl)carbamate |
| 12. | 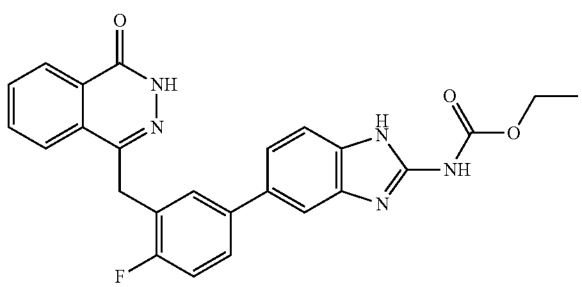 [SMILES: CCOC(=O)Nc1nc2cc(-c3ccc(F)c(Cc4n[nH]c(=O)c5ccccc45)c3)ccc2[nH]1] | Ethyl (5-(4-fluoro-3-((4-oxo-3,4-dihydrophthalazin-1-yl)methyl)phenyl)-1H-benzoimidazol-2-yl)carbamate |
| 13. | 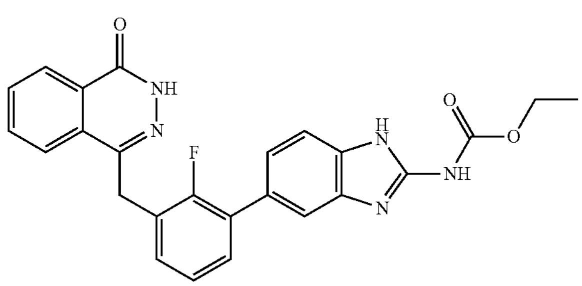 | Ethyl (5-(2-fluoro-3-((4-oxo-3,4-dihydrophthalazin-1-yl)methyl)phenyl)-1H-benzoimidazol-2-yl)carbamate |
| 14. | 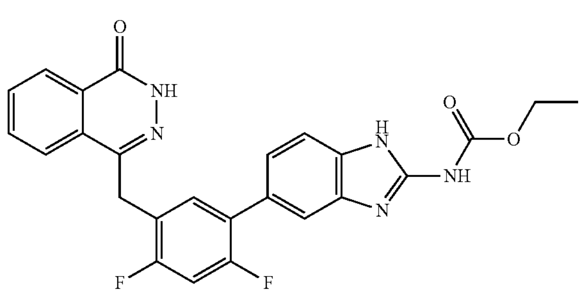 [SMILES: CCOC(=O)Nc1nc2cc(-c3cc(Cc4n[nH]c(=O)c5ccccc45)c(F)cc3F)ccc2[nH]1] | Ethyl (5-(2,4-difluoro-5-((4-oxo-3,4-dihydrophthalazin-1-yl)methyl)phenyl)-1H-benzoimidazol-2-yl)carbamate |

| Cmpd No. | Structure | Name |
|---|---|---|
| 15. | 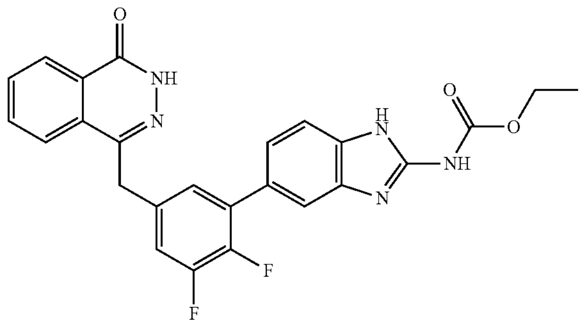 [SMILES: CCOC(=O)Nc1nc2cc(-c3cc(Cc4n[nH]c(=O)c5ccccc45)cc(F)c3F)ccc2[nH]1] | Ethyl (5-(2,3-difluoro-5-((4-oxo-3,4-dihydrophthalazin-1-yl)methyl)phenyl)-1H-benzoimidazol-2-yl)carbamate |
| 16. | 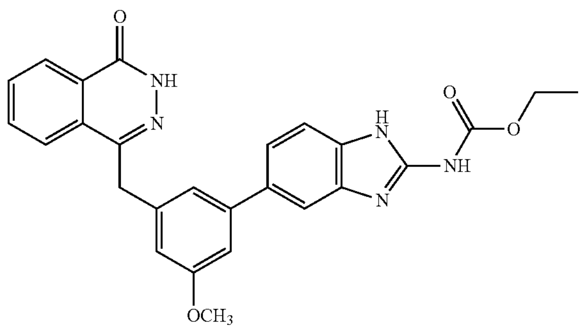 [SMILES: CCOC(=O)Nc1nc2cc(-c3cc(Cc4n[nH]c(=O)c5ccccc45)cc(OC)c3)ccc2[nH]1] | Ethyl (5-(3-methoxy-5-((4-oxo-3,4-dihydrophthalazin-1-yl)methyl)phenyl)-1H-benzoimidazol-2-yl)carbamate |
| 17. | 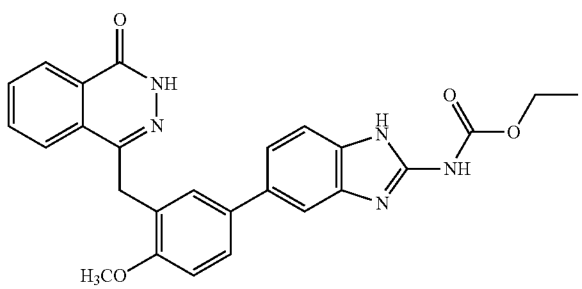 [SMILES: CCOC(=O)Nc1nc2cc(-c3ccc(OC)c(Cc4n[nH]c(=O)c5ccccc45)c3)ccc2[nH]1] | Ethyl (5-(4-methoxy-3-((4-oxo-3,4-dihydrophthalazin-1-yl)methyl)phenyl)-1H-benzoimidazol-2-yl)carbamate |
| 18. | 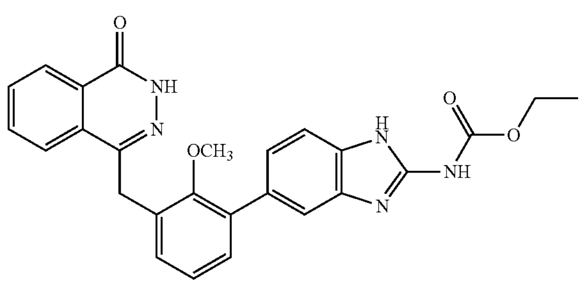 [SMILES: CCOC(=O)Nc1nc2cc(-c3cccc(Cc4n[nH]c(=O)c5ccccc45)c3OC)ccc2[nH]1] | Ethyl (5-(2-methoxy-3-((4-oxo-3,4-dihydrophthalazin-1-yl)methyl)phenyl)-1H-benzoimidazol-2-yl)carbamate |
| 19. | 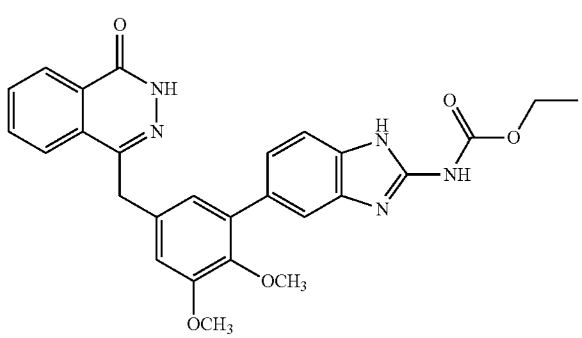 [SMILES: CCOC(=O)Nc1nc2cc(-c3cc(Cc4n[nH]c(=O)c5ccccc45)cc(OC)c3OC)ccc2[nH]1] | Ethyl (5-(2,3-dimethoxy-5-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 20. | 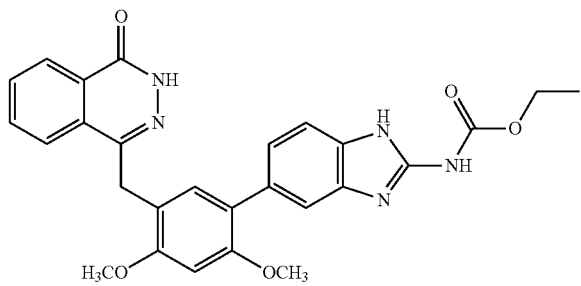 [SMILES: CCOC(=O)Nc1nc2cc(-c3cc(Cc4n[nH]c(=O)c5ccccc45)c(OC)cc3OC)ccc2[nH]1] | Ethyl (5-(2,4-dimethoxy-5-((4-oxo-3,4-dihydrophthalazin-1-yl)methyl)phenyl)-1H-benzoimidazol-2-yl)carbamate |
| 21. | 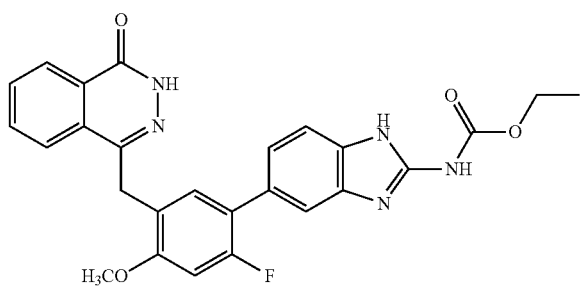 [SMILES: CCOC(=O)Nc1nc2cc(-c3cc(Cc4n[nH]c(=O)c5ccccc45)c(OC)cc3F)ccc2[nH]1] | Ethyl (5-(2-fluoro-4-methoxy-5-((4-oxo-3,4-dihydrophthalazin-1-yl)methyl)phenyl)-1H-benzoimidazol-2-yl)carbamate |
| 22. | 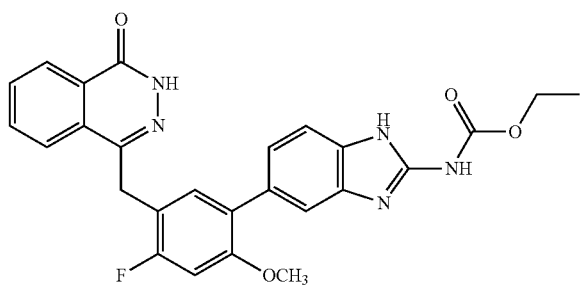 [SMILES: CCOC(=O)Nc1nc2cc(-c3cc(Cc4n[nH]c(=O)c5ccccc45)c(F)cc3OC)ccc2[nH]1] | Ethyl (5-(4-fluoro-2-methoxy-5-((4-oxo-3,4-dihydrophthalazin-1-yl)methyl)phenyl)-1H-benzoimidazol-2-yl)carbamate |
| 23. | 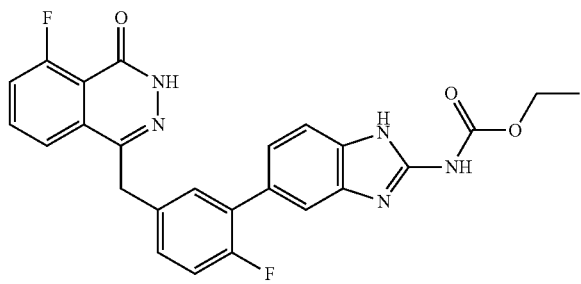 [SMILES: CCOC(=O)Nc1nc2cc(-c3cc(Cc4n[nH]c(=O)c5c(F)cccc45)ccc3F)ccc2[nH]1] | Ethyl (5-(2-fluoro-5-((5-fluoro-4-oxo-3,4-dihydrophthalazin-1-yl)methyl)phenyl)-1H-benzoimidazol-2-yl)carbamate |
| 24. | 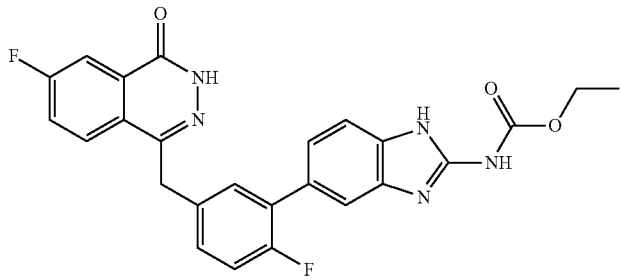 [SMILES: CCOC(=O)Nc1nc2cc(-c3cc(Cc4n[nH]c(=O)c5cc(F)ccc45)ccc3F)ccc2[nH]1] | Ethyl (5-(2-fluoro-5-((6-fluoro-4-oxo-3,4-dihydrophthalazin-1-yl)methyl)phenyl)-1H-benzoimidazol-2-yl)carbamate |

-continued

| Cmpd No. | Structure | Name |
|---|---|---|
| 25. | 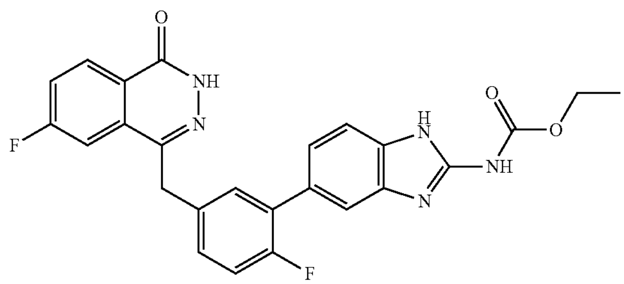 [SMILES: CCOC(=O)Nc1nc2cc(-c3cc(Cc4n[nH]c(=O)c5ccc(F)cc45)ccc3F)ccc2[nH]1] | Ethyl (5-(2-fluoro-5-((7-fluoro-4-oxo-3,4-dihydrophthalazin-1-yl)methyl)phenyl)-1H-benzoimidazol-2-yl)carbamate |
| 26. | 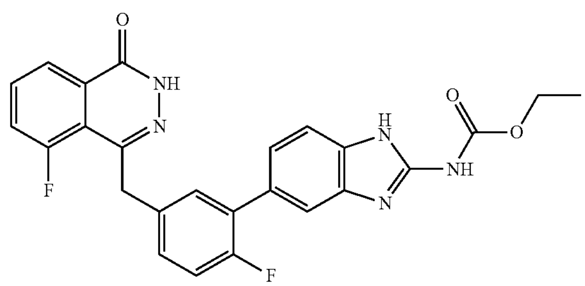 [SMILES: CCOC(=O)Nc1nc2cc(-c3cc(Cc4n[nH]c(=O)c5cccc(F)c45)ccc3F)ccc2[nH]1] | Ethyl (5-(2-fluoro-5-((8-fluoro-4-oxo-3,4-dihydrophthalazin-1-yl)methyl)phenyl)-1H-benzoimidazol-2-yl)carbamate |
| 27. | 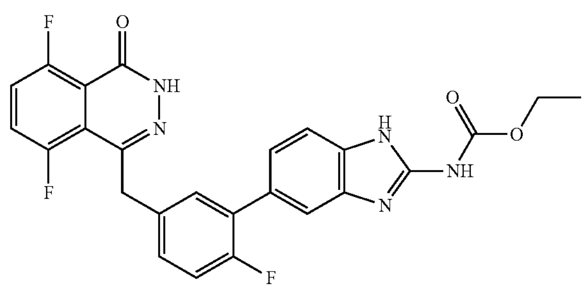 [SMILES: CCOC(=O)Nc1nc2cc(-c3cc(Cc4n[nH]c(=O)c5c(F)ccc(F)c45)ccc3F)ccc2[nH]1] | Ethyl (5-(5-((5,8-difluoro-4-oxo-3,4-dihydrophthalazin-1-yl)methyl)-2-fluorophenyl)-1H-benzoimidazol-2-yl)carbamate |
| 28. | 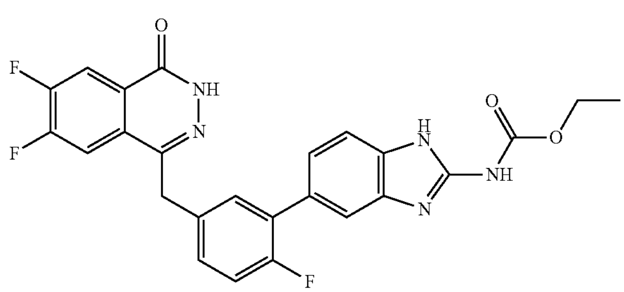 [SMILES: CCOC(=O)Nc1nc2cc(-c3cc(Cc4n[nH]c(=O)c5cc(F)c(F)cc45)ccc3F)ccc2[nH]1] | Ethyl (5-(5-((6,7-difluoro-4-oxo-3,4-dihydrophthalazin-1-yl)methyl)-2-fluorophenyl)-1H-benzoimidazol-2-yl)carbamate |
| 29. | 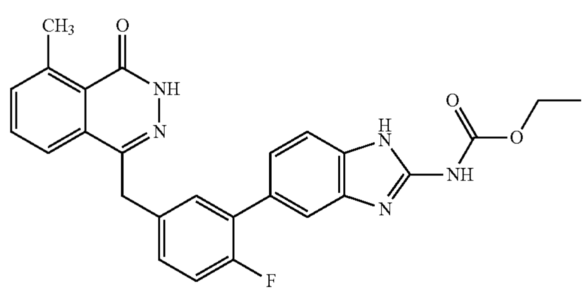 [SMILES: CCOC(=O)Nc1nc2cc(-c3cc(Cc4n[nH]c(=O)c5c(C)cccc45)ccc3F)ccc2[nH]1] | Ethyl (5-(2-fluoro-5-((5-methyl-4-oxo-3,4-dihydrophthalazin-1-yl)methyl)phenyl)-1H-benzoimidazol-2-yl)carbamate |

-continued

| Cmpd No. | Structure | Name |
|---|---|---|
| 30. | 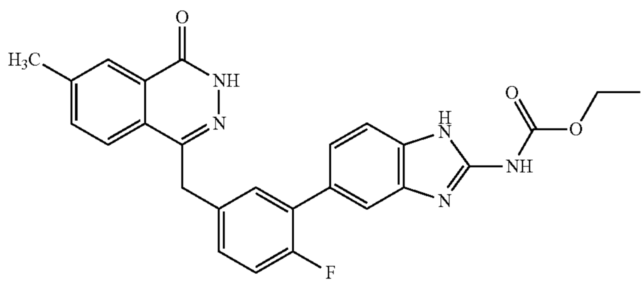 [SMILES: CCOC(=O)Nc1nc2cc(-c3cc(Cc4n[nH]c(=O)c5cc(C)ccc45)ccc3F)ccc2[nH]1] | Ethyl (5-(2-fluoro-5-((6-methyl-4-oxo-3,4-dihydrophthalazin-1-yl)methyl)phenyl)-1H-benzoimidazol-2-yl)carbamate |
| 31. | 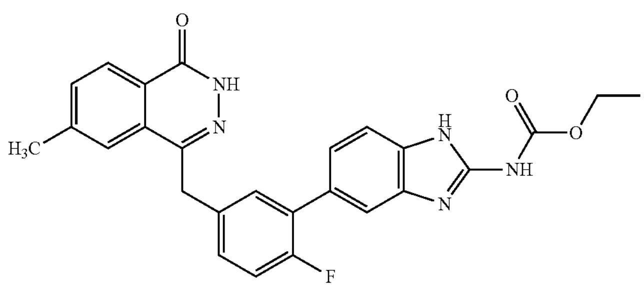 [SMILES: CCOC(=O)Nc1nc2cc(-c3cc(Cc4n[nH]c(=O)c5ccc(C)cc45)ccc3F)ccc2[nH]1] | Ethyl (5-(2-fluoro-5-((7-methyl-4-oxo-3,4-dihydrophthalazin-1-yl)methyl)phenyl)-1H-benzoimidazol-2-yl)carbamate |
| 32. | 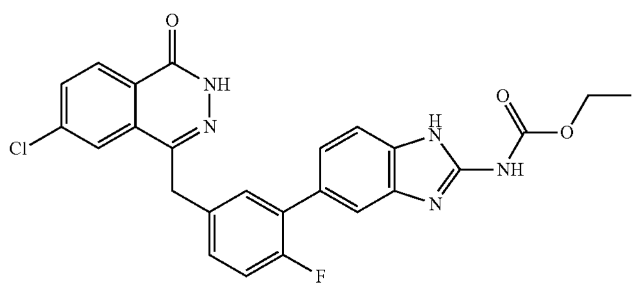 [SMILES: CCOC(=O)Nc1nc2cc(-c3cc(Cc4n[nH]c(=O)c5ccc(Cl)cc45)ccc3F)ccc2[nH]1] | Ethyl (5-(5-((7-chloro-4-oxo-3,4-dihydrophthalazin-1-yl)methyl)-2-fluorophenyl)-1H-benzoimidazol-2-yl)carbamate |
| 33. | 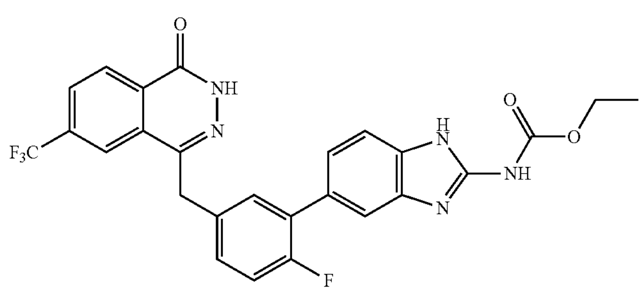 [SMILES: CCOC(=O)Nc1nc2cc(-c3cc(Cc4n[nH]c(=O)c5ccc(C(F)(F)F)cc45)ccc3F)ccc2[nH]1] | Ethyl (5-(2-fluoro-5-((4-oxo-7-(trifluoromethyl)-3,4-dihydrophthalazin-1-yl)methyl)phenyl)-1H-benzoimidazol-2-yl)carbamate |
| 34. | 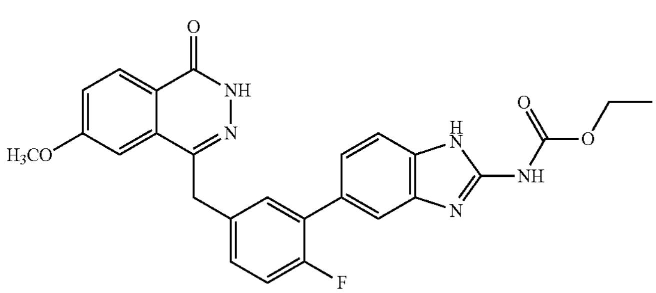 [SMILES: CCOC(=O)Nc1nc2cc(-c3cc(Cc4n[nH]c(=O)c5ccc(OC(F)(F)F)cc45)ccc3F)ccc2[nH]1] | Ethyl (5-(2-fluoro-5-((7-methoxy-4-oxo-3,4-dihydrophthalazin-1-yl)methyl)phenyl)-1H-benzoimidazol-2-yl)carbamate |

| Cmpd No. | Structure | Name |
|---|---|---|
| 35. | 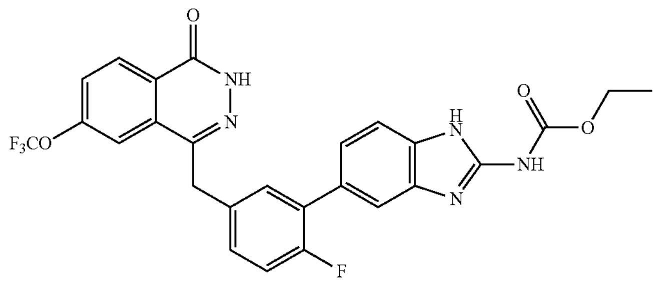 | Ethyl (5-(2-fluoro-5-((4-oxo-7-(trifluoromethoxy)-3,4-dihydrophthalazin-1-yl)methyl)phenyl)-1H-benzoimidazol-2-yl)carbamate |
| 36. | 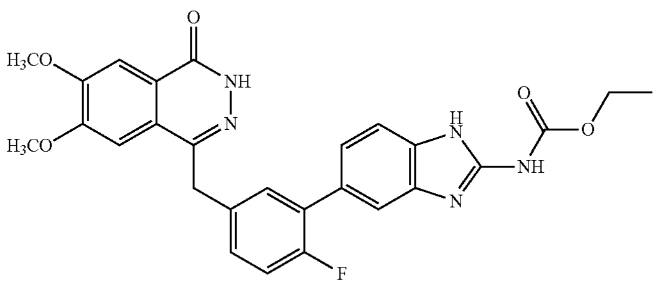 [SMILES: CCOC(=O)Nc1nc2cc(-c3cc(Cc4n[nH]c(=O)c5cc(OC)c(OC)cc45)ccc3F)ccc2[nH]1] | Ethyl (5-(5-((6,7-dimethoxy-4-oxo-3,4-dihydrophthalazin-1-yl)methyl)-2-fluorophenyl)-1H-benzoimidazol-2-yl)carbamate |
| 37. | 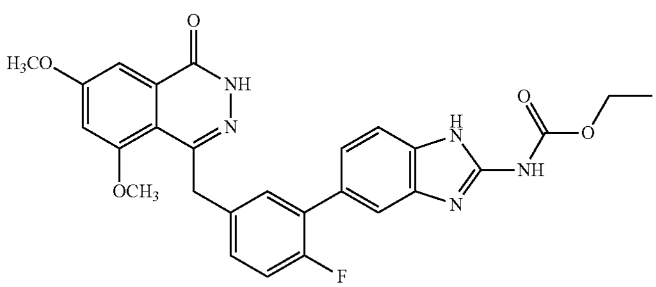 [SMILES: CCOC(=O)Nc1nc2cc(-c3cc(Cc4n[nH]c(=O)c5cc(OC)cc(OC)c45)ccc3F)ccc2[nH]1] | Ethyl (5-(5-((6,8-dimethoxy-4-oxo-3,4-dihydrophthalazin-1-yl)methyl)-2-fluorophenyl)-1H-benzoimidazol-2-yl)carbamate |
| 38. | 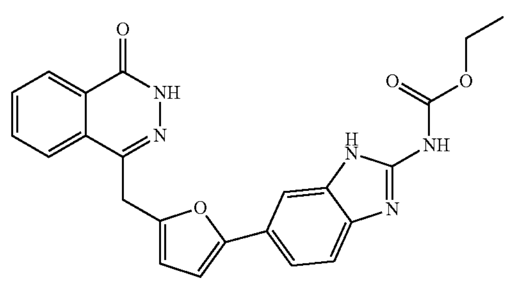 [SMILES: CCOC(=O)Nc1nc2ccc(-c3ccc(Cc4n[nH]c(=O)c5ccccc45)o3)cc2[nH]1] | Ethyl (6-(5-((4-oxo-3,4-dihydrophthalazin-1-yl)methyl)furan-2-yl)-1H-benzoimidazol-2-yl)carbamate |
| 39. | 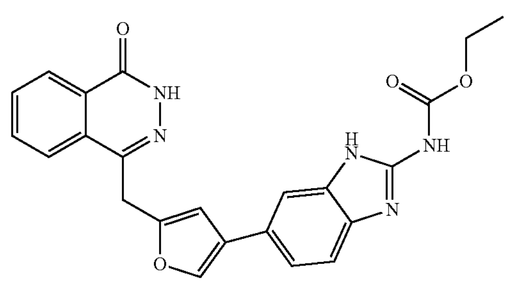 [SMILES: CCOC(=O)Nc1nc2ccc(-c3coc(Cc4n[nH]c(=O)c5ccccc45)c3)cc2[nH]1] | Ethyl (6-(5-((4-oxo-3,4-dihydrophthalazin-1-yl)methyl)furan-3-yl)-1H-benzoimidazol-2-yl)carbamate |

| Cmpd No. | Structure | Name |
|---|---|---|
| 40. | 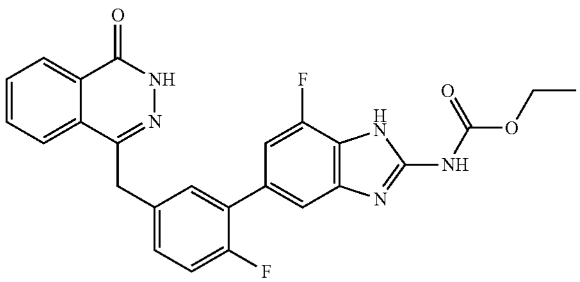 [SMILES: CCOC(=O)Nc1nc2cc(-c3cc(Cc4n[nH]c(=O)c5ccccc45)ccc3F)cc(F)c2[nH]1] | Ethyl (7-fluoro-5-(2-fluoro-5-((4-oxo-3,4-dihydrophthalazin-1-yl)methyl)phenyl)-1H-benzoimidazol-2-yl)carbamate |
| 41. | 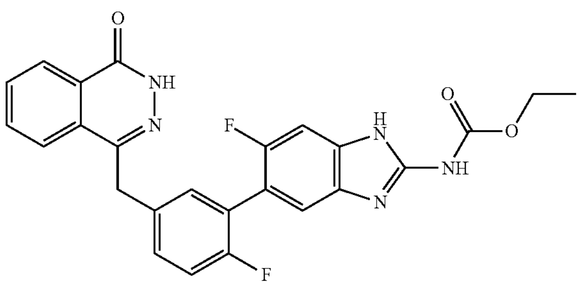 [SMILES: CCOC(=O)Nc1nc2cc(-c3cc(Cc4n[nH]c(=O)c5ccccc45)ccc3F)c(F)cc2[nH]1] | Ethyl (6-fluoro-5-(2-fluoro-5-((4-oxo-3,4-dihydrophthalazin-1-yl)methyl)phenyl)-1H-benzoimidazol-2-yl)carbamate |
| 42. | 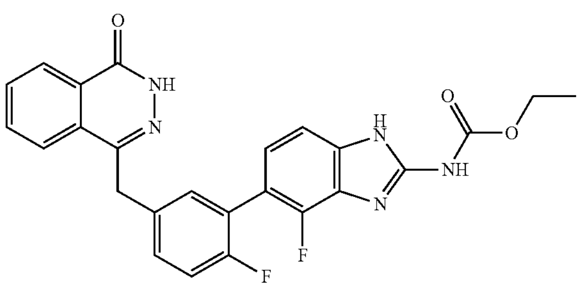 [SMILES: CCOC(=O)Nc1nc2c(F)c(-c3cc(Cc4n[nH]c(=O)c5ccccc45)ccc3F)ccc2[nH]1] | Ethyl (4-fluoro-5-(2-fluoro-5-((4-oxo-3,4-dihydrophthalazin-1-yl)methyl)phenyl)-1H-benzoimidazol-2-yl)carbamate |
| 43. | 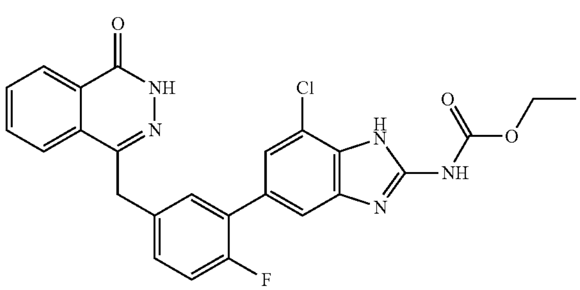 [SMILES: CCOC(=O)Nc1nc2cc(-c3cc(Cc4n[nH]c(=O)c5ccccc45)ccc3F)cc(Cl)c2[nH]1] | Ethyl (7-chloro-5-(2-fluoro-5-((4-oxo-3,4-dihydrophthalazin-1-yl)methyl)phenyl)-1H-benzoimidazol-2-yl)carbamate |
| 44. | 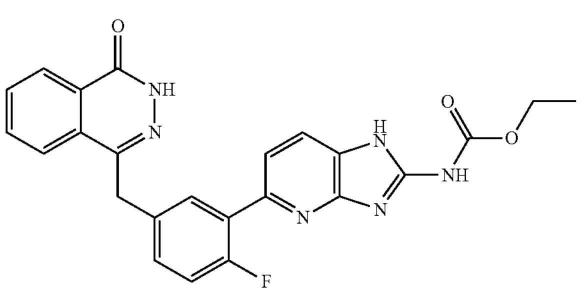 [SMILES: CCOC(=O)Nc1nc2nc(-c3cc(Cc4n[nH]c(=O)c5ccccc45)ccc3F)ccc2[nH]1] | Ethyl (5-(2-fluoro-5-((4-oxo-3,4-dihydrophthalazin-1-yl)methyl)phenyl)-1H-imidazo[4,5-b]pyridin-2-yl)carbamate |

| Cmpd No. | Structure | Name |
|---|---|---|
| 45. | 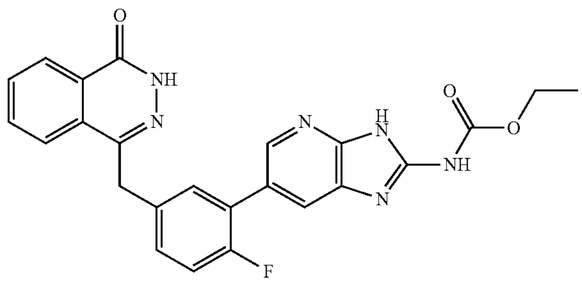 [SMILES: CCOC(=O)Nc1nc2cc(-c3cc(Cc4n[nH]c(=O)c5ccccc45)ccc3F)cnc2[nH]1] | Ethyl (6-(2-fluoro-5-((4-oxo-3,4-dihydrophthalazin-1-yl)methyl)phenyl)-3H-imidazo[4,5-b]pyridin-2-yl)carbamate |
| 46. | 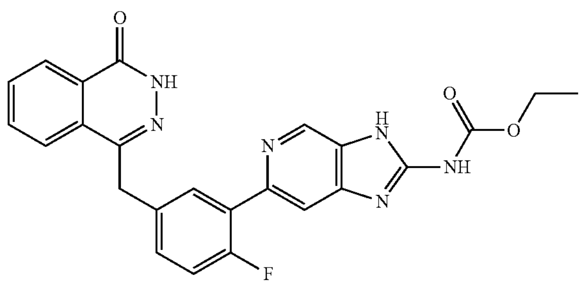 | Ethyl (6-(2-fluoro-5-((4-oxo-3,4-dihydrophthalazin-1-yl)methyl)phenyl)-3H-imidazo[4,5-c]pyridin-2-yl)carbamate |
| 47. | 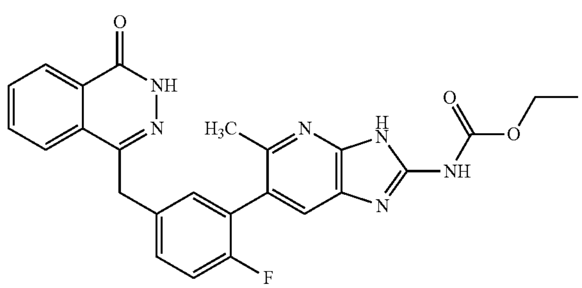 [SMILES: CCOC(=O)Nc1nc2cc(-c3cc(Cc4n[nH]c(=O)c5ccccc45)ccc3F)c(C)nc2[nH]1] | Ethyl (6-(2-fluoro-5-((4-oxo-3,4-dihydrophthalazin-1-yl)methyl)phenyl)-5-methyl-3H-imidazo[4,5-b]pyridin-2-yl)carbamate |
| 48. | 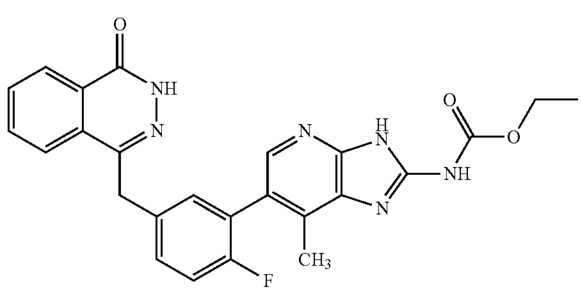 [SMILES: CCOC(=O)Nc1nc2c(C)c(-c3cc(Cc4n[nH]c(=O)c5ccccc45)ccc3F)cnc2[nH]1] | Ethyl (6-(2-fluoro-5-((4-oxo-3,4-dihydrophthalazin-1-yl)methyl)phenyl)-7-methyl-3H-imidazo[4,5-b]pyridin-2-yl)carbamate |
| 49. | 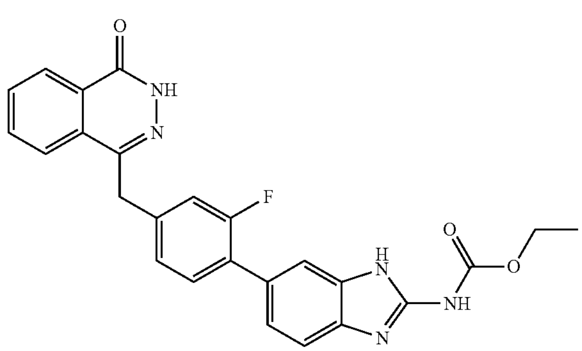 [SMILES: CCOC(=O)Nc1nc2ccc(-c3ccc(Cc4n[nH]c(=O)c5ccccc45)cc3F)cc2[nH]1] | Ethyl (6-(2-fluoro-4-((4-oxo-3,4-dihydrophthalazin-1-yl)methyl)phenyl)-1H-benzoimidazol-2-yl)carbamate |

-continued

| Cmpd No. | Structure | Name |
|---|---|---|
| Example 3. | | |
| 1. | | 2-Methoxyethyl (5-(2-fluoro-5-((4-oxo-3,4-dihydrophthalazin-1-yl)methyl)phenyl)-1H-benzoimidazol-2-yl)carbamate |
| 2. | 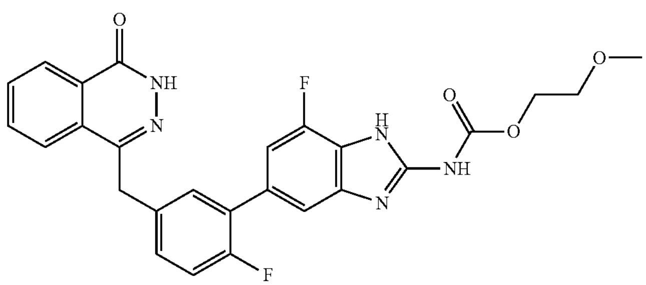 [SMILES: COCCOC(=O)Nc1nc2cc(-c3cc(Cc4n[nH]c(=O)c5ccccc45)ccc3F)cc(F)c2[nH]1] | 2-Methoxyethyl (7-fluoro-5-(2-fluoro-5-((4-oxo-3,4-dihydrophthalazin-1-yl)methyl)phenyl)-1H-benzoimidazol-2-yl)carbamate |
| 3. | 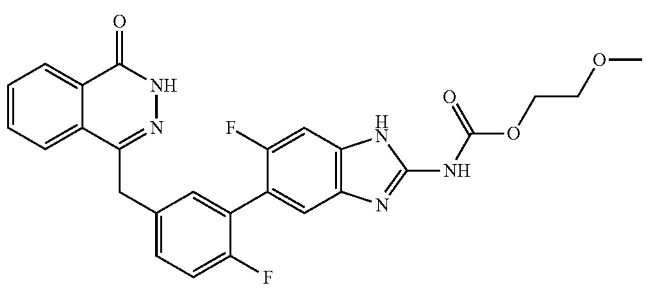 [SMILES: COCCOC(=O)Nc1nc2cc(-c3cc(Cc4n[nH]c(=O)c5ccccc45)ccc3F)c(F)cc2[nH]1] | 2-Methoxyethyl (6-fluoro-5-(2-fluoro-5-((4-oxo-3,4-dihydrophthalazin-1-yl)methyl)phenyl)-1H-benzoimidazol-2-yl)carbamate |
| 4. | 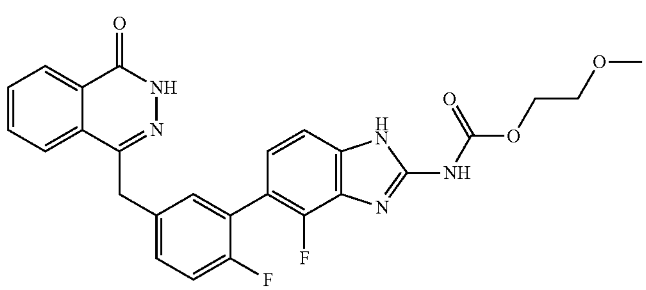 [SMILES: COCCOC(=O)Nc1nc2c(F)c(-c3cc(Cc4n[nH]c(=O)c5ccccc45)ccc3F)ccc2[nH]1] | 2-Methoxyethyl (4-fluoro-5-(2-fluoro-5-((4-oxo-3,4-dihydrophthalazin-1-yl)methyl)phenyl)-1H-benzoimidazol-2-yl)carbamate |
| Example 4. | | |
| 1. | | Propyl (5-(2-fluoro-5-((4-oxo-3,4-dihydrophthalazin-1-yl)methyl)phenyl)-1H-benzoimidazol-2-yl)carbamate |

-continued

| Cmpd No. | Structure | Name |
|---|---|---|
| 2. | 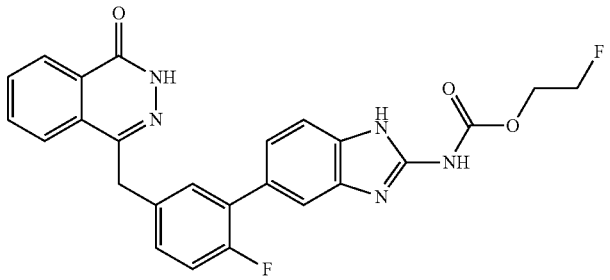 [SMILES: O=C(Nc1nc2cc(-c3cc(Cc4n[nH]c(=O)c5ccccc45)ccc3F)ccc2[nH]1)OCCF] | 2-Fluoroethyl (5-(2-fluoro-5-((4-oxo-3,4-dihydrophthalazin-1-yl)methyl)phenyl)-1H-benzoimidazol-2-yl)carbamate |
| 3. | 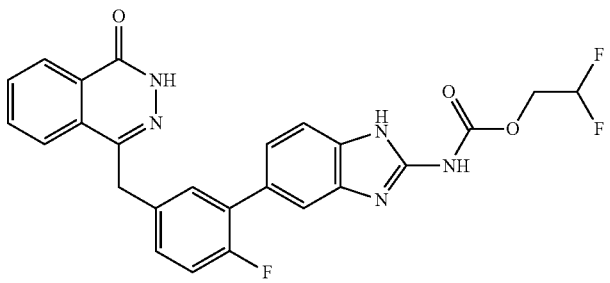 [SMILES: O=C(Nc1nc2cc(-c3cc(Cc4n[nH]c(=O)c5ccccc45)ccc3F)ccc2[nH]1)OCC(F)F] | 2,2-Difluoroethyl (5-(2-fluoro-5-((4-oxo-3,4-dihydrophthalazin-1-yl)methyl)phenyl)-1H-benzoimidazol-2-yl)carbamate |
| 4. | 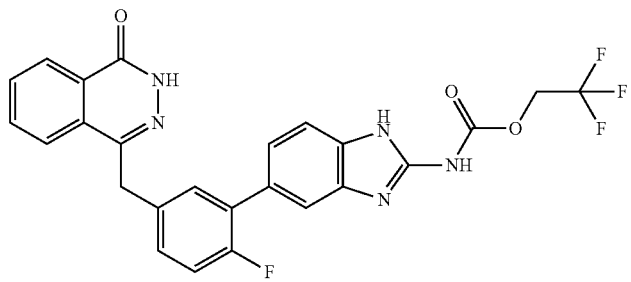 [SMILES: O=C(Nc1nc2cc(-c3cc(Cc4n[nH]c(=O)c5ccccc45)ccc3F)ccc2[nH]1)OCC(F)(F)F] | 2,2,2-Trifluoroethyl (5-(2-fluoro-5-((4-oxo-3,4-dihydrophthalazin-1-yl)methyl)phenyl)-1H-benzoimidazol-2-yl)carbamate |
| 5. | 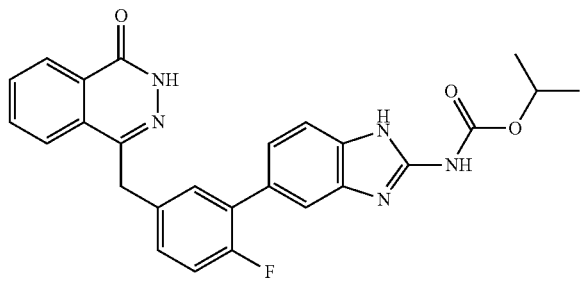 [SMILES: CC(C)OC(=O)Nc1nc2cc(-c3cc(Cc4n[nH]c(=O)c5ccccc45)ccc3F)ccc2[nH]1] | Isopropyl (5-(2-fluoro-5-((4-oxo-3,4-dihydrophthalazin-1-yl)methyl)phenyl)-1H-benzoimidazol-2-yl)carbamate |
| 6. | 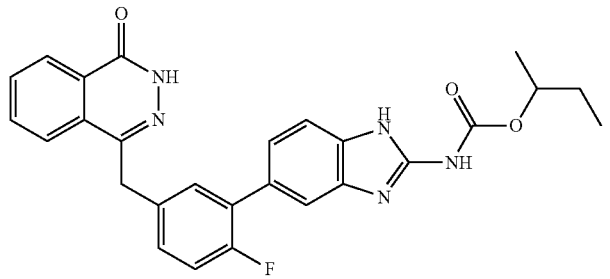 [SMILES: CCC(C)OC(=O)Nc1nc2cc(-c3cc(Cc4n[nH]c(=O)c5ccccc45)ccc3F)ccc2[nH]1] | sec-Butyl (5-(2-fluoro-5-((4-oxo-3,4-dihydrophthalazin-1-yl)methyl)phenyl)-1H-benzoimidazol-2-yl)carbamate |

| Cmpd No. | Structure | Name |
|---|---|---|
| 7. | 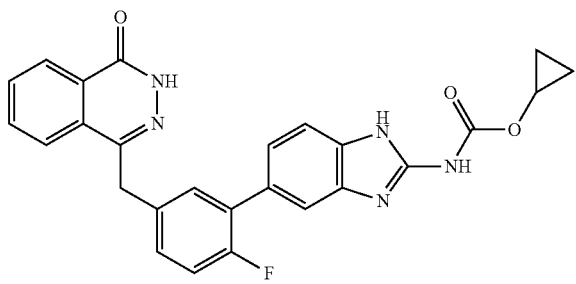 [SMILES: O=C(Nc1nc2cc(-c3cc(Cc4n[nH]c(=O)c5ccccc45)ccc3F)ccc2[nH]1)OC1CC1] | Cyclopropyl (5-(2-fluoro-5-((4-oxo-3,4-dihydrophthalazin-1-yl)methyl)phenyl)-1H-benzoimidazol-2-yl)carbamate |
| 8. | 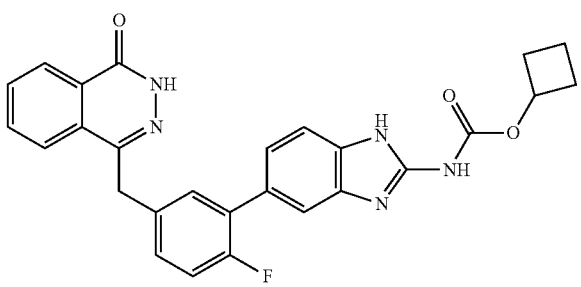 [SMILES: O=C(Nc1nc2cc(-c3cc(Cc4n[nH]c(=O)c5ccccc45)ccc3F)ccc2[nH]1)OC1CCC1] | Cyclobutyl (5-(2-fluoro-5-((4-oxo-3,4-dihydrophthalazin-1-yl)methyl)phenyl)-1H-benzoimidazol-2-yl)carbamate |
| 9. | 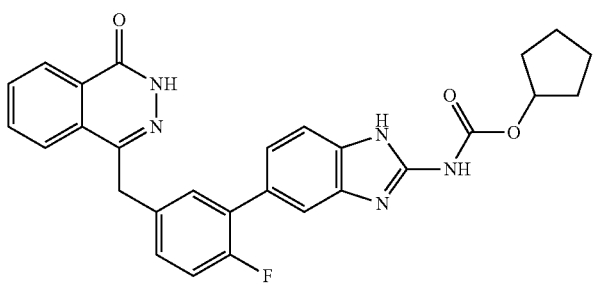 [SMILES: O=C(Nc1nc2cc(-c3cc(Cc4n[nH]c(=O)c5ccccc45)ccc3F)ccc2[nH]1)OC1CCCC1] | Cyclopentyl (5-(2-fluoro-5-((4-oxo-3,4-dihydrophthalazin-1-yl)methyl)phenyl)-1H-benzoimidazol-2-yl)carbamate |
| 10. | 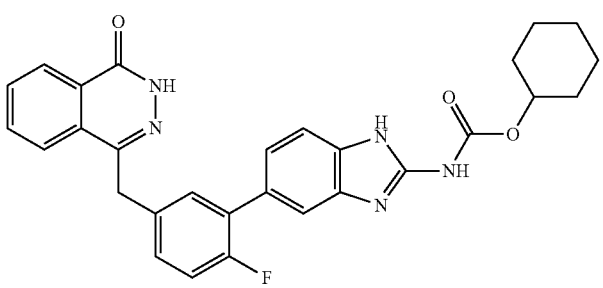 [SMILES: O=C(Nc1nc2cc(-c3cc(Cc4n[nH]c(=O)c5ccccc45)ccc3F)ccc2[nH]1)OC1CCCCC1] | Cyclohexyl (5-(2-fluoro-5-((4-oxo-3,4-dihydrophthalazin-1-yl)methyl)phenyl)-1H-benzoimidazol-2-yl)carbamate |
| 11. | 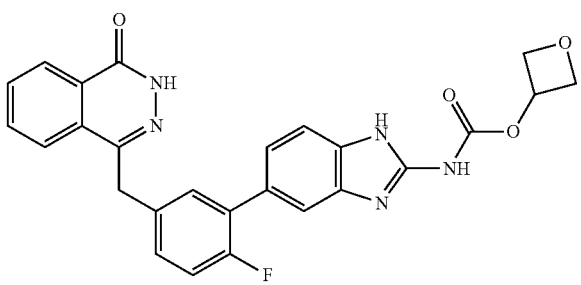 [SMILES: O=C(Nc1nc2cc(-c3cc(Cc4n[nH]c(=O)c5ccccc45)ccc3F)ccc2[nH]1)OC1COC1] | Oxetan-3-yl (5-(2-fluoro-5-((4-oxo-3,4-dihydrophthalazin-1-yl)methyl)phenyl)-1H-benzoimidazol-2-yl)carbamate |

| Cmpd No. | Structure | Name |
|---|---|---|
| 12. | 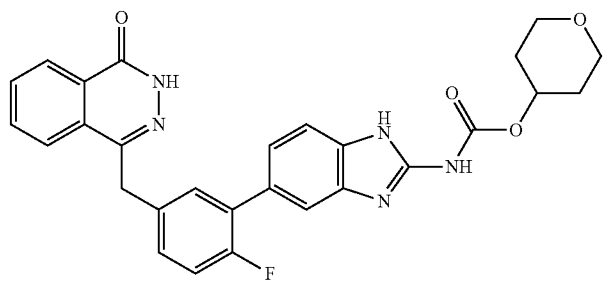 [SMILES: O=C(Nc1nc2cc(-c3cc(Cc4n[nH]c(=O)c5ccccc45)ccc3F)ccc2[nH]1)OC1CCOCC1] | Tetrahydro-2H-pyran-4-yl (5-(2-fluoro-5-((4-oxo-3,4-dihydrophthalazin-1-yl)methyl)phenyl)-1H-benzoimidazol-2-yl)carbamate |
| 13. | 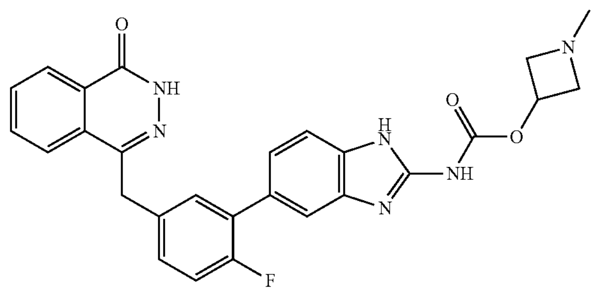 [SMILES: CN1CC(OC(=O)Nc2nc3cc(-c4cc(Cc5n[nH]c(=O)c6ccccc56)ccc4F)ccc3[nH]2)C1] | 1-Methylazetidin-3-yl (5-(2-fluoro-5-((4-oxo-3,4-dihydrophthalazin-1-yl)methyl)phenyl)-1H-benzoimidazol-2-yl)carbamate |
| 14. | 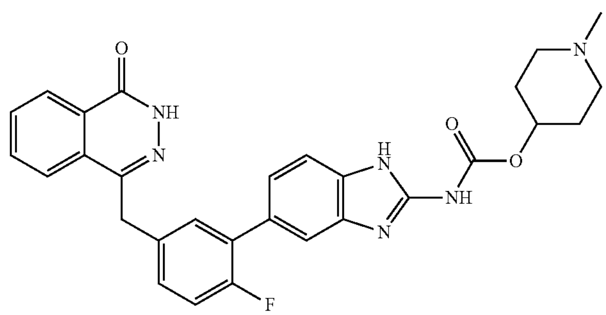 [SMILES: CN1CCC(OC(=O)Nc2nc3cc(-c4cc(Cc5n[nH]c(=O)c6ccccc56)ccc4F)ccc3[nH]2)CC1] | 1-Methylpiperidin-4-yl (5-(2-fluoro-5-((4-oxo-3,4-dihydrophthalazin-1-yl)methyl)phenyl)-1H-benzoimidazol-2-yl)carbamate |
| 15. | 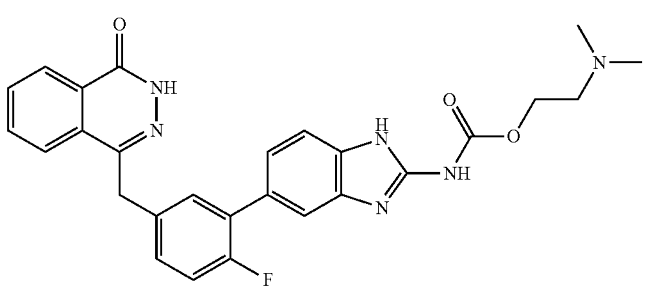 [SMILES: CN(C)CCOC(=O)Nc1nc2cc(-c3cc(Cc4n[nH]c(=O)c5ccccc45)ccc3F)ccc2[nH]1] | 2-(Dimethylamino)ethyl (5-(2-fluoro-5-((4-oxo-3,4-dihydrophthalazin-1-yl)methyl)phenyl)-1H-benzoimidazol-2-yl)carbamate |
| 16. | 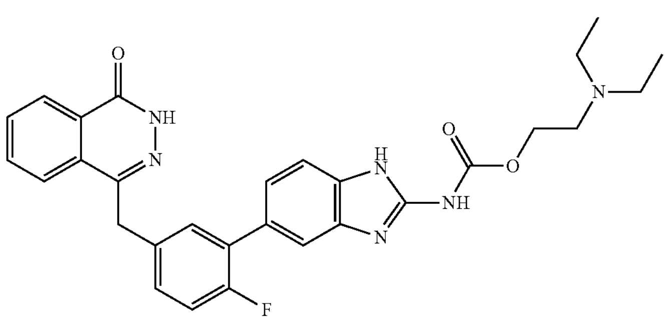 [SMILES: CCN(CC)CCOC(=O)Nc1nc2cc(-c3cc(Cc4n[nH]c(=O)c5ccccc45)ccc3F)ccc2[nH]1] | 2-(Diethylamino)ethyl (5-(2-fluoro-5-((4-oxo-3,4-dihydrophthalazin-1-yl)methyl)phenyl)-1H-benzoimidazol-2-yl)carbamate |

| Cmpd No. | Structure | Name |
|---|---|---|
| 17. | 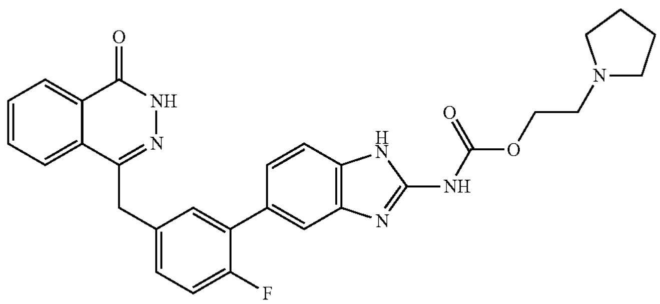 [SMILES: O=C(Nc1nc2cc(-c3cc(Cc4n[nH]c(=O)c5ccccc45)ccc3F)ccc2[nH]1)OCCN1CCCC1] | 2-(Pyrrolidin-1-yl)ethyl (5-(2-fluoro-5-((4-oxo-3,4-dihydrophthalazin-1-yl)methyl)phenyl)-1H-benzoimidazol-2-yl)carbamate |
| 18. | 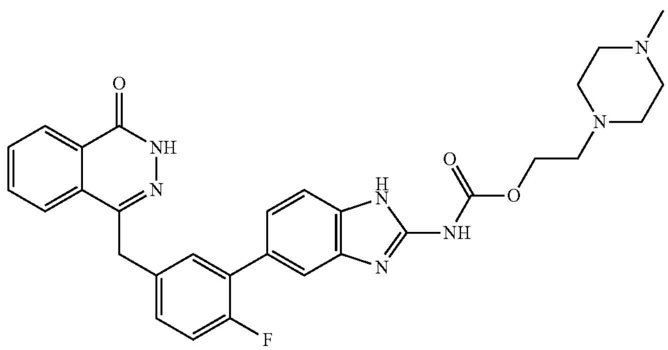 [SMILES: CN1CCN(CCOC(=O)Nc2nc3cc(-c4cc(Cc5n[nH]c(=O)c6ccccc56)ccc4F)ccc3[nH]2)CC1] | 2-(4-Methylpiperazin-1-yl)ethyl (5-(2-fluoro-5-((4-oxo-3,4-dihydrophthalazin-1-yl)methyl)phenyl)-1H-benzoldlimidazol-2-yl)carbamate |
| 19. | 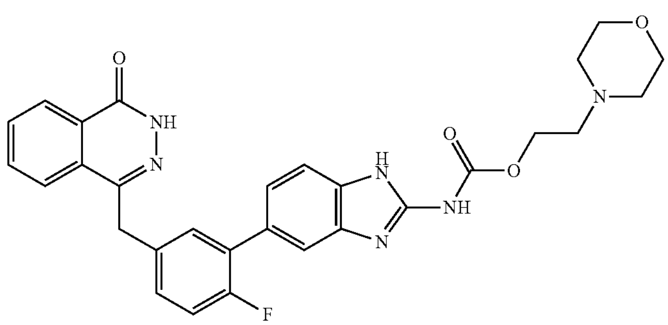 [SMILES: O=C(Nc1nc2cc(-c3cc(Cc4n[nH]c(=O)c5ccccc45)ccc3F)ccc2[nH]1)OCCN1CCOCC1] | 2-Morpholinoethyl (5-(2-fluoro-5-((4-oxo-3,4-dihydrophthalazin-1-yl)methyl)phenyl)-1H-benzoimidazol-2-yl)carbamate |
| 20. | 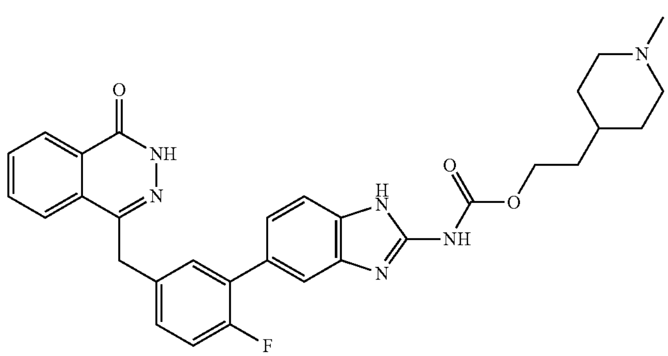 [SMILES: CN1CCC(CCOC(=O)Nc2nc3cc(-c4cc(Cc5n[nH]c(=O)c6ccccc56)ccc4F)ccc3[nH]2)CC1] | 2-(1-Methylpiperidin-4-yl)ethyl (5-(2-fluoro-5-((4-oxo-3,4-dihydrophthalazin-1-yl)methyl)phenyl)-1H-benzoimidazol-2-yl)carbamate |

| Cmpd No. | Structure | Name |
|---|---|---|
| 21. | 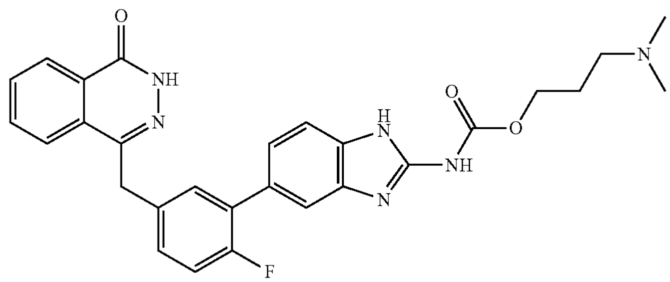 [SMILES: CN(C)CCCOC(=O)Nc1nc2cc(-c3cc(Cc4n[nH]c(=O)c5ccccc45)ccc3F)ccc2[nH]1] | 3-(Dimethylamino)propyl (5-(2-fluoro-5-((4-oxo-3,4-dihydrophthalazin-1-yl)methyl)phenyl)-1H-benzoimidazol-2-yl)carbamate |
| 22. | 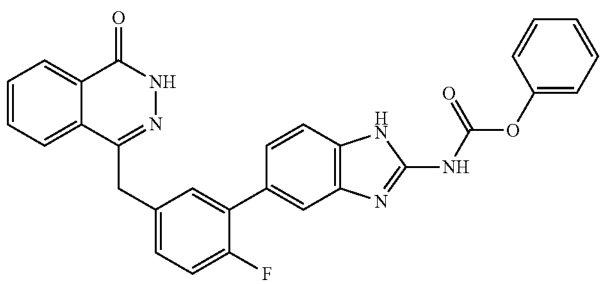 [SMILES: O=C(Nc1nc2cc(-c3cc(Cc4n[nH]c(=O)c5ccccc45)ccc3F)ccc2[nH]1)Oc1ccccc1] | Phenyl (5-(2-fluoro-5-((4-oxo-3,4-dihydrophthalazin-1-yl)methyl)phenyl)-1H-benzoimidazol-2-yl)carbamate |
| 23. | 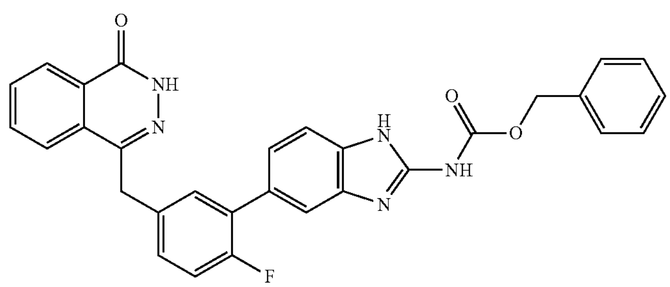 [SMILES: O=C(Nc1nc2cc(-c3cc(Cc4n[nH]c(=O)c5ccccc45)ccc3F)ccc2[nH]1)OCc1ccccc1] | Benzyl (5-(2-fluoro-5-((4-oxo-3,4-dihydrophthalazin-1-yl)methyl)phenyl)-1H-benzoimidazol-2-yl)carbamate |

Example 5.

| | | |
|---|---|---|
| 1. | | 1-Ethyl-3-(5-(2-fluoro-5-((4-oxo-3,4-dihydrophthalazin-1-yl)methyl)phenyl)-1H-benzoimidazol-2-yl)urea |
| 2. | | 1-Ethyl-3-(5-(3-((4-oxo-3,4-dihydrophthalazin-1-yl)methyl)phenyl)-1H-benzoimidazol-2-yl)urea |

-continued

| Cmpd No. | Structure | Name |
|---|---|---|
| 3. | 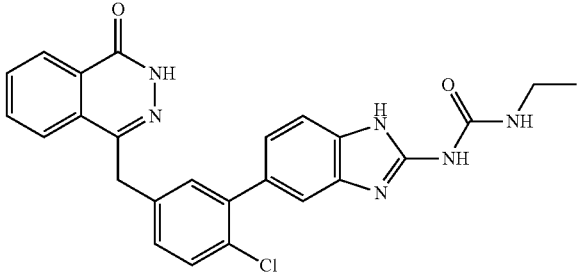 [SMILES: CCNC(=O)Nc1nc2cc(-c3cc(Cc4n[nH]c(=O)c5ccccc45)ccc3F)ccc2[nH]1] | 1-(5-(2-Chloro-5-((4-oxo-3,4-dihydrophthalazin-1-yl)methyl)phenyl)-1H-benzoimidazol-2-yl)-3-ethylurea |
| 4. | 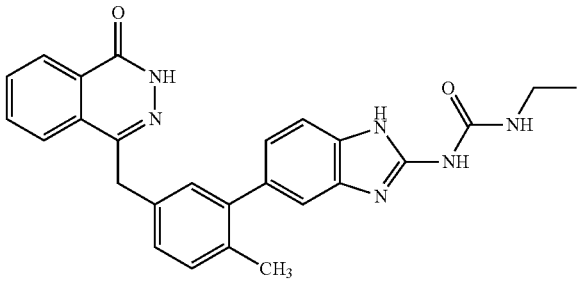 | 1-Ethyl-3-(5-(2-methyl-5-((4-oxo-3,4-dihydrophthalazin-1-yl)methyl)phenyl)-1H-benzoimidazol-2-yl)urea |
| 5. | 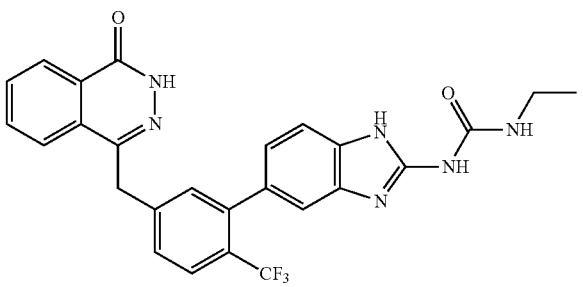 | 1-Ethyl-3-(5-(5-((4-oxo-3,4-dihydrophthalazin-1-yl)methyl)-2-(trifluoromethyl)phenyl)-1H-benzoimidazol-2-yl)urea |
| 6. | 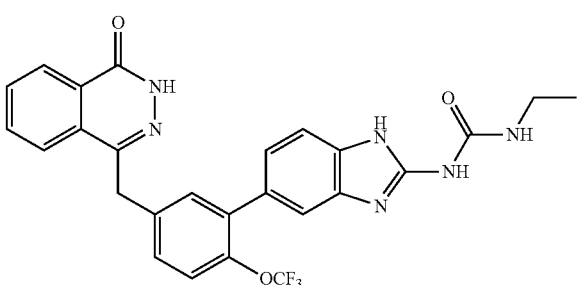 [SMILES: CCNC(=O)Nc1nc2cc(-c3cc(Cc4n[nH]c(=O)c5ccccc45)ccc3Cl)ccc2[nH]1] | 1-thyl-3-(5-(5-((4-oxo-3,4-dihydrophthalazin-1-yl)methyl)-2-(trifluoromethoxy)phenyl)-1H-benzoimidazol-2-yl)urea |
| 7. | 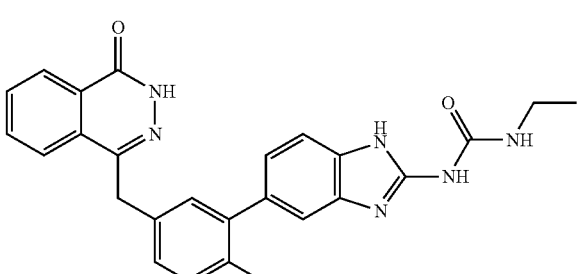 | 1-Ethyl-3-(5-(2-methoxy-5-((4-oxo-3,4-dihydrophthalazin-1-yl)methyl)phenyl)-1H-benzoimidazol-2-yl)urea |

| Cmpd No. | Structure | Name |
|---|---|---|
| 8. | 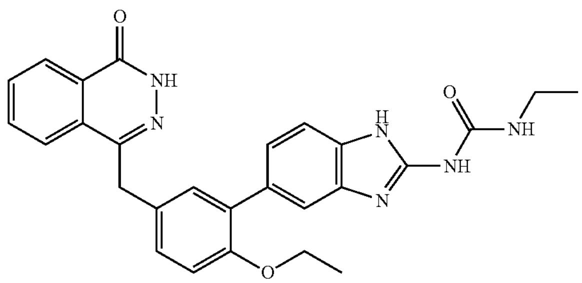 | 1-(5-(2-Ethoxy-5-((4-oxo-3,4-dihydrophthalazin-1-yl)methyl)phenyl)-1H-benzoimidazol-2-yl)-3-ethylurea |
| 9. | 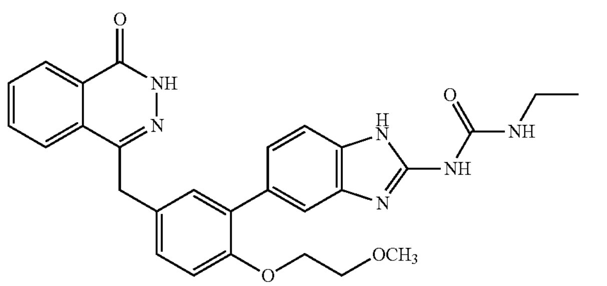 [SMILES: CCNC(=O)Nc1nc2cc(-c3cc(Cc4n[nH]c(=O)c5ccccc45)ccc3OCCOC)ccc2[nH]1] | 1-Ethyl-3-(5-(2-(2-methoxyethoxy)-5-((4-oxo-3,4-dihydrophthalazin-1-yl)methyl)phenyl)-1H-benzoimidazol-2-yl)urea |
| 10. | 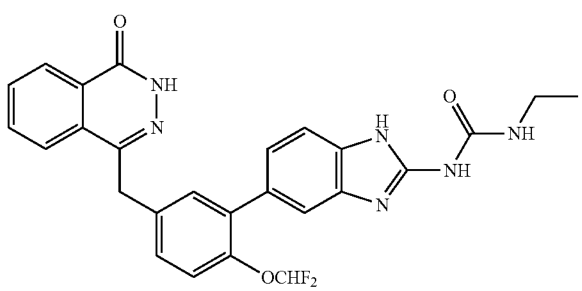 | 1-(5-(2-(Difluoromethoxy)-5-((4-oxo-3,4-dihydrophthalazin-1-yl)methyl)phenyl)-1H-benzoimidazol-2-yl)-3-ethylurea |
| 11. | 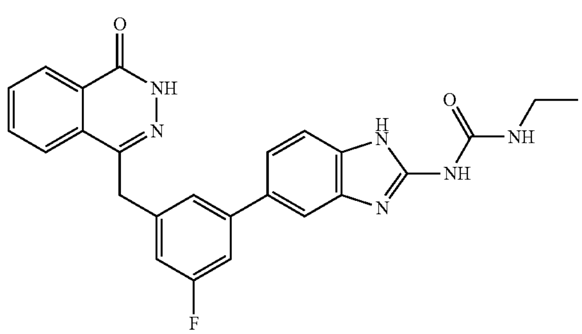 | 1-Ethyl-3-(5-(3-fluoro-5-((4-oxo-3,4-dihydrophthalazin-1-yl)methyl)phenyl)-1H-benzoimidazol-2-yl)urea |
| 12. | 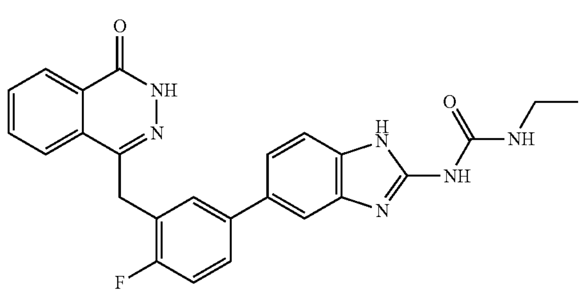 [SMILES: CCNC(=O)Nc1nc2cc(-c3ccc(F)c(Cc4n[nH]c(=O)c5ccccc45)c3)ccc2[nH]1] | 1-Ethyl-3-(5-(4-fluoro-3-((4-oxo-3,4-dihydrophthalazin-1-yl)methyl)phenyl)-1H-benzoimidazol-2-yl)urea |

-continued

| Cmpd No. | Structure | Name |
|---|---|---|
| 13. | 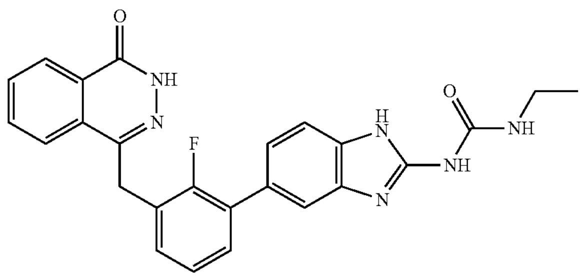 [SMILES: CCNC(=O)Nc1nc2cc(-c3cccc(Cc4n[nH]c(=O)c5ccccc45)c3F)ccc2[nH]1] | 1-Ethyl-3-(5-(2-fluoro-3-((4-oxo-3,4-dihydrophthalazin-1-yl)methyl)phenyl)-1H-benzoimidazol-2-yl)urea |
| 14. | 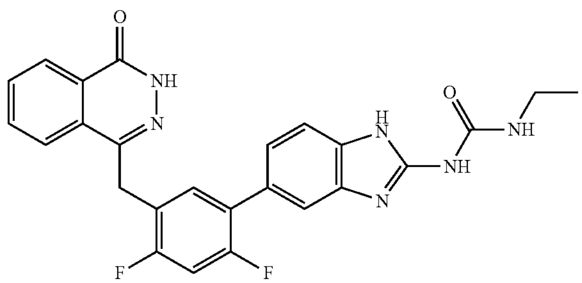 | 1-(5-(2,4-Difluoro-5-((4-oxo-3,4-dihydrophthalazin-1-yl)methyl)phenyl)-1H-benzoimidazol-2-yl)-3-ethylurea |
| 15. | 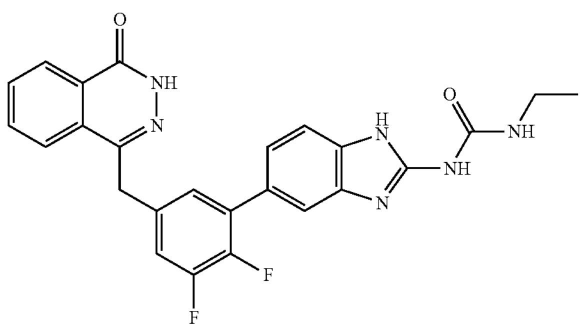 | 1-(5-(2,3-Difluoro-5-((4-oxo-3,4-dihydrophthalazin-1-yl)methyl)phenyl)-1H-benzoimidazol-2-yl)-3-ethylurea |
| 16. | 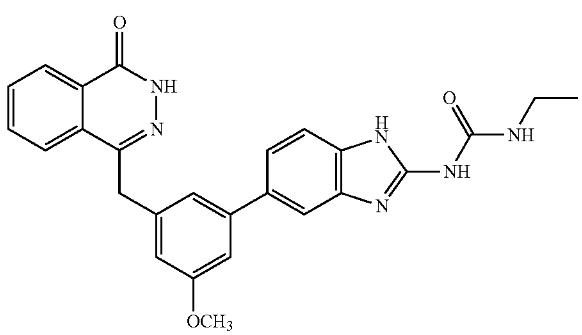 [SMILES: CCNC(=O)Nc1nc2cc(-c3cc(Cc4n[nH]c(=O)c5ccccc45)cc(OC)c3)ccc2[nH]1] | 1-Ethyl-3-(5-(3-methoxy-5-((4-oxo-3,4-dihydrophthalazin-1-yl)methyl)phenyl)-1H-benzoimidazol-2-yl)urea |
| 17. | 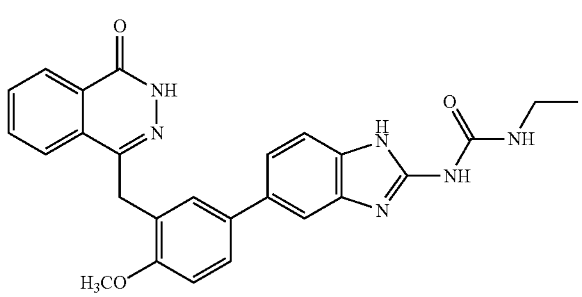 | 1-Ethyl-3-(5-(4-methoxy-3-((4-oxo-3,4-dihydrophthalazin-1-yl)methyl)phenyl)-1H-benzoimidazol-2-yl)urea |

-continued

| Cmpd No. | Structure | Name |
|---|---|---|
| 18. | 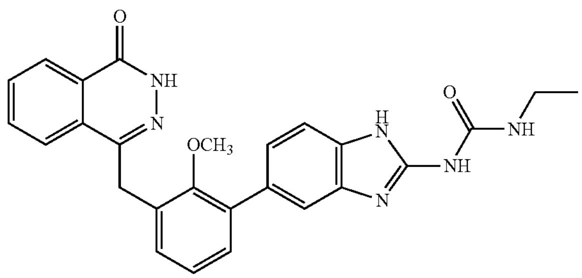 [SMILES: CCNC(=O)Nc1nc2cc(-c3cccc(Cc4n[nH]c(=O)c5ccccc45)c3OC)ccc2[nH]1] | 1-Ethyl-3-(5-(2-methoxy-3-((4-oxo-3,4-dihydrophthalazin-1-yl)methyl)phenyl)-1H-benzoimidazol-2-yl)urea |
| 19. | 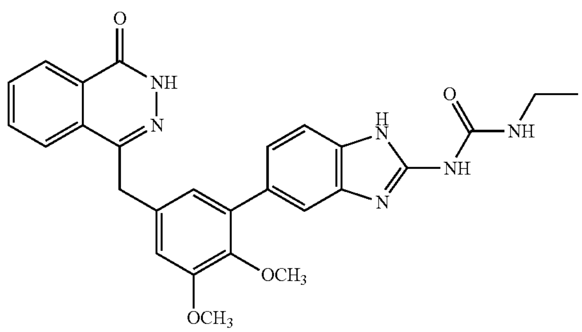 [SMILES: CCNC(=O)Nc1nc2cc(-c3cc(Cc4n[nH]c(=O)c5ccccc45)cc(OC)c3OC)ccc2[nH]1] | 1-(5-(2,3-Dimethoxy-5-((4-oxo-3,4-dihydrophthalazin-1-yl)methyl)phenyl)-1H-benzoimidazol-2-yl)-3-ethylurea |
| 20. | 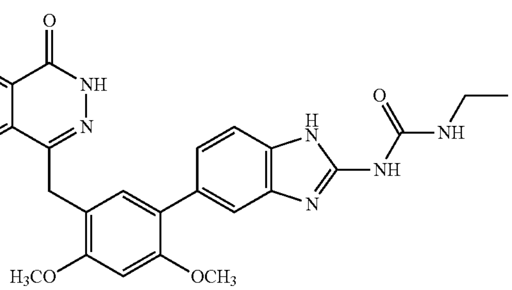 | 1-(5-(2,4-Dimethoxy-5-((4-oxo-3,4-dihydrophthalazin-1-yl)methyl)phenyl)-1H-benzoimidazol-2-yl)-3-ethylurea |
| 21. | 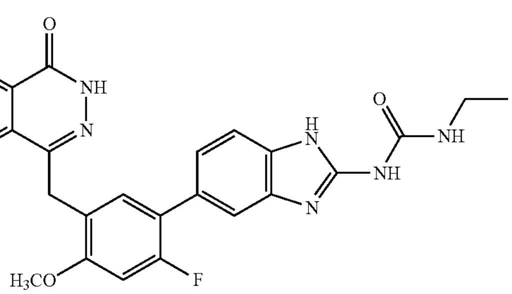 | 1-Ethyl-3-(5-(2-fluoro-4-methoxy-5-((4-oxo-3,4-dihydrophthalazin-1-yl)methyl)phenyl)-1H-benzoimidazol-2-yl)urea |
| 22. | 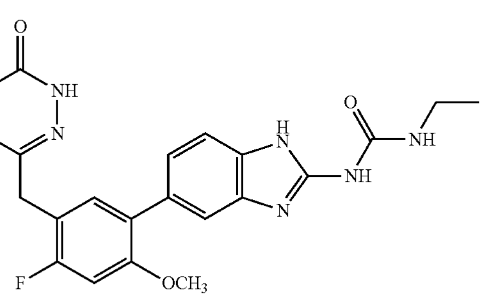 | 1-Ethyl-3-(5-(4-fluoro-2-methoxy-5-((4-oxo-3,4-dihydrophthalazin-1-yl)methyl)phenyl)-1H-benzoimidazol-2-yl)urea |

-continued

| Cmpd No. | Structure | Name |
|---|---|---|
| 23. | 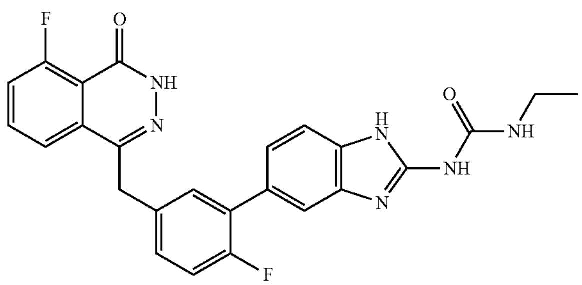 | 1-Ethyl-3-(5-(2-fluoro-5-((5-fluoro-4-oxo-3,4-dihydrophthalazin-1-yl)methyl)phenyl)-1H-benzoimidazol-2-yl)urea |
| 24. | 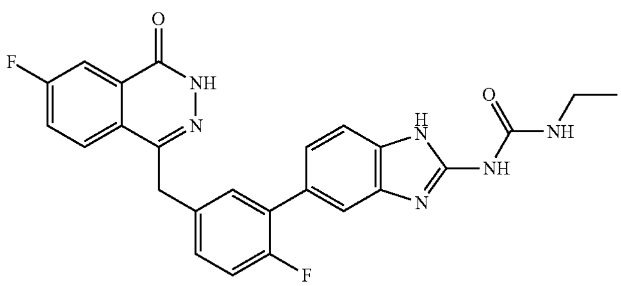 [SMILES: CCNC(=O)Nc1nc2cc(-c3cc(Cc4n[nH]c(=O)c5cc(F)ccc45)ccc3F)ccc2[nH]1] | 1-Ethyl-3-(5-(2-fluoro-5-((6-fluoro-4-oxo-3,4-dihydrophthalazin-1-yl)methyl)phenyl)-1H-benzoimidazol-2-yl)urea |
| 25. | 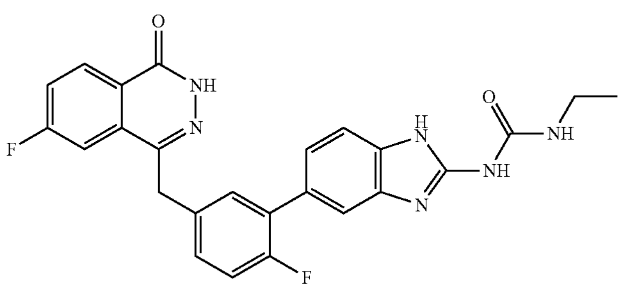 | 1-Ethyl-3-(5-(2-fluoro-5-((7-fluoro-4-oxo-3,4-dihydrophthalazin-1-yl)methyl)phenyl)-1H-benzoimidazol-2-yl)urea |
| 26. | 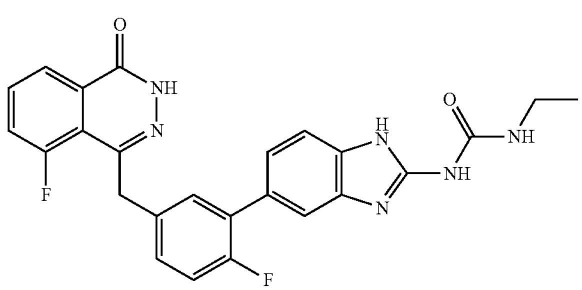 [SMILES: CCNC(=O)Nc1nc2cc(-c3cc(Cc4n[nH]c(=O)c5cccc(F)c45)ccc3F)ccc2[nH]1] | 1-Ethyl-3-(5-(2-fluoro-5-((8-fluoro-4-oxo-3,4-dihydrophthalazin-1-yl)methyl)phenyl)-1H-benzoimidazol-2-yl)urea |
| 27. | 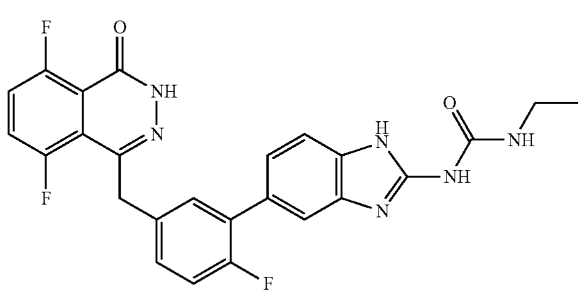 [SMILES: CCNC(=O)Nc1nc2cc(-c3cc(Cc4n[nH]c(=O)c5c(F)ccc(F)c45)ccc3F)ccc2[nH]1] | 1-(5-(5-((5,8-Difluoro-4-oxo-3,4-dihydrophthalazin-1-yl)methyl)-2-fluorophenyl)-1H-benzoimidazol-2-yl)-3-ethylurea |

| Cmpd No. | Structure | Name |
|---|---|---|
| 28. | 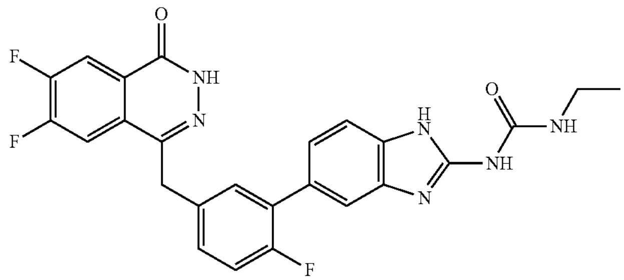 [SMILES: CCNC(=O)Nc1nc2cc(-c3cc(Cc4n[nH]c(=O)c5cc(F)c(F)cc45)ccc3F)ccc2[nH]1] | 1-(5-(5-((6,7-Difluoro-4-oxo-3,4-dihydrophthalazin-1-yl)methyl)-2-fluorophenyl)-1H-benzoimidazol-2-yl)-3-ethylurea |
| 29. | 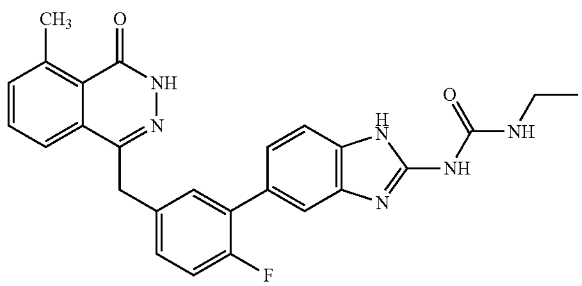 [SMILES: CCNC(=O)Nc1nc2cc(-c3cc(Cc4n[nH]c(=O)c5c(C)cccc45)ccc3F)ccc2[nH]1] | 1-Ethyl-3-(5-(2-fluoro-5-((5-methyl-4-oxo-3,4-dihydrophthalazin-1-yl)methyl)phenyl)-1H-benzoimidazol-2-yl)urea |
| 30. | 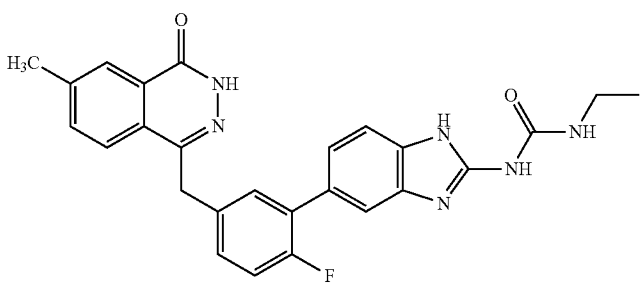 [SMILES: CCNC(=O)Nc1nc2cc(-c3cc(Cc4n[nH]c(=O)c5cc(C)ccc45)ccc3F)ccc2[nH]1] | 1-Ethyl-3-(5-(2-fluoro-5-((6-methyl-4-oxo-3,4-dihydrophthalazin-1-yl)methyl)phenyl)-1H-benzoimidazol-2-yl)urea |
| 31. | 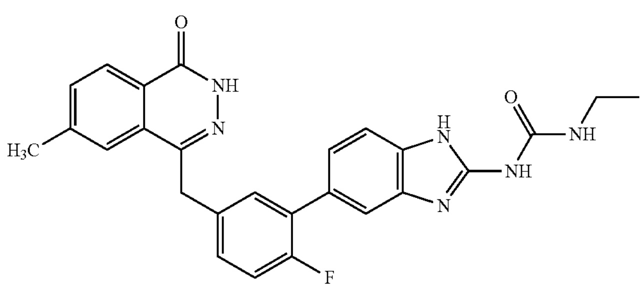 [SMILES: CCNC(=O)Nc1nc2cc(-c3cc(Cc4n[nH]c(=O)c5ccc(C)cc45)ccc3F)ccc2[nH]1] | 1-Ethyl-3-(5-(2-fluoro-5-((7-methyl-4-oxo-3,4-dihydrophthalazin-1-yl)methyl)phenyl)-1H-benzoimidazol-2-yl)urea |
| 32. | 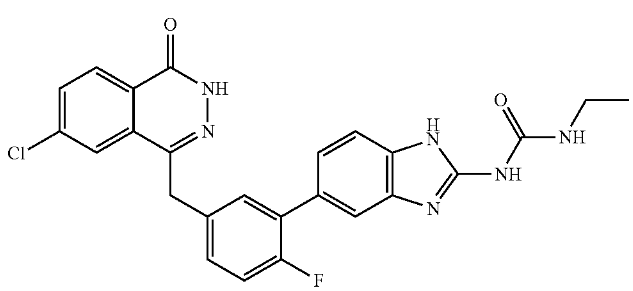 [SMILES: CCNC(=O)Nc1nc2cc(-c3cc(Cc4n[nH]c(=O)c5ccc(Cl)cc45)ccc3F)ccc2[nH]1] | 1-(5-(5-((7-Chloro-4-oxo-3,4-dihydrophthalazin-1-yl)methyl)-2-fluorophenyl)-1H-benzoimidazol-2-yl)-3-ethylurea |

-continued

| Cmpd No. | Structure | Name |
|---|---|---|
| 33. | 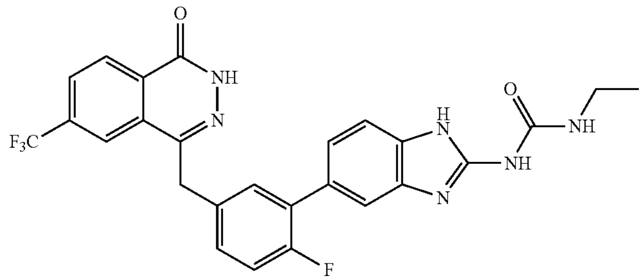 [SMILES: CCNC(=O)Nc1nc2cc(-c3cc(Cc4n[nH]c(=O)c5ccc(C(F)(F)F)cc45)ccc3F)ccc2[nH]1] | 1-Ethyl-3-(5-(2-fluoro-5-((4-oxo-7-(trifluoromethyl)-3,4-dihydrophthalazin-1-yl)methyl)phenyl)-1H-benzoimidazol-2-yl)urea |
| 34. | 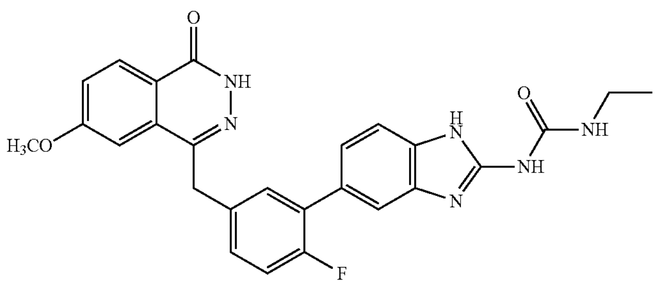 [SMILES: CCNC(=O)Nc1nc2cc(-c3cc(Cc4n[nH]c(=O)c5ccc(OC)cc45)ccc3F)ccc2[nH]1] | 1-Ethyl-3-(5-(2-fluoro-5-((7-methoxy-4-oxo-3,4-dihydrophthalazin-1-yl)methyl)phenyl)-1H-benzoimidazol-2-yl)urea |
| 35. | 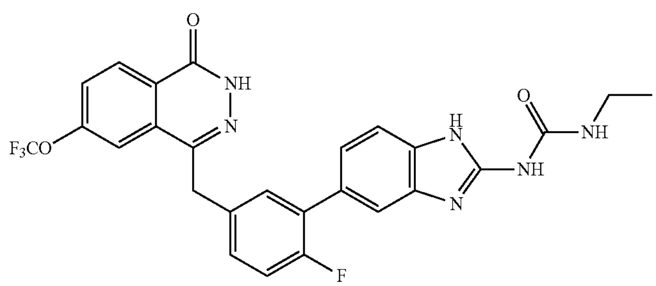 [SMILES: CCNC(=O)Nc1nc2cc(-c3cc(Cc4n[nH]c(=O)c5ccc(OC(F)(F)F)cc45)ccc3F)ccc2[nH]1] | 1-Ethyl-3-(5-(2-fluoro-5-((4-oxo-7-(trifluoromethoxy)-3,4-dihydrophthalazin-1-yl)methyl)phenyl)-1H-benzoimidazol-2-yl)urea |
| 36. | 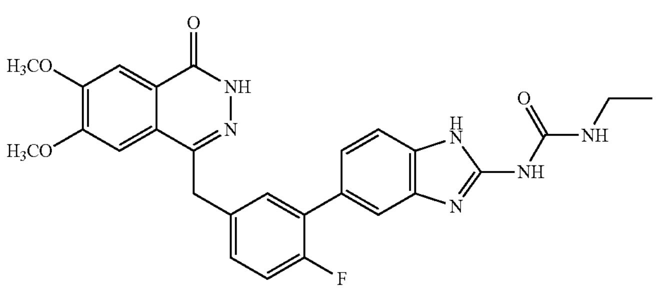 [SMILES: CCNC(=O)Nc1nc2cc(-c3cc(Cc4n[nH]c(=O)c5cc(OC)c(OC)cc45)ccc3F)ccc2[nH]1] | 1-(5-(5-((6,7-Dimethoxy-4-oxo-3,4-dihydrophthalazin-1-yl)methyl)-2-fluorophenyl)-1H-benzoimidazol-2-yl)-3-ethylurea |
| 37. | 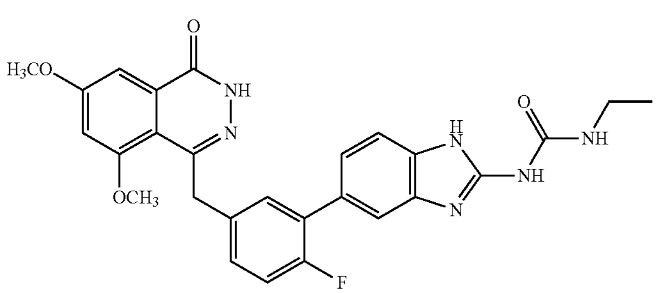 [SMILES: CCNC(=O)Nc1nc2cc(-c3cc(Cc4n[nH]c(=O)c5cc(OC)cc(OC)c45)ccc3F)ccc2[nH]1] | 1-(5-(5-((6,8-Dimethoxy-4-oxo-3,4-dihydrophthalazin-1-yl)methyl)-2-fluorophenyl)-1H-benzoimidazol-2-yl)-3-ethylurea |

| Cmpd No. | Structure | Name |
|---|---|---|
| 38. | 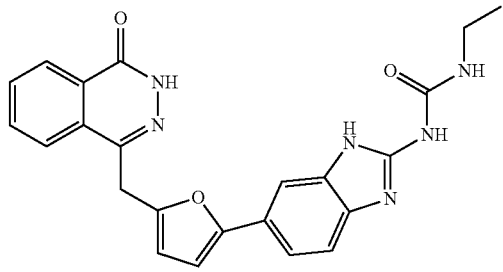 [SMILES: CCNC(=O)Nc1nc2ccc(-c3ccc(Cc4n[nH]c(=O)c5ccccc45)o3)cc2[nH]1] | 1-Ethyl-3-(6-(5-((4-oxo-3,4-dihydrophthalazin-1-yl)methyl)furan-2-yl)-1H-benzoimidazol-2-yl)urea |
| 39. | 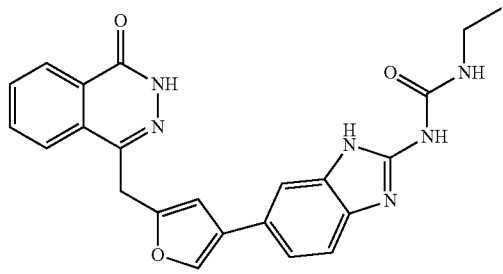 [SMILES: CCNC(=O)Nc1nc2ccc(-c3coc(Cc4n[nH]c(=O)c5ccccc45)c3)cc2[nH]1] | 1-Ethyl-3-(6-(5-((4-oxo-3,4-dihydrophthalazin-1-yl)methyl)furan-3-yl)-1H-benzoimidazol-2-yl)urea |
| 40. | 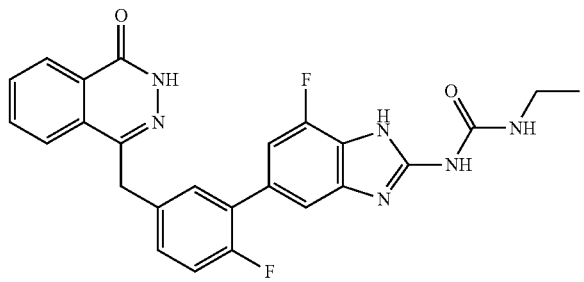 [SMILES: CCNC(=O)Nc1nc2cc(-c3cc(Cc4n[nH]c(=O)c5ccccc45)ccc3F)cc(F)c2[nH]1] | 1-Ethyl-3-(7-fluoro-5-(2-fluoro-5-((4-oxo-3,4-dihydrophthalazin-1-yl)methyl)phenyl)-1H-benzoimidazol-2-yl)urea |
| 41. | 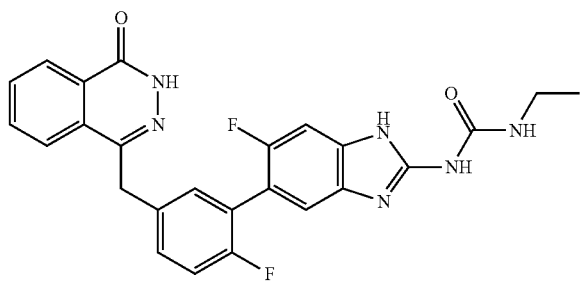 [SMILES: CCNC(=O)Nc1nc2cc(-c3cc(Cc4n[nH]c(=O)c5ccccc45)ccc3F)c(F)cc2[nH]1] | 1-Ethyl-3-(6-fluoro-5-(2-fluoro-5-((4-oxo-3,4-dihydrophthalazin-1-yl)methyl)phenyl)-1H-benzoimidazol-2-yl)urea |
| 42. | 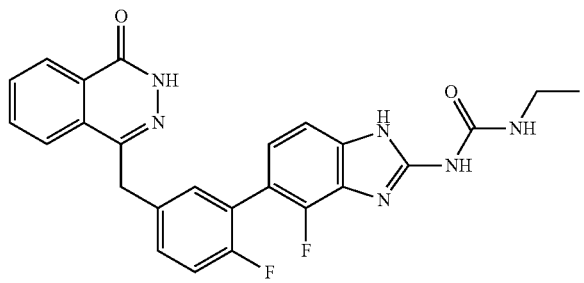 [SMILES: CCNC(=O)Nc1nc2c(F)c(-c3cc(Cc4n[nH]c(=O)c5ccccc45)ccc3F)ccc2[nH]1] | 1-Ethyl-3-(4-fluoro-5-(2-fluoro-5-((4-oxo-3,4-dihydrophthalazin-1-yl)methyl)phenyl)-1H-benzoimidazol-2-yl)urea |

| Cmpd No. | Structure | Name |
|---|---|---|
| 43. | 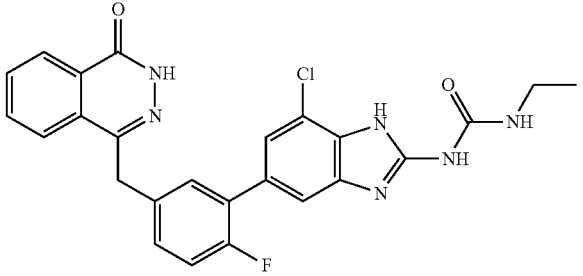 [SMILES: CCNC(=O)Nc1nc2cc(-c3cc(Cc4n[nH]c(=O)c5ccccc45)ccc3F)cc(Cl)c2[nH]1] | 1-(7-Chloro-5-(2-fluoro-5-((4-oxo-3,4-dihydrophthalazin-1-yl)methyl)phenyl)-1H-benzoimidazol-2-yl)-3-ethylurea |
| 44. | 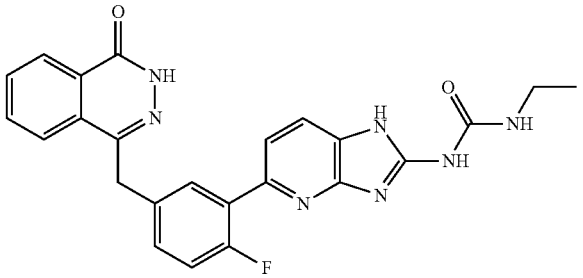 [SMILES: CCNC(=O)Nc1nc2nc(-c3cc(Cc4n[nH]c(=O)c5ccccc45)ccc3F)ccc2[nH]1] | 1-Ethyl-3-(5-(2-fluoro-5-((4-oxo-3,4-dihydrophthalazin-1-yl)methyl)phenyl)-1H-imidazo[4,5-b]pyridin-2-yl)urea |
| 45. | 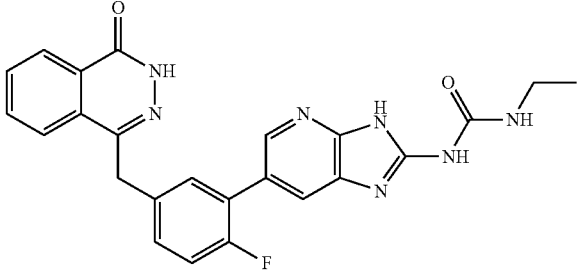 [SMILES: CCNC(=O)Nc1nc2cc(-c3cc(Cc4n[nH]c(=O)c5ccccc45)ccc3F)cnc2[nH]1] | 1-Ethyl-3-(6-(2-fluoro-5-((4-oxo-3,4-dihydrophthalazin-1-yl)methyl)phenyl)-3H-imidazo[4,5-b]pyridin-2-yl)urea |
| 46. | 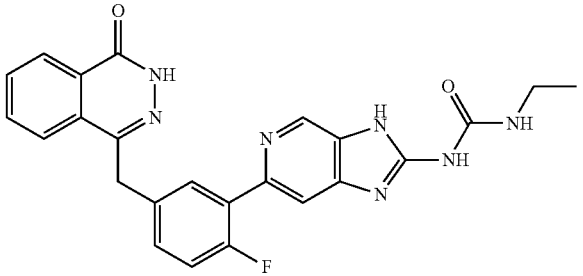 [SMILES: CCNC(=O)Nc1nc2cc(-c3cc(Cc4n[nH]c(=O)c5ccccc45)ccc3F)ncc2[nH]1] | 1-Ethyl-3-(6-(2-fluoro-5-((4-oxo-3,4-dihydrophthalazin-1-yl)methyl)phenyl)-3H-imidazo[4,5-c]pyridin-2-yl)urea |
| 47. | 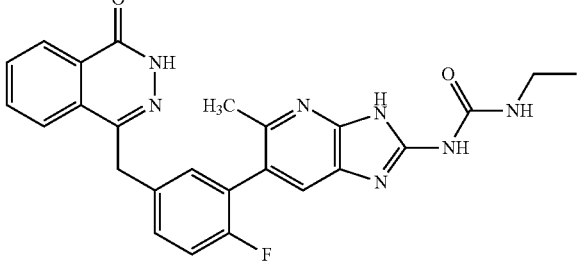 | 1-Ethyl-3-(6-(2-fluoro-5-((4-oxo-3,4-dihydrophthalazin-1-yl)methyl)phenyl)-5-methyl-3H-imidazo[4,5-b]pyridin-2-yl)urea |

| Cmpd No. | Structure | Name |
|---|---|---|
| 48. | 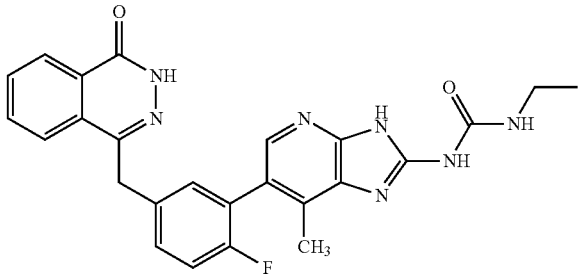 [SMILES: CCNC(=O)Nc1nc2c(C)c(-c3cc(Cc4n[nH]c(=O)c5ccccc45)ccc3F)cnc2[nH]1] | 1-Ethyl-3-(5-(2-fluoro-5-((4-oxo-4,5-dihydrofuro[2,3-d]pyridazin-7-yl)methyl)phenyl)-1H-benzoimidazol-2-yl)urea |
| 49. | 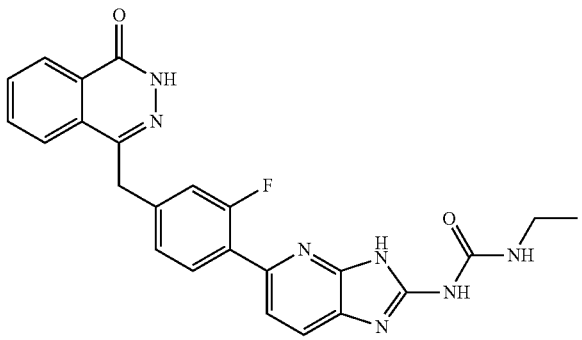 [SMILES: CCNC(=O)Nc1nc2ccc(-c3ccc(Cc4n[nH]c(=O)c5ccccc45)cc3F)nc2[nH]1] | 1-Ethyl-3-(6-(2-fluoro-4-((4-oxo-3,4-dihydrophthalazin-1-yl)methyl)phenyl)-1H-benzo[d]imidazol-2-yl)urea |

Example 6.

| | | |
|---|---|---|
| 1. | 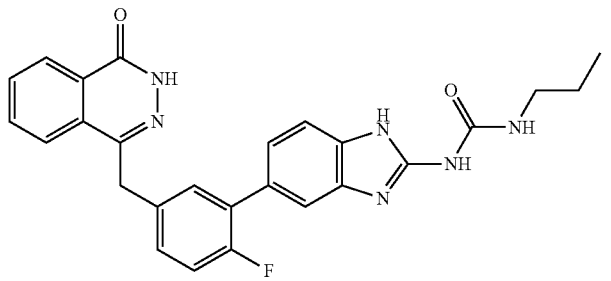 [SMILES: CCCNC(=O)Nc1nc2cc(-c3cc(Cc4n[nH]c(=O)c5ccccc45)ccc3F)ccc2[nH]1] | 1-(5-(2-Fluoro-5-((4-oxo-3,4-dihydrophthalazin-1-yl)methyl)phenyl)-1H-benzoimidazol-2-yl)-3-propylurea |
| 2. | 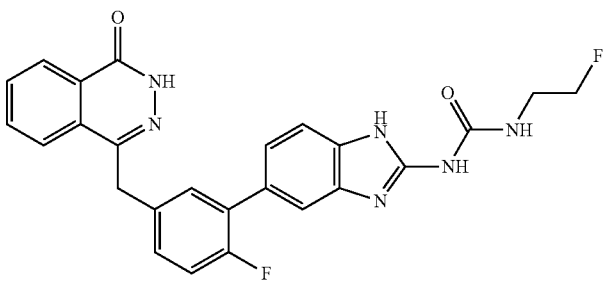 [SMILES: O=C(NCCF)Nc1nc2cc(-c3cc(Cc4n[nH]c(=O)c5ccccc45)ccc3F)ccc2[nH]1] | 1-(5-(2-Fluoro-5-((4-oxo-3,4-dihydrophthalazin-1-yl)methyl)phenyl)-1H-benzoimidazol-2-yl)-3-(2-fluoroethyl)urea |
| 3. | 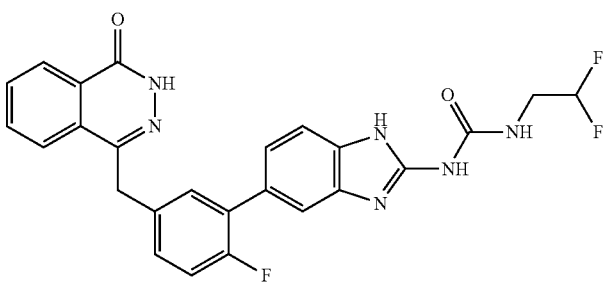 [SMILES: O=C(NCC(F)F)Nc1nc2cc(-c3cc(Cc4n[nH]c(=O)c5ccccc45)ccc3F)ccc2[nH]1] | 1-(2,2-Difluoroethyl)-3-(5-(2-fluoro-5-((4-oxo-3,4-dihydrophthalazin-1-yl)methyl)phenyl)-1H-benzoimidazol-2-yl)urea |

-continued

| Cmpd No. | Structure | Name |
|---|---|---|
| 4. | 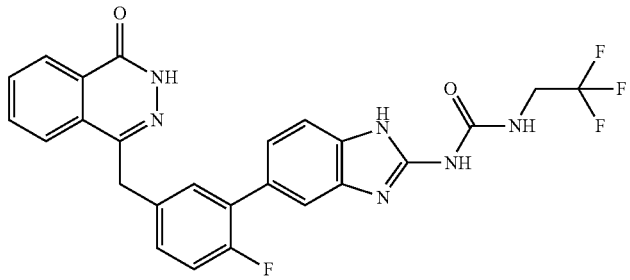 [SMILES: O=C(NCC(F)(F)F)Nc1nc2cc(-c3cc(Cc4n[nH]c(=O)c5ccccc45)ccc3F)ccc2[nH]1] | 1-(5-(2-Fluoro-5-((4-oxo-3,4-dihydrophthalazin-1-yl)methyl)phenyl)-1H-benzoimidazol-2-yl)-3-(2,2,2-trifluoroethyl)urea |
| 5. | 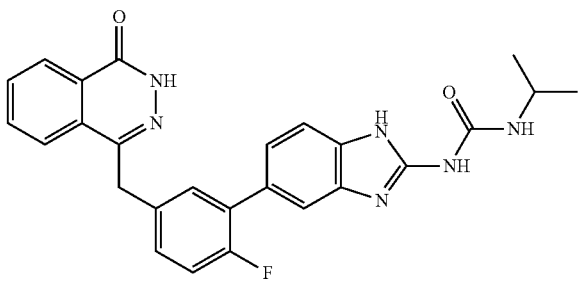 [SMILES: CC(C)NC(=O)Nc1nc2cc(-c3cc(Cc4n[nH]c(=O)c5ccccc45)ccc3F)ccc2[nH]1] | 1-(5-(2-Fluoro-5-((4-oxo-3,4-dihydrophthalazin-1-yl)methyl)phenyl)-1H-benzoimidazol-2-yl)-3-isopropylurea |
| 6. | 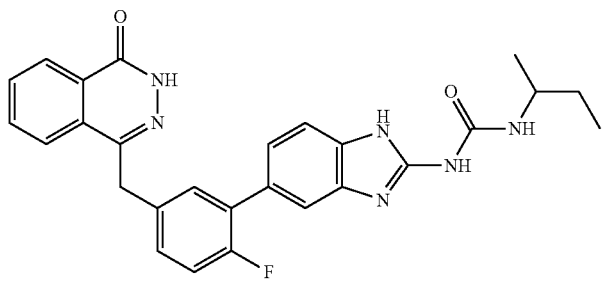 [SMILES: CCC(C)NC(=O)Nc1nc2cc(-c3cc(Cc4n[nH]c(=O)c5ccccc45)ccc3F)ccc2[nH]1] | 1-(sec-Butyl)-3-(5-(2-fluoro-5-((4-oxo-3,4-dihydrophthalazin-1-yl)methyl)phenyl)-1H-benzoimidazol-2-yl)urea |
| 7. | 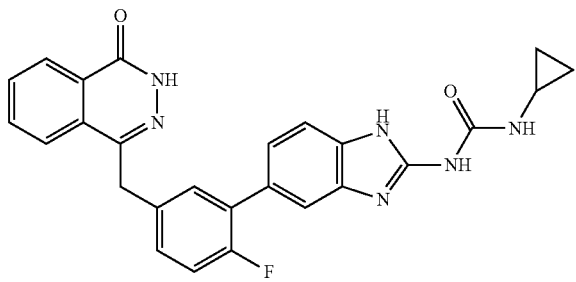 [SMILES: O=C(Nc1nc2cc(-c3cc(Cc4n[nH]c(=O)c5ccccc45)ccc3F)ccc2[nH]1)NC1CC1] | 1-Cyclopropyl-3-(5-(2-fluoro-5-((4-oxo-3,4-dihydrophthalazin-1-yl)methyl)phenyl)-1H-benzoimidazol-2-yl)urea |
| 8. | 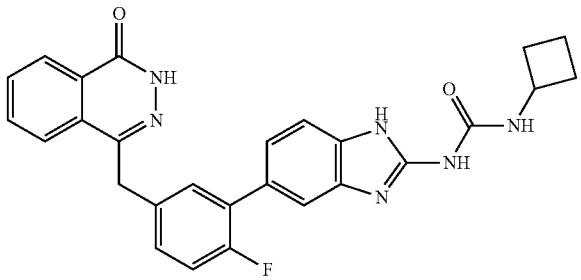 [SMILES: O=C(Nc1nc2cc(-c3cc(Cc4n[nH]c(=O)c5ccccc45)ccc3F)ccc2[nH]1)NC1CCC1] | 1-Cyclobutyl-3-(5-(2-fluoro-5-((4-oxo-3,4-dihydrophthalazin-1-yl)methyl)phenyl)-1H-benzoimidazol-2-yl)urea |

-continued

| Cmpd No. | Structure | Name |
|---|---|---|
| 9. | 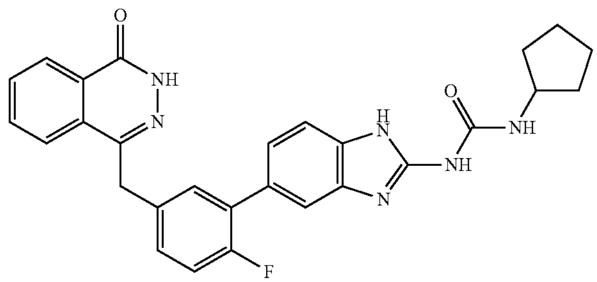 [SMILES: O=C(Nc1nc2cc(-c3cc(Cc4n[nH]c(=O)c5ccccc45)ccc3F)ccc2[nH]1)NC1CCCC1] | 1-Cyclopentyl-3-(5-(2-fluoro-5-((4-oxo-3,4-dihydrophthalazin-1-yl)methyl)phenyl)-1H-benzoimidazol-2-yl)urea |
| 10. | 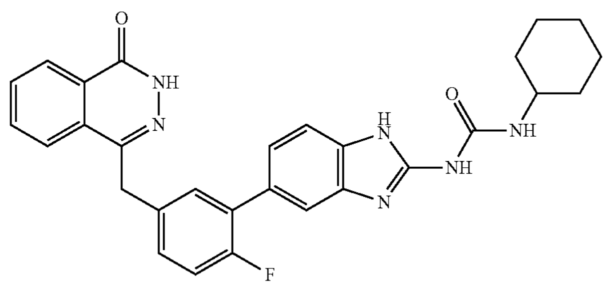 [SMILES: O=C(Nc1nc2cc(-c3cc(Cc4n[nH]c(=O)c5ccccc45)ccc3F)ccc2[nH]1)NC1CCCCC1] | 1-Cyclohexyl-3-(5-(2-fluoro-5-((4-oxo-3,4-dihydrophthalazin-1-yl)methyl)phenyl)-1H-benzoimidazol-2-yl)urea |
| 11. | 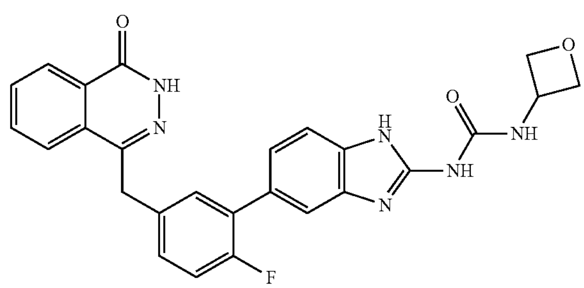 [SMILES: O=C(Nc1nc2cc(-c3cc(Cc4n[nH]c(=O)c5ccccc45)ccc3F)ccc2[nH]1)NC1COC1] | 1-(5-(2-Fluoro-5-((4-oxo-3,4-dihydrophthalazin-1-yl)methyl)phenyl)-1H-benzoimidazol-2-yl)-3-(oxetan-3-yl)urea |
| 12. | 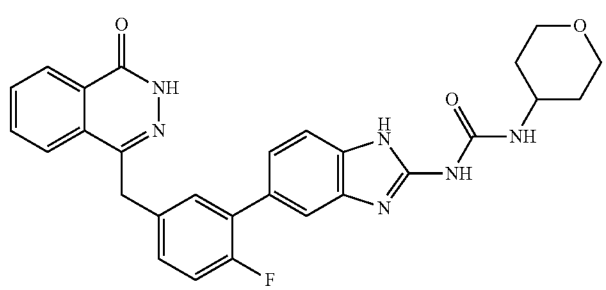 [SMILES: O=C(Nc1nc2cc(-c3cc(Cc4n[nH]c(=O)c5ccccc45)ccc3F)ccc2[nH]1)NC1CCOCC1] | 1-(5-(2-Fluoro-5-((4-oxo-3,4-dihydrophthalazin-1-yl)methyl)phenyl)-1H-benzoimidazol-2-yl)-3-(tetrahydro-2H-pyran-4-yl)urea |
| 13. | 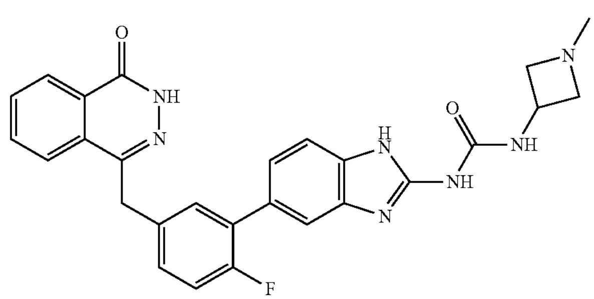 [SMILES: CN1CC(NC(=O)Nc2nc3cc(-c4cc(Cc5n[nH]c(=O)c6ccccc56)ccc4F)ccc3[nH]2)C1] | 1-(5-(2-Fluoro-5-((4-oxo-3,4-dihydrophthalazin-1-yl)methyl)phenyl)-1H-benzoimidazol-2-yl)-3-(1-methylazetidin-3-yl)urea |

| Cmpd No. | Structure | Name |
|---|---|---|
| 14. | 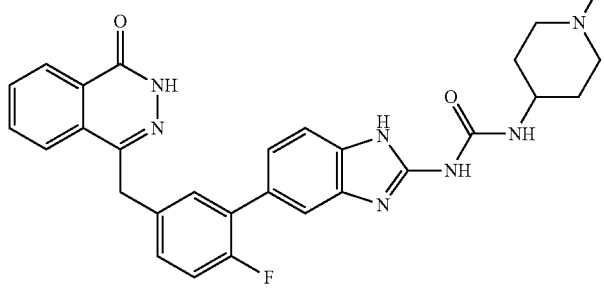 | 1-(5-(2-Fluoro-5-((4-oxo-3,4-dihydrophthalazin-1-yl)methyl)phenyl)-1H-benzoimidazol-2-yl)-3-(1-methylpiperidin-4-yl)urea |
| 15. | 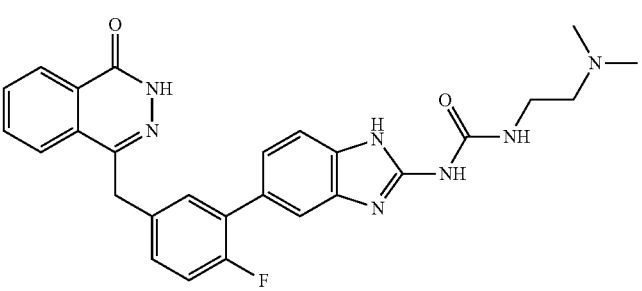 [SMILES: CN(C)CCNC(=O)Nc1nc2cc(-c3cc(Cc4n[nH]c(=O)c5ccccc45)ccc3F)ccc2[nH]1] | 1-(2-(Dimethylamino)ethyl)-3-(5-(2-fluoro-5-((4-oxo-3,4-dihydrophthalazin-1-yl)methyl)phenyl)-1H-benzoimidazol-2-yl)urea |
| 16. | 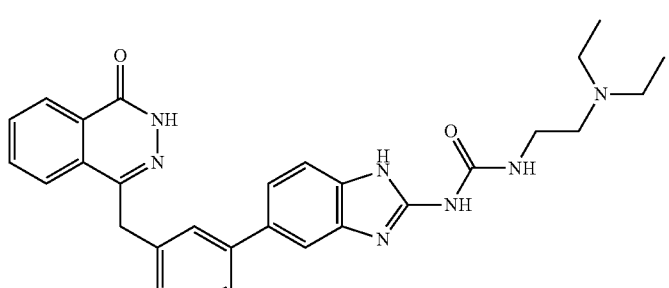 | 1-(2-(Diethylamino)ethyl)-3-(5-(2-fluoro-5-((4-oxo-3,4-dihydrophthalazin-1-yl)methyl)phenyl)-1H-benzoimidazol-2-yl)urea |
| 17. | 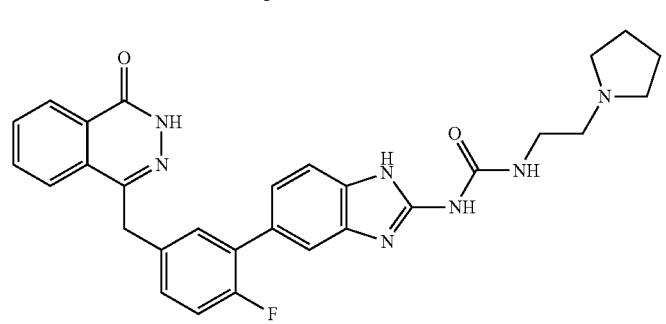 | 1-(5-(2-Fluoro-5-((4-oxo-3,4-dihydrophthalazin-1-yl)methyl)phenyl)-1H-benzoimidazol-2-yl)-3-(2-(pyrrolidin-1-yl)ethyl)urea |
| 18. | 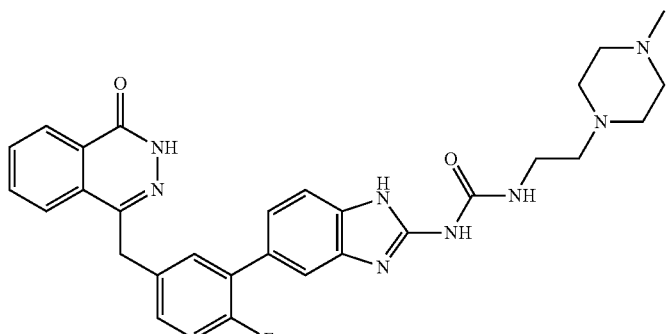 | 1-(5-(2-Fluoro-5-((4-oxo-3,4-dihydrophthalazin-1-yl)methyl)phenyl)-1H-benzoimidazol-2-yl)-3-(2-(4-methylpiperazin-1-yl)ethyl)urea |

-continued

| Cmpd No. | Structure | Name |
|---|---|---|
| 19. | 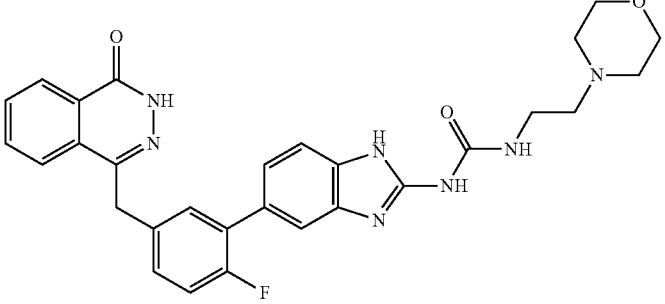 | 1-(5-(2-Fluoro-5-((4-oxo-3,4-dihydrophthalazin-1-yl)methyl)phenyl)-1H-benzoimidazol-2-yl)-3-(2-morpholinoethyl)urea |
| 20. | 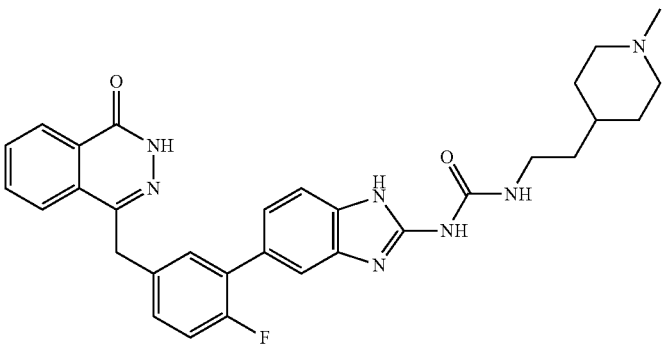 | 1-(5-(2-Fluoro-5-((4-oxo-3,4-dihydrophthalazin-1-yl)methyl)phenyl)-1H-benzoimidazol-2-yl)-3-(2-(1-methylpiperidin-4-yl)ethyl)urea |
| 21. | 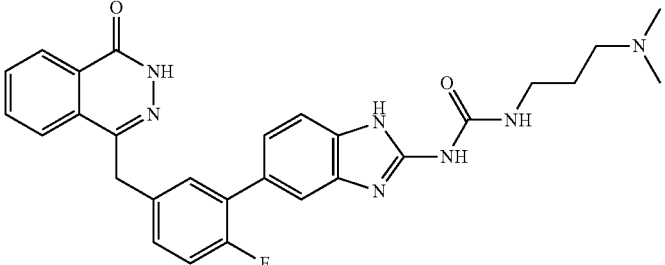 | 1-(3-(Dimethylamino)propyl)-3-(5-(2-fluoro-5-((4-oxo-3,4-dihydrophthalazin-1-yl)methyl)phenyl)-1H-benzoimidazol-2-yl)urea |
| 22. | 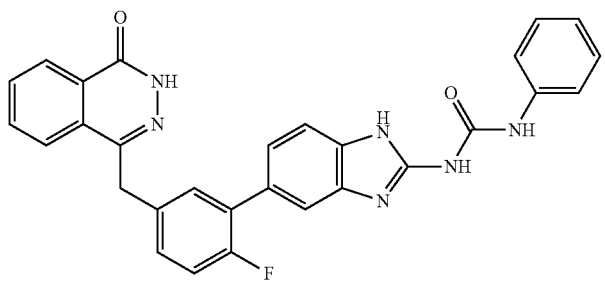 [SMILES: O=C(Nc1ccccc1)Nc1nc2cc(-c3cc(Cc4n[nH]c(=O)c5ccccc45)ccc3F)ccc2[nH]1] | 1-(5-(2-Fluoro-5-((4-oxo-3,4-dihydrophthalazin-1-yl)methyl)phenyl)-1H-benzoimidazol-2-yl)-3-phenylurea |
| 23. | 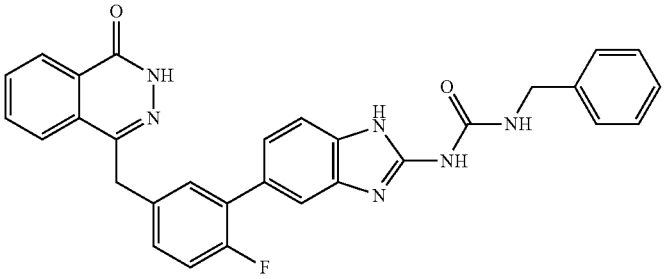 [SMILES: O=C(NCc1ccccc1)Nc1nc2cc(-c3cc(Cc4n[nH]c(=O)c5ccccc45)ccc3F)ccc2[nH]1] | 1-Benzyl-3-(5-(2-fluoro-5-((4-oxo-3,4-dihydrophthalazin-1-yl)methyl)phenyl)-1H-benzoimidazol-2-yl)urea |

| Cmpd No. | Structure | Name |
|---|---|---|
| 24. | 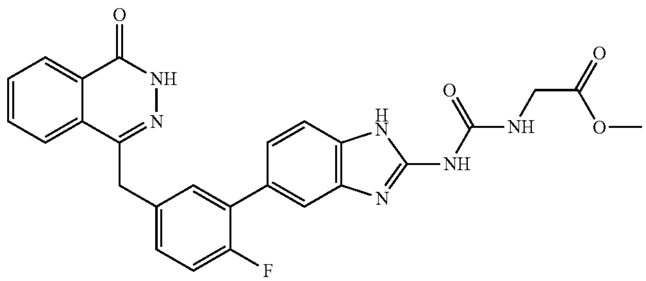 [SMILES: COC(=O)CNC(=O)Nc1nc2cc(-c3cc(Cc4n[nH]c(=O)c5ccccc45)ccc3F)ccc2[nH]1] | Methyl ((5-(2-fluoro-5-((4-oxo-3,4-dihydrophthalazin-1-yl)methyl)phenyl)-1H-benzoimidazol-2-yl)carbamoyl)glycinate |
| 25. | 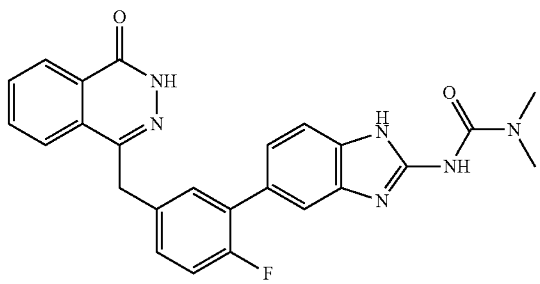 [SMILES: CN(C)C(=O)Nc1nc2cc(-c3cc(Cc4n[nH]c(=O)c5ccccc45)ccc3F)ccc2[nH]1] | 3-(5-(2-Fluoro-5-((4-oxo-3,4-dihydrophthalazin-1-yl)methyl)phenyl)-1H-benzoimidazol-2-yl)-1,1-dimethylurea |
| 26. | 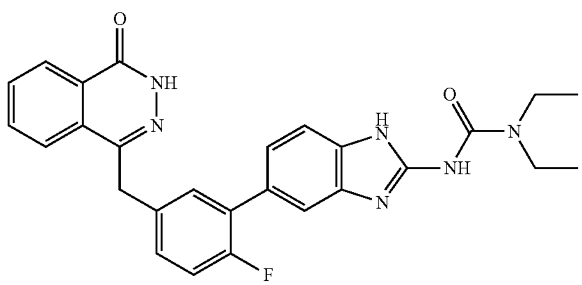 [SMILES: CCN(CC)C(=O)Nc1nc2cc(-c3cc(Cc4n[nH]c(=O)c5ccccc45)ccc3F)ccc2[nH]1] | 1,1-Diethyl-3-(5-(2-fluoro-5-((4-oxo-3,4-dihydrophthalazin-1-yl)methyl)phenyl)-1H-benzoimidazol-2-yl)urea |

Example 7.

| | | |
|---|---|---|
| 1. | | N-(5-(2-fluoro-5-((4-oxo-3,4-dihydrophthalazin-1-yl)methyl)phenyl)-1H-benzimidazol-2-yl) methanesulfonamide |

Example 8.

| | | |
|---|---|---|
| 1. | | N-(5-(2-fluoro-5-((4-oxo-3,4-dihydrophthalazin-1-yl)methyl)phenyl)-1H-benzoimidazol-2-yl)butyramide |

Example 9

PARP1 Enzymatic Activity Inhibition: Determination of IC50 Values for Selected Compounds The half maximal inhibitory concentration (IC50) with respect to PARP1 inhibition was determined for each test compound by using Trevigen's HT Universal PARP Assay Kit, according to the manufacturer's protocol (Cat #4677-096-K, Gaithersburg, Md.). This assay measures the incorporation of biotinylated poly(ADP-ribose) onto histone proteins in a 96-well strip well format. This assay is ideal for the determination of IC50 values of known or suspected PARP inhibitors. Briefly, stock solutions of each test compound were prepared in DMSO. Histone strip wells were incubated for 30 minutes at room temperature with 50 l/well of 1×PARP Buffer to rehydrate the histones. Serial dilutions of either test compound were added to appropriate wells. Diluted PARP enzyme (0.5 Unit/well) was then added to the wells containing compounds, and incubated for 10 minutes at room temperature. Subsequently, 25 µl of 1×PARP Cocktail, containing activated DNA, was distributed into each well. Three types of control wells were also analyzed; i. A negative control without PARP was prepared to determine background absorbance. ii. An activity control for PARP Inhibitor Study: 0.5 Unit/well PARP-HSA without inhibitors. These wells provided the 100% activity reference point. iii. And a PARP Standard Curve: Serial dilution of the PARP-HAS standard were prepared in cold microtubes with IX PARP Buffer such that the total activity is 1 Unit/25 µl, 0.5 Units/25 µl, 0.25 Units/25 µl, 0.1 Units/25 µl, 0.05 Units/25 µl, 0.025 Units/25 µl, and 0.01 Units/25 µl. 25 µl of each standard was added to triplicate wells. Following a 60 minutes incubation at room temperature, the strip wells were washed twice with 1×PBS+0.1% Triton X-100, and twice with IX PBS. For activity detection, 50 µl per well of diluted Strep-HRP was added, and then incubated at room temperature for 60 minutes. Subsequently, 50 µl per well of pre-warmed TACS-Sapphire™ colorimetric substrate was added followed by a 15 minutes incubation, in the dark, at room temperature. The reactions were then stopped by adding 50 µl per well of 0.2M HCl or 5% Phosphoric Acid and read the absorbance at 450 nm.

The IC50 values were determined by performing non-linear regression analysis fitting velocities and the logarithm of inhibitor concentrations to a sigmoidal dose response with a variable slope model using the GraphPad Prism 6.0 software.

PARP 2 Enzymatic Activity Inhibition: Determination of IC50 Values for Selected Compounds The half maximal inhibitory concentration (IC50) with respect to PARP2 inhibition was determined for each test compound by using BPS Bioscience PARP2 Assay Kit, according to the manufacturer's protocol (Cat #80552, San Diego, Calif.). This assay measures the incorporation of biotinylated poly(ADP-ribose) onto histone proteins in a 96-well strip well format. This assay is ideal for the determination of IC50 values of known or suspected PARP inhibitors. Briefly, stock solutions of each test compound were prepared in DMSO. Histone strip wells were incubated for 30 minutes at room temperature with 50 l/well of 1×PARP Buffer to rehydrate the histones. Serial dilutions of either test compound were added to appropriate wells. Diluted PARP enzyme (0.5 Unit/well) was then added to the wells containing compounds, and incubated for 10 minutes at room temperature. Subsequently, 25 µl of 1×PARP Cocktail, containing activated DNA, was distributed into each well. Three types of control wells were also analyzed; i. A negative control without PARP was prepared to determine background absorbance. ii. An activity control for PARP Inhibitor Study: 0.5 Unit/well PARP-HSA without inhibitors. These wells provided the 100% activity reference point. iii. And a PARP Standard Curve: Serial dilution of the PARP-HAS standard were prepared in cold microtubes with 1×PARP Buffer such that the total activity is 1 Unit/25 µl, 0.5 Units/25 µl, 0.25 Units/25 µl, 0.1 Units/25 µl, 0.05 Units/25 µl, 0.025 Units/25 µl, and 0.01 Units/25 µl. 25 µl of each standard was added to triplicate wells. Following a 60 minutes incubation at room temperature, the strip wells were washed twice with IX PBS+0.1% Triton X-100, and twice with IX PBS. For activity detection, 50 µl per well of diluted Strep-HRP was added, and then incubated at room temperature for 60 minutes. Subsequently, 50 µl per well of pre-warmed TACS-Sapphire™ colorimetric substrate was added followed by al 5 minutes incubation, in the dark, at room temperature. The reactions were then stopped by adding 50 µl per well of 0.2M HCl or 5% Phosphoric Acid and read the absorbance at 450 nm.

The IC50 values were determined by performing non-linear regression analysis fitting velocities and the logarithm of inhibitor concentrations to a sigmoidal dose response with a variable slope model using the GraphPad Prism 6.0 software. PARP2 inhibition by Ex. 1.1 is 0.05 nM.

Trapping of PARP-DNA Complexes Formation Assay

Trapping PARP on damaged DNA has recently been proposed as a mechanism accounting for the cytotoxicity of many PARP inhibitors. Using a cellular Western Blot assay to measure PARP trapping on damaged DNA, we examined chromatin-bound PARP1. To prepare chromatin-bound subcellular fraction, semiconfluent MDA-MB-436 human breast cancer cells with 10 mL medium in 10 cm dish were exposed to various concentrations of the drugs for 4 hours. Cells were then collected and fractionated using a Subcellular Protein Fractionation Kit from Thermo Scientific (78840) following the manufacturer's instructions. Immunoblotting was carried out using standard procedures. Histone H3 was used as positive markers for chromatin-bound fractions and as loading control. Topoisomerase 1 was used as positive markers for soluble nuclear fractions and as loading control. Rabbit polyclonal anti-PARP1 antibody (#9542) was purchased from cell signaling technology. Rabbit polyclonal anti-histone H3 antibody (#4499) was from cell signaling technology. Mouse monoclonal anti-topoisomerase I antibody [23B11] was purchased from Abcam. Secondary antibodies were horseradish peroxidase (HRP)-conjugated antibodies to rabbit immunoglobulin G (IgG; GE Healthcare).

Tubulin Polymerization Assay

The high-throughput screening-tubulin polymerization assay kit (Cytoskeleton, Cat. #BK011P) is an economical one step procedure for determining the effects of drugs or proteins on tubulin polymerization. Polymerization is followed by fluorescence enhancement due to the incorporation of a fluorescent reporter into microtubules as polymerization occurs. The standard assay tubulin generates a polymerization curve representing the three phases of microtubule formation, namely nucleation, growth, and steady state equilibrium. Compounds that interact with tubulin will often alter one or more of the characteristic phases of polymerization. For example, the anti-mitotic drug paclitaxel eliminates the nucleation phase and enhances the Vmax of the growth phase. Similarly, the microtubule destabilizing drug, vinblastine (also antimitotic) causes a decrease in Vmax and a reduction in final polymer mass. Thus, one application of this assay is the identification of novel anti-mitotics.

The direct effects of the test compounds on tubulin polymerization were investigated using the abovementioned Tubulin polymerization assay kit (Cytoskeleton, Cat. #BK011P), as indicated by the manufacturer protocol. Briefly, bovine brain tubulin (400 μg/sample) in the presence of either 0.5% DMSO treated (control), or increasing concentrations of each test compounds was incubated in PEM buffer [80 mm PIPES, 1 mm EGTA, 1 mm MgCl$_2$ (pH 6.8)] containing 1.0 mm GTP (G-PEM) and 15% glycerol, at 37 C. All samples (wells) contained 15% glycerol. The degree of polymerization over time was measured in a spectrophotometer (Biotek synergy HT plate reader) at 350 nm. All time points were plotted and analyzed using GraphPad Prism 6.0 software.

The IC50 values were determined by performing non-linear regression analysis fitting velocities and the logarithm of inhibitor concentrations to a sigmoidal dose response with a variable slope model using the GraphPad Prism 6.0 software.

Cell Viability Assay in Solid Tumors Cell Lines

Human cancer cell lines (lung, ovarian, breast pancreatic and mesothelioma) were purchased from the ATCC. The cell lines were cultured in RPMI 1640 (Life Technologies, Carlsbad, Calif.) supplemented with 10% fetal bovine serum (FBS) and antibiotics. 2000 cells were seeded in 96 well costar plate one day before treatment with test compounds, Olaparib (Selleck Chemicals), Imatnib Mesylate (Selleck Chemicals) or ponatinib at different concentrations for 72 hours, with vehicle (DMSO) as controls. At the end of treatment, cell proliferation was determined by an intracellular adenosine triphosphate monitoring system (Cell-Titer Glo-Promega). Cell lines tested included A549 cells=Human lung adenocarcinoma; OVCAR-8 Cells=Human Ovarian adenocarcinoma; MDA-MB-436 Cells=Human Breast adenocarcinoma cell line with BRCA1-mutation.

Inhibitory activity was evaluated comparing treated versus control data using the GraphPad Prism 6.0 software. The dose inhibiting 50% (IC50) of cell viability was calculated using non-linear regression curve. Results show the mean IC50 value from three different experiments.

Data obtained from these assays for compounds of the invention are provided in FIG. 1A-FIG. 1O.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt thereof, having a structure according to formula (I):

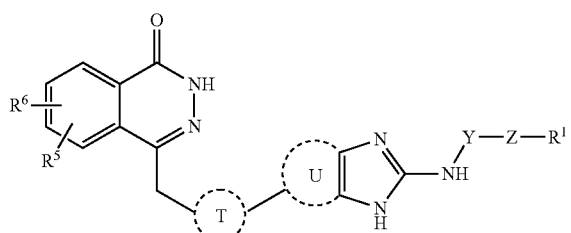

(I)

wherein T has a structure which is

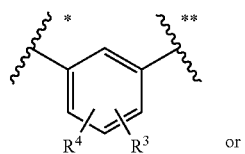

(A)

or

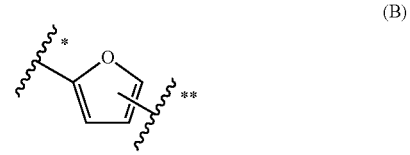

(B)

wherein $\vert^*$ represents a covalent bond to the methylene group in formula (I) and $\vert^{**}$ represents a covalent bond to the U ring in formula (I)

wherein formula (C)

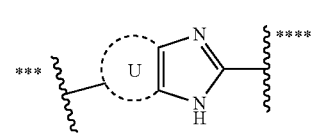

(C)

wherein $\vert^{*}$ represents a covalent bond to the T ring in formula (I) and $\vert^{**}$ represents a covalent bond to —NH—Y—Z—R$^1$ in formula (I), has a structure which is

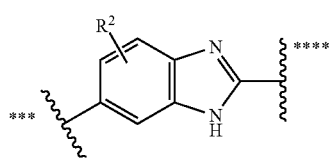

(D)

or

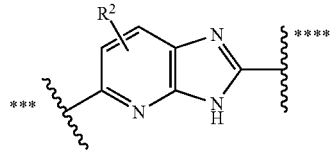

(E)

or

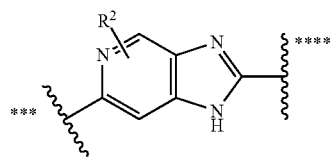

(F)

or

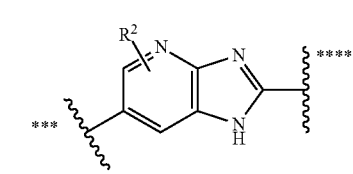

(G)

wherein Y is C(O) or S(O)$_2$;

Z is —O— or —CH$_2$— or —NH— or —N(CH$_2$R$^7$)—
wherein R$^7$ is hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl;

R$^1$ is unsubstituted C$_2$ or C$_1$ or C$_3$ or C$_4$ or C$_5$ or C$_6$ or C$_7$ or C$_8$ or C$_9$ or C$_{10}$ alkyl or hydrogen or substituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ heteroalkyl or substituted or unsubstituted aryl or substituted or unsubstituted arylalkyl or substituted or unsubstituted cycloalkyl or substituted or unsubstituted heterocycloalkyl;

R$^2$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl;

R$^3$ is halogen or hydrogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ alkoxy;

R$^4$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl or substituted or unsubstituted C$_1$ or C$_2$ or C$_3$ or C$_4$ or C$_5$ or C$_6$ or C$_7$ or C$_8$ or C$_9$ or C$_{10}$ alkoxy;

R$^5$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl; and R$^6$ is hydrogen or halogen or substituted or unsubstituted C$_1$ or C$_2$ or C$_3$ or C$_4$ or C$_5$ or C$_6$ or C$_7$ or C$_8$ or C$_9$ or C$_{10}$ alkyl.

2. The compound of claim 1, or a salt thereof, having a structure which is (VIII)

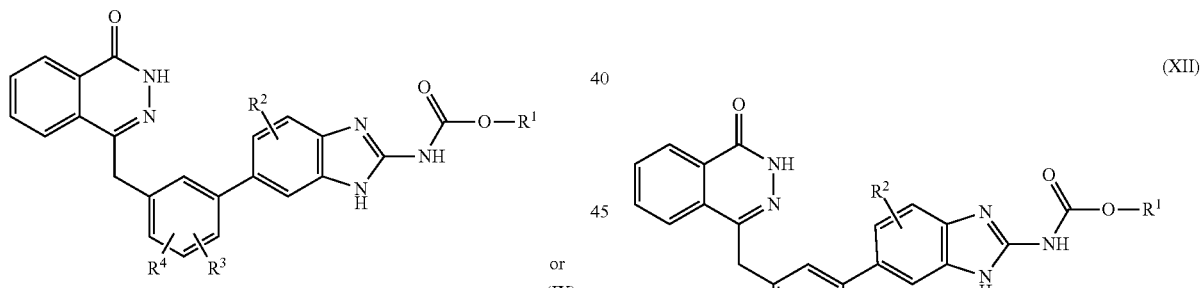

or (IX)

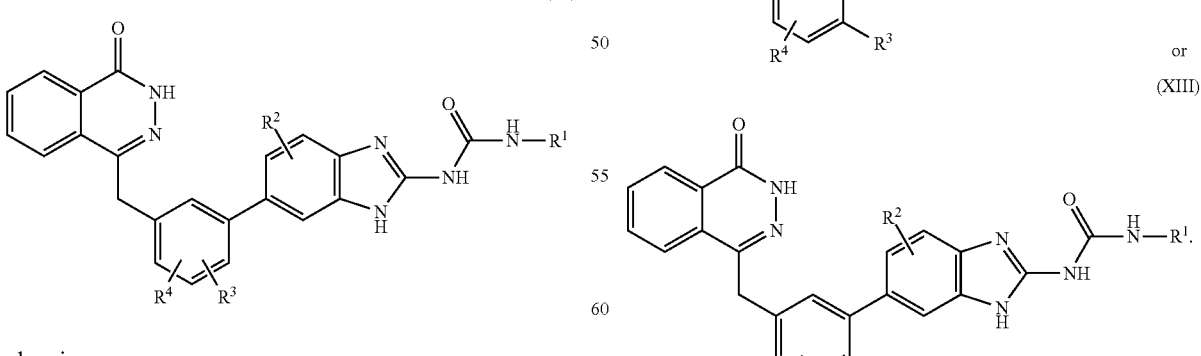

wherein
R$^2$ is hydrogen or F or Cl or unsubstituted C$_1$ or C$_2$ or C$_3$ alkyl;
R$^3$ is hydrogen or F or Cl or unsubstituted C$_1$ or C$_2$ or C$_3$ or alkyl or substituted or unsubstituted C$_1$ or C$_2$ or C$_3$ alkoxy; and R$^4$ is hydrogen or F or Cl or unsubstituted C$_1$ or C$_2$ or C$_3$ or alkyl or substituted or unsubstituted C$_1$ or C$_2$ or C$_3$ alkoxy.

3. The compound of claim 1, or a salt thereof, having a structure which is (X)

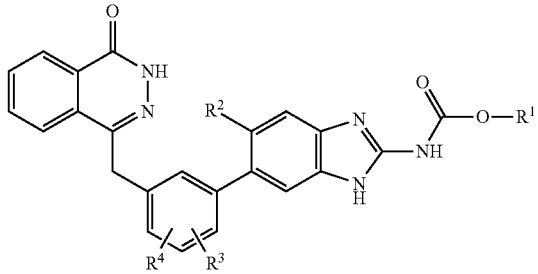

or (XI)

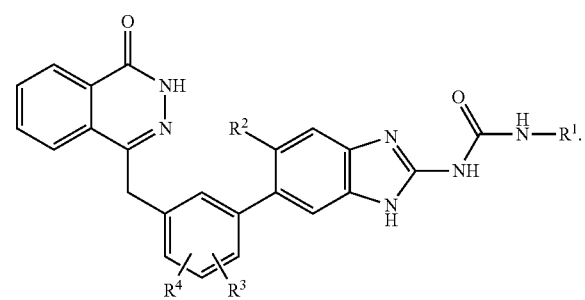

4. The compound of claim 1, or a salt thereof, having a structure which is (XII)

or (XIII)

5. The compound of claim 1, or a salt thereof, having a structure which is (XIV)
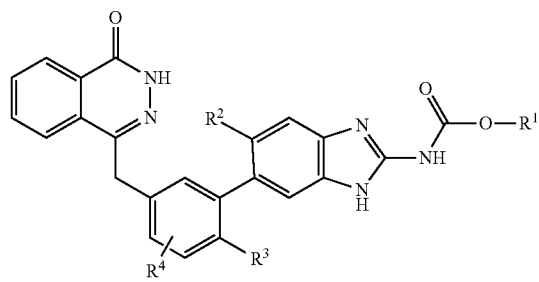
or
(XV)
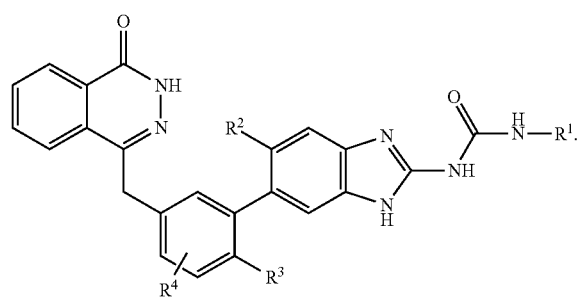
6. The compound of claim 1, or a salt thereof, having a structure which is
(XVI)
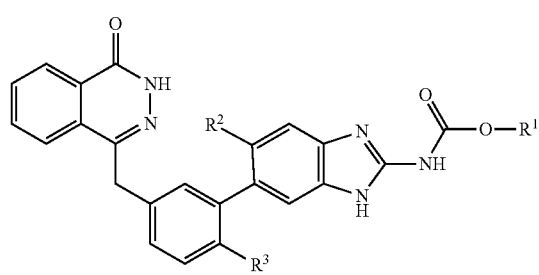
or
(XVII)
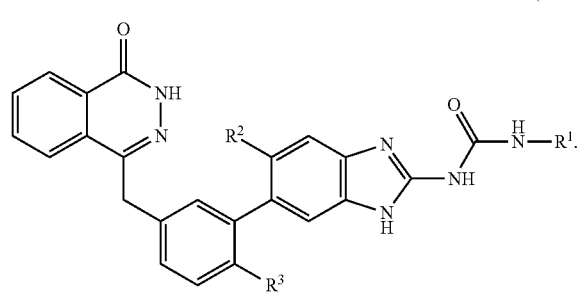
(XVIII)
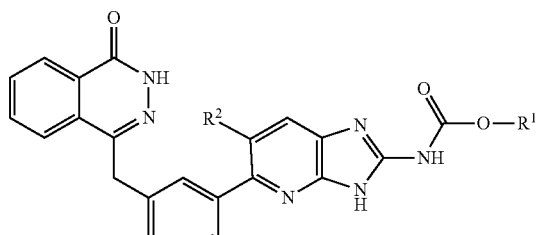
or
(XIX)
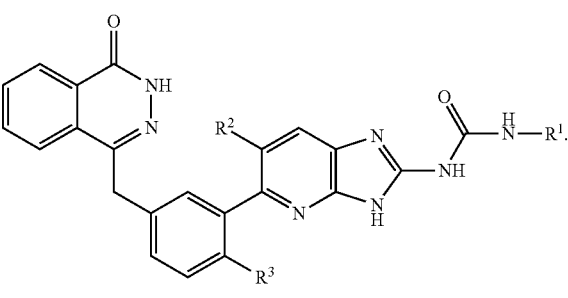
8. The compound of claim 1, or a salt thereof, having a structure which is
(XX)
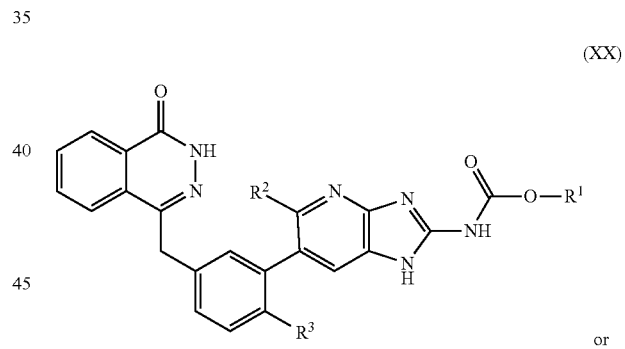
or
(XXI)
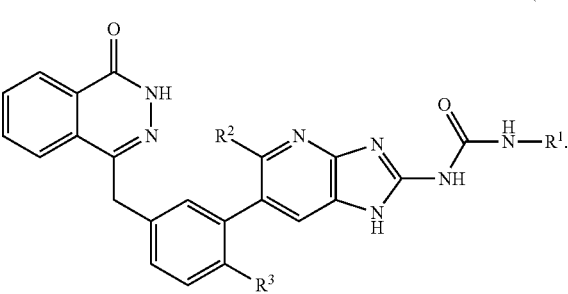
7. The compound of claim 1, or a salt thereof, having a structure which is
9. The compound of claim 1, or a salt thereof, having a structure which is (XXII)

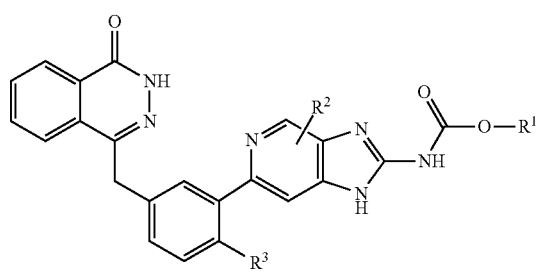

or (XXIII)

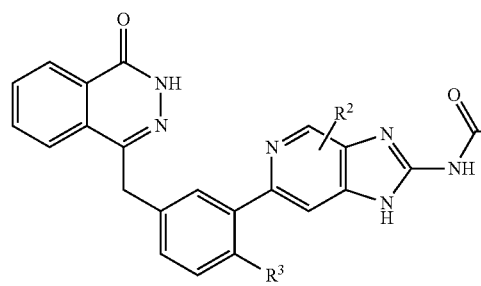

10. The compound of claim 1, or a salt thereof, having a structure which is (II)

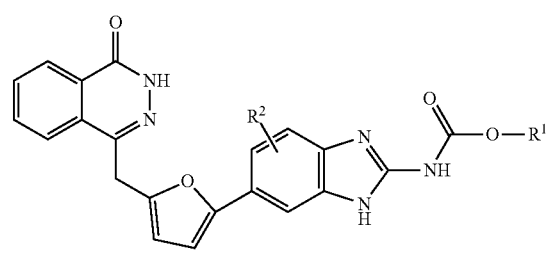

or (III)

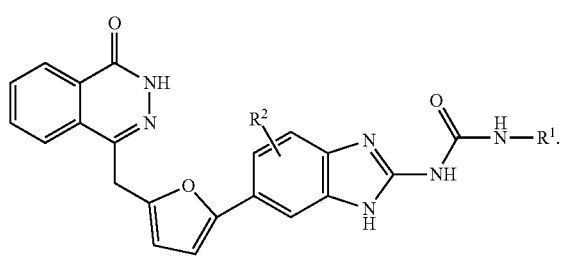

11. The compound of claim 1, or a salt thereof, having a structure which is (IV)

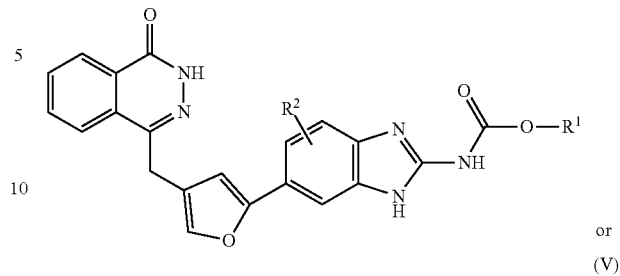

or (V)

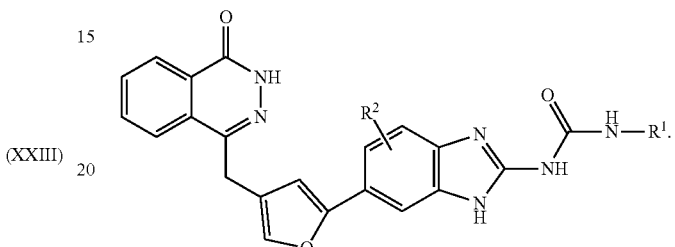

12. The compound of claim 1, or a salt thereof, having a structure which is (VI)

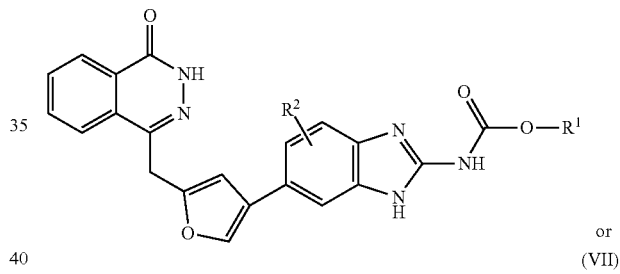

or (VII)

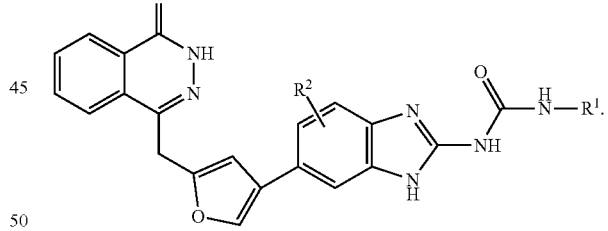

13. The compound of claim 1, or a salt thereof, wherein
$R^2$ is H and $R^3$ is H; or
$R^2$ is F and $R^3$ is H; or
$R^2$ is H and $R^3$ is F; or
$R^2$ is F and $R^3$ is F; or
$R^2$ is H and $R^3$ is Cl; or
$R^2$ is F and $R^3$ is Cl; or
$R^2$ is H and $R^3$ is —OCH$_3$; or
$R^2$ is H and $R^3$ is —OCHF$_2$; or
$R^2$ is H and $R^3$ is —OCF$_3$; or
$R^2$ is H and $R^3$ is —CH$_3$; or
$R^2$ is H and $R^3$ is —OCH$_2$CH$_3$; or
$R^2$ is H and $R^3$ is —CF$_3$.

14. The compound of claim 1, or a salt thereof, wherein $R^1$ is substituted or unsubstituted $C_1$ or $C_2$ or $C_3$ or $C_4$ or $C_5$ or $C_6$ or $C_7$ or $C_8$ or $C_9$ or $C_{10}$ alkyl or substituted or unsubstituted $C_1$ or $C_2$ or $C_3$ or $C_4$ or $C_5$ or $C_6$ or $C_7$ or $C_8$ or $C_9$ or $C_{10}$ heteroalkyl or substituted or unsubstituted aryl or substituted or unsubstituted arylalkyl or substituted or unsubstituted cycloalkyl or substituted or unsubstituted heterocycloalkyl.

15. The compound of claim 1, or a salt thereof, wherein $R^1$ is methyl.

16. The compound of claim 1, or a salt thereof, wherein $R^1$ is ethyl.

17. The compound of claim 1, or a salt thereof, wherein $R^1$ is —$(CH_2)_mOR^{1a}$, wherein $R^{1a}$ is substituted or unsubstituted $C_1$ or $C_2$ or $C_3$ alkyl, and m is 2 or 3.

18. The compound of claim 1, or a salt thereof, wherein $R^1$ is —$(CH_2)_2OCH_3$.

19. The compound of claim 1, or a salt thereof, wherein $R^1$ is propyl or —$CH_2CH_2F$ or —$CH_2CHF_2$ or —$CH_2CF_3$ or —$CH(CH_3)_2$ or —$CH(CH_3)(CH_2CH_3)$ or cyclopropyl or cyclobutyl or cyclopentyl or cyclohexyl or oxetanyl or tetrahydropyranyl or azetidinyl or methylazetidinyl or piperidinyl or methylpiperidinyl or phenyl or benzyl or —$(CH_2)_mNR^{1b}R^{1c}$, wherein $R^{1b}$ is hydrogen or substituted or unsubstituted $C_1$ or $C_2$ or $C_3$ alkyl and $R^{1c}$ is hydrogen or substituted or unsubstituted $C_1$ or $C_2$ or $C_3$ alkyl and m is 1 or 2 or 3, with the proviso that $R^{1b}$ and $R^{1c}$ can optionally be joined to form a 4-7 membered ring.

20. The compound of claim 1, or a salt thereof, wherein
$R^1$ is —$(CH_2)_2OCH_3$, $R^2$ is H, and $R^3$ is H; or
$R^1$ is —$(CH_2)_2OCH_3$, $R^2$ is H, and $R^3$ is F; or
$R^1$ is methyl, $R^2$ is F, and $R^3$ is F; or
$R^1$ is ethyl, $R^2$ is F, and $R^3$ is F; or
$R^1$ is —$(CH_2)_2OCH_3$, $R^2$ is F, and $R^3$ is F; or
$R^1$ is methyl; $R^2$ is H; and $R^3$ is —$CH_3$; or
$R^1$ is ethyl; $R^2$ is H; and $R^3$ is —$CH_3$; or
$R^1$ is —$(CH_2)_2OCH_3$, $R^2$ is H; and $R^3$ is —$CH_3$; or
$R^1$ is methyl; $R^2$ is H; and $R^3$ is —$OCH_3$; or
$R^1$ is ethyl; $R^2$ is H; and $R^3$ is —$OCH_3$; or
$R^1$ is —$(CH_2)_2OCH_3$, $R^2$ is H; and $R^3$ is —$OCH_3$; or
$R^1$ is methyl; $R^2$ is H; and $R^3$ is —$OCHF_2$; or
$R^1$ is ethyl; $R^2$ is H; and $R^3$ is —$OCHF_2$; or
$R^1$ is —$(CH_2)_2OCH_3$, $R^2$ is H; and $R^3$ is —$OCHF_2$; or
$R^1$ is methyl; $R^2$ is H; and $R^3$ is —$OCH_2CH_3$; or
$R^1$ is ethyl; $R^2$ is H; and $R^3$ is —$OCH_2CH_3$; or
$R^1$ is —$(CH_2)_2OCH_3$, $R^2$ is H; and $R^3$ is —$OCH_2CH_3$.

21. The compound of claim 1, or a salt thereof, wherein $R^1$ is methyl; $R^2$ is H; and $R^3$ is F.

22. The compound of claim 1, or a salt thereof, wherein $R^1$ is ethyl; $R^2$ is H; and $R^3$ is F.

23. A pharmaceutical formulation comprising:
a) the compound, or a salt thereof, of claim 1; and
b) a pharmaceutically acceptable excipient.

24. The pharmaceutical formulation of claim 23, wherein the pharmaceutical formulation is a unit dosage form.

25. The pharmaceutical formulation of claim 23, wherein the salt of the compound is a pharmaceutically acceptable salt.

26. A method of inhibiting PARP1 and/or PARP2 and/or tubulin, comprising: contacting said PARP1 and/or PARP2 and/or tubulin with an effective amount of the compound of claim 1, thereby inhibiting said PARP1 and/or PARP2 and/or tubulin.

27. A method of treating a cancer in an animal, comprising: administering to an animal in need of treatment thereof a therapeutically effective amount of the compound of claim 1, or a salt thereof, thereby treating the cancer, and wherein the cancer is a sarcoma, adrenal cortical cancer, anal cancer, bile duct cancer, bladder cancer, bone cancer, bone metastasis, breast cancer, a central nervous system (CNS) cancer, a peripheral nervous system (PNS) cancer, Castleman's Disease, cervical cancer, colon cancer, rectum cancer, endometrial cancer, esophagus cancer, Ewing's family of tumors, eye cancer, gallbladder cancer, a gastrointestinal carcinoid tumor, a gastrointestinal stromal tumor, gestational trophoblastic disease, hairy cell leukemia, Hodgkin's disease, kidney cancer, laryngeal cancer, a hypopharyngeal cancer, acute lymphocytic leukemia, acute myeloid leukemia, children's leukemia, chronic lymphocytic leukemia, chronic myeloid leukemia, liver cancer, lung cancer, a lung carcinoid tumor, malignant mesothelioma, multiple myeloma, myelodysplastic syndrome, myeloproliferative disorders, a nasal cavity cancer, a paranasal cancer, nasopharyngeal cancer, neuroblastoma, an oral cavity cancer, an oropharyngeal cancer, osteosarcoma, ovarian cancer, pancreatic cancer, penile cancer, pituitary tumor, prostate cancer, retinoblastoma, rhabdomyosarcoma, salivary gland cancer, soft tissue cancer, melanoma skin cancer, non-melanoma skin cancer, stomach cancer, testicular cancer, thymus cancer, thyroid cancer, uterine cancer, vaginal cancer, vulvar cancer, or Waldenstrom's macroglobulinemia.

28. The method of claim 27, wherein the animal is a human.

29. The method of claim 27, wherein
the cancer is of the Ewing's family of tumors, and wherein the Ewing's family of tumors is Ewing's sarcoma; or
the cancer is uterine cancer, and wherein the uterine cancer is uterine sarcoma.

30. A method of treating a cancer in an animal, comprising: administering to an animal in need of treatment thereof a therapeutically effective amount of the compound of claim 1, or a salt thereof, thereby treating the cancer, and, wherein the cancer is cancer of the blood, cancer of the skin, cancer of the colon, cancer of the lung, cancer of the ovary, cancer of the uterus, cancer of the breast, cancer of the prostate, cancer of the pancreas, cancer of the central nervous system, or cancer of the renal system.

31. The method of claim 30, wherein the cancer is a cancer of the blood, and the cancer of the blood is leukemia; or the cancer is a cancer of the skin, and the cancer of the skin is melanoma.

32. The method of claim 27, wherein the cancer is a soft tissue cancer, and the soft tissue cancer is adult soft tissue cancer.

33. The method of claim 27, wherein the cancer is multiple myeloma, ovarian cancer, uterine cancer, pancreatic cancer, lung cancer, melanoma skin cancer, non-melanoma skin cancer, colon cancer, or brain cancer when the cancer is a central nervous system cancer.

34. The method of claim 27, wherein the cancer is derived from cancer stem cells.

35. The method of claim 27, wherein the cancer is breast cancer.

36. The method of claim 27, wherein the cancer is breast cancer, and the breast cancer is negative for one or more of Estrogen Receptor (ER), Progesterone Receptor (PR), or Human Epidermal Growth Factor Receptor 2 (HER2).

37. The method of claim 27, wherein the cancer is breast cancer, and the breast cancer is negative for one or more of ER, PR or HER2; and wherein the breast cancer is positive for one or more of ER, PR or HER2.

38. The method of claim 27, wherein the cancer is breast cancer, and the breast cancer is negative for two of ER, PR or HER2.

39. The method of claim 27, wherein the cancer is breast cancer, and the breast cancer is ER negative and PR-negative, or the breast cancer is ER-negative and HER2-negative, or the breast cancer is PR-negative and HER2-negative, or the breast cancer is an ER-negative breast cancer, or the breast cancer is an HER2-negative breast cancer.

40. A method of treating a cancer in an animal, comprising: administering to an animal in need of treatment thereof a therapeutically effective amount of the compound of claim 1, or a salt thereof, thereby treating the cancer, wherein the cancer is deficient in Homologous Recombination (HR) dependent DNA double strand repair (DSB).

41. The method of claim 30, wherein the animal is a human.

42. The method of claim 40, wherein the animal is a human.

* * * * *